(12) United States Patent
Bouckaert et al.

(10) Patent No.: US 10,273,313 B2
(45) Date of Patent: Apr. 30, 2019

(54) MULTIMERIC MANNOSIDES, A PROCESS FOR PREPARING THE SAME AND THEIR USES AS A DRUG

(71) Applicants: CENTRE NATIONAL DE LA RECHERCHE SCIENTIFIQUE, Paris (FR); UNIVERSITE DE NANTES, Nantes (FR); UNIVERSITE DE PICARDIE JULES VERNE, Amiens (FR); UNIVERSITE LILLE 1-SCIENCES ET TECHNOLOGIES, Villeneuve d'Ascq (FR); UNIVERSITE D'AUVERGNE, Clermont-Ferrand (FR); INSERM (INSTITUT NATIONAL DE LA SANTE ET DE LA RECHERCHE MEDICALE), Paris (FR)

(72) Inventors: Julie Bouckaert, Kortrijk (BE); Sebastien Gouin, Thouare sur Loire (FR); David Deniaud, Saint Herblain (FR); Rostyslav Bilyy, Lviv (UA); Tetiana Dumych, Volyn Oblast (UA); Adeline Sivignon, Gerzat (FR); Arlette Darfeuille-Michaud, La Roche-Blanche (FR)

(73) Assignees: CENTRE NATIONAL DE LA RECHERCHE SCIENTIFIQUE, Paris (FR); UNIVERSITE DE NANTES, Nantes (FR); UNIVERSITE DE PICARDIE JULES VERNE, Amiens (FR); UNIVERSITE LILLE 1-SCIENCES ET TECHNOLOGIES, Villeneuve d'Ascq (FR); UNIVERSITE D'AUVERGNE, Clermont-Ferrand (FR)

( * ) Notice: Subject to any disclaimer, the term of this patent is extended or adjusted under 35 U.S.C. 154(b) by 250 days.

(21) Appl. No.: 14/416,529

(22) PCT Filed: Jul. 24, 2013

(86) PCT No.: PCT/EP2013/065668
§ 371 (c)(1),
(2) Date: Jan. 22, 2015

(87) PCT Pub. No.: WO2014/016361
PCT Pub. Date: Jan. 30, 2014

(65) Prior Publication Data
US 2015/0210781 A1    Jul. 30, 2015

(30) Foreign Application Priority Data
Jul. 24, 2012  (EP) .................... 12305906

(51) Int. Cl.
*A61K 47/61* (2017.01)
*C07H 15/26* (2006.01)
*A61K 39/385* (2006.01)
*C08B 37/16* (2006.01)
*C07H 17/00* (2006.01)
*C07H 19/06* (2006.01)

(52) U.S. Cl.
CPC ........ *C08B 37/0012* (2013.01); *A61K 39/385* (2013.01); *A61K 47/61* (2017.08); *C07H 15/26* (2013.01); *C07H 17/00* (2013.01); *C07H 19/06* (2013.01)

(58) Field of Classification Search
CPC .............. C08B 37/0012; A61K 31/724; A61K 47/4823
See application file for complete search history.

(56) References Cited

U.S. PATENT DOCUMENTS

2007/0049552 A1*  3/2007 Babu .................... A61K 9/0014
                                                         514/58

OTHER PUBLICATIONS

Almant, M. et al "Clustering of *Escherichia coli* Type-1 fimbrial . . . " Chem. Eur. J. (2011) vol. 17, pp. 10029-10038.*
Ortiz Mellet, C. et al "Multivalent cyclooligosaccharides: versatile carbohydrate clusters . . . " Chem. Eur. J. (2002) vol. 8, No. 9, pp. 1983-1990.*

(Continued)

*Primary Examiner* — Leigh C Maier
(74) *Attorney, Agent, or Firm* — Young & Thompson

(57) ABSTRACT

The present invention relates to multimeric mannosides, a process for preparing the same and their uses in medicine for treating *Escherichia coli* infections. Exemplary compounds are:

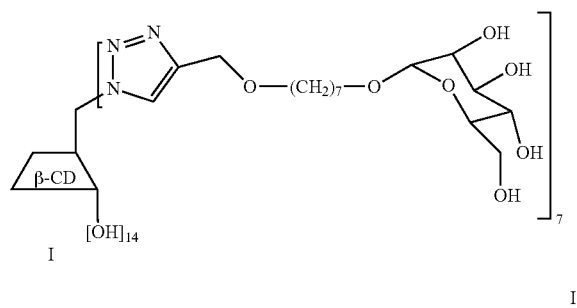

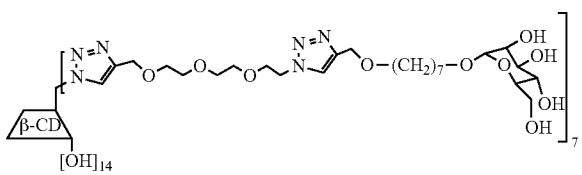

21 Claims, 23 Drawing Sheets

(56) References Cited

OTHER PUBLICATIONS

Christensen, H. et al "Recognition of peptides by cyclodextrin trimers" (2011) pp. 5279-5290.*
Wellens, A. et al "Intervening with urinary tract infections . . . " PLoS One, vol. 3, No. 4, pp. 1-13. (Year: 2008).*
Gouin, S. et al "Synthetic multimeric heptyl mannosides . . . " ChemMedChem, vol. 4, pp. 749-755. (Year: 2009).*

* cited by examiner

Figure 3
Figure 3A
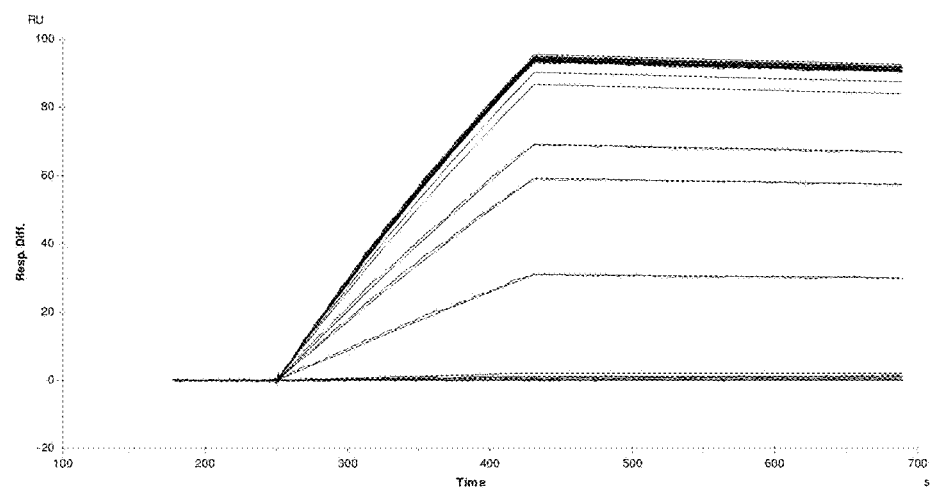
Figure 3B
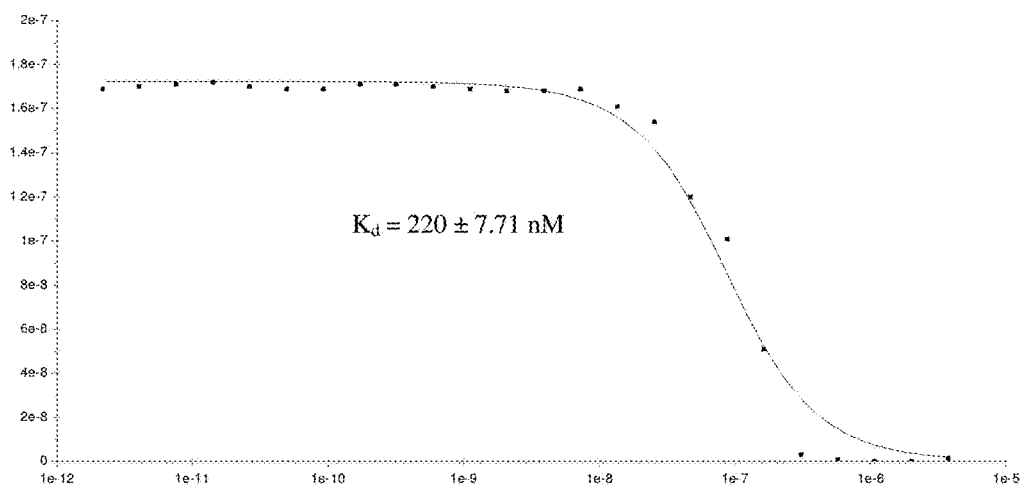
$K_d = 220 \pm 7.71$ nM

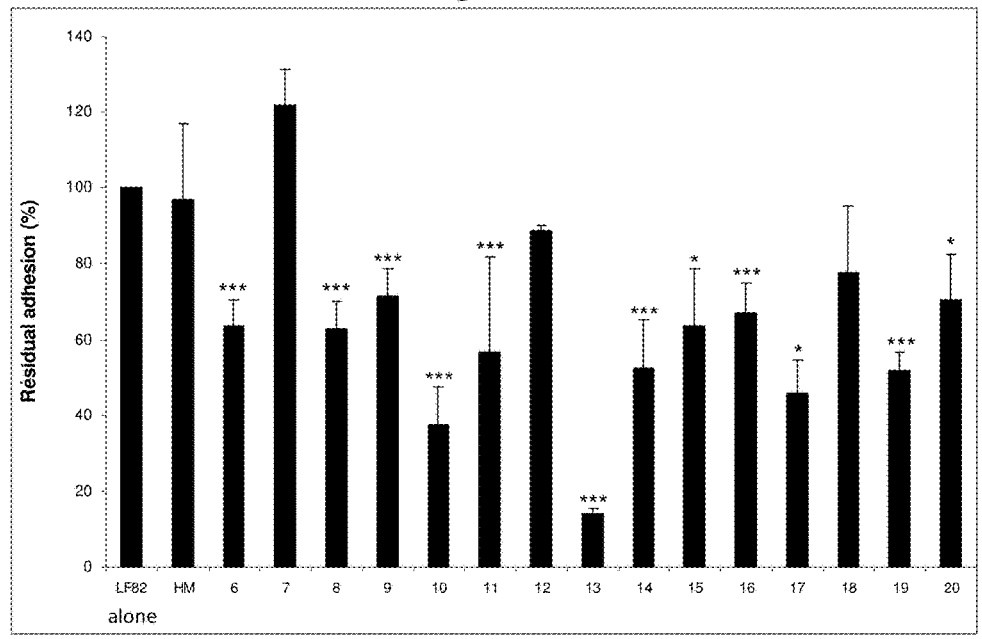
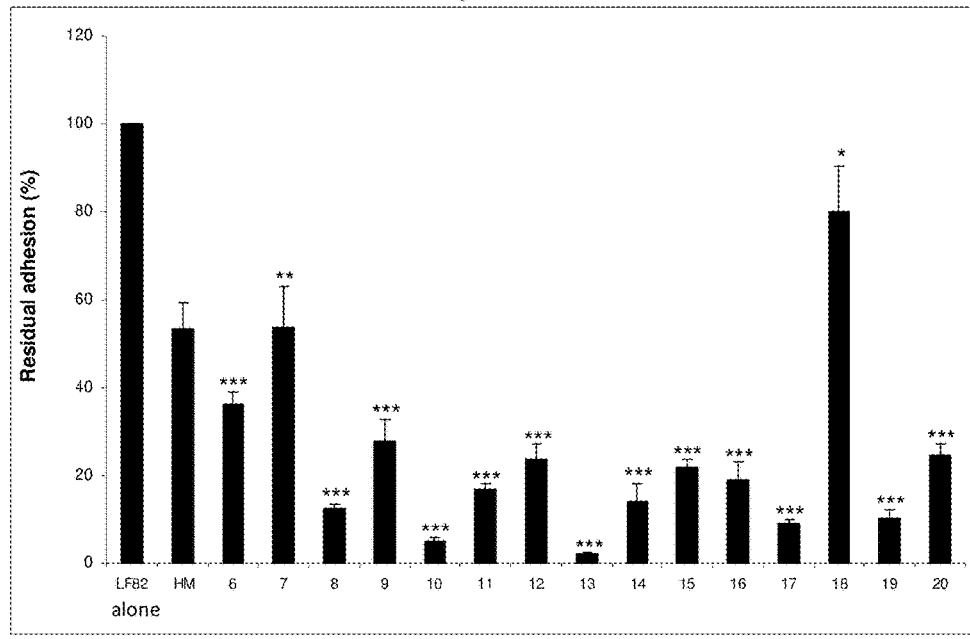

MULTIMERIC MANNOSIDES, A PROCESS FOR PREPARING THE SAME AND THEIR USES AS A DRUG

The present invention relates to mannose derivatives, a process for preparing the same and their uses as a drug.

Most *E. coli* express on their cell surface a few hundreds of proteinaceous, rod-like organelles, of up to 1 μm long, that are called type-1 fimbriae. Type-1 fimbriae carry an adhesin at the edge of a flexible tip fibrillum that is a lectin having a high-affinity for mannose, FimH. The receptors of FimH are high-mannosylated glycoproteins. Well-known receptors of FimH are uroplakin 1a on the bladder epithelium and CEACAM6 on the colon epithelium. FimH binding to its receptor transduces signaling in the cytoplasm of the infected epithelial cell and allows invasion of the bacteria. Epithelial cell invasion and intracellular survival and replication of the bacterium are paired with severe early inflammatory responses that are the prelude to recurrent and persistent infections by *Escherichia coli*.

The specificity of FimH lectin has been identified (Bouckaert, J. et al. *Mol. Microbiol.* 61: 1556-1568 (2006); Wellens, A. et al. *PloS One* 3(4): e2040. (2008). The FimH adhesin has been structurally and functionally characterized and a series of inhibitors with nanomolar affinities has been developed (Bouckaert, J. et al. *Mol. Microbiol.* 55(2): 441-455 (2005); Gouin, S. G. et al. *Chem Med Chem* 4 (5), 749-755 (2009). US2008171706 describes alkyl α-D-mannoside compounds that are effectively inhibiting binding of *E. coli* to its human cell targets. Heptyl α-D-mannoside is to date one of the best in vitro characterised monomeric mannose-based inhibitors of FimH. In vivo efficiency is however limited and millimolar concentrations of this compound are required to inhibit bacterial colonization of the bladder.

The unprotected and hydrophobic aglycones of these compounds tend to interact in serum or absorb into biological membranes, through which they need multiple passages to end up in bladder or colon upon oral administration. Moreover, aforesaid inhibitors are not easily adaptable to the required pharmacological properties (log P, log O, permeability, solubility, affinity and retention) because the mannoside moiety needs to be conserved to maintain specificity and a large part of the hydrophobic aglycone moiety is not permissive to structural changes to maintain affinity for FimH.

The human urinary tract is a normally sterile environment. However, the urinary tract is the most prevalent focus for bacteremia. At times, bacteria invade it from the intestinal tract and cause urinary tract infections (UTIs). Women are more prone to UTI than men due to differences in anatomy. *Escherichia coli* is the most prevalent causative agent of infection in the bladder or cystitis, in more than 75% of the cases. *E. coli* bacteria may attach to densely displayed glycans on urinary epithelial cells via hundreds of fimbriae simultaneously, and thus act in a multivalent fashion. When *E. coli* enters the bladder, the initial encounter of the bacterium with the urothelium is made with the uroplakins. This host-pathogen interaction can induce phosphorylation of the cytoplasmic tail of uroplakin IIIa in bladder cells. Uroplakin Ia is in ring-shaped complexes with three other uroplakins on the bladder epithelium and carries a single high-mannosylated glycosylation site, in embryonic tissue shown to consist of a mixture of oligomannosides-6, -7, -8 and -9. The attachment of type-1 fimbriae can provoke conformational changes in the mannosylated glycoprotein receptor, which subsequently translates into signaling in the cytoplasm of the infected epithelial cell and invasion of the bacteria. These conformational changes in the glycoprotein receptor translate into signaling in the infected epithelial cell, with subsequent uptake of the successful *E. coli* being the prelude to chronic, recurrent or persistent *E. coli* infections in humans from now on almost insensible to antibiotic treatment.

Crohn's disease is a chronic and lifelong disease which affects 4 millions of people worldwide with a prevalence of about 100 cases per 100,000 individuals. It has a major impact on the quality of life, extending into the old age and 80% of patients will require surgery. Crohn's disease represents an important economic impact on the healthcare system and the economy as a whole, with direct costs ($18,022-18,932 per year for patients living in the US, "Inflammatory bowel disease-attributable costs and cost-effective strategies in the united states: a review" K. T. Park, MD, and Dorsey Bass, MD, IBD 2011) and indirect costs because of the effect on employability.

Crohn's disease is characterized by an aberrant immune response occurring in a genetically predisposed host in response to microbes and/or microbial compounds. Adherent-Invasive *E. coli* (AIEC) bacteria are found abnormally associated with the ileal mucosa in 36.4% of the Crohn's disease patients with an ileal involvement. As these bacteria possess invasive, anti-phagocytic and pro-inflammatory properties, this is of a crucial importance to elaborate a strategy to eradicate AIEC bacteria from the digestive tract, in inhibiting the bacterial adhesion. The role of type 1 fimbriae was well established in these *E. coli* strains associated with Crohn's disease. It has been shown that the ileum of CD patients is abnormally colonized by *E. coli* bacteria in results from overexpression of carcinoembryonic antigen-related cell adhesion molecule 6 (CEACAM6) acting as receptors for *E. coli* adhesion via type 1 pili. Bacterial adhesion to intestinal epithelial cells is mediated by the FimH adhesin on the tip of the type 1 pili from the bacteria. Several amino acid substitutions modify type 1 pili FimH adhesin affinity for various mannose residues [Bouckaert, Berglund, Schembri, De Genst, Cools, Wuhrer, Hung, Pinkner, Slattegard, Zavialov, Choudhury, Langermann, Hultgren, Wyns, Klemm, Oscarson, Knight and De Greve, Receptor binding studies disclose a novel class of high-affinity inhibitors of the *Escherichia coli* FimH adhesin. Mol Microbiol, 2005. 55.441-55, Schembri, Christiansen and Klemm, FimH-mediated auto aggregation of *Escherichia coli*. Mol Microbiol, 2001. 41.1419-30, Sokurenko, Schembri, Trintchina, Kjaergaard, Hasty and Klemm, Valency conversion in the type 1 fimbrial adhesin of *Escherichia coli*. Mol Microbiol, 2001. 41.675-86], under conditions of shear force. The AIEC reference strain LF82 expresses type 1 pili variant with four amino acid substitutions (V27A; N70S; S78N; T158P) that could favour the binding of the bacteria to the abnormally expressed CEACAM6 receptor in CD patients. The host/bacteria crosstalk in the context of host susceptibility to CD can be mimicked using CEABAC10 transgenic mouse expressing human CEACAM6 receptor. In this model, it has been reported that AIEC infected CEABAC10 mice develop severe colitis and are abundantly colonized by bacteria only when AIEC bacteria express type 1 pili.

One objective of the present invention is to provide mannose derivatives liable to treat pathologies caused by *Escherichia coli* and mediated by interactions between *Escherichia coli* lectins and host cell surface glycans, in particular pathologies caused by *Escherichia coli* and mediated by interactions between *Escherichia coli* FimH adhesin and host cell surface glycans.

Another aim of the present invention is to provide mannose derivatives enabling to reduce the intake of antibiotics when treating *Escherichia coli* infection.

Another aim of the invention is to provide mannose derivatives liable to constitute a treatment of urinary tract infections, in particular for those patients suffering from interstitial cystitis and/or painful bladder syndrome.

Another aim of the invention is to provide mannose derivatives liable to constitute a treatment for those patients suffering from a urinary tract infection in the context of a metabolic disease correlated with enhanced apoptosis, especially diabetes.

Still another aim of the invention is to provide mannose derivatives liable to constitute a treatment of inflammatory bowel disease, especially Crohn's disease.

The present invention relates to a compound of the following formula (I):

$$A\text{-}X_n \quad (I)$$

wherein:
A is a scaffold;
n is an integer comprised from 3 to 10, in particular from 3 to 8, more particularly from 3 to 7;
X represents a group of the following formula (1):

$$-W_p\text{-}L_r\text{-}Y_s-Z \quad (1)$$

wherein:
p, r, and s are integers independently from each other equal to 0 or 1, provided that:
the sum p+r+s is different from 0, and
when r is equal to 0, p and s are such as the sum p+s is equal to 1;
W is chosen from:

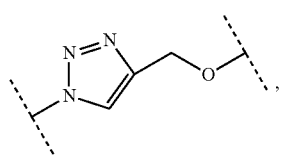 (1')

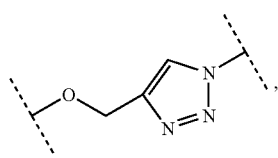 (2')

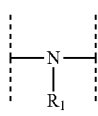 (3')

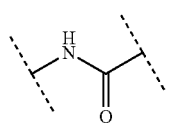 (4')

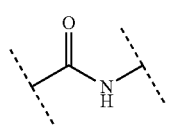 (4bis')

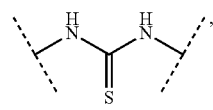 (5')

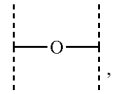 (6')

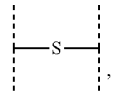 (7')

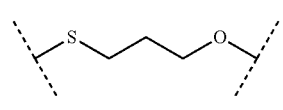 (8')

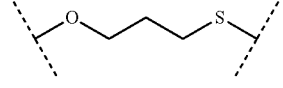 (8bis')

and, when r and s are equal to 0, W can also represent:

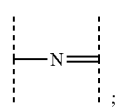 (3bis')

Y is chosen from:

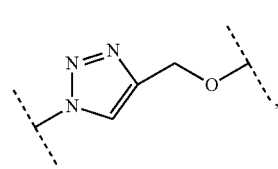 (1')

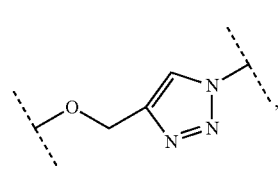 (2')

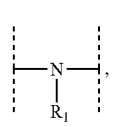 (3')

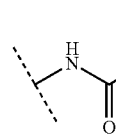 (4')

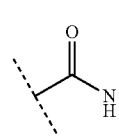 (4bis')

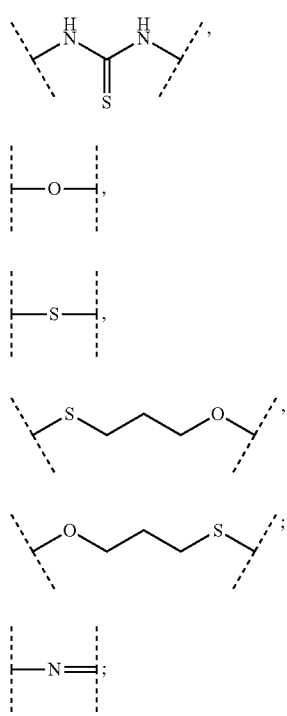

R1 representing:
  a hydrogen, or
  a linear or branched $(C_1-C_7)$-alkyl;
Z is chosen from:

(1″)

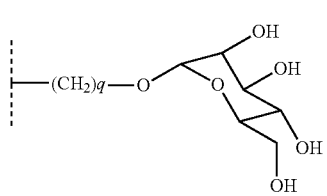

(2″)

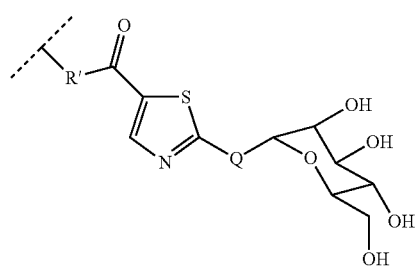

(3″)

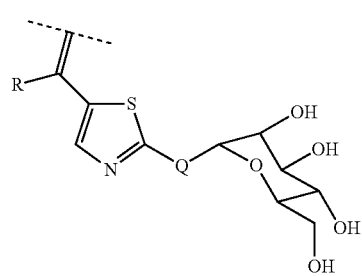

(4″)

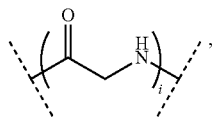

provided Z represents (3″):

(3″)

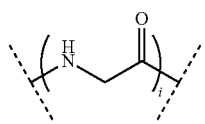

if and only if Y or W represents (3bis′):

(3bis′)

$\vdash\!\!-N\!=\!\!\dashv$ ;

L represents a linker of one of the following formulae:

when p+s=0, corresponding to X=-L-Z, ($1_2$)

or, providing Z is different from (4″), ($1_4$)

i being an integer comprised from 0 to 20, in particular from 0 to 10, when p+s=1, corresponding to X=—W-L-Z or -L-Y—Z, when p=0, corresponding to X=-L-Y—Z,

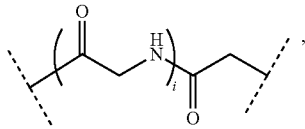
(1₃)

or, providing Y is chosen from (3'), (6'), (7'), (8') and (8bis'),

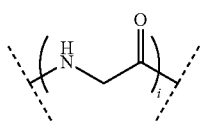
(1₄)

i being an integer comprised from 0 to 20, in particular from 0 to 10, when p=1, corresponding to X=—W-L-Z,

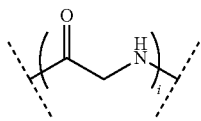
(1₂)

i being an integer comprised from 0 to 20, in particular from 0 to when p+s=2, corresponding to X=—W-L-Y—Z,

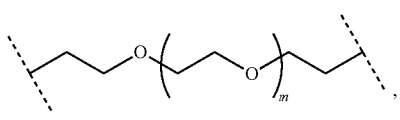
(1₁)

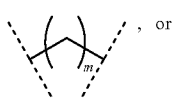, or
(1₅)

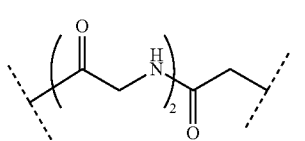
(1₃)

m being an integer comprised from 0 to 20, in particular from 0 to 10, i being an integer comprised from 0 to 20, in particular from 0 to 10, provided L represents (l₃) only when Z represents a group selected from (3'), (6'), (7'), (8') and (8bis'):

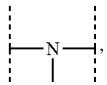
(3')

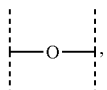
(6')

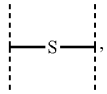
(7')

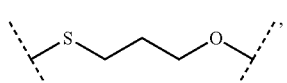
(8')

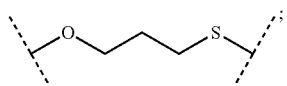
(8bis')

q being an integer chosen from 6, 7 and 8, q being in particular equal to 7;

Q representing NH, O or S, in particular NH;

R' representing a group selected from:
- a linear or branched $(C_1-C_7)$-alkane diyl,
- a linear or branched $(C_2-C_7)$-alkene diyl,
- a linear or branched $(C_2-C_7)$-alkyne diyl,
- a $(C_3-C_7)$-cycloalkane diyl,
- a $(C_5-C_7)$-cycloalkene diyl,
- a $(C_3-C_7)$-heterocycloalkane diyl,
- a $(C_5-C_7)$-heterocycloalkene diyl,
- an arene diyl, said arene being an aromatic or heteroaromatic group,
- a group -arene₁-arene₂- wherein arene₁ and arene₂ are independently to each other an aromatic or heteroaromatic arene;

said $(C_1-C_7)$-alkane diyl, $(C_2-C_7)$-alkene diyl, $(C_2-C_7)$-alkyne diyl, $(C_3-C_7)$-cycloalkane diyl, $(C_5-C_7)$-cycloalkene diyl, $(C_3-C_7)$-heterocycloalkane diyl, $(C_5-C_7)$-heterocycloalkene diyl, arene diyl, arene₁ and arene₂ being substituted or not by one or more substituent(s), each independently selected from:
- a linear or branched $(C_1-C_7)$-alkyl,
- a linear or branched $(C_2-C_7)$-alkenyl,
- a linear or branched $(C_2-C_7)$-alkynyl,
- a $(C_3-C_7)$-cycloalkyl,
- a $(C_5-C_7)$-cycloalkenyl,
- a $(C_3-C_7)$-heterocycloalkyl,
- a $(C_5-C_7)$-heterocycloalkenyl,
- an aryl, wherein the aryl is an aromatic or heteroaromatic group
- an alkyl aryl, wherein the aryl is an aromatic or heteroaromatic group,
- a CHO,
- a CO—$(C_1-C_7)$-alkyl,
- a CO-aryl, wherein aryl is an aromatic or heteroaromatic group,
- a $CO_2H$,
- a $CO_2$—$(C_1-C_7)$-alkyl,
- a CONH—$(C_1-C_7)$-alkyl,
- a halogen selected from the group comprising F, Cl, Br, and I, CF$_3$,
OR$_a$, wherein R$_a$ represents:
  H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
NR$_b$R$_c$, wherein R$_b$ and R$_c$ represent independently from each other:
  H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
NO$_2$,
CN;
R representing a group selected from:
  a linear or branched (C$_1$-C$_7$)-alkyl,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl,
  an aryl, said aryl being an aromatic or heteroaromatic group,
  an alkyl aryl, wherein the aryl is an aromatic or heteroaromatic group,
  a CO—(C$_1$-C$_7$)-alkyl,
  a CO-aryl, wherein aryl is an aromatic or heteroaromatic group,
  a CO$_2$H,
  a CO$_2$—(C$_1$-C$_7$)-alkyl,
  a CONH—(C$_1$-C$_7$)-alkyl,
  CF$_3$,
  adamantyl,
said (C$_1$-C$_7$)-alkyl, (C$_2$-C$_7$)-alkenyl, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl and CO-aryl being substituted or not by one or more substituent(s), each independently selected from:
  a linear or branched (C$_1$-C$_7$)-alkyl,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl,
  an aryl, wherein the aryl is an aromatic or heteroaromatic group
  an alkyl aryl, wherein the aryl is an aromatic or heteroaromatic group,
  a CHO,
  a CO—(C$_1$-C$_7$)-alkyl,
  a CO-aryl, wherein aryl is an aromatic or heteroaromatic group,
  a CO$_2$H,
  a CO$_2$—(C$_1$-C$_7$)-alkyl,
  a CONH—(C$_1$-C$_7$)-alkyl,
  a halogen selected from the group comprising F, Cl, Br, and I,
  CF$_3$,
  OR$_a$, wherein R$_a$ represents:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NR$_b$R$_c$, wherein R$_b$ and R$_c$ represent independently from each other:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NO$_2$,
  CN,
A being such as the n bonds between A and the n groups X are, considering the mean position of aforesaid bonds, substantially equidistant,
provided that aforesaid compound is different from:

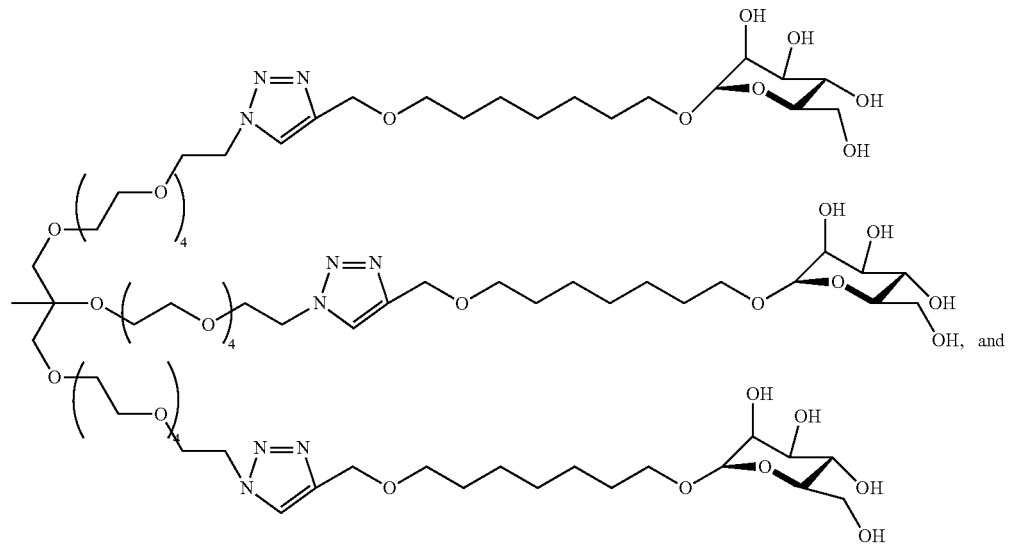

-continued

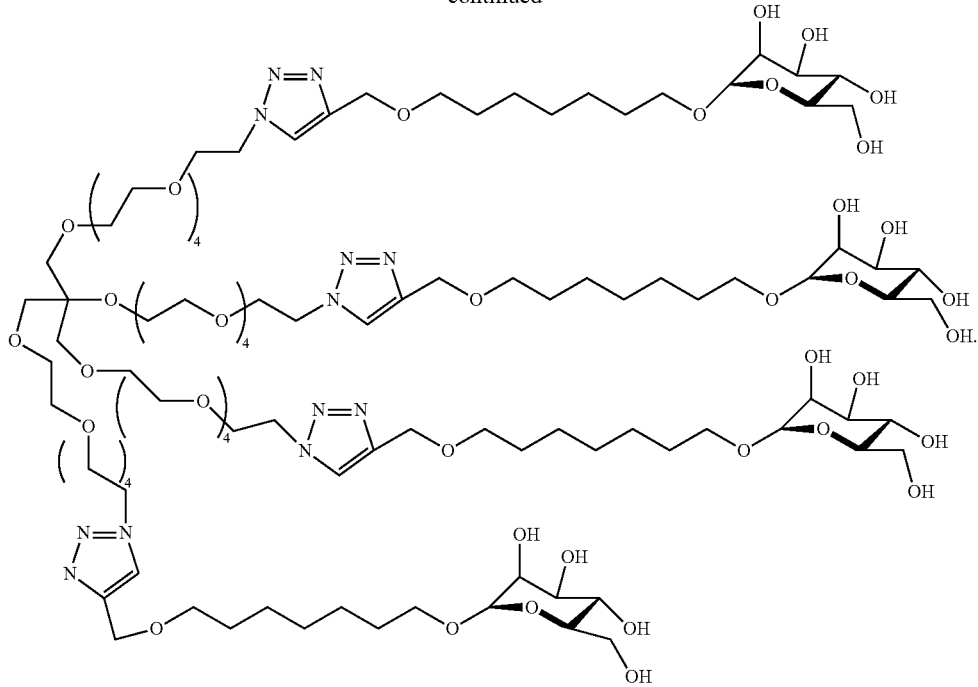

By "scaffold" is meant a chemical moiety which displays the n substituents X in a particular special geometry, aforesaid substituents X being covalently bound to aforesaid scaffold.

By linear ($C_1$-$C_7$) alkyl group is meant a group such as methyl, ethyl, propyl, butyl, pentyl, hexyl or heptyl.

By branched alkyl group is meant an alkyl group as defined above bearing substituents selected from the list of linear alkyl groups defined above, said linear alkyl group being also liable to be branched.

By linear ($C_2$-$C_7$) alkenyl group is meant a linear hydrocarbon group constituted by 2 to 7 carbon atoms, with one or more carbon-carbon double bond(s).

By branched alkenyl group is meant an alkenyl group as defined above bearing substituents selected from the list of linear alkyl groups defined above, said linear alkyl group being also liable to be branched.

By linear ($C_2$-$C_7$) alkynyl group is meant a linear hydrocarbon group constituted by 2 to 7 carbon atoms, with one or more carbon-carbon triple bond(s).

By branched alkynyl group is meant an alkynyl group as defined above bearing substituents selected from the list of linear alkyl groups defined above, said linear alkyl group being also liable to be branched.

By ($C_3$-$C_7$)-cycloalkyl group is meant a group such as cyclopropyl, cyclobutyl, cyclopentyl, cyclohexyl or cycloheptyl.

By ($C_5$-$C_7$)-cycloalkenyl group is meant a cyclic hydrocarbon group constituted by 5 to 7 carbon atoms, with one or more carbon-carbon double bond(s).

By ($C_3$-$C_7$)-heterocycloalkyl group is meant a ($C_3$-$C_7$)- cyclic group having at least one non-carbon atom in the ring.

By ($C_5$-$C_7$)-heterocycloalkenyl group is meant a heterocyclic group constituted by 5 to 7 carbon atoms, with one or more double bond(s).

The term "aryl" refers to any functional group or substituent derived from a simple aromatic ring, aforesaid aromatic ring comprising from 6 to 16 carbon atoms.

The term "heteroaromatic" refers to a compound comprising from 5 to 16 atoms, having the characteristics of an aromatic compound whilst having at least one non-carbon atom in the ring, aforesaid non-carbon atom being in particular N, S or O.

By alkyl aryl group is meant a linear or branched alkyl group that is substituted by an aryl group.

By

is meant that the atom At is bound through a covalent bond to another atom or group that is not represented.

For instance, considering:

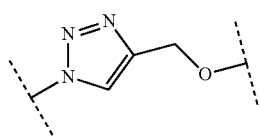

by

is meant that the oxygen atom is bound to another atom or group through a covalent bond involving aforesaid oxygen atom;

by

is meant that the nitrogen atom is bound to another atom or group through a covalent bond involving aforesaid nitrogen atom.

The above-mentioned definitions apply to the entire specification.

Surprisingly, the inventors have found that compounds of the invention are considerably more potent than monovalent heptylmannoside, for instance to reduce bacterial load in the bladder of mice suffering from urinary tract infection, whereas FimH is known to possess a single available binding centre and thus is not a candidate to consider for multivalent effect investigations.

The present invention also relates to a compound of the following formula (I):

$$A\text{-}X_n \quad (I)$$

wherein:
A is a scaffold;
n is an integer comprised from 3 to 10, in particular from 3 to 8, more particularly from 3 to 7;
X represents a group of the following formula (1):

$$-W_p\text{-}L_r\text{-}Y_s-Z \quad (1)$$

wherein:
p, r, and s are integers independently from each other equal to 0 or 1, provided that:
the sum p+r+s is different from 0, and
when r is equal to 0, p and s are such as the sum p+s is equal to 1;
W is chosen from:

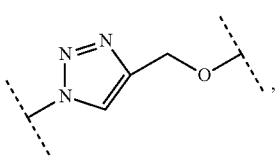 (1')

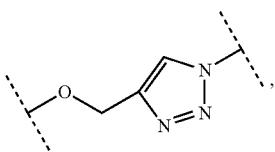 (2')

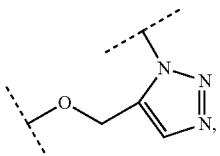 (2bis')

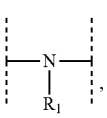 (3')

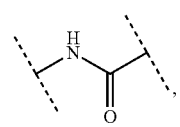 (4')

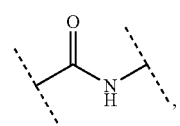 (4bis')

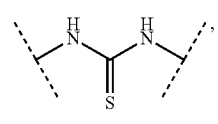 (5')

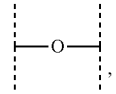 (6')

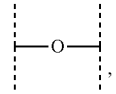 (7')

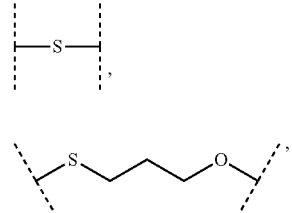 (8')

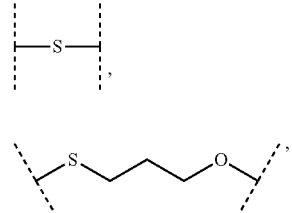 (8bis')

and, when r and s are equal to 0, W can also represent:

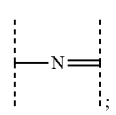 (3bis')

Y is chosen from:

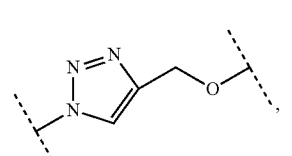 (1')

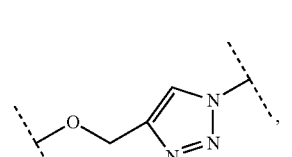 (2')

-continued
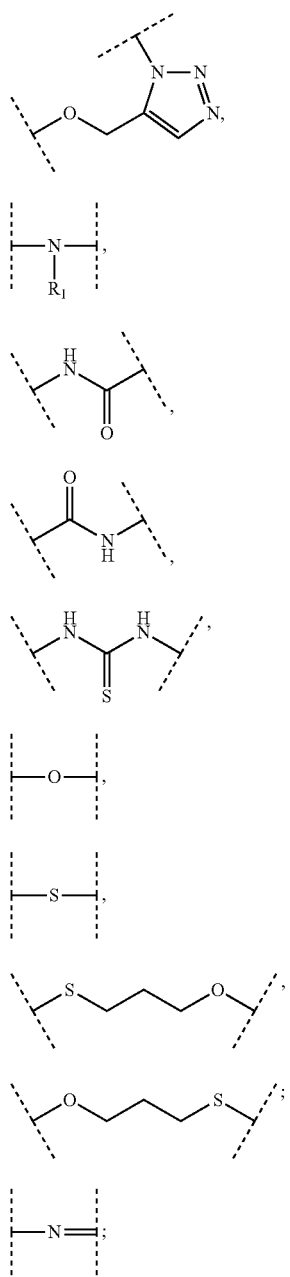
R1 representing:
 a hydrogen, or
 a linear or branched $(C_1\text{-}C_7)$-alkyl;
Z is chosen from:
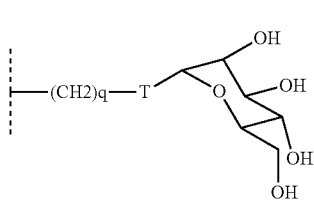
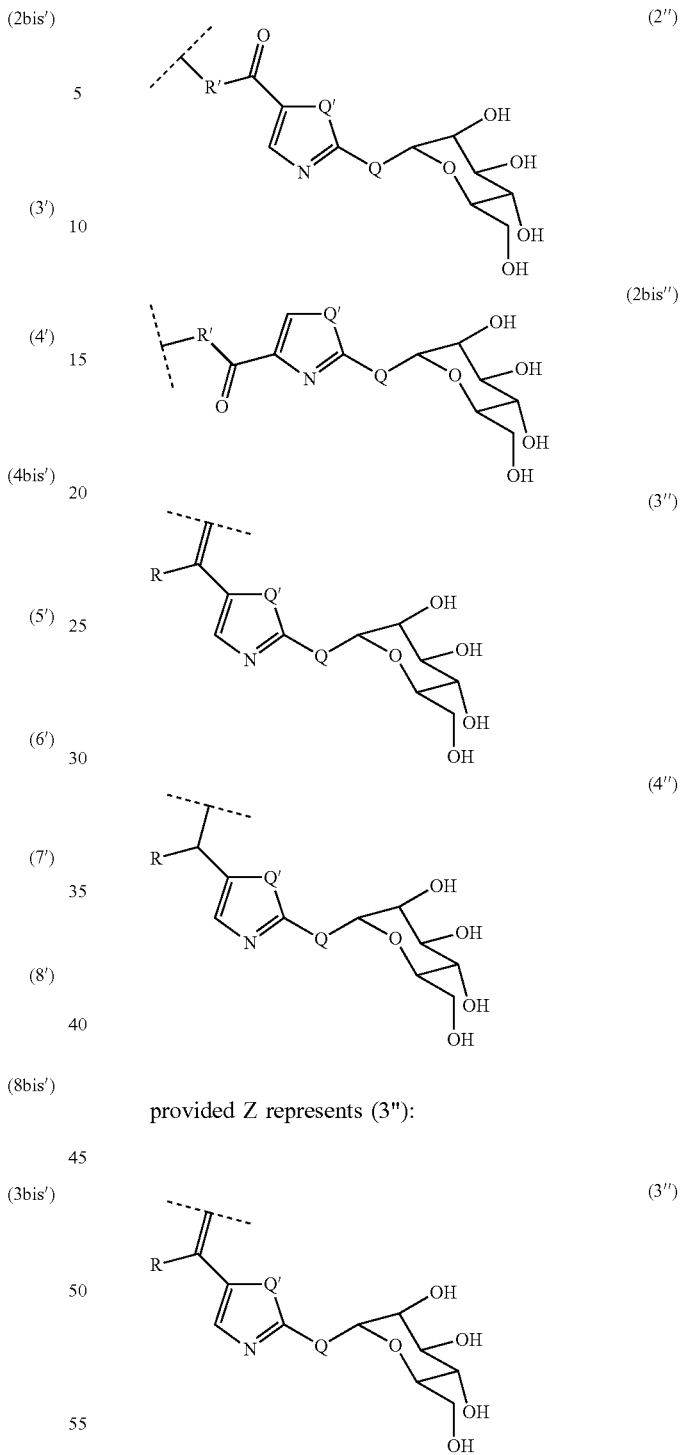
provided Z represents (3"):
if and only if Y or W represents (3bis'):

L represents a linker of one of the following formulae:

when p+s=0, corresponding to X=-L-Z,

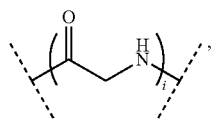

(1₂)

or, providing Z is different from (4″),

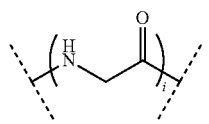

(1₄)

i being an integer comprised from 0 to 20, in particular from 0 to 10, when p+s=1, corresponding to X=—W-L-Z or -L-Y—Z, when p=0, corresponding to X=-L-Y—Z,

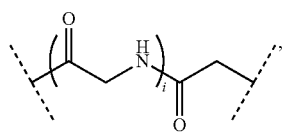

(1₃)

or, providing Y is chosen from (3'), (6'), (7'), (8') and (8bis'),

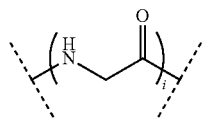

(1₄)

i being an integer comprised from 0 to 20, in particular from 0 to 10, when p=1, corresponding to X=—W-L-Z,

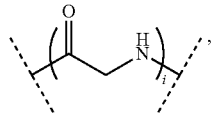

(1₂)

i being an integer comprised from 0 to 20, in particular from 0 to 10, when p+s=2, corresponding to X=—W-L-Y—Z,

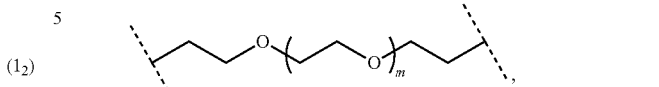

(1₁)

(1₅)

or

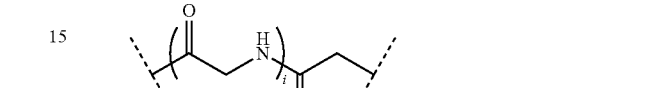

(1₃)

m being an integer comprised from 0 to 20, in particular from 0 to 10, i being an integer comprised from 0 to 20, in particular from 0 to 10, provided L represents (l₃) only when Z represents a group selected from (3'), (6'), (7'), (8') and (8bis'):

(3')

(6')

(7')

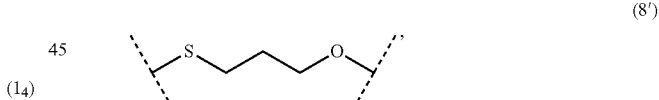

(8')

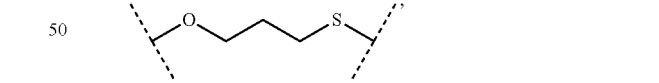

(8bis')

q being an integer chosen from 6, 7 and 8, q being in particular equal to 7;

Q and Q' representing independently from each other NH, O or S;

Q and Q' representing in particular NH and S, respectively;

T representing O, S or $CH_2$, in particular O;

R' representing a group selected from:
- a linear or branched $(C_1-C_7)$-alkane diyl,
- a linear or branched $(C_2-C_7)$-alkene diyl,
- a linear or branched $(C_2-C_7)$-alkyne diyl,
- a $(C_3-C_7)$-cycloalkane diyl,
- a $(C_5-C_7)$-cycloalkene diyl,
- a $(C_3-C_7)$-heterocycloalkane diyl, a ($C_5$-$C_7$)-heterocycloalkene diyl,
an arene diyl, said arene being an aromatic or heteroaromatic group,
a group -$arene_1$-$arene_2$- wherein $arene_1$ and $arene_2$ are independently to each other an aromatic or heteroaromatic arene;
a group of the following formula:

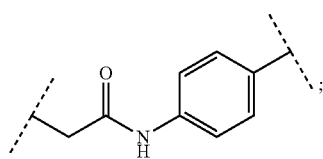

said ($C_1$-$C_7$)-alkane diyl, ($C_2$-$C_7$)-alkene diyl, ($C_2$-$C_7$)-alkyne diyl, ($C_3$-$C_7$)-cycloalkane diyl, ($C_5$-$C_7$)-cycloalkene diyl, ($C_3$-$C_7$)-heterocycloalkane diyl, ($C_5$-$C_7$)-heterocycloalkene diyl, arene diyl, $arene_1$ and $arene_2$ being substituted or not by one or more substituent(s), each independently selected from:
a linear or branched ($C_1$-$C_7$)-alkyl,
a linear or branched ($C_2$-$C_7$)-alkenyl,
a linear or branched ($C_2$-$C_7$)-alkynyl,
a ($C_3$-$C_7$)-cycloalkyl,
a ($C_5$-$C_7$)-cycloalkenyl,
a ($C_3$-$C_7$)-heterocycloalkyl,
a ($C_5$-$C_7$)-heterocycloalkenyl,
an aryl, wherein the aryl is an aromatic or heteroaromatic group
an alkyl aryl, wherein the aryl is an aromatic or heteroaromatic group,
a CHO,
a CO—($C_1$-$C_7$)-alkyl,
a CO-aryl, wherein aryl is an aromatic or heteroaromatic group,
a $CO_2H$,
a $CO_2$—($C_1$-$C_7$)-alkyl,
a CONH—($C_1$-$C_7$)-alkyl,
a halogen selected from the group comprising F, Cl, Br, and I,
$CF_3$,
$OR_a$, wherein $R_a$ represents:
H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
$NR_bR_c$, wherein $R_b$ and $R_c$ represent independently from each other:
H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
$NO_2$,
CN;

R representing a group selected from:
a linear or branched ($C_1$-$C_7$)-alkyl,
a linear or branched ($C_2$-$C_7$)-alkenyl,
a linear or branched ($C_2$-$C_7$)-alkynyl,
a ($C_3$-$C_7$)-cycloalkyl,
a ($C_5$-$C_7$)-cycloalkenyl,
a ($C_3$-$C_7$)-heterocycloalkyl,
a ($C_5$-$C_7$)-heterocycloalkenyl,
an aryl, said aryl being an aromatic or heteroaromatic group,
an alkyl aryl, wherein the aryl is an aromatic or heteroaromatic group,
a CO—($C_1$-$C_7$)-alkyl,
a CO-aryl, wherein aryl is an aromatic or heteroaromatic group,
a $CO_2H$,
a $CO_2$—($C_1$-$C_7$)-alkyl,
a CONH—($C_1$-$C_7$)-alkyl,
$CF_3$,
adamantyl,
said ($C_1$-$C_7$)-alkyl, ($C_2$-$C_7$)-alkenyl, ($C_2$-$C_7$)-alkynyl, ($C_3$-$C_7$)-cycloalkyl, ($C_5$-$C_7$)-cycloalkenyl, ($C_3$-$C_7$)-heterocycloalkyl, ($C_5$-$C_7$)-heterocycloalkenyl, CO—($C_1$-$C_7$)-alkyl, $CO_2$—($C_1$-$C_7$)-alkyl, CONH—($C_1$-$C_7$)-alkyl, aryl, alkyl aryl and CO-aryl being substituted or not by one or more substituent(s), each independently selected from:
a linear or branched ($C_1$-$C_7$)-alkyl,
a linear or branched ($C_2$-$C_7$)-alkenyl,
a linear or branched ($C_2$-$C_7$)-alkynyl,
a ($C_3$-$C_7$)-cycloalkyl,
a ($C_5$-$C_7$)-cycloalkenyl,
a ($C_3$-$C_7$)-heterocycloalkyl,
a ($C_5$-$C_7$)-heterocycloalkenyl,
an aryl, wherein the aryl is an aromatic or heteroaromatic group
an alkyl aryl, wherein the aryl is an aromatic or heteroaromatic group,
a CHO,
a CO—($C_1$-$C_7$)-alkyl,
a CO-aryl, wherein aryl is an aromatic or heteroaromatic group,
a $CO_2H$,
a $CO_2$—($C_1$-$C_7$)-alkyl,
a CONH—($C_1$-$C_7$)-alkyl,
a halogen selected from the group comprising F, Cl, Br, and I,
$CF_3$,
$OR_a$, wherein $R_a$ represents:
H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
$NR_bR_c$, wherein $R_b$ and $R_c$ represent independently from each other:
H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
$NO_2$,
CN, A being such as the n bonds between A and the n groups X are, considering the mean position of aforesaid bonds, substantially equidistant,
provided that aforesaid compound is different from:

when r is equal to 0, p and s are such as the sum p+s is equal to 1,
when r is equal to 1, p and s are such as the sum p+s is equal to 2;

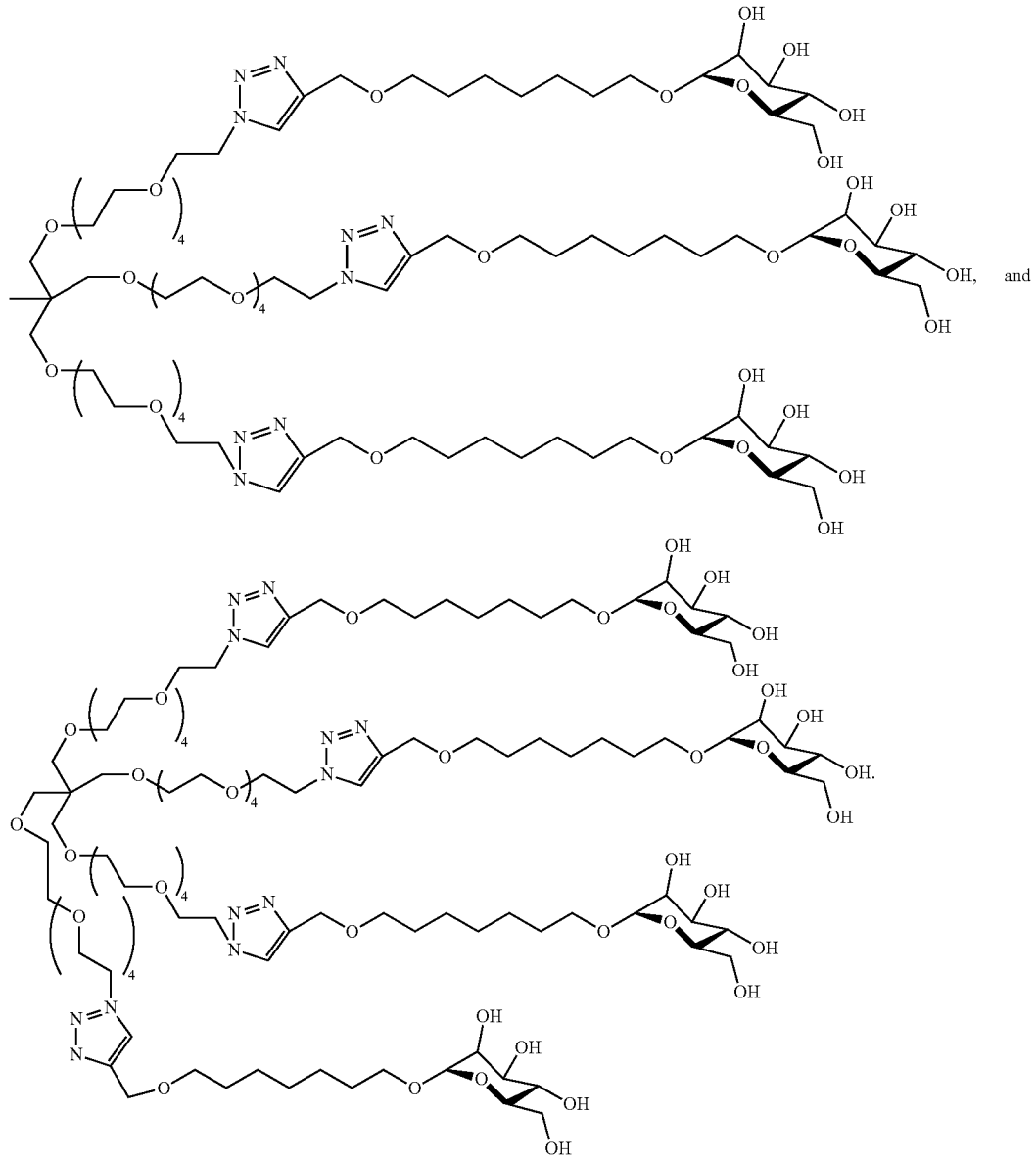

In an advantageous embodiment, the present invention relates to a compound of the following formula (I):

A-X$_n$     (I)

wherein:
A is a scaffold;
n is an integer comprised from 3 to 10, in particular from 3 to 8, more particularly from 3 to 7;
X represents a group of the following formula (1):

—W$_p$-L$_r$-Y$_s$—Z     (1)

wherein:
p, r, and s are integers independently from each other equal to 0 or 1, provided that:

W is chosen from:

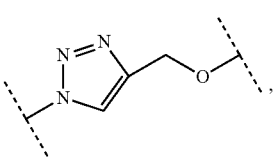

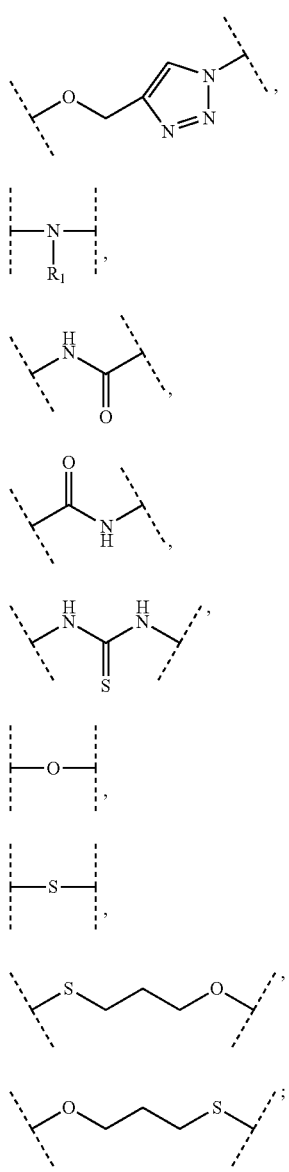
and, when r and s are equal to 0, W can also represent:
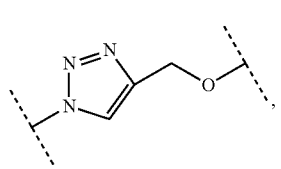
Y is chosen from:
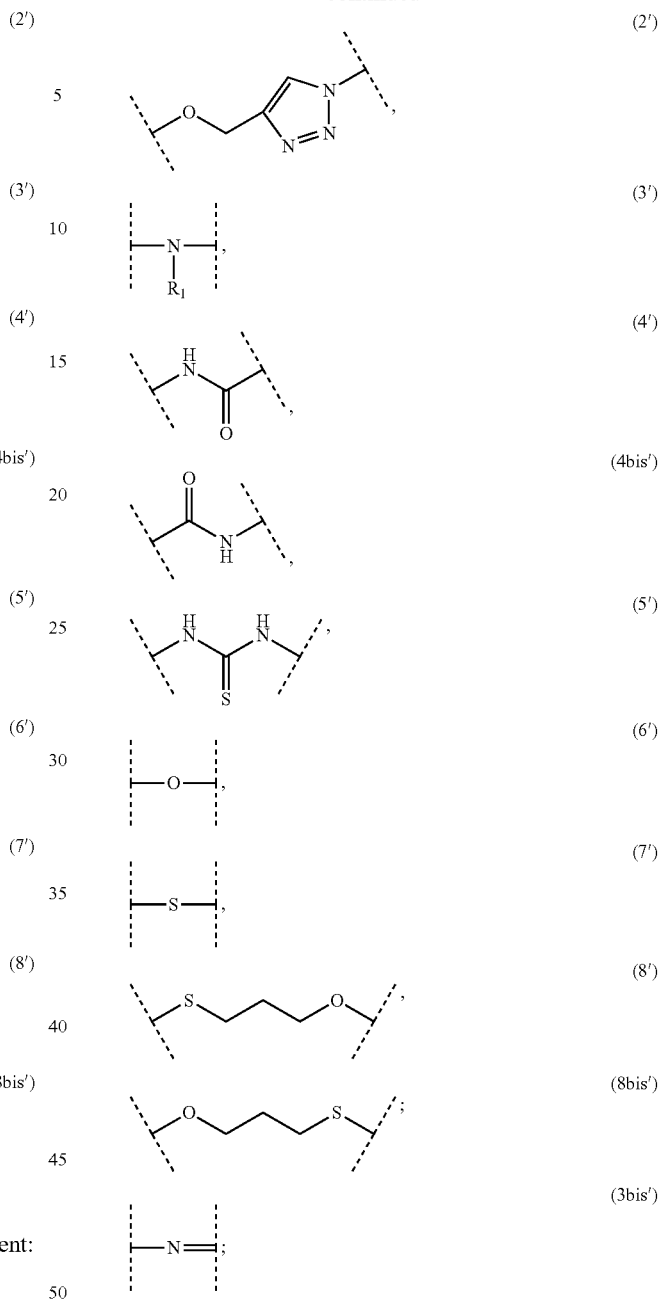
R1 representing:
  a hydrogen, or
  a linear or branched $(C_1-C_7)$-alkyl;
Z is chosen from:
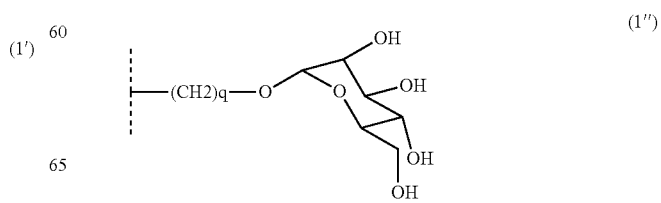

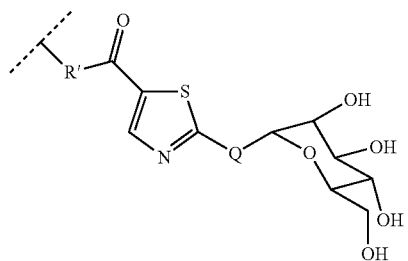
(2″)

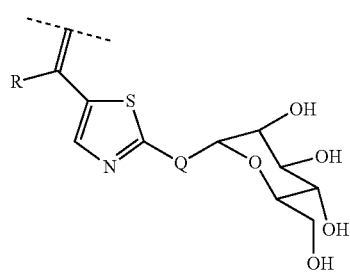
(3″)

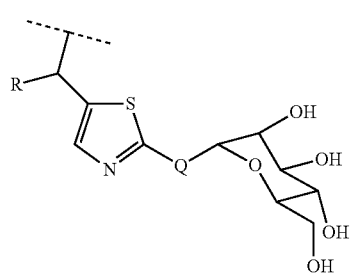
(4″)

provided Z represents (3″):

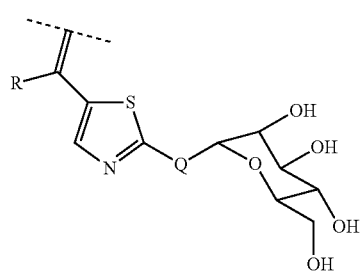
(3″)

if and only if Y or W represents (3bis'):

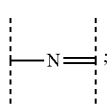
(3bis')

L represents a linker of one of the following formulae:

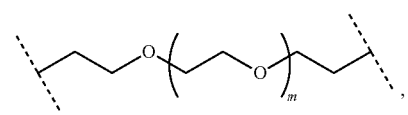
(1₁)

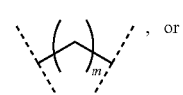, or
(1₅)

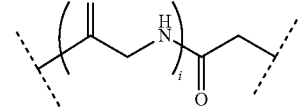
(1₃)

m being an integer comprised from 0 to 20, in particular from 0 to 10, i being an integer comprised from 0 to 20, in particular from 0 to 10, provided L represents (l₃) only when Z represents a group selected from (3'), (6'), (7'), (8') and (8bis'):

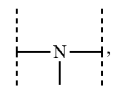
(3')

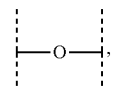
(6')

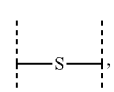
(7')

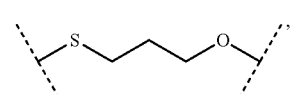
(8')

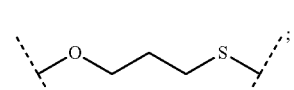
(8bis')

q being an integer chosen from 6, 7 and 8, q being in particular equal to 7;

Q representing NH, O or S, in particular NH;

R' representing a group selected from:
- a linear or branched $(C_1$-$C_7)$-alkane diyl,
- a linear or branched $(C_2$-$C_7)$-alkene diyl,
- a linear or branched $(C_2$-$C_7)$-alkyne diyl,
- a $(C_3$-$C_7)$-cycloalkane diyl,
- a $(C_5$-$C_7)$-cycloalkene diyl,
- a $(C_3$-$C_7)$-heterocycloalkane diyl,
- a $(C_5$-$C_7)$-heterocycloalkene diyl,
- an arene diyl, said arene being an aromatic or heteroaromatic group,
- a group -arene₁-arene₂- wherein arene₁ and arene₂ are independently to each other an aromatic or heteroaromatic arene;

said ($C_1$-$C_7$)-alkane diyl, ($C_2$-$C_7$)-alkene diyl, ($C_2$-$C_7$)-alkyne diyl, ($C_3$-$C_7$)-cycloalkane diyl, ($C_5$-$C_7$)-cycloalkene diyl, ($C_3$-$C_7$)-heterocycloalkane diyl, ($C_5$-$C_7$)-heterocycloalkene diyl, arene diyl, $arene_1$ and $arene_2$ being substituted or not by one or more substituent(s), each independently selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, wherein the aryl is an aromatic or heteroaromatic group
- an alkyl aryl, wherein the aryl is an aromatic or heteroaromatic group,
- a CHO,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- a halogen selected from the group comprising F, Cl, Br, and I,
- $CF_3$,
- $OR_a$, wherein $R_a$ represents:
  - H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
- $NR_bR_c$, wherein $R_b$ and $R_c$ represent independently from each other:
  - H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
- $NO_2$,
- CN;

R representing a group selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, said aryl being an aromatic or heteroaromatic group,
- an alkyl aryl, wherein the aryl is an aromatic or heteroaromatic group,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- $CF_3$,
- adamantyl, said ($C_1$-$C_7$)-alkyl, ($C_2$-$C_7$)-alkenyl, ($C_2$-$C_7$)-alkynyl, ($C_3$-$C_7$)-cycloalkyl, ($C_5$-$C_7$)-cycloalkenyl, ($C_3$-$C_7$)-heterocycloalkyl, ($C_5$-$C_7$)-heterocycloalkenyl, CO—($C_1$-$C_7$)-alkyl, $CO_2$—($C_1$-$C_7$)-alkyl, CONH—($C_1$-$C_7$)-alkyl, aryl, alkyl aryl and CO-aryl being substituted or not by one or more substituent(s), each independently selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, wherein the aryl is an aromatic or heteroaromatic group
- an alkyl aryl, wherein the aryl is an aromatic or heteroaromatic group,
- a CHO,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- a halogen selected from the group comprising F, Cl, Br, and I,
- $CF_3$,
- $OR_a$, wherein $R_a$ represents:
  - H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
- $NR_bR_c$, wherein $R_b$ and $R_c$ represent independently from each other:
  - H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
- $NO_2$,
- CN, A being such as the n bonds between A and the n groups X are, considering the mean position of aforesaid bonds, substantially equidistant, provided that aforesaid compound is different from:

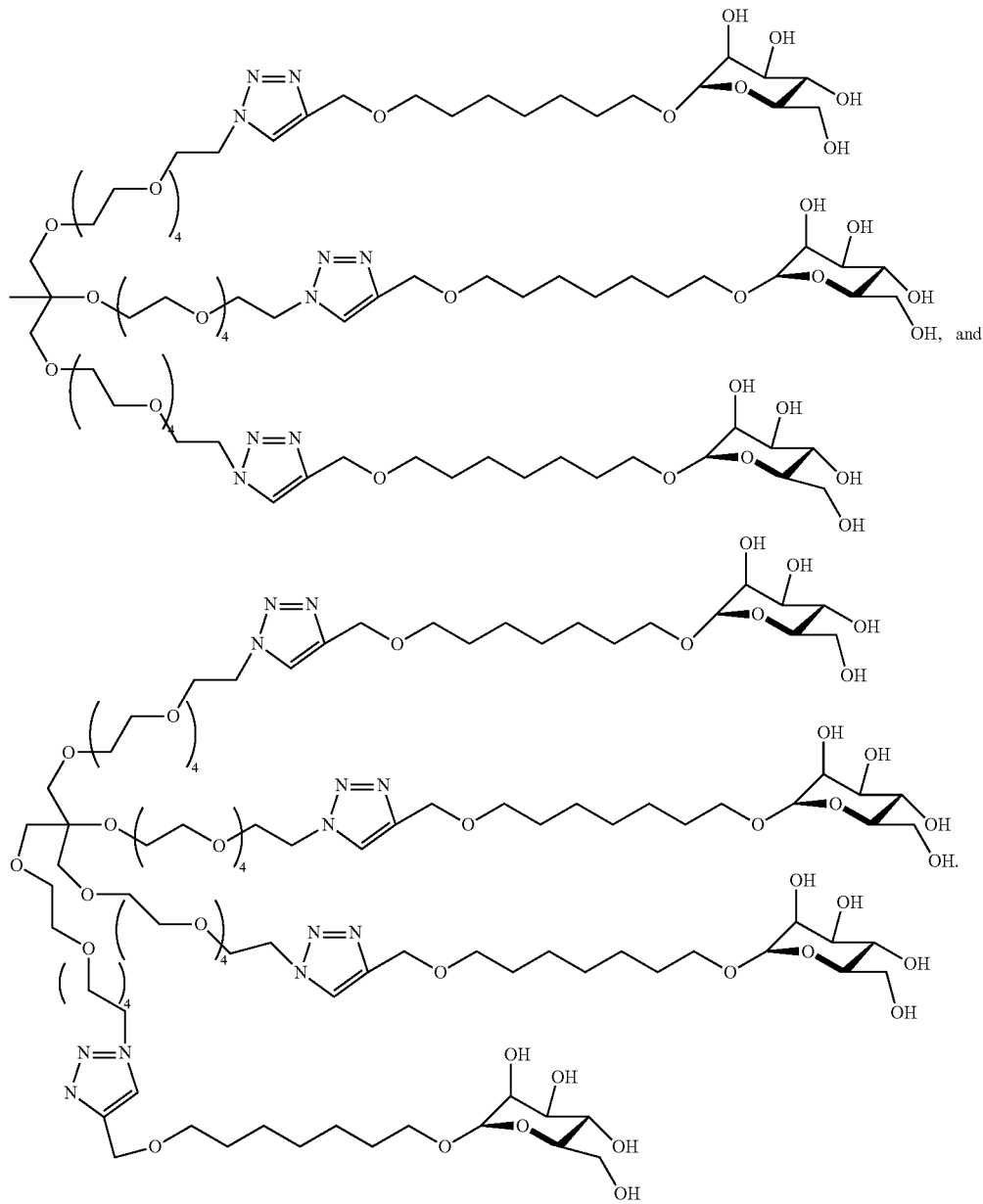

In an advantageous embodiment, the present invention relates to a compound of the following formula (I):

A-X$_n$      (I)

wherein:
A is a scaffold;
n is an integer comprised from 3 to 10, in particular from 3 to 8, more particularly from 3 to 7;
X represents a group of the following formula (1):

—W$_p$-L$_r$-Y$_s$—Z      (1)

wherein:
p, r, and s are integers independently from each other equal to 0 or 1, provided that:

when r is equal to 0, p and s are such as the sum p+s is equal to 1,
when r is equal to 1, p and s are such as the sum p+s is equal to 2;

W is chosen from:

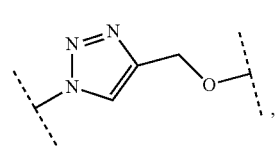

(1')

-continued
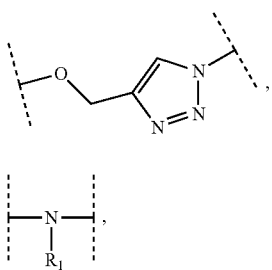 (2′)
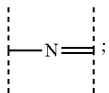 (3′)
and, when r and s are equal to 0, W can also represent:
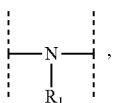 (3bis′)
Y is chosen from:
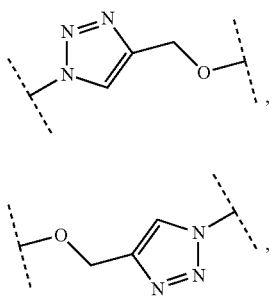 (1′)
(2′)
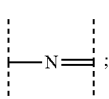 (3′)
(3bis′)
R1 representing:
  a hydrogen, or
  a linear or branched (C₁-C₇)-alkyl;
Z is chosen from:
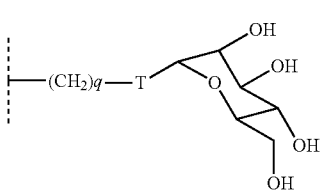 (1″)
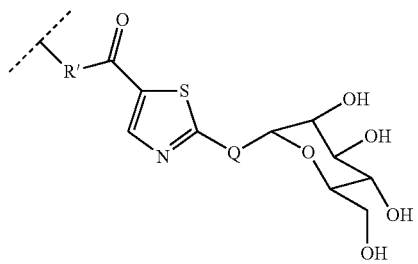 (2″)
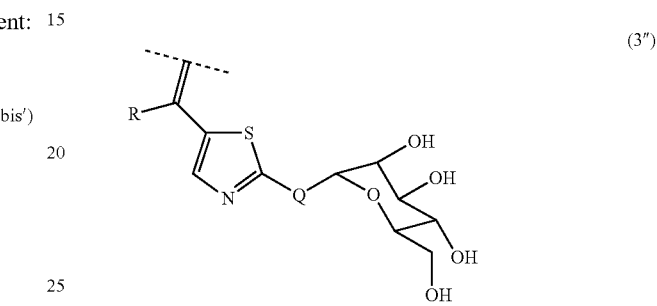 (3″)
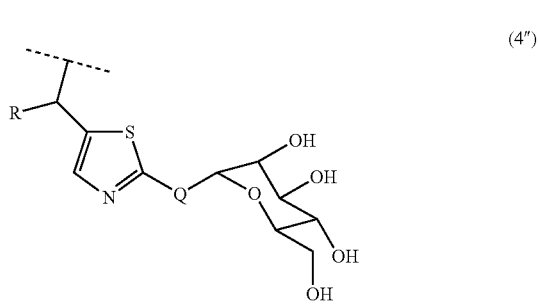 (4″)
provided Z represents (3″):
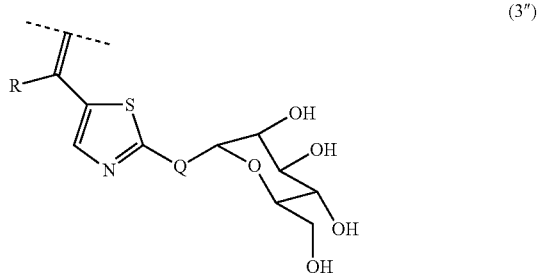 (3″)
if and only if Y or W represents (3bis′):
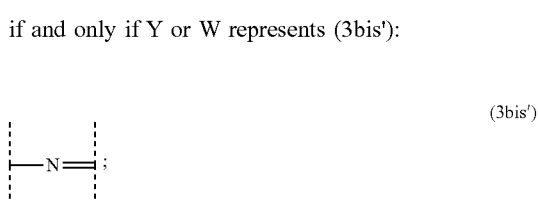 (3bis′)
L represents a linker of one of the following formulae.

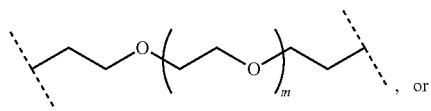
(1₁) , or m being an integer comprised from 0 to 20, in particular from 0 to 10, q being an integer chosen from 6, 7 and 8, q being in particular equal to 7;

Q representing NH, O or S, in particular NH;

R' and R being as described above;

A being such as the n bonds between A and the n groups X are, considering the mean position of aforesaid bonds, substantially equidistant, provided that aforesaid compound is different from:

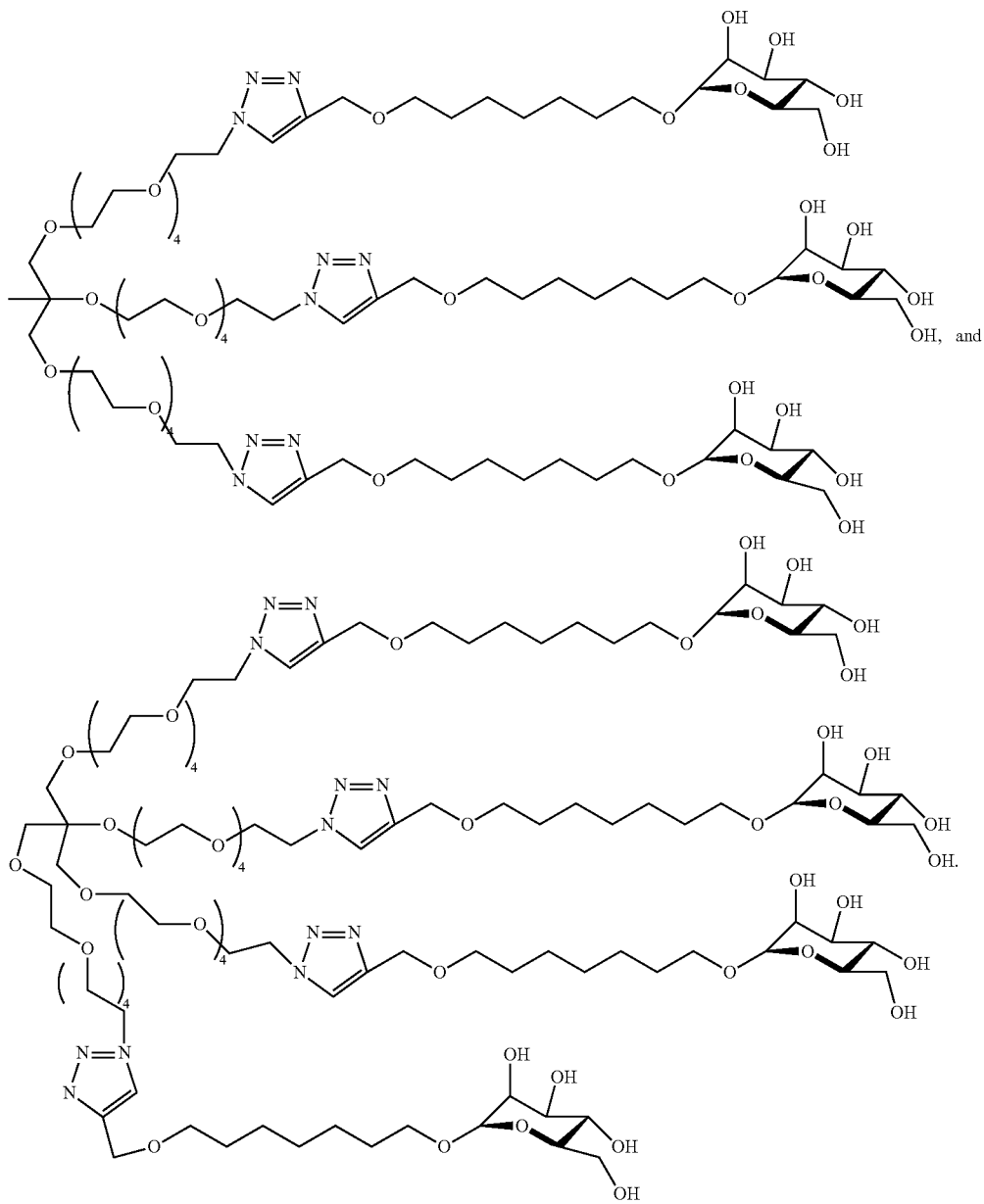

(1₅)

In an advantageous embodiment, the present invention relates to a compound of formula (I) wherein A is cyclic, A being in particular chosen from cyclodextrins and their derivatives, in particular alkylated cyclodextrins, calixarenes and their derivatives, in particular alkylated calixarenes, porphyrines, cyclic peptides, octasilsesquioxane, azacycles and carbohydrate derivatives.

By "derivative" is meant a chemical substance related structurally to another substance. For instance, an alkylated or an acylated compound is a derivative of the original compound.
In an advantageous embodiment, the present invention relates to a compound of formula (I), wherein A is selected from the group comprising:
(A1)
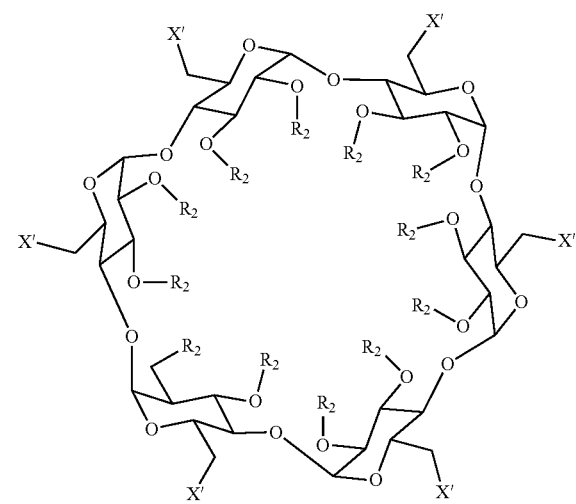
(A2)
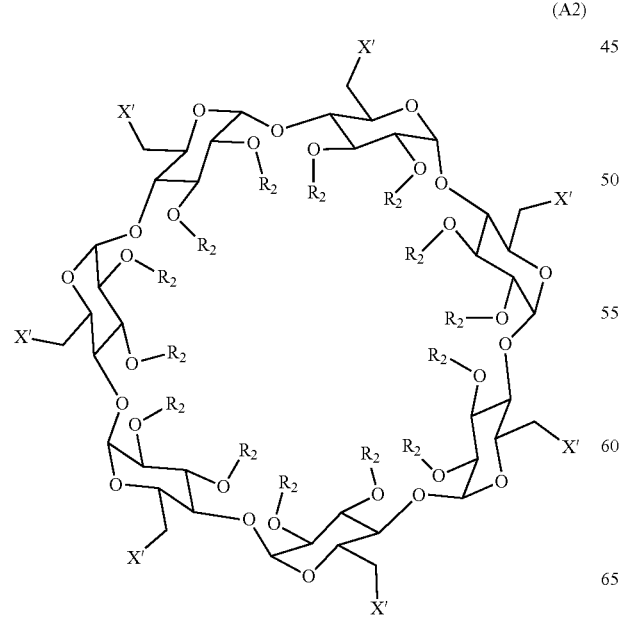
(A3)
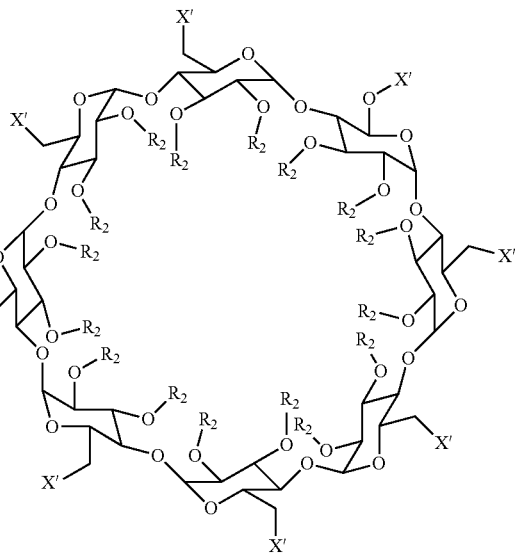
(A4)
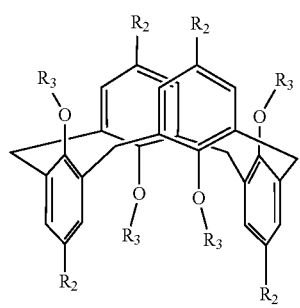
(A5)
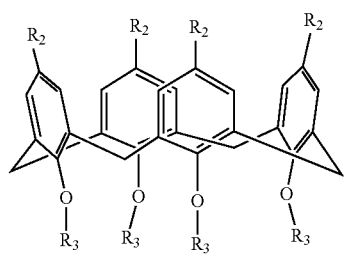
(A6)
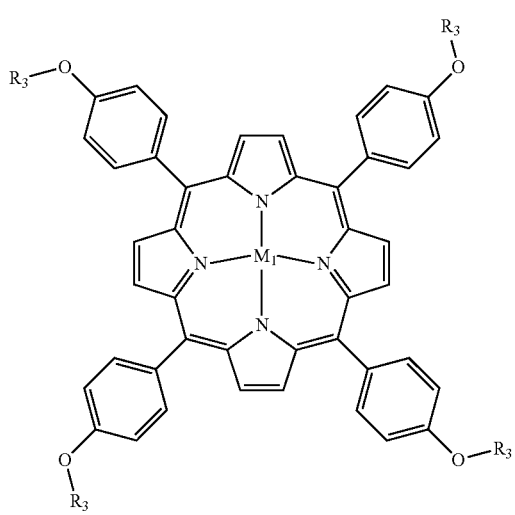

(A7) 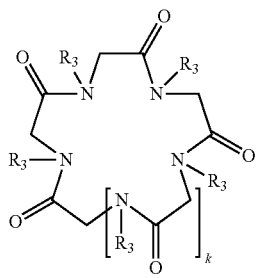

(A8) 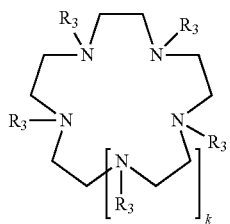

(A9) 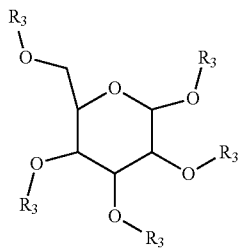

(A10) 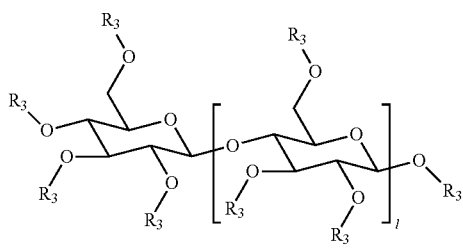

(A11) 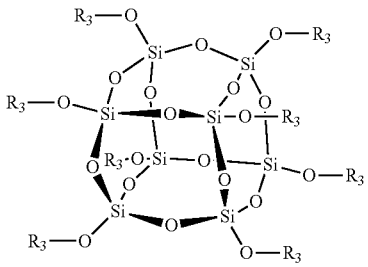

wherein
X' is chosen from the group comprising —OH and -----, wherein ----- represents a bond to X;
$R_2$ is chosen from the group comprising hydrogen and a linear or branched ($C_1$-$C_7$)-alkyl;
$R_3$ are independently from each other chosen from the group comprising hydrogen and the alkane diyl group $R_4$ of the following formula:

wherein j represents an integer comprised from 1 to 7 and ----- represents a bond to X; $R_3$ groups being in particular identical;
$M_1$ is a metal chosen from the group comprising Zn and Cu;
k is an integer comprised from 0 to 2;
l is an integer comprised from 0 to 7.

In an advantageous embodiment, the present invention relates to a compound of formula (I), wherein A is a dendrimer.

In an advantageous embodiment, the present invention relates to a compound of formula (I), wherein A is a poly(amido amine) (PAMAM) dendrimer of generation 0, 1, 2, 3, 4 or 5.

In an advantageous embodiment, the present invention relates to a compound of formula (I), wherein A is selected from the group comprising:

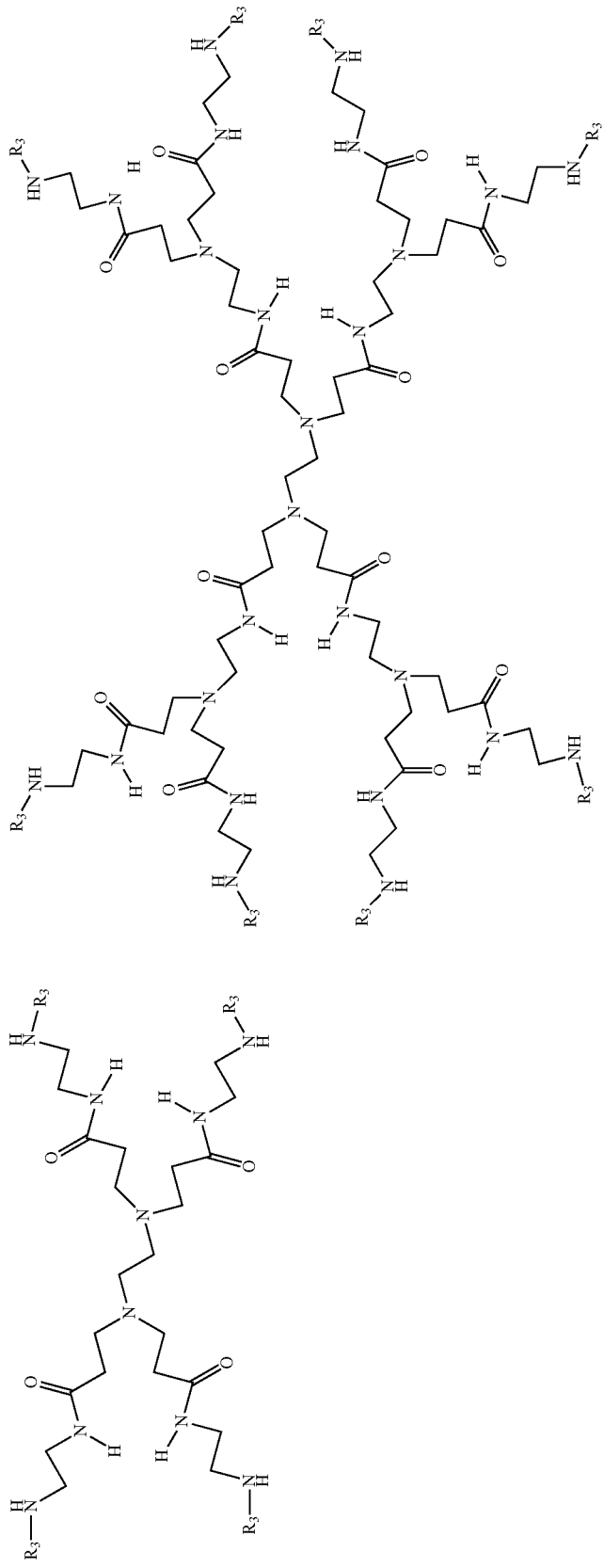

-continued
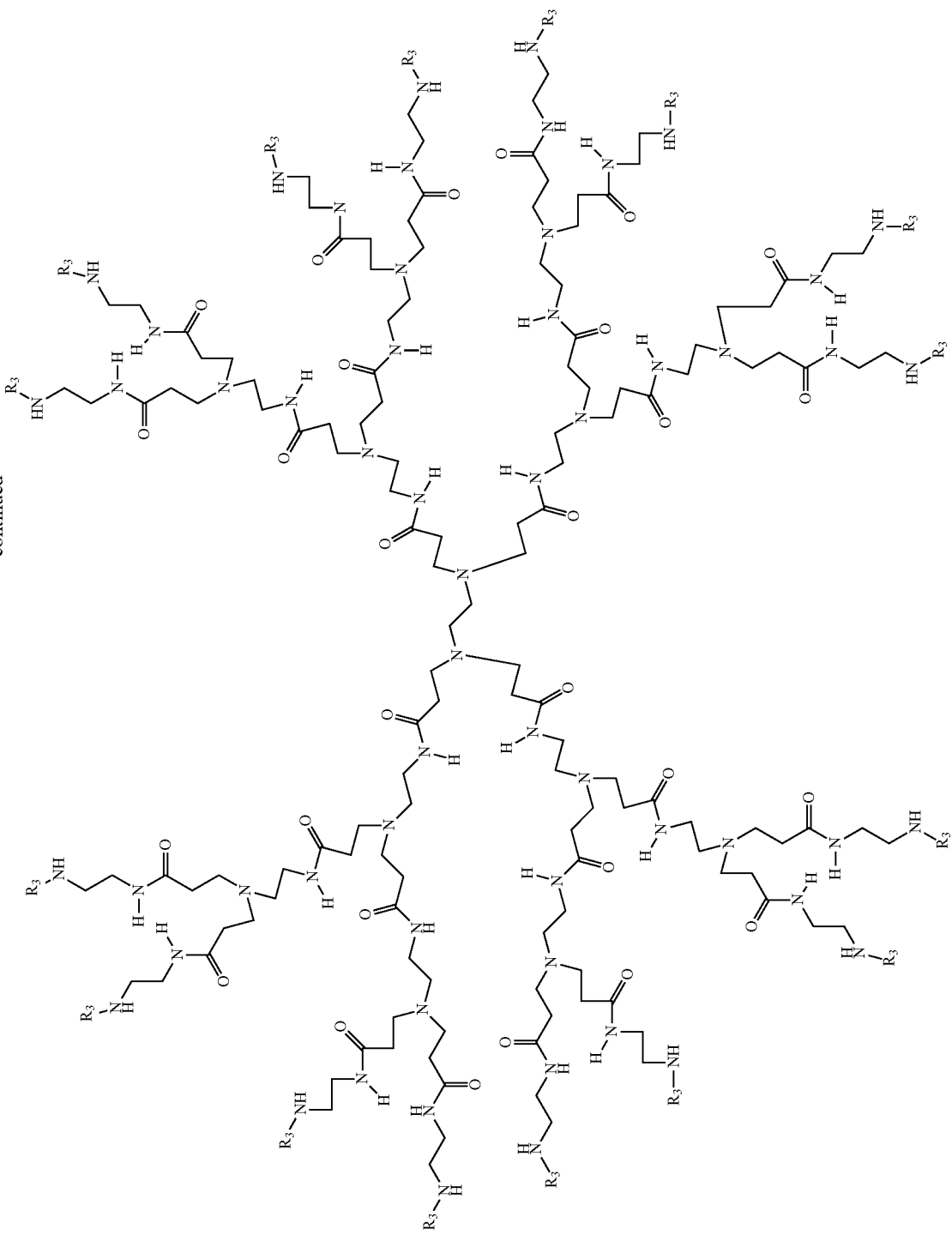

-continued
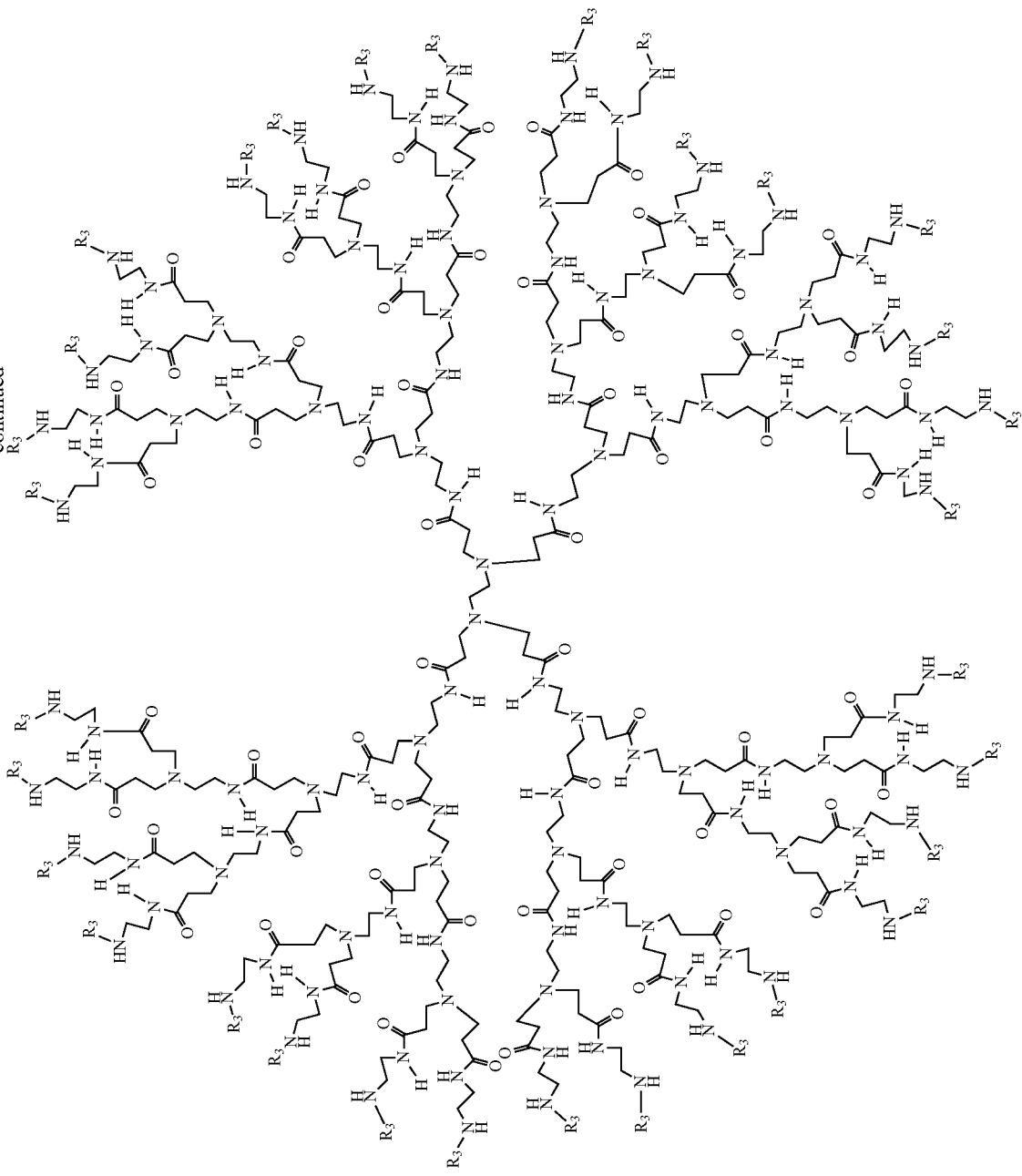

wherein R₃ is as described above.

In an advantageous embodiment, the present invention also relates to a compound of the following formula (I):

$$A\text{-}X_n \quad (I)$$

wherein:

A is chosen from cyclodextrins and their derivatives, in particular alkylated cyclodextrins, A being more particularly selected from the group comprising:

(A1)

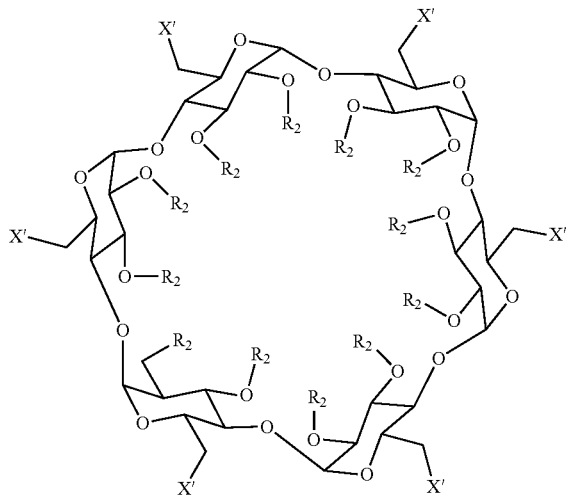

(A2)

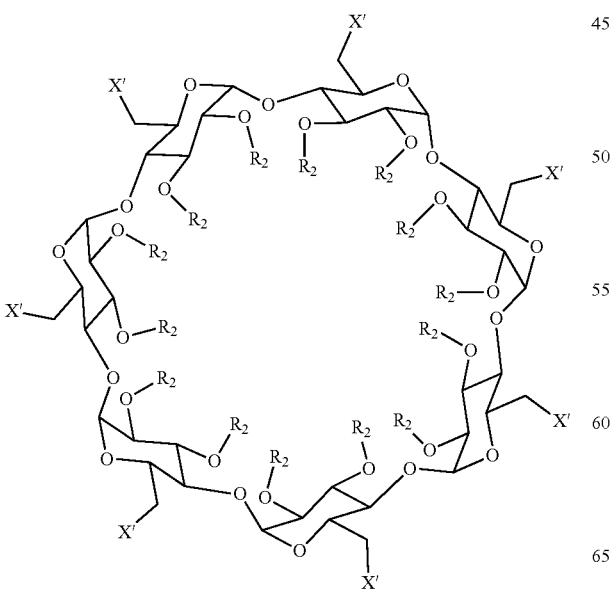

(A3)

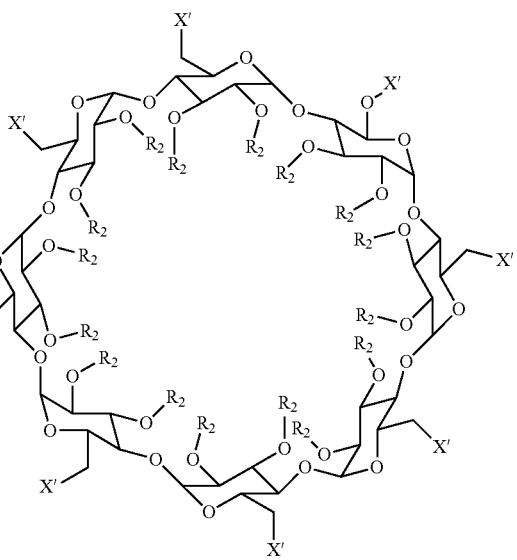

wherein

X' is chosen from the group comprising —OH and -----, wherein ----- represents a bond to X;

$R_2$ is chosen from the group comprising hydrogen and a linear or branched $(C_1\text{-}C_7)$-alkyl;

n is an integer comprised from 3 to 8, in particular from 6 to 8;

X represents a group of the following formula (1):

$$-W_p\text{-}L_r\text{-}Y_s-Z \quad (1)$$

wherein:

p, r, and s are integers independently from each other equal to 0 or 1, provided that:

when r is equal to 0, p and s are such as the sum p+s is equal to 1, when r is equal to 1, p and s are such as the sum p+s is equal to 2;

W is chosen from:

(1')

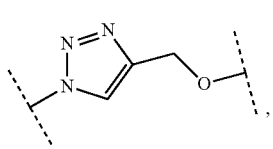

(2')

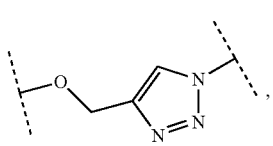

(2bis')

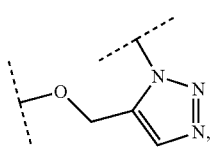

Y is chosen from:

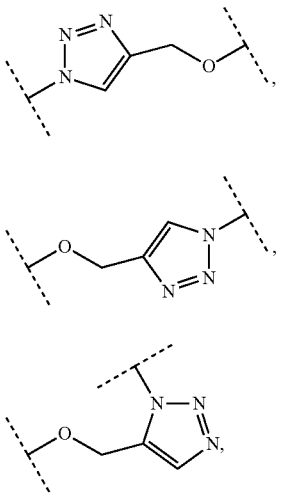

(1')

(2')

(2bis')

Z is chosen from:

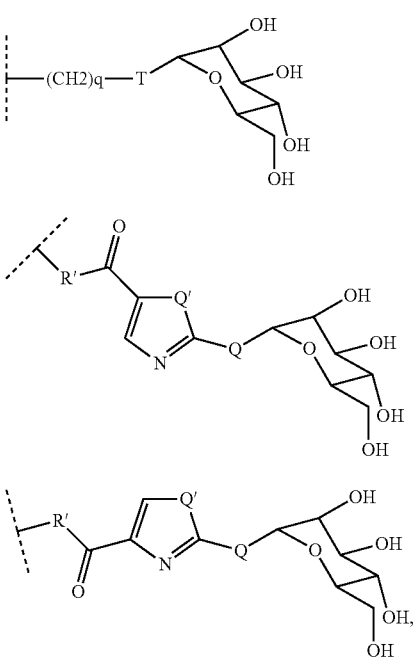

(1'')

(2'')

(2bis'')

R being in particular equal to 0 when Z represents (2'') or (2bis'');

L represents a linker of one of the following formulae:

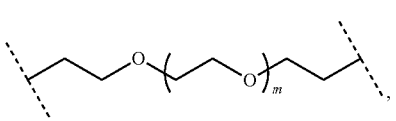

(1$_1$)

(1$_5$)

m being an integer comprised from 0 to 20, in particular from 0 to 10,

Q and Q' representing independently from each other NH, O or S;

Q and Q' representing in particular NH and S, respectively;

T representing O, S or $CH_2$, in particular O;

R' representing a group selected from:
- a linear or branched ($C_1$-$C_7$)-alkane diyl,
- a linear or branched ($C_2$-$C_7$)-alkene diyl,
- a linear or branched ($C_2$-$C_7$)-alkyne diyl,
- a ($C_3$-$C_7$)-cycloalkane diyl,
- a ($C_5$-$C_7$)-cycloalkene diyl,
- a ($C_3$-$C_7$)-heterocycloalkane diyl,
- a ($C_5$-$C_7$)-heterocycloalkene diyl,
- an arene diyl, said arene being an aromatic or heteroaromatic group,
- a group -arene$_1$-arene$_2$- wherein arene$_1$ and arene$_2$ are independently to each other an aromatic or heteroaromatic arene;
- a group of the following formula:

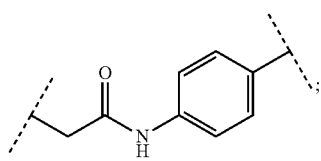

said ($C_1$-$C_7$)-alkane diyl, ($C_2$-$C_7$)-alkene diyl, ($C_2$-$C_7$)-alkyne diyl, ($C_3$-$C_7$)-cycloalkane diyl, ($C_5$-$C_7$)-cycloalkene diyl, ($C_3$-$C_7$)-heterocycloalkane diyl, ($C_5$-$C_7$)-heterocycloalkene diyl, arene diyl, arene$_1$ and arene$_2$ being substituted or not by one or more substituent(s), each independently selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, wherein the aryl is an aromatic or heteroaromatic group
- an alkyl aryl, wherein the aryl is an aromatic or heteroaromatic group,
- a CHO,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- a halogen selected from the group comprising F, Cl, Br, and I,
- $CF_3$, $OR_a$, wherein $R_a$ represents:
   H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NR_bR_c$, wherein $R_b$ and $R_c$ represent independently from each other:
   H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NO_2$,
CN;
R' representing in particular a linear or branched $(C_1-C_7)$-alkane diyl, more particularly —$CH_2$—, or a group of the following formula:

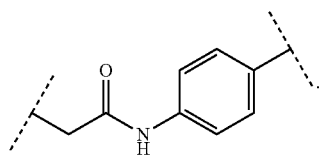

In an advantageous embodiment, the present invention relates to a compound of formula (I), wherein X is of the following formula (1a):

—Y—Z (1a)

wherein Y and Z are as defined above.

In an advantageous embodiment, the present invention relates to a compound of formula (I), wherein X is of the following formula (1b):

—W-L-Y—Z (1b)

wherein W, L, Y and Z are as defined in above.

In an advantageous embodiment, the present invention relates to a compound of formula (I), wherein Z is of formula (1″):

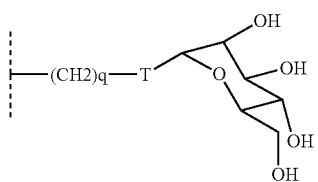

T representing O, S or $CH_2$, in particular S or $CH_2$.

In an advantageous embodiment, the present invention relates to a compound of formula (I), wherein Z is of formula (1″):

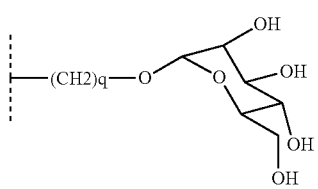

wherein q is as defined above, q being in particular equal to 7.

In an advantageous embodiment, the present invention relates to a compound of formula (I) wherein X is of formula (1), wherein p equals 0 and Z is of formula (1″), corresponding to the following formula (2a):

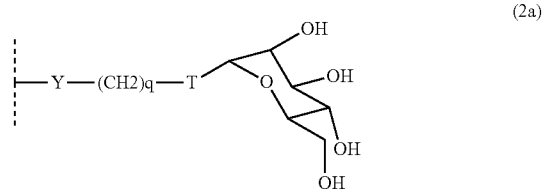

wherein Y and q are as defined above, q being in particular equal to 7,

T representing O, S or $CH_2$, in particular S or $CH_2$.

In an advantageous embodiment, the present invention relates to a compound of formula (I) wherein X is of formula (1), wherein p equals 0 and Z is of formula (1″), corresponding to the following formula (2a):

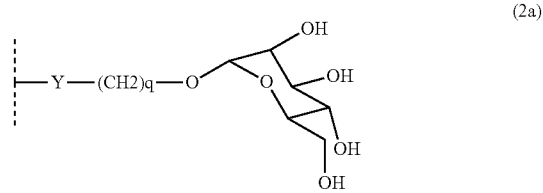

wherein Y and q are as defined above, q being in particular equal to 7.

In an advantageous embodiment, the present invention relates to a compound of formula (I) wherein X is of formula (1), wherein p equals 1 and Z is of formula (1″), corresponding to the following formula (2b):

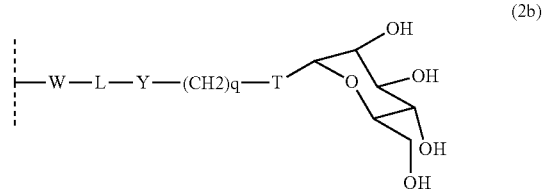

wherein W, L, Y and q are as defined above, q being in particular equal to 7,

T representing O, S or $CH_2$, in particular S or $CH_2$.

In an advantageous embodiment, the present invention relates to a compound of formula (I) wherein X is of formula (1), wherein p equals 1 and Z is of formula (1″), corresponding to the following formula (2b):

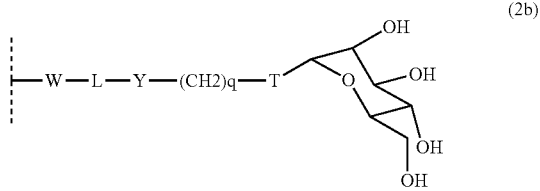

(2b)

wherein W, L, Y and q are as defined above, q being in particular equal to 7.

In an advantageous embodiment, the present invention relates to a compound of formula (I) wherein X is of formula (1), wherein p equals 0, Y represents (1') and Z is of formula (1"), corresponding to the following formula (2c):

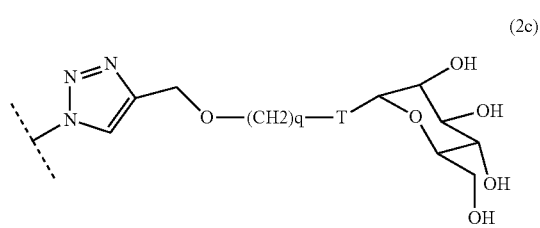

(2c)

wherein q is as defined in above, q being in particular equal to 7,

T representing O, S or $CH_2$, in particular S or $CH_2$.

In an advantageous embodiment, the present invention relates to a compound of formula (I) wherein X is of formula (1), wherein p equals 0, Y represents (1') and Z is of formula (1"), corresponding to the following formula (2c):

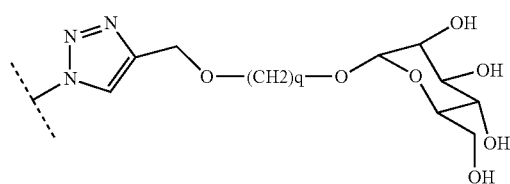

(2c)

wherein q is as defined in above, q being in particular equal to 7.

In an advantageous embodiment, the present invention relates to a compound of formula (I), wherein X is of formula (1), wherein p equals 1, L is of formula ($l_1$), and Z is of formula (1"), corresponding to the following formula (2d):

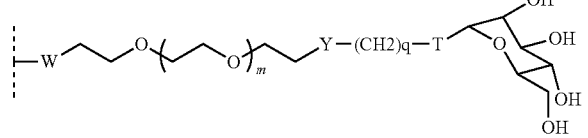

(2d)

wherein W, L, Y, m and q are as defined above, m being in particular equal to 1, q being in particular equal to 7, T representing O, S or $CH_2$, in particular S or $CH_2$.

In an advantageous embodiment, the present invention relates to a compound of formula (I), wherein X is of formula (1), wherein p equals 1, L is of formula ($l_1$), and Z is of formula (1"), corresponding to the following formula (2d):

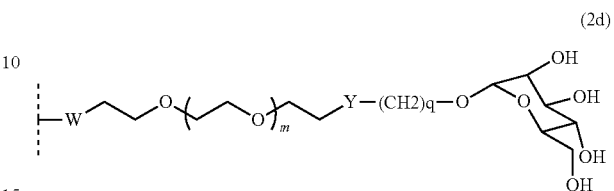

(2d)

wherein W, L, Y, m and q are as defined above, m being in particular equal to 1, q being in particular equal to 7.

In an advantageous embodiment, the present invention relates to a compound of formula (I), wherein X is of formula (1), wherein p equals 1, W and Y are of formula (1'), and Z is of formula (1"), corresponding to the following formula (2e):

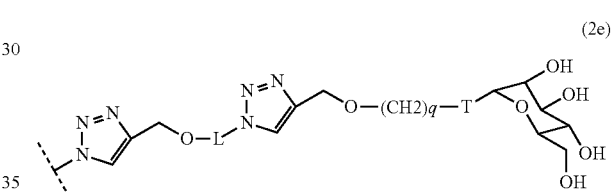

(2e)

wherein L and q are as defined above, q being in particular equal to 7,

T representing O, S or $CH_2$, in particular S or $CH_2$.

In an advantageous embodiment, the present invention relates to a compound of formula (I), wherein X is of formula (1), wherein p equals 1, W and Y are of formula (1'), and Z is of formula (1"), corresponding to the following formula (2e):

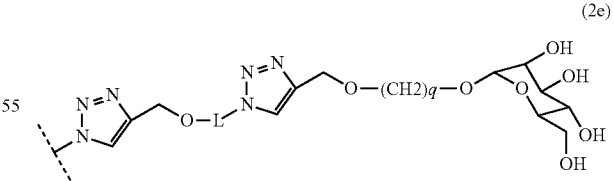

(2e)

wherein L and q are as defined above, q being in particular equal to 7.

In an advantageous embodiment, the present invention relates to a compound of formula (I), wherein X is of formula (1), wherein p equals 1, W and Y are of formula (1'), and Z is of formula (1"), corresponding to the following formula (2f):

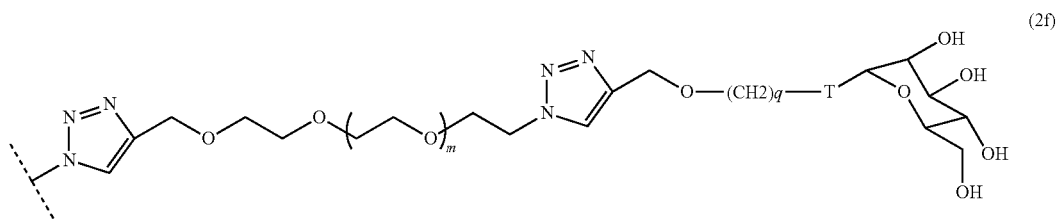

(2f)

wherein m and q are as defined in above, m being in particular equal to 1, q being in particular equal to 7,
T representing O, S or $CH_2$, in particular S or $CH_2$.

In an advantageous embodiment, the present invention relates to a compound of formula (I), wherein X is of formula (1), wherein p equals 1, W and Y are of formula (1'), and Z is of formula (1"), corresponding to the following formula (2f):

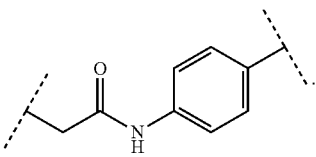

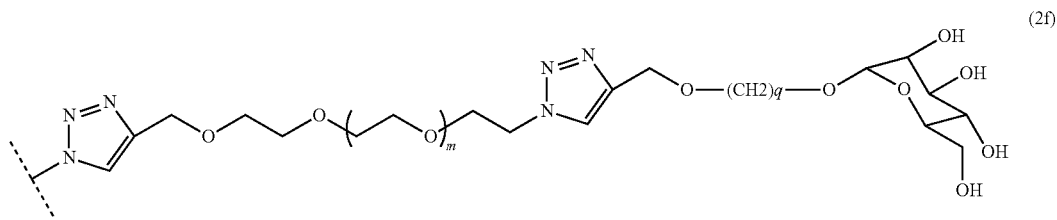

(2f)

wherein m and q are as defined in above, m being in particular equal to 1, q being in particular equal to 7.

In an advantageous embodiment, the present invention relates to a compound of formula (I), wherein Z is of formula (2") or (2bis"):

In an advantageous embodiment, the present invention relates to a compound of formula (I), wherein Z is of formula (1"):

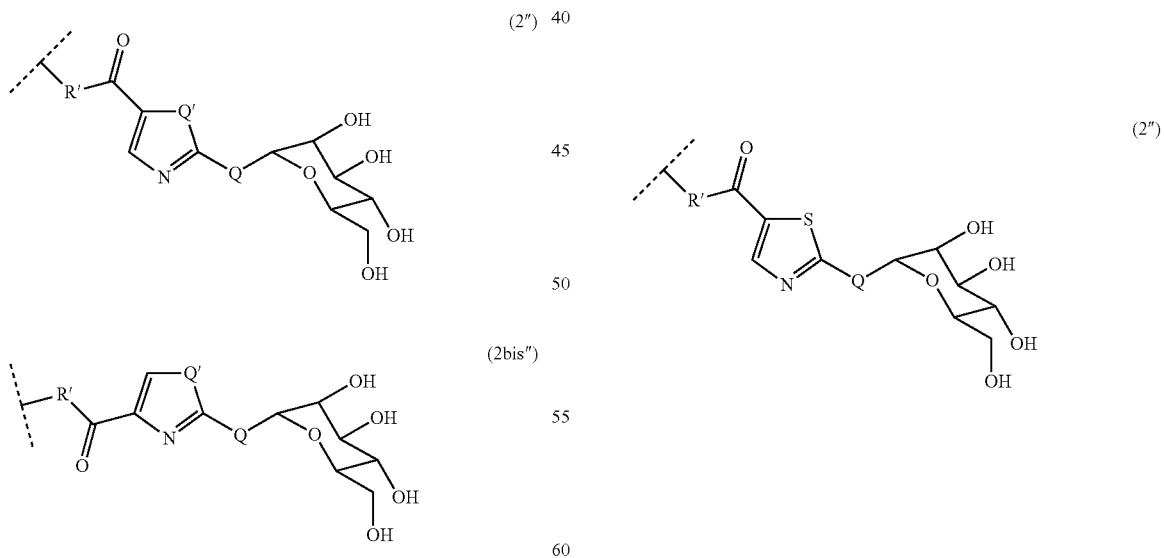

wherein R', Q and Q' are as defined above,
Q and Q' representing in particular NH and S, respectively,
R' representing in particular a linear or branched ($C_1$-$C_7$)-alkane diyl, more particularly —$CH_2$—, or a group of the following formula:

wherein R' and Q are as defined above.

In an advantageous embodiment, the present invention relates to a compound of formula (I), wherein Z is of formula (3"):

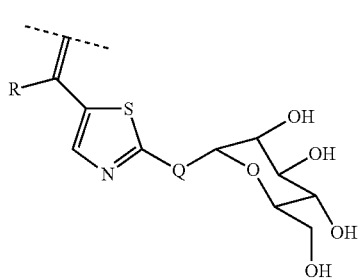
(3″)

wherein R and Q are as defined above.

In an advantageous embodiment, the present invention relates to a compound of formula (I), wherein X is of formula (1), wherein p equals 0 and Z is of formula (2″), corresponding to the following formula (3a):

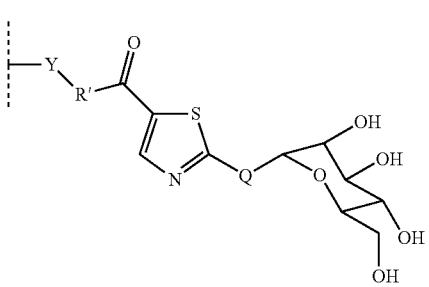
(3a)

wherein Y, R' and Q are as defined in above.

In an advantageous embodiment, the present invention relates to a compound of formula (I), wherein X is of formula (1), wherein p equals 0, Y is of formula (3bis') and Z is of formula (3″), corresponding to the following formula (3″a):

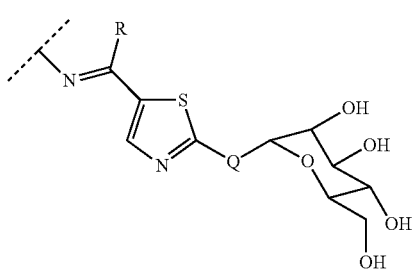
(3″a)

wherein Y, R and Q are as defined above.

In an advantageous embodiment, the present invention relates to a compound of formula (I), wherein X is of formula (1), wherein p equals 1 and Z is of formula (2″) or (2bis″), corresponding respectively to the following formula (3b) or (3b-bis):

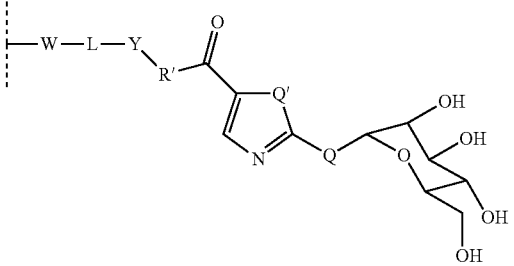
(3b)

(3b-bis)

wherein W, L, Y, R', Q and Q' are as defined above,

Q and Q' representing in particular NH and S, respectively,

R' representing in particular a linear or branched ($C_1$-$C_7$)-alkane diyl, more particularly —$CH_2$—, or a group of the following formula:

In an advantageous embodiment, the present invention relates to a compound of formula (I), wherein X is of formula (1), wherein p equals 1 and Z is of formula (2″), corresponding to the following formula (3b):

(3b)

wherein W, L, Y, R' and Q are as defined above.

In an advantageous embodiment, the present invention relates to a compound of formula (I), wherein X is of formula (1), wherein p equals 1, Y is of formula (3bis') and Z is of formula (3″), corresponding to the following formula (3″b):

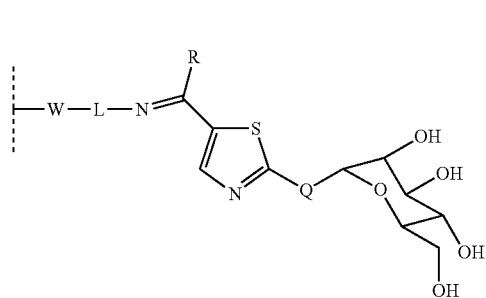

(3"b)

wherein W, L, Y, R and Q are as defined above.

In an advantageous embodiment, the present invention relates to a compound of formula (I), wherein X is of formula (1), wherein p equals 0, Y represents (1') and Z is of formula (2"), corresponding to the following formula (3c):

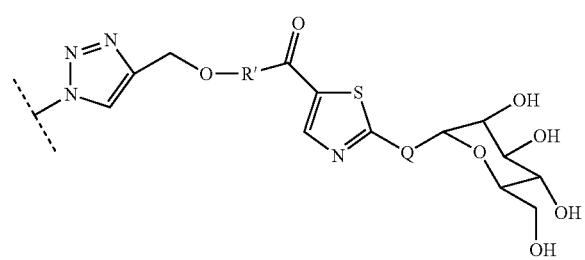

(3c)

wherein R' and Q are as defined above.

In an advantageous embodiment, the present invention relates to a compound of formula (I), wherein X is of formula (1), wherein p equals 0, Y represents (2') and Z is of formula (2"), corresponding to the following formula (3c'):

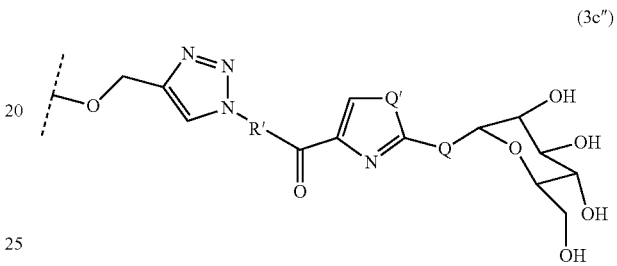

(3c')

wherein R', Q and Q' are as defined above,
Q and Q' representing in particular NH and S, respectively,
R' representing in particular a linear or branched (C$_1$-C$_7$)-alkane diyl, more particularly —CH$_2$—, or a group of the following formula:

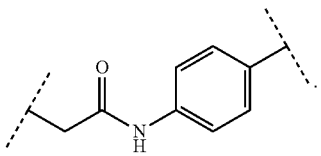

In an advantageous embodiment, the present invention relates to a compound of formula (I), wherein X is of formula (1), wherein p equals 0, Y represents (2') and Z is of formula (2bis"), corresponding to the following formula (3c"):

(3c")

wherein R', Q and Q' are as defined above,
Q and Q' representing in particular NH and S, respectively,
R' representing in particular a linear or branched (C$_1$-C$_7$)-alkane diyl, more particularly —CH$_2$—, or a group of the following formula:

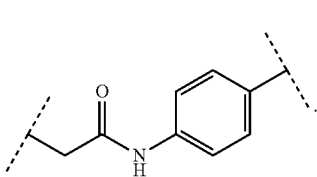

In an advantageous embodiment, the present invention relates to a compound of formula (I), wherein X is of formula (1), wherein p equals 0, Y represents (2bis') and Z is of formula (2"), corresponding to the following formula (3c'-bis):

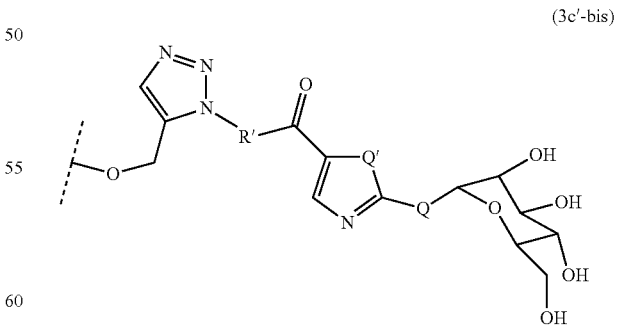

(3c'-bis)

wherein R', Q and Q' are as defined above,
Q and Q' representing in particular NH and S, respectively,
R' representing in particular a linear or branched (C$_1$-C$_7$)-alkane diyl, more particularly —CH$_2$—, or a group of the following formula:

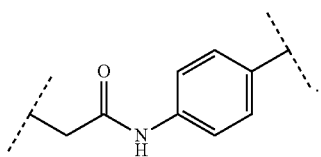 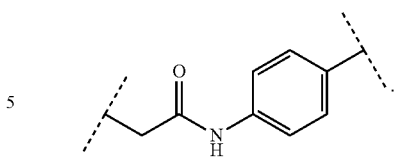

In an advantageous embodiment, the present invention relates to a compound of formula (I), wherein X is of formula (1), wherein p equals 0, Y represents (2bis') and Z is of formula (2bis"), corresponding to the following formula (3c"-bis):

In an advantageous embodiment, the present invention relates to a compound of formula (I), wherein X is of formula (1), wherein p equals 1, L is of formula ($l_1$), and Z is of formula (2"), corresponding to the following formula (3d):

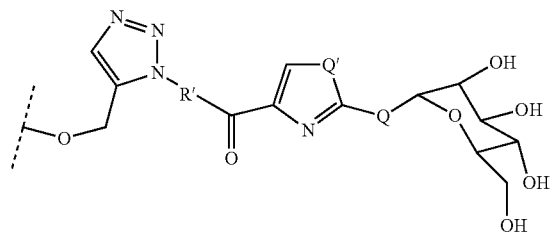

(3c"-bis)

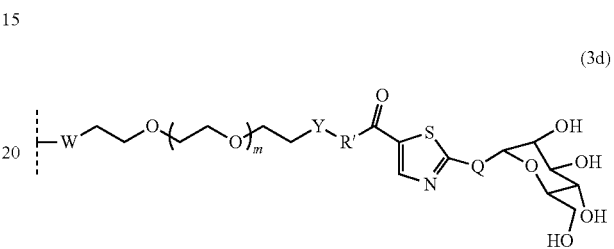

(3d)

wherein W, Y, m, R' and Q are as defined above, m being in particular equal to 1.

wherein R', Q and Q' are as defined above,
Q and Q' representing in particular NH and S, respectively, R' representing in particular a linear or branched ($C_1$-$C_7$)-alkane diyl, more particularly —$CH_2$—, or a group of the following formula:

In an advantageous embodiment, the present invention relates to a compound of formula (I), wherein X is of formula (1), wherein p equals 1, W and Y are of formula (1'), and Z is of formula (2"), corresponding to the following formula (3e):

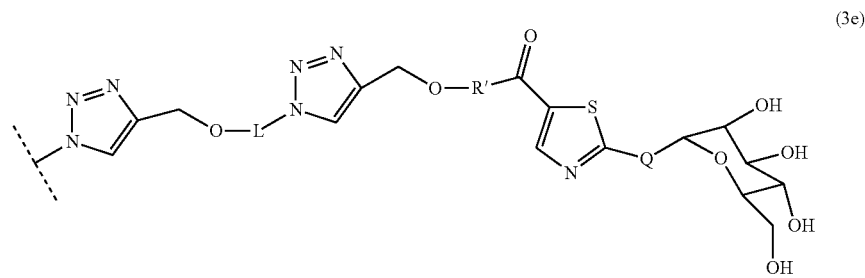

(3e)

wherein L, R' and Q are as defined above.

In an advantageous embodiment, the present invention relates to a compound of formula (I), wherein X is of formula (1), wherein p equals 1, W and Y are of formula (1'), and Z is of formula (2"), corresponding to the following formula (3f):

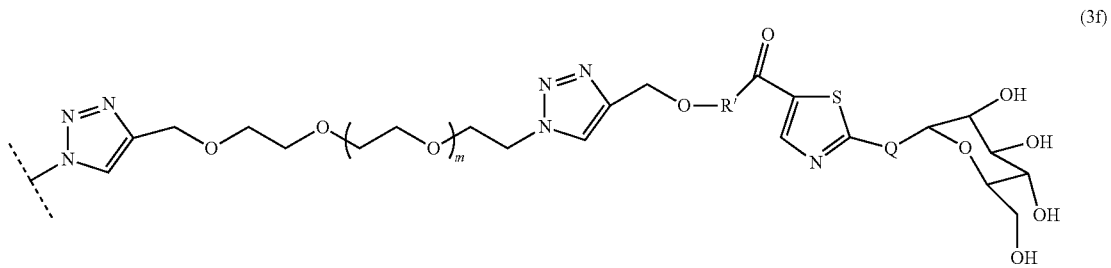

(3f)

wherein m, R' and Q are as defined above, m being in particular equal to 1.

In an advantageous embodiment, the present invention relates to a compound of formula (I), wherein A is a cyclodextrin (CD), or a cyclodextrin derivative, in particular an alkylated cyclodextrin.

In an advantageous embodiment, the present invention relates to a compound of formula (I):

wherein A is a cyclodextrin chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, A being preferably a β-cyclodextrin or an alkylated β-cyclodextrin, n being chosen from 3, 4, 5, and 6 when A is α-cyclodextrin or a α-cyclodextrin derivative, n being preferably 6;

n being chosen from 3, 4, 5, 6 and 7 when A is β-cyclodextrin or a β-cyclodextrin derivative, n being preferably 7;

n being chosen from 3, 4, 5, 6, 7 and 8 when A is γ-cyclodextrin or a γ-cyclodextrin derivative, n being preferably 8.

In an advantageous embodiment, the present invention relates to a compound of formula (I), wherein A is a cyclodextrin or a cyclodextrin derivative, X is of formula (1), wherein Z is of formula (1"), corresponding to the following formula:

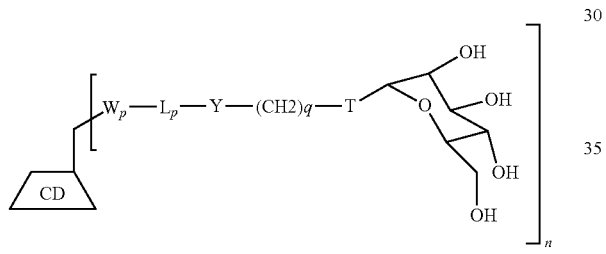

wherein p, n, W, L, Y and q are as defined above, q being in particular equal to 7, T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein Z is of formula (1"), corresponding to the following formula:

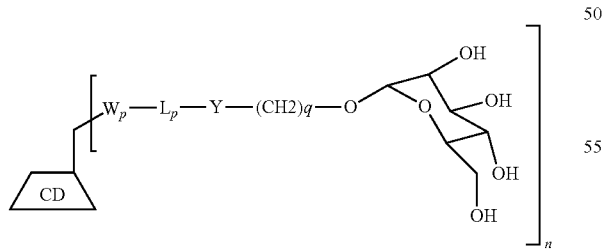

wherein p, n, W, L, Y and q are as defined above, q being in particular equal to 7.

In an advantageous embodiment, the present invention relates to a compound of formula (I), wherein A is a cyclodextrin or a cyclodextrin derivative, X is of formula (1), wherein p equals 0 and Z is of formula (1"), corresponding to the following formula (IIa):

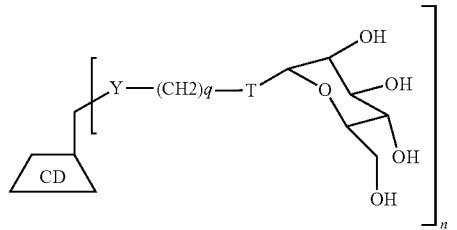

wherein n, Y and q are as defined above, q being in particular equal to 7,

T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 0 and Z is of formula (1"), corresponding to the following formula (IIa):

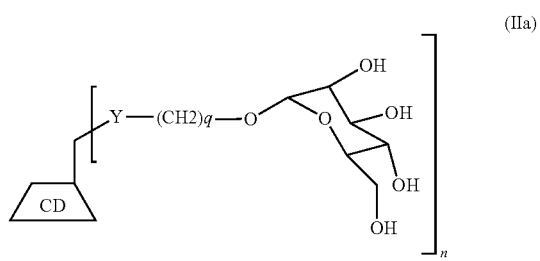

wherein n, Y and q are as defined above, q being in particular equal to 7.

In an advantageous embodiment, the present invention relates to a compound of formula (I), wherein A is a cyclodextrin or a cyclodextrin derivative, X is of formula (1), wherein p equals 1 and Z is of formula (1"), corresponding to the following formula (IIb):

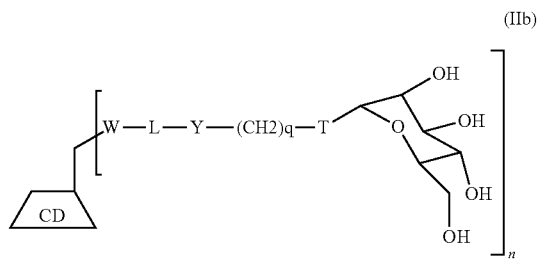

wherein n, W, L, Y and q are as defined above, q being in particular equal to 7, T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 1 and Z is of formula (1"), corresponding to the following formula (IIb):

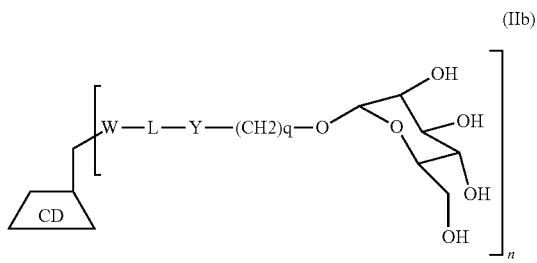

(IIb)

wherein n, W, L, Y and q are as defined above, q being in particular equal to 7.

In an advantageous embodiment, the present invention relates to a compound of formula (I), wherein A is a cyclodextrin or a cyclodextrin derivative, X is of formula (1), wherein p equals 0, Y represents (1') and Z is of formula (1"), corresponding to the following formula (IIc):

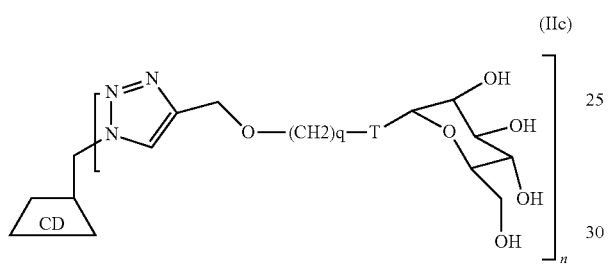

(IIc)

wherein n and q are as defined above, q being in particular equal to 7,

T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 0, Y represents (1') and Z is of formula (1"), corresponding to the following formula (IIc):

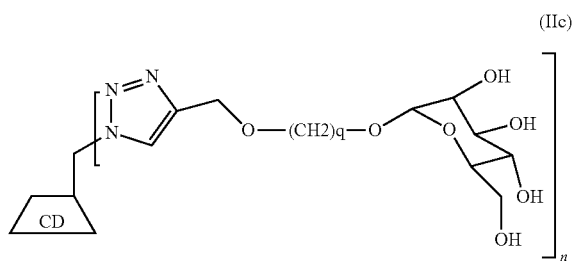

(IIc)

wherein n and q are as defined above, q being in particular equal to 7.

In an advantageous embodiment, the present invention relates to a compound of formula (I), wherein A is a cyclodextrin or a cyclodextrin derivative, X is of formula (1), wherein p equals 1, L is of formula ($l_1$), and Z is of formula (1"), corresponding to the following formula (IId):

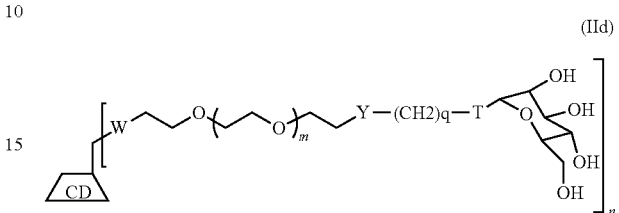

(IId)

wherein n, W, L, Y, m and q are as defined above, m being in particular equal to 1, q being in particular equal to 7, T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 1, L is of formula ($l_1$), and Z is of formula (1"), corresponding to the following formula (IId):

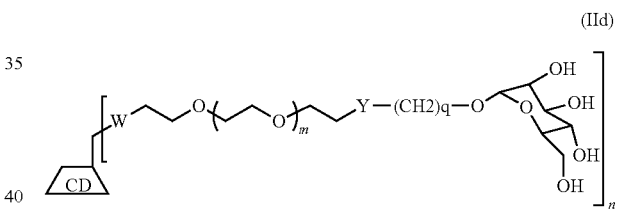

(IId)

wherein n, W, L, Y, m and q are as defined above, m being in particular equal to 1, q being in particular equal to 7.

In an advantageous embodiment, the present invention relates to a compound of formula (I), wherein A is a cyclodextrin or a cyclodextrin derivative, X is of formula (1), wherein p equals 1, W and Y are of formula (1'), and Z is of formula (1"), corresponding to the following formula (IIe):

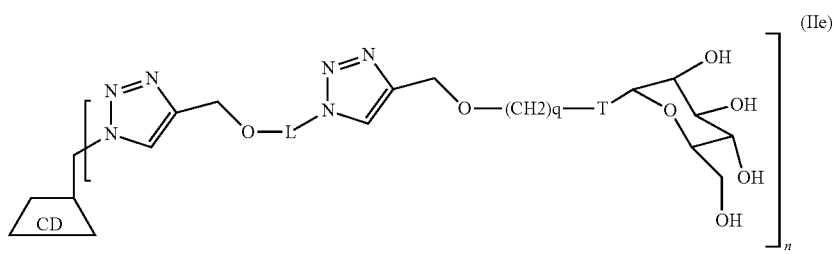

(IIe)

wherein n, L and q are as defined above, q being in particular equal to 7,
T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 1, W and Y are of formula (1'), and Z is of formula (1"), corresponding to the following formula (IIe):

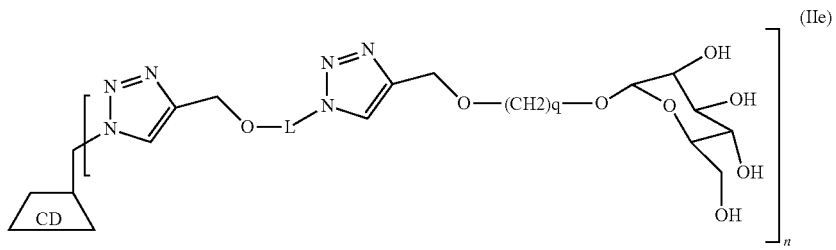

wherein n, L and q are as defined above, q being in particular equal to 7.

In an advantageous embodiment, the present invention relates to a compound of formula (I), wherein A is a cyclodextrin or a cyclodextrin derivative, X is of formula (1), wherein p equals 1, W and Y are of formula (1'), and Z is of formula (1"), corresponding to the following formula (IIf):

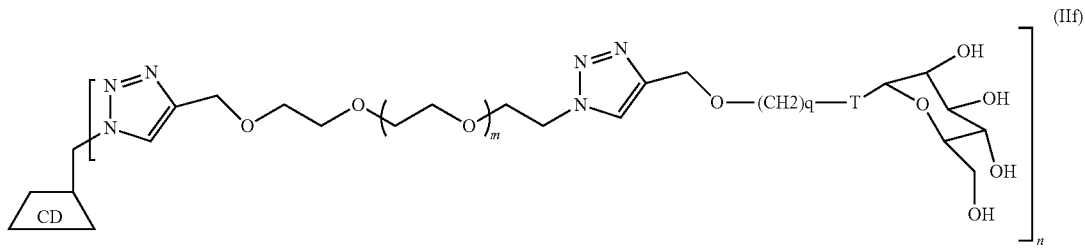

wherein n, m and q are as defined above, m being in particular equal to 1, q being in particular equal to 7,
T representing O, S or $CH_2$, in particular S or $CH_2$.

In an advantageous embodiment, the present invention relates to a compound of formula (I), wherein A is a cyclodextrin or a cyclodextrin derivative, X is of formula (1), wherein p equals 1, W and Y are of formula (1'), and Z is of formula (1"), corresponding to the following formula (IIf):

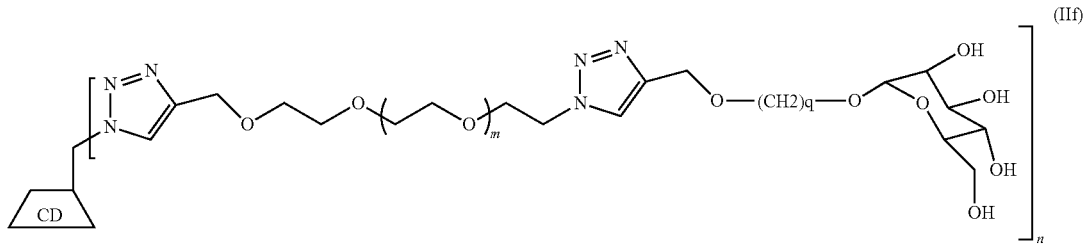

wherein n, m and q are as defined above, m being in particular equal to 1, q being in particular equal to 7.

In an advantageous embodiment, the present invention relates to a compound of formula (I), wherein A is a cyclodextrin, X is of formula (1), wherein p equals 0, Y represents (1') and Z is of formula (1"), corresponding to the following formula (IIg):

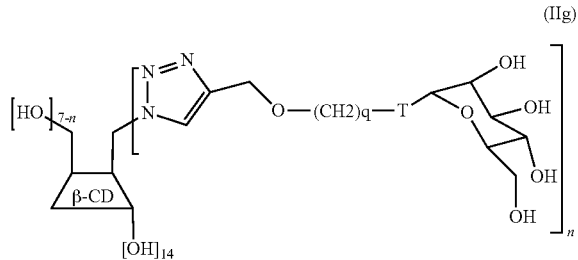

wherein n and q are as defined above, q being in particular equal to 7, n being in particular equal to 7,
T representing O, S or $CH_2$, in particular S or $CH_2$.

In an advantageous embodiment, the present invention relates to a compound of formula (I), wherein A is a cyclodextrin, X is of formula (1), wherein p equals 0, Y represents (1') and Z is of formula (1"), corresponding to the following formula (IIg):

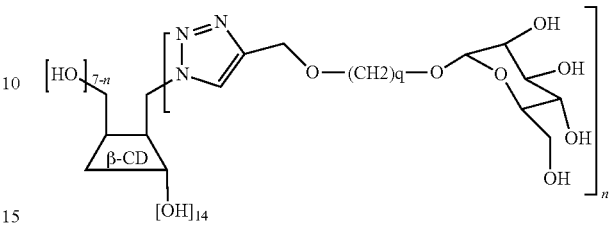

wherein n and q are as defined above, q being in particular equal to 7, n being in particular equal to 7.

In an advantageous embodiment, the present invention relates to a compound of formula (I), wherein A is a cyclodextrin, X is of formula (1), wherein p equals 1, W and Y are of formula (1'), and Z is of formula (1"), corresponding to the following formula (IIh):

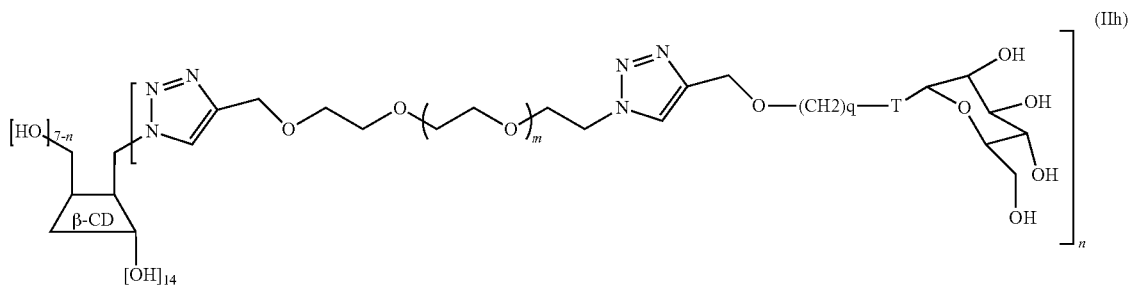

wherein n, m and q are as defined above, m being in particular equal to 1, q being in particular equal to 7, n being in particular equal to 7,
T representing O, S or $CH_2$, in particular S or $CH_2$.

In an advantageous embodiment, the present invention relates to a compound of formula (I), wherein A is a cyclodextrin, X is of formula (1), wherein p equals 1, W and Y are of formula (1'), and Z is of formula (1"), corresponding to the following formula (IIh):

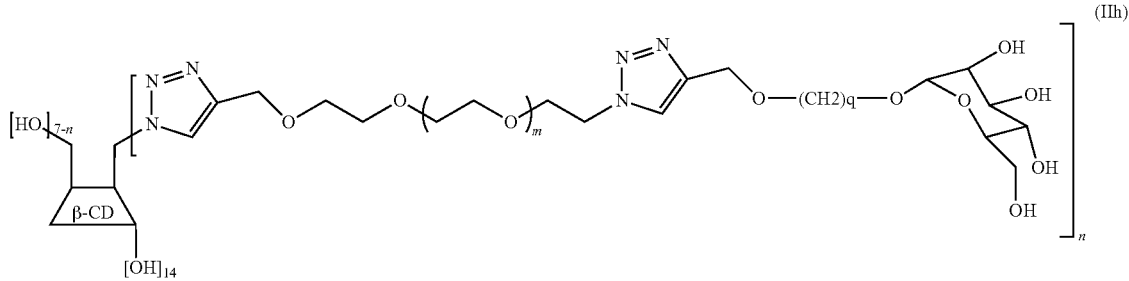

wherein n, m and q are as defined above, m being in particular equal to 1, q being in particular equal to 7, n being in particular equal to 7.

In an advantageous embodiment, the present invention relates to a compound of formula (I), wherein A is a cyclodextrin derivative, X is of formula (1), wherein p equals 0, Y represents (1') and Z is of formula (1"), corresponding to the following formula (IIg-bis):

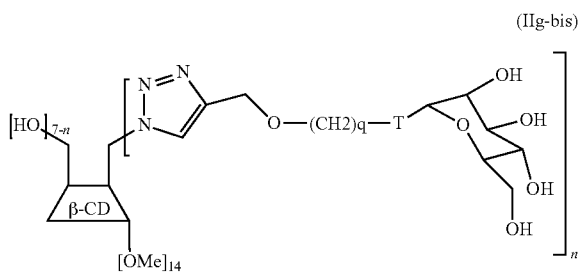

(IIg-bis)

wherein n and q are as defined above, q being in particular equal to 7,
T representing O, S or CH$_2$, in particular S or CH$_2$.

In an advantageous embodiment, the present invention relates to a compound of formula (I), wherein A is a cyclodextrin derivative, X is of formula (1), wherein p equals 0, Y represents (1') and Z is of formula (1"), corresponding to the following formula (IIg-bis):

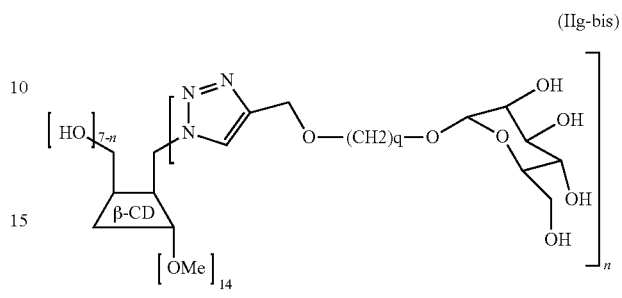

(IIg-bis)

wherein n and q are as defined above, q being in particular equal to 7.

In an advantageous embodiment, the present invention relates to a compound of formula (I), wherein A is a cyclodextrin derivative, X is of formula (1), wherein p equals 1, W and Y are of formula (1'), and Z is of formula (1"), corresponding to the following formula (IIh-bis):

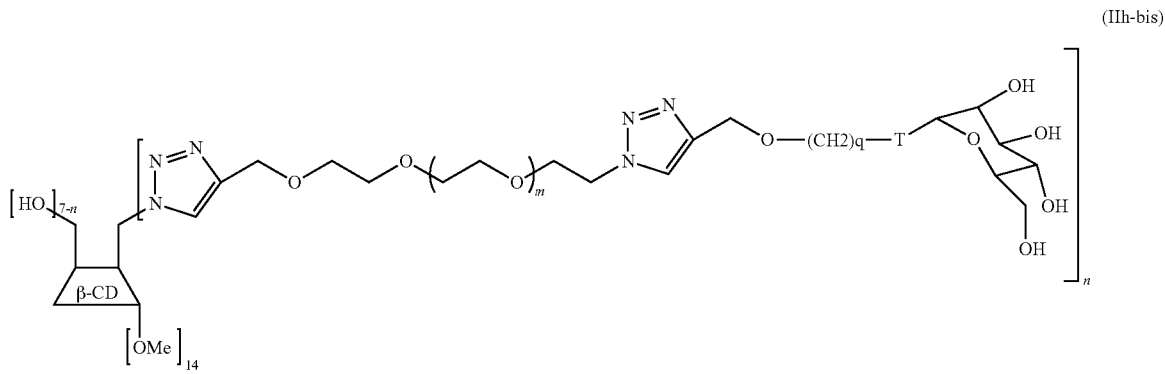

(IIh-bis)

wherein n, m and q are as defined above, m being in particular equal to 1, q being in particular equal to 7,
T representing O, S or CH$_2$, in particular S or CH$_2$.

In an advantageous embodiment, the present invention relates to a compound of formula (I), wherein A is a cyclodextrin derivative, X is of formula (1), wherein p equals 1, W and Y are of formula (1'), and Z is of formula (1"), corresponding to the following formula (IIh-bis):

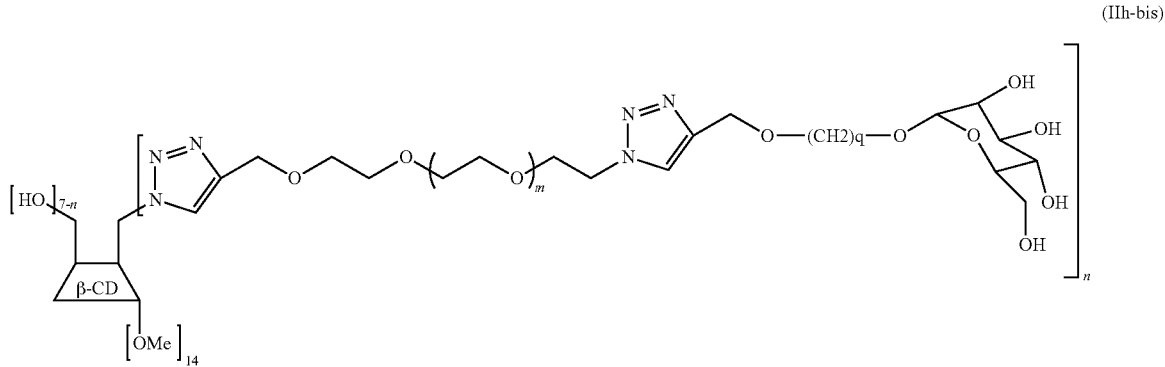

(IIh-bis)

wherein n, m and q are as defined above, m being in particular equal to 1, q being in particular equal to 7.

In an advantageous embodiment, the present invention relates to a compound of formula (I), wherein A is a cyclodextrin, X is of formula (1), wherein Z is of formula (2″) or (2bis″), corresponding respectively to the following formula (II-1) or (II-2):

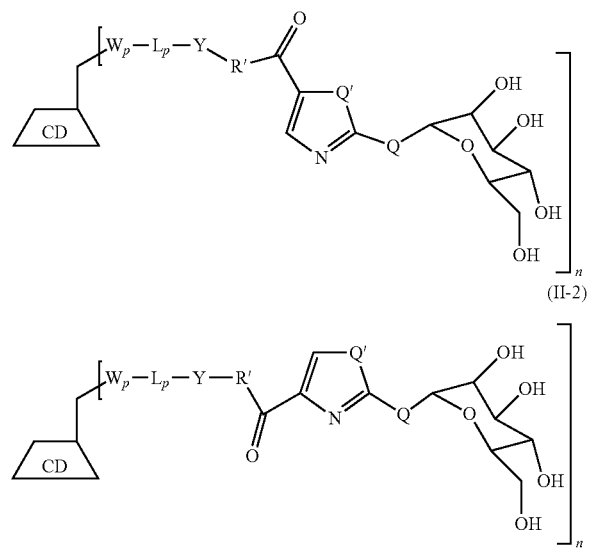

wherein p, n, W, L, Y, R', Q and Q' are as defined above, Q and Q' representing in particular NH and S, respectively, R' representing in particular a linear or branched $(C_1-C_7)$-alkane diyl, more particularly —$CH_2$—, or a group of the following formula:

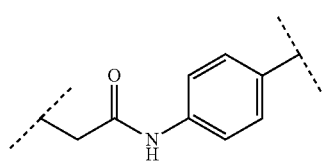

In an advantageous embodiment, the present invention relates to a compound of formula (I), wherein A is a cyclodextrin, X is of formula (1), wherein Z is of formula (2″), corresponding to the following formula:

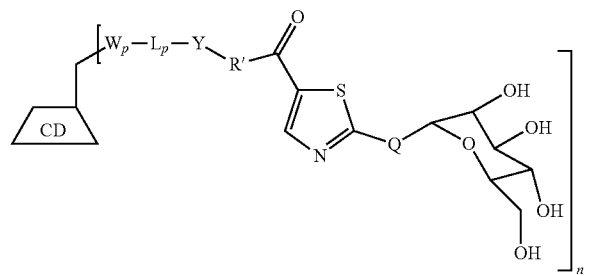

wherein p, n, W, L, Y, R' and Q are as defined above.

In an advantageous embodiment, the present invention relates to a compound of formula (I), wherein A is a cyclodextrin, X is of formula (1), wherein Y is of formula (3bis') and Z is of formula (3″), corresponding to the following formula:

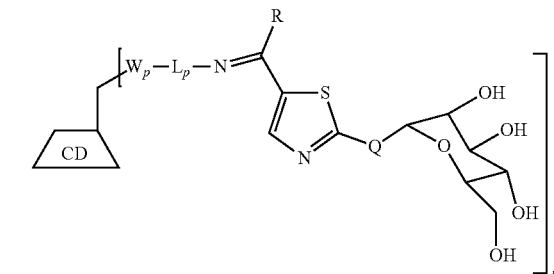

wherein p, n, W, L, Y, R and Q are as defined above.

In an advantageous embodiment, the present invention relates to a compound of formula (I), wherein A is a cyclodextrin, X is of formula (1), wherein p equals 0 and Z is of formula (2″) or (2bis″), corresponding respectively to the following formula (IIa) or (IIa-bis):

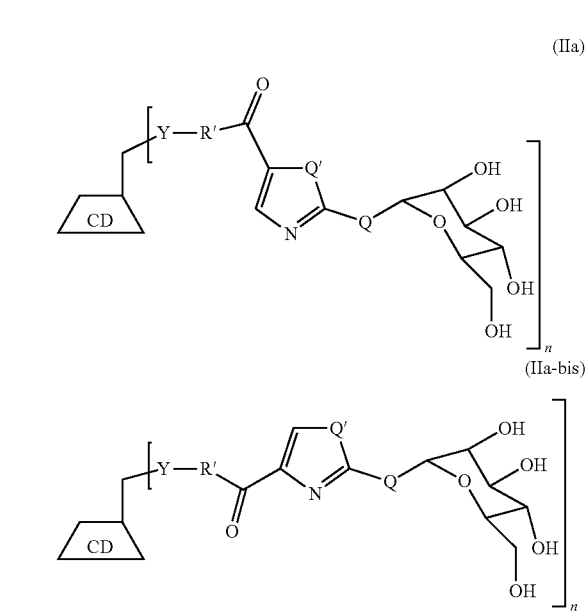

wherein n, Y, R', Q and Q' are as defined above, Q and Q' representing in particular NH and S, respectively, R' representing in particular a linear or branched $(C_1-C_7)$-alkane diyl, more particularly —$CH_2$—, or a group of the following formula:

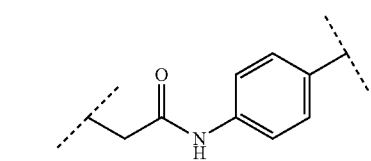

In an advantageous embodiment, the present invention relates to a compound of formula (I), wherein A is a cyclodextrin, X is of formula (1), wherein p equals 0 and Z is of formula (2″), corresponding to the following formula (IIa):

(IIa)

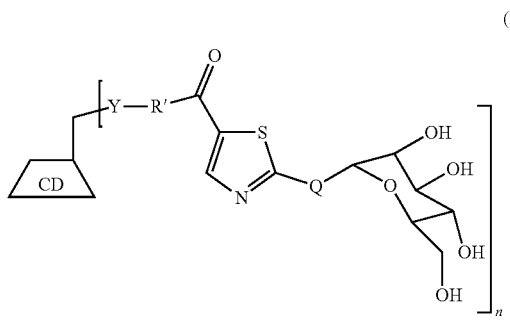

wherein n, Y, R' and Q are as defined above.

In an advantageous embodiment, the present invention relates to a compound of formula (I), wherein A is a cyclodextrin, X is of formula (1), wherein p equals 0, Y is of formula (3bis') and Z is of formula (3"), corresponding to the following formula (IIa):

(IIa)

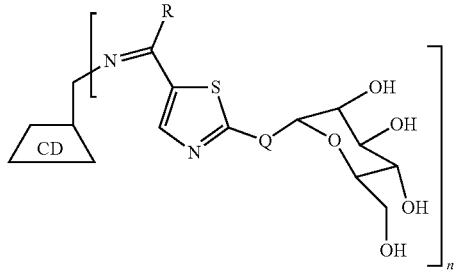

wherein n, Y, R and Q are as defined above.

In an advantageous embodiment, the present invention relates to a compound of formula (I), wherein A is a cyclodextrin, X is of formula (1), wherein p equals 1 and Z is of formula (2"), corresponding to the following formula (IIb):

(IIb)

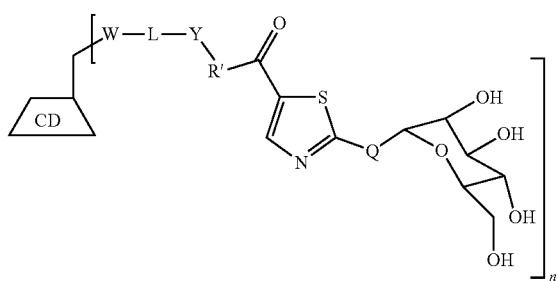

wherein n, W, L, Y, R' and Q are as defined above.

In an advantageous embodiment, the present invention relates to a compound of formula (I), wherein A is a cyclodextrin, X is of formula (1), wherein p equals 1 and Z is of formula (3"), corresponding to the following formula:

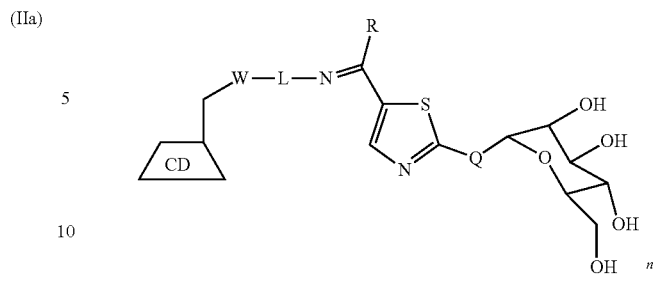

wherein n, W, L, Y, R and Q are as defined above.

In an advantageous embodiment, the present invention relates to a compound of formula (I), wherein A is a cyclodextrin, X is of formula (1), wherein p equals 0, Y represents (1') and Z is of formula (2"), corresponding to the following formula (IIc):

(IIc)

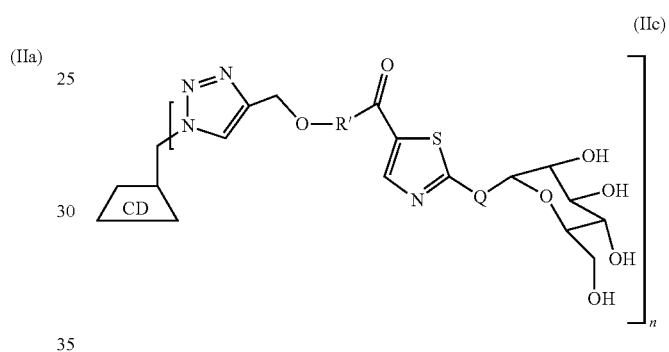

wherein n, R' and Q are as defined above.

In an advantageous embodiment, the present invention relates to a compound of formula (I), wherein A is a cyclodextrin, X is of formula (1), wherein p equals 0, Y represents (2') and Z is of formula (2"), corresponding to the following formula (IIc'):

(IIc')

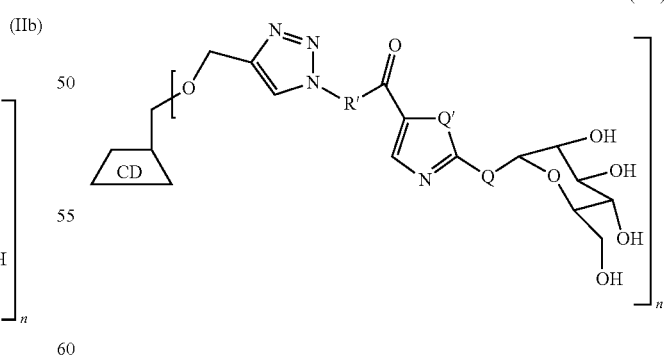

wherein n, R', Q and Q' are as defined above,

Q and Q' representing in particular NH and S, respectively,

R' representing in particular a linear or branched $(C_1\text{-}C_7)$-alkane diyl, more particularly $-CH_2-$, or a group of the following formula:

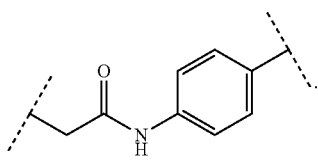

In an advantageous embodiment, the present invention relates to a compound of formula (I), wherein A is a cyclodextrin, X is of formula (1), wherein p equals 0, Y represents (2') and Z is of formula (2bis"), corresponding to the following formula (IIc"):

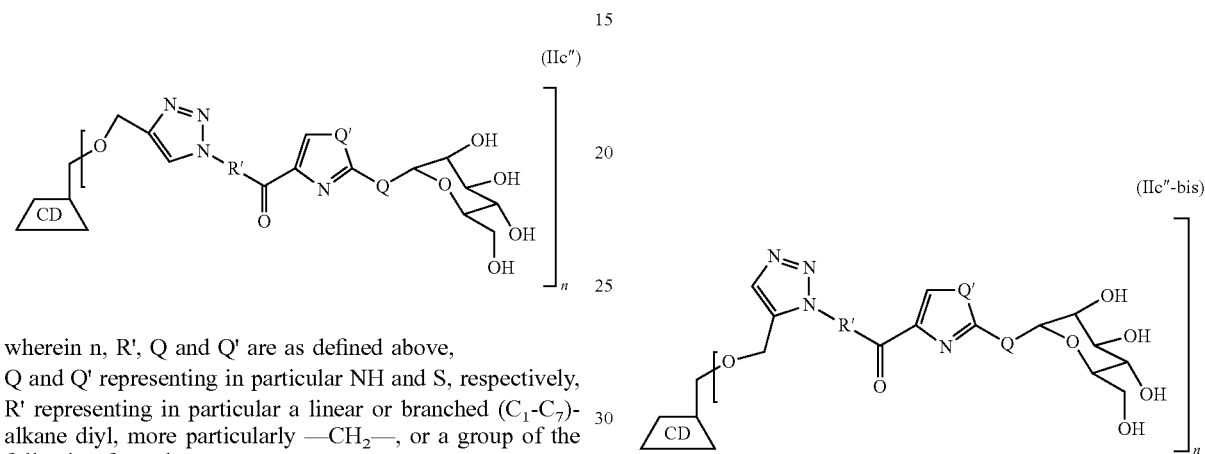

wherein n, R', Q and Q' are as defined above,
Q and Q' representing in particular NH and S, respectively,
R' representing in particular a linear or branched $(C_1-C_7)$-alkane diyl, more particularly —$CH_2$—, or a group of the following formula:

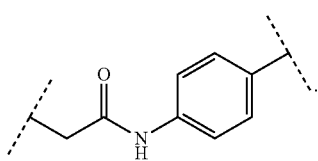

In an advantageous embodiment, the present invention relates to a compound of formula (I), wherein A is a cyclodextrin, X is of formula (1), wherein p equals 0, Y represents (2bis') and Z is of formula (2"), corresponding to the following formula (IIc'-bis):

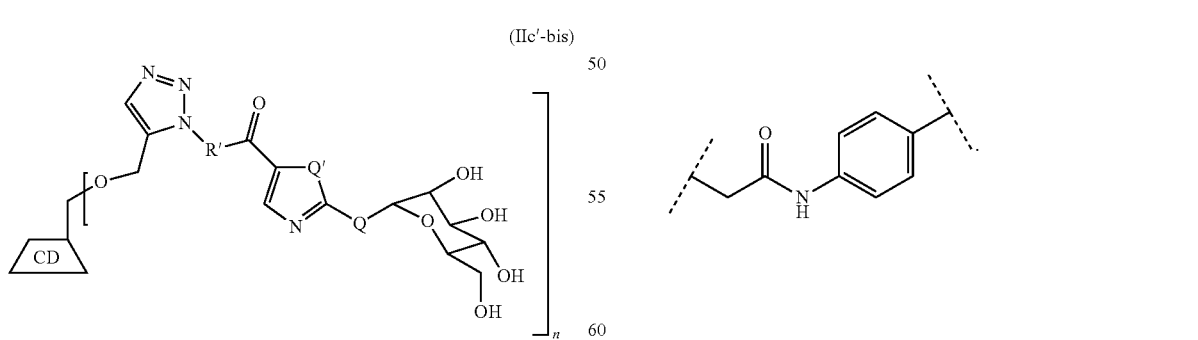

wherein n, R', Q and Q' are as defined above,
Q and Q' representing in particular NH and S, respectively,
R' representing in particular a linear or branched $(C_1-C_7)$-alkane diyl, more particularly —$CH_2$—, or a group of the following formula:

In an advantageous embodiment, the present invention relates to a compound of formula (I), wherein A is a cyclodextrin, X is of formula (1), wherein p equals 0, Y represents (2bis') and Z is of formula (2bis"), corresponding to the following formula (IIc"-bis):

wherein n, R', Q and Q' are as defined above,
Q and Q' representing in particular NH and S, respectively,
R' representing in particular a linear or branched $(C_1-C_7)$-alkane diyl, more particularly —$CH_2$—, or a group of the following formula:

In an advantageous embodiment, the present invention relates to a compound of formula (I), wherein A is a cyclodextrin, X is of formula (1), wherein p equals 1, L is of formula $(l_1)$, and Z is of formula (2"), corresponding to the following formula (IId):

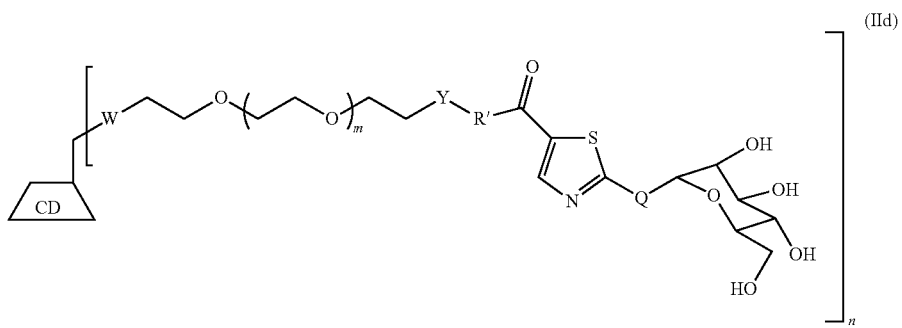

wherein R', n, W, L, Y, m and q are as defined above, m being in particular equal to 1, q being in particular equal to 7.

In an advantageous embodiment, the present invention relates to a compound of formula (I), wherein A is a cyclodextrin, X is of formula (1), wherein p equals 1, W and Y are of formula (1'), and Z is of formula (2"), corresponding to the following formula (IIe):

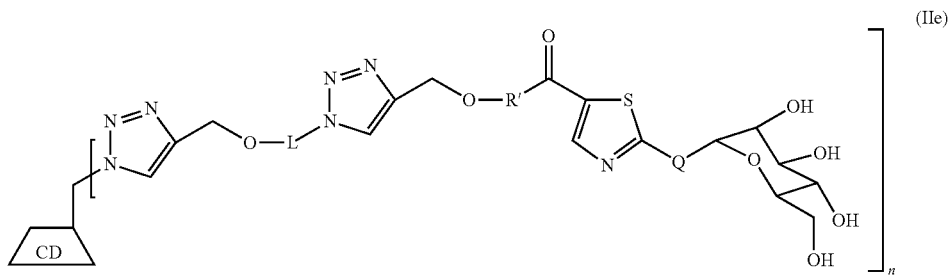

wherein n, L, R' and Q are as defined above.

In an advantageous embodiment, the present invention relates to a compound of formula (I), wherein A is a cyclodextrin, X is of formula (1), wherein p equals 1, W and Y are of formula (1'), and Z is of formula (2"), corresponding to the following formula (IIf):

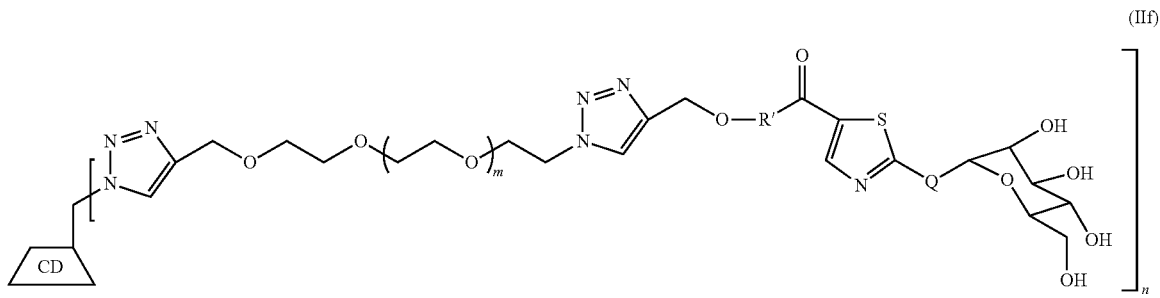

wherein n, m, R' and Q are as defined above, m being in particular equal to 1.

In an advantageous embodiment, the present invention relates to a compound of formula (I), wherein A is a cyclodextrin, X is of formula (1), wherein p equals 0, Y represents (1') and Z is of formula (2"), corresponding to the following formula (IIg):

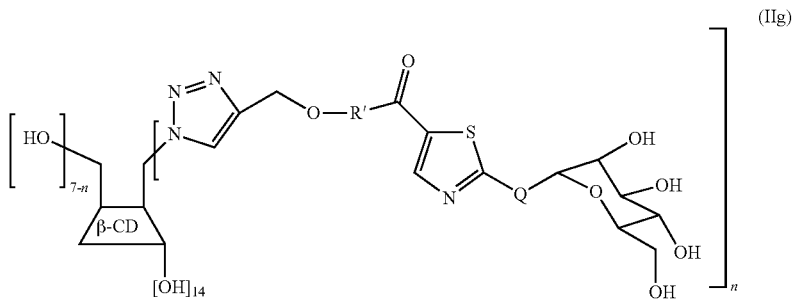

wherein n, R' and Q are as defined above.

In an advantageous embodiment, the present invention relates to a compound of formula (I), wherein A is a cyclodextrin, X is of formula (1), wherein p equals 0, Y represents (2') and Z is of formula (2"), corresponding to the following formula (IIg'):

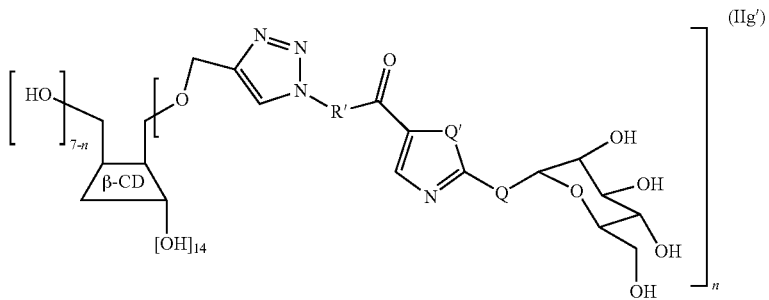

wherein n, R', Q and Q' are as defined above,
Q and Q' representing in particular NH and S, respectively,
R' representing in particular a linear or branched $(C_1-C_7)$-alkane diyl, more particularly —$CH_2$—, or a group of the following formula:

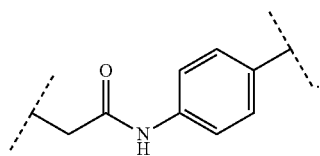

In an advantageous embodiment, the present invention relates to a compound of formula (I), wherein A is a cyclodextrin, X is of formula (1), wherein p equals 0, Y represents (2') and Z is of formula (2bis"), corresponding to the following formula (IIg"):

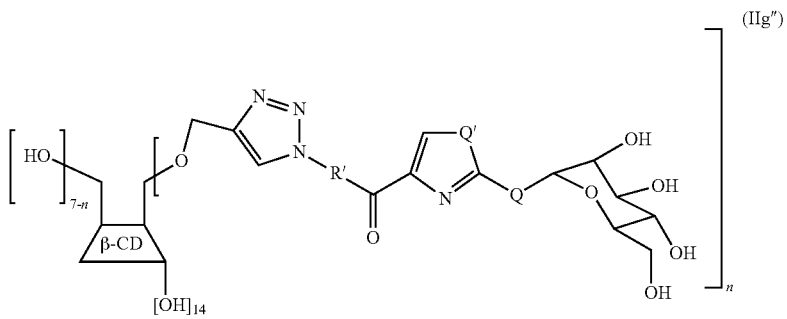

wherein n, R', Q and Q' are as defined above,
Q and Q' representing in particular NH and S, respectively, R' representing in particular a linear or branched (C$_1$-C$_7$)-alkane diyl, more particularly —CH$_2$—, or a group of the following formula:

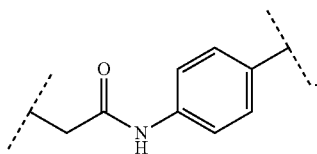

In an advantageous embodiment, the present invention relates to a compound of formula (I), wherein A is a cyclodextrin, X is of formula (1), wherein p equals 0, Y represents (2bis') and Z is of formula (2"), corresponding to the following formula (IIg'-bis):

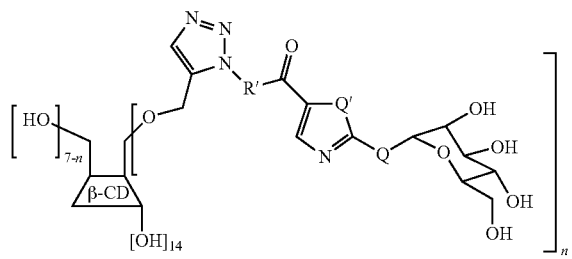

(IIg'-bis)

wherein n, R', Q and Q' are as defined above,
Q and Q' representing in particular NH and S, respectively, R' representing in particular a linear or branched (C$_1$-C$_7$)-alkane diyl, more particularly —CH$_2$—, or a group of the following formula:

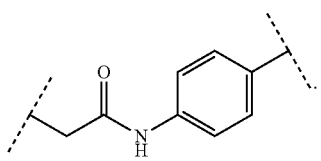

In an advantageous embodiment, the present invention relates to a compound of formula (I), wherein A is a cyclodextrin, X is of formula (1), wherein p equals 0, Y represents (2bis') and Z is of formula (2bis"), corresponding to the following formula (IIg"-bis):

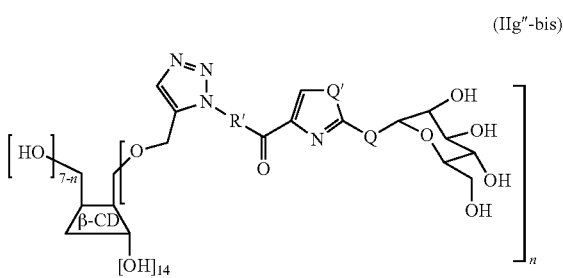

(IIg"-bis)

wherein n, R', Q and Q' are as defined above,
Q and Q' representing in particular NH and S, respectively, R' representing in particular a linear or branched (C$_1$-C$_7$)-alkane diyl, more particularly —CH$_2$—, or a group of the following formula:

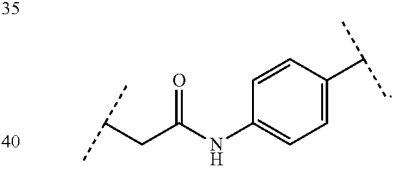

In an advantageous embodiment, the present invention relates to a compound of formula (I), wherein A is a cyclodextrin, X is of formula (1), wherein p equals 1, W and Y are of formula (1'), and Z is of formula (2"), corresponding to the following formula (IIh):

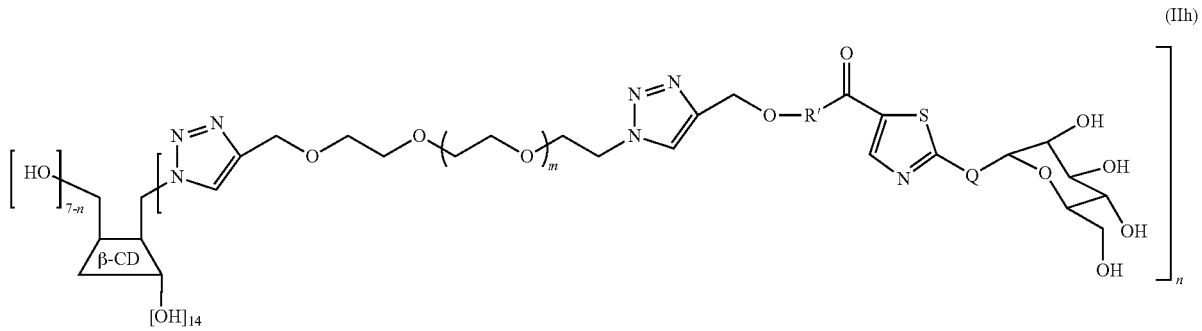

(IIh)

wherein n, m, R and Q are as defined above, m being in particular equal to 1.

In an advantageous embodiment, the present invention relates to a compound of formula (I), selected from the group comprising:
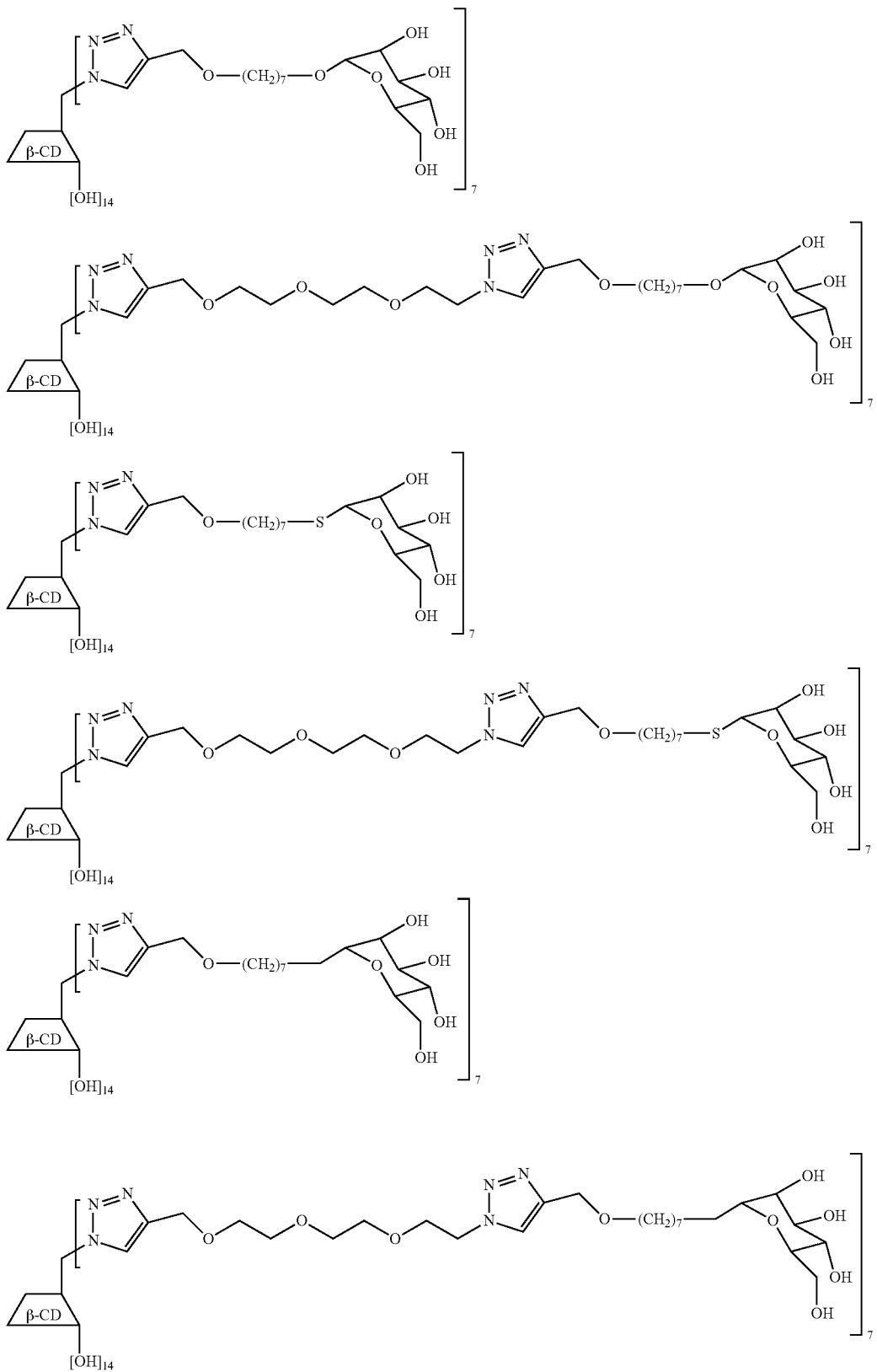

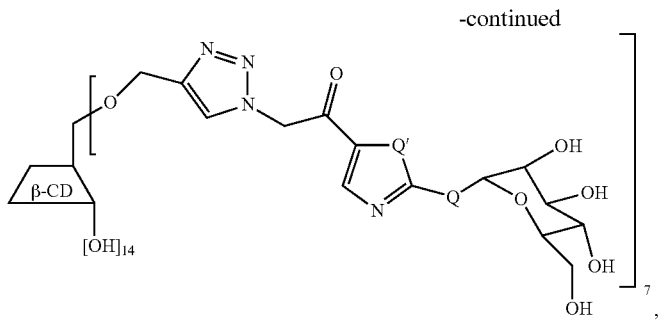

wherein Q and Q' are as defined above, Q and Q' representing in particular NH and S, respectively,

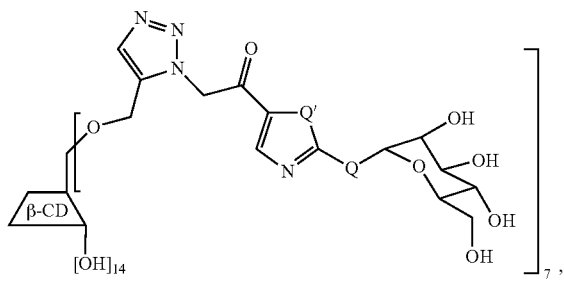

wherein Q and Q' are as defined above, Q and Q' representing in particular NH and S, respectively,

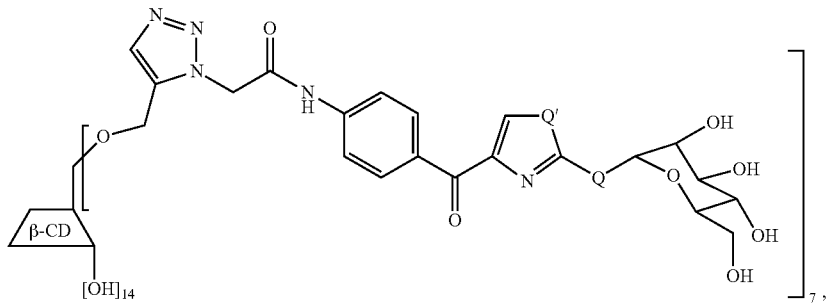

wherein Q and Q' are as defined above, Q and Q' representing in particular NH and S, respectively.

In another aspect, the present invention relates to a pharmaceutical composition comprising, as active substance, a compound of formula (I) described above, in association with a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semisynthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical composition, wherein said active compound is of the following formula:

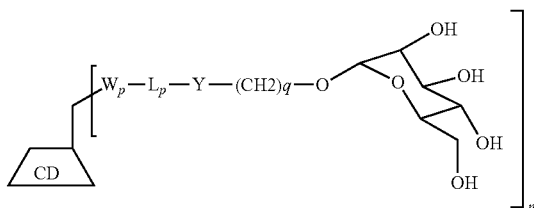

wherein p, n, W, L, Y and q are as defined above, q being in particular equal to 7.

In an advantageous embodiment, the present invention relates to a pharmaceutical composition, wherein said active compound is of the following formula:

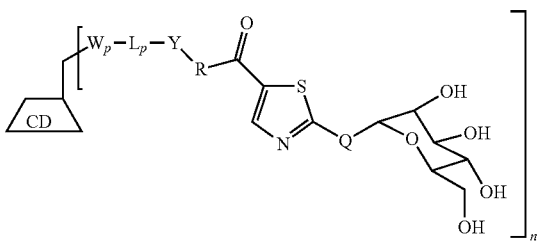

wherein p, n, W, L, Y, R and Q are as defined above.

In an advantageous embodiment, the present invention relates to a pharmaceutical composition, wherein said active compound is of the following formula:

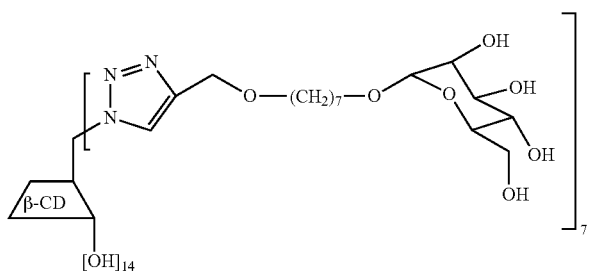

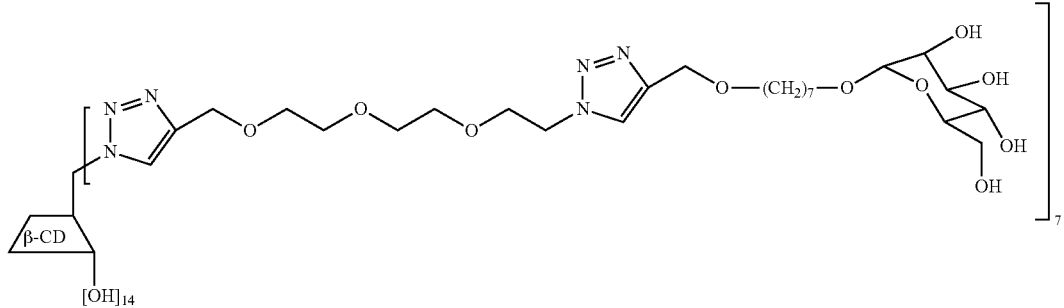

In an advantageous embodiment, the present invention relates to a pharmaceutical composition, said composition being in a form administrable by at least one route selected from the group consisting of oral, intravenous, subcutaneous, nasal, inhalatory, intramuscular, intraperitoneal and suppository, in particular oral or intravenous route.

In an advantageous embodiment, the present invention relates to a pharmaceutical composition, administrable by oral route at a dose comprised from about 0.1 mg/kg to about 100 mg/kg of body weight.

In an advantageous embodiment, the present invention relates to a pharmaceutical composition, under a form liable to be administrable by oral route, under the form of a unit dose comprised from 5 mg to 7,500 mg, in particular from 10 mg to 2,000 mg, in particular from 50 to 1000 mg.

Said pharmaceutical composition can be administered 1 to 4 times per day, preferably 2 or 3 times per day.

In an advantageous embodiment, the present invention relates to a pharmaceutical composition, administrable by intravenous route at a dose comprised from about 10 µg/kg to about 10 mg/kg.

In an advantageous embodiment, the present invention relates to a pharmaceutical composition, under a form liable to be administrable by intravenous, under the form of a unit dose comprised from 0.1 mg to 1000 mg, in particular from 10 mg to 1,000 mg, in particular from 10 to 500 mg, in particular from 10 to 100 mg.

Said pharmaceutical composition can be administered 1 to 4 times per day, preferably 2 or 3 times per day.

In another aspect, the present invention relates to a vaccine composition comprising, as active substance, a compound of formula (I) described above, in association with a pharmaceutically acceptable adjuvant.

By "adjuvant" is meant any substance that enhances the immune response to an antigen. Adjuvants useful in the vaccine composition according to the present invention include mineral compounds including mineral salts such as calcium or aluminium salts, mineral or non-mineral oils, bacterial products, liposomes, saponins, iscoms and biodegradable microparticles. Well known adjuvants include Quil A, Marcol 52, Montanide 103 and pluronic polymers, such as L121 (BASF, N.J.).

The vaccine composition may include other adjuvants, including adjuvants in liquid form. Such other adjuvants that may be used include squalene, Adjuvant 65 (containing peanut oil, mannide monooleate and aluminium monostearate), surfactants such as hexadecylamine, octadecylamine, lysolecithin, dimethyl-dioctadecylammonium bromide, N,N-dioctradecyl-N,N¹-bis(2-hydroxyethyl)-propanediamine, methoxy-hexadecylglycerol and pluronic polyols, polyanions such as pyran, dextran sulfate, polyacrylic acid and carbopol, peptides and amino acids such as muramyl dipeptide, demethylglycine, tuftsin and trehalose dimycolate, Adju-Phos, Algal Glucan, Algammulin, aluminium salts including aluminium hydroxide (Al(OH)$_3$), aluminium phosphate (AlPO$_4$), Alhydrogel, Antigen Formulation, Avridine, Bay R1005, Calcitriol, Calcium Phosphate, Calcium Phosphate Gel, Cholera Holotoxin (CT), Cholera Toxin B Subunit (CTB), CRL1005, DDA, DHEA, DMPC, DMPG, DOC/Alum Complex, Gamma Inulin, Gerbu Adjuvant, GMDP, Imiquimod, ImmTher, Interferon-gamma, Iscoprep 7.0.3, Loxoribine, LT-OA or LT Oral Adjuvant, MF59, Mannan, MONTANIDE ISA 51, MONTANIDE ISA 720, MPL, MTP-PE, MTP-PE, Muramamide, Murapalmitine, D-Murapalmitine, NAGO, Nonionic Surfactant Vesicles, Pleuran, PLGA, PGA and PLA, PMMA, PODDS, Poly Ra: Poly rU, Polyphosphazene, Polysorbate 80, Protein Cochleates, QS-21, Rehydragel HPA, Rehydragel LV, S-28463, SAF-1, Sclavo Peptide, Sendai Proteoliposomes, Sendai-Containing Lipid Matrices, Span 85, Specol, Stearyl Tyrosine, Theramide, Threonyl-MDP and Ty Particles.

In another aspect, the present invention relates to a compound of formula (I) described above, for its use for the treatment of pathologies caused by *Escherichia coli* and mediated by interactions between *Escherichia coli* lectins and host cell surface glycans, in particular pathologies caused by *Escherichia coli* and mediated by interactions between *Escherichia coli* FimH adhesin and host cell surface glycans.

In an advantageous embodiment, the present invention relates to a compound of formula (I) described above, for its use for the treatment, for patients living with diabetes or another disease involving increased apoptosis rate, of pathologies caused by *Escherichia coli* and mediated by interactions between *Escherichia coli* lectins and host cell surface glycans, in particular pathologies caused by *Escherichia coli* and mediated by interactions between *Escherichia coli* FimH adhesin and host cell surface glycans.

In an advantageous embodiment, said pathologies belong to the group consisting of:
  inflammatory bowel diseases, in particular Crohn's disease,
  urinary tract infections, in particular painful bladder syndrome and cystitis, more particularly interstitial cystitis, and
  urinary tract infections in patients with a metabolic disease correlated with enhanced apoptosis, in particular diabetes.

Examples of inflammatory bowel diseases are Crohn's disease and ulcerative colitis.

Examples of urinary tract infections are painful bladder syndrome and cystitis, in particular interstitial cystitis.

Heightened apoptosis frequency in diabetics was described by Ustuner M C et al. (Urology 2010; 75(4):902-6).

Heightened urinary tract infections frequency in diabetics was described in Geerlings S E Int J Antimicrob Agents. 2008; 31 Suppl 1:S54-7.

Heightened apoptosis in (interstitial) cystitis was described in Shi J H et al. Urology. 2012, 79 (2), 484 and in Klumpp D J et al., Infect Immun. 2006, 74 (9), 5106-5113.

In another aspect, the present invention relates to a combination of a compound of formula (I) described above, and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides, for simultaneous, separated or sequential use in treatment of said diseases.

In another aspect, the present invention relates to a complex between a compound of formula (I) described above and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides.

The present invention also relates to a process of preparation of a compound of formula (I):

$$A\text{-}X_n \qquad (I)$$

wherein:
  A is a scaffold;
  n is an integer comprised from 3 to 10, in particular from 3 to 8, more particularly from 3 to 7;
and wherein X represents:
  a group of the following formula:

$$-Y-Z \qquad (1a),$$

or $$-W-Z$$

wherein:
  Y or W is chosen from:

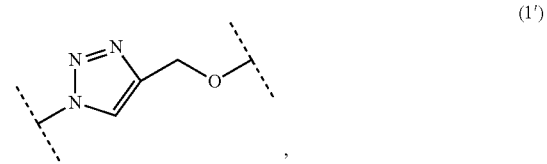
(1')

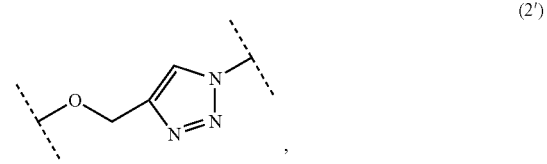
(2')

(3')

(4')

(4bis')

(5')

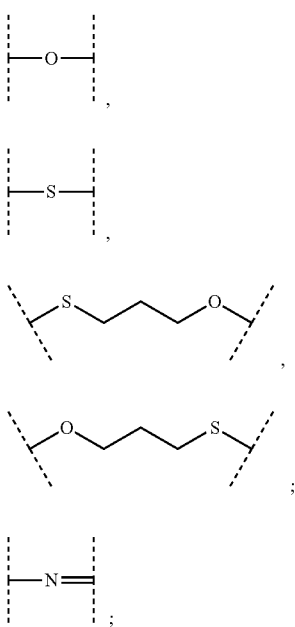

R1 representing:
  a hydrogen, or
  a linear or branched (C$_1$-C$_7$)-alkyl;
Z is chosen from:

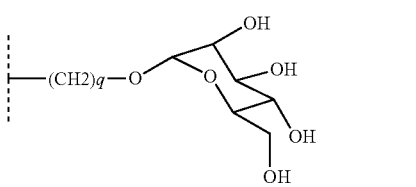

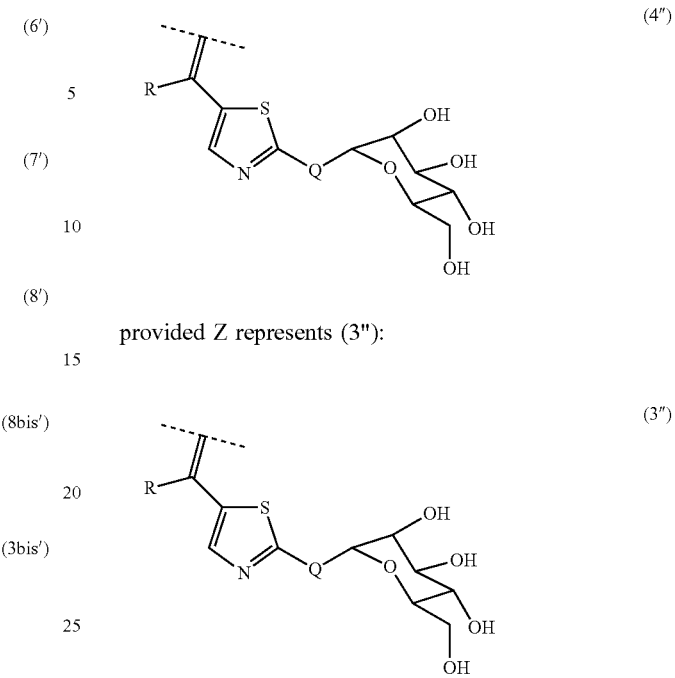

provided Z represents (3″):

only when Y or W represents (3bis′):

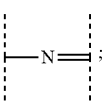

q being an integer chosen from 6, 7 and 8, q being in particular equal to 7;
Q representing NH, O or S, in particular NH;
R' representing a group selected from:
  a linear or branched (C$_1$-C$_7$)-alkane diyl,
  a linear or branched (C$_2$-C$_7$)-alkene diyl,
  a linear or branched (C$_2$-C$_7$)-alkyne diyl,
  a (C$_3$-C$_7$)-cycloalkane diyl,
  a (C$_5$-C$_7$)-cycloalkene diyl,
  a (C$_3$-C$_7$)-heterocycloalkane diyl,
  a (C$_5$-C$_7$)-heterocycloalkene diyl,
  an arene diyl, said arene being an aromatic or heteroaromatic group,
  a group -arene$_1$-arene$_2$- wherein arene$_1$ and arene$_2$ are independently to each other an aromatic or heteroaromatic arene;
said (C$_1$-C$_7$)-alkane diyl, (C$_2$-C$_7$)-alkene diyl, (C$_2$-C$_7$)-alkyne diyl, (C$_3$-C$_7$)-cycloalkane diyl, (C$_5$-C$_7$)-cycloalkene diyl, (C$_3$-C$_7$)-heterocycloalkane diyl, (C$_5$-C$_7$)-heterocycloalkene diyl, arene diyl, arene$_1$ and arene$_2$ being substituted or not by one or more substituent(s), each independently selected from:
  a linear or branched (C$_1$-C$_7$)-alkyl,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl, an aryl, wherein the aryl is an aromatic or heteroaromatic group
an alkyl aryl, wherein the aryl is an aromatic or heteroaromatic group,
a CHO,
a CO—$(C_1$-$C_7)$-alkyl,
a CO-aryl, wherein aryl is an aromatic or heteroaromatic group,
a $CO_2H$,
a $CO_2$—$(C_1$-$C_7)$-alkyl,
a CONH—$(C_1$-$C_7)$-alkyl,
a halogen selected from the group comprising F, Cl, Br, and I,
$CF_3$,
$OR_a$, wherein $R_a$ represents:
  H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group,
$NR_bR_c$, wherein $R_b$ and $R_c$ represent independently from each other:
  H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group,
$NO_2$,
CN;
R representing a group selected from:
  a linear or branched $(C_1$-$C_7)$-alkyl,
  a linear or branched $(C_2$-$C_7)$-alkenyl,
  a linear or branched $(C_2$-$C_7)$-alkynyl,
  a $(C_3$-$C_7)$-cycloalkyl,
  a $(C_5$-$C_7)$-cycloalkenyl,
  a $(C_3$-$C_7)$-heterocycloalkyl,
  a $(C_5$-$C_7)$-heterocycloalkenyl,
  an aryl, said aryl being an aromatic or heteroaromatic group,
  an alkyl aryl, wherein the aryl is an aromatic or heteroaromatic group,
  a CO—$(C_1$-$C_7)$-alkyl,
  a CO-aryl, wherein aryl is an aromatic or heteroaromatic group,
  a $CO_2H$,
  a $CO_2$—$(C_1$-$C_7)$-alkyl,
  a CONH—$(C_1$-$C_7)$-alkyl,
  $CF_3$,
  adamantyl,
said $(C_1$-$C_7)$-alkyl, $(C_2$-$C_7)$-alkenyl, $(C_2$-$C_7)$-alkynyl, $(C_3$-$C_7)$-cycloalkyl, $(C_5$-$C_7)$-cycloalkenyl, $(C_3$-$C_7)$-heterocycloalkyl, $(C_5$-$C_7)$-heterocycloalkenyl, CO—$(C_1$-$C_7)$-alkyl, $CO_2$—$(C_1$-$C_7)$-alkyl, CONH—$(C_1$-$C_7)$-alkyl, aryl, alkyl aryl and CO-aryl being substituted or not by one or more substituent(s), each independently selected from:
  a linear or branched $(C_1$-$C_7)$-alkyl,
  a linear or branched $(C_2$-$C_7)$-alkenyl,
  a linear or branched $(C_2$-$C_7)$-alkynyl,
  a $(C_3$-$C_7)$-cycloalkyl,
  a $(C_5$-$C_7)$-cycloalkenyl,
  a $(C_3$-$C_7)$-heterocycloalkyl,
  a $(C_5$-$C_7)$-heterocycloalkenyl,
  an aryl, wherein the aryl is an aromatic or heteroaromatic group
  an alkyl aryl, wherein the aryl is an aromatic or heteroaromatic group,
  a CHO,
  a CO—$(C_1$-$C_7)$-alkyl,
  a CO-aryl, wherein aryl is an aromatic or heteroaromatic group,
  a $CO_2H$,
  a $CO_2$—$(C_1$-$C_7)$-alkyl,
  a CONH—$(C_1$-$C_7)$-alkyl,
  a halogen selected from the group comprising F, Cl, Br, and I,
  $CF_3$,
  $OR_a$, wherein $R_a$ represents:
    H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group,
  $NR_bR_c$, wherein $R_b$ and $R_c$ represent independently from each other:
    H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group,
  $NO_2$,
  CN,
A being such as the n bonds between A and the n groups $X_n$ are, considering the mean position of aforesaid bonds, substantially equidistant,
provided that aforesaid compound is different from:

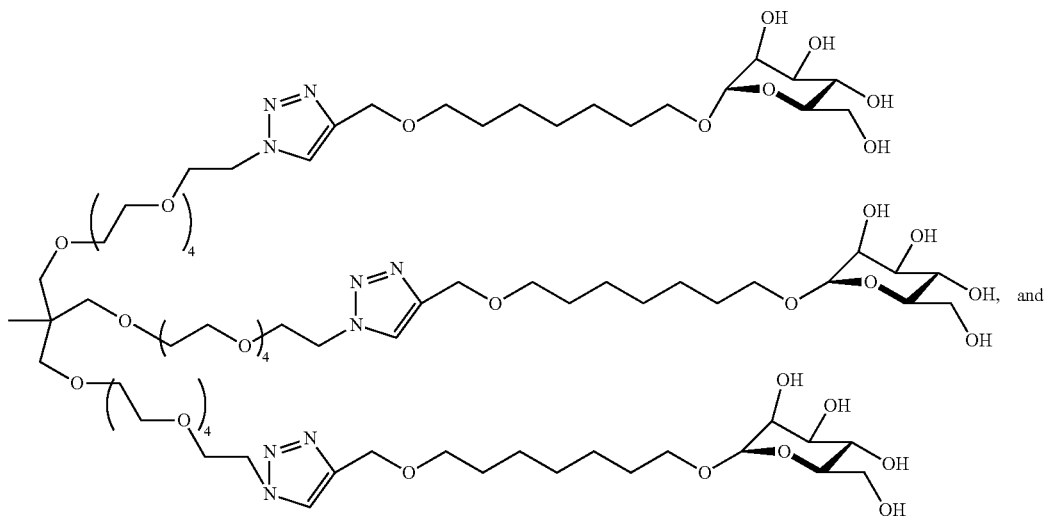

-continued

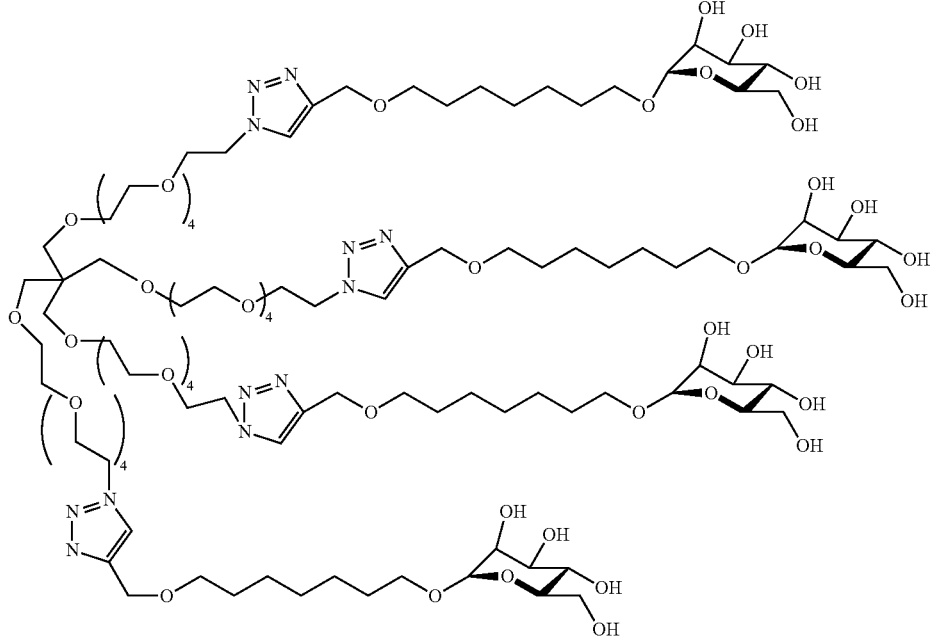

said process of preparation comprising a reaction between:
A-(G$_1$)$_n$, wherein A and n are as defined above and G$_1$ is the first co-precursor of Y or W;
G$_2$-Z, wherein Z is as defined above and G$_2$ is the second co-precursor of Y or W
to obtain a compound of formula (I) A-(X)$_n$, wherein X corresponds to formula —Y—Z (1a) or —W—Z, G$_1$ and G$_2$ having reacted together to form Y or W,
or
wherein X represents a group of the following formula (1b):

—W-L-Y—Z    (1b)

wherein
W, Y and Z are as defined above,
L represents a linker of the following formula:
when p+s=0, corresponding to X=-L-Z, (1$_2$)

i being an integer comprised from 0 to 20, in particular from 0 to 10,
when p+s=1, corresponding to X=—W-L-Z or -L-Y—Z,
when p=0, corresponding to X=-L-Y—Z, (1$_3$)

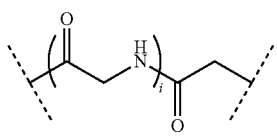

i being an integer comprised from 0 to 20, in particular from 0 to 10,
when p=1, corresponding to X=—W-L-Z, (1$_2$)

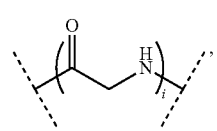

i being an integer comprised from 0 to 20, in particular from 0 to 10,
when p+s=2, corresponding to X=—W-L-Y—Z, (1$_1$)

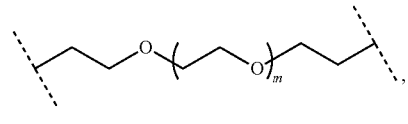

(1$_5$)

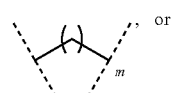  or (1$_3$)

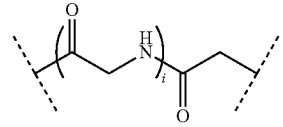

m being an integer comprised from 0 to 20, in particular from 0 to 10,
i being an integer comprised from 0 to 20, in particular from 0 to 10, provided L represents (l₃) only when Z represents a group selected from (3'), (6'), (7'), (8') and (8bis'):

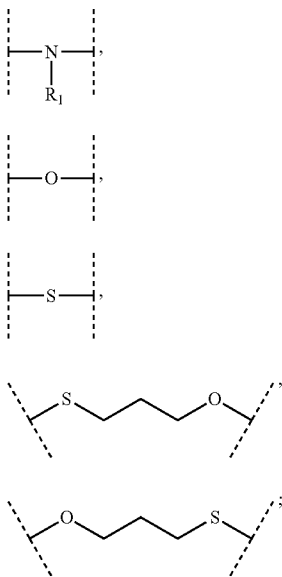

said process of preparation comprising:
a) a reaction between:
- A-(G₁)ₙ, wherein A and n are as defined above and G₁ is the first co-precursor of W;
- F₂-L-F₃, wherein L is as defined above, F₂ is the second co-precursor of W, and F₃ is a precursor of the first co-precursor F₄ of Y, F₃ being in particular a leaving group or the first co-precursor of Y bearing an appropriate protective group;
to obtain a compound of formula A-(W-L-F₃)ₙ; G₁ and F₂ having reacted together to form W;
b) a reaction, in particular a reaction of substitution or deprotection, starting from A-(W-L-F₃)ₙ to obtain A-(W-L-F₄)ₙ, wherein F₄ is the first co-precursor of Y;
c) a reaction between:
- A-(W-L-F₄)ₙ, and
- G₂-Z, wherein Z is as defined above and G₂ is the second co-precursor of Y
to obtain a compound of formula (I) A-(X)ₙ, wherein X corresponds to formula (1b) —W-L-Y—Z, F₄ and G₂ having reacted together to form Y;
or
wherein X represents a group of the following formula:

L-Z wherein L and Z are as defined above,
said process of preparation comprising:
a) a reaction between A-(J₁)ₙ and J₂-L-J₃, wherein A, L and n are as defined above, J₁ and J₂ are chemical functions able to react together to form the n bonds between A and L, and J₃ is a chemical function able to react with a chemical function J₄ to form a bond between L and Z, to obtain a compound of formula A-(L-J₃)ₙ,
b) a reaction between A-(L-J₃)ₙ and J₄-Z, wherein J₄ and Z are described above, to obtain a compound of formula (I) A-(X)ₙ, wherein X corresponds to -L-Z;
or
wherein X represents a group of the following formula (1b):

—W-L-Z wherein
W, L and Z are as defined above,
said process of preparation comprising:
a) a reaction between:
- A-(G₁)ₙ, wherein A and n are as defined above and G₁ is the first co-precursor of W;
- F₂-L-J₃, wherein F₂ and J₃ are described above, to obtain a compound of formula A-(W-L-J₃)ₙ,
b) a reaction between A-(W-L-J₃)ₙ and J₄-Z, wherein J₄ and Z are described above, to obtain a compound of formula (I) A-(X)ₙ, wherein X corresponds to —W-L-Z;
or
wherein X represents a group of the following formula:

-L-Y—Z wherein
L, Y and Z are as defined above,
said process of preparation comprising:
a) a reaction between A-(J₁)ₙ and J₂-L-F₄, wherein A, J1, L, n, J2 and F4 are as defined above, to obtain a compound of formula A-(L-F4)ₙ,
b) a reaction between:
- A-(L-F₄)ₙ, and
- G₂-Z, wherein Z is as defined above and G₂ is the second co-precursor of Y to obtain a compound of formula (I) A-(X)ₙ, wherein X corresponds to formula -L-Y—Z.

Examples of co-precursors of Y or W, when Y or W represents:

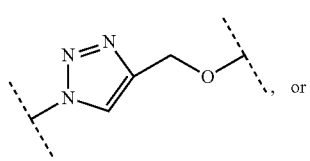

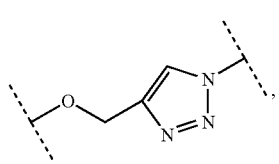

are —(N₃) and

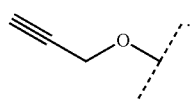

Examples of co-precursors of Y or W, when Y or W represents:

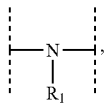

are

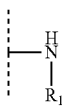

and a leaving group, such as a halide, a mesyl or a tosyl.
Examples of co-precursors of Y or W, when Y or W represents:

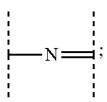
(3bis')

are —NH$_2$ and a ketone, in particular a R—CO— ketone, wherein R is as described above.
Examples of co-precursors of Y or W, when Y or W represents:

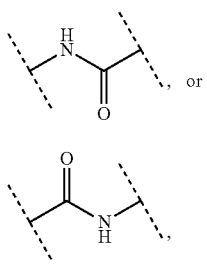
(4')
(4bis')

are —NH2 and an activated ester, aforesaid activated ester being chosen from all the activated esters known by those skilled in the art, in particular an activated ester obtain from the corresponding carboxylic acid, N,N'-Dicyclohexylcarbodiimide (DCC) and 4-dimethylaminopyridine (DMAP).
When Y represents

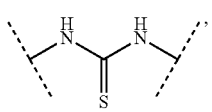
(5')

Y co-precursors of for instance an amine —NH2 and a isothiocyanate —NCS.
When Y represents (6')

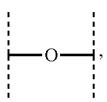

Y co-precursor are for instance an hydroxyle —OH and a leaving group, such as a halide, a mesyl or a tosyl, in particular a bromide.

When Y represents

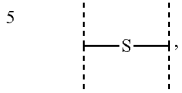
(7')

Y co-precursor are for instance:
a thiol —SH and a leaving group, such as a halide, a mesyl or a tosyl, in particular a bromide,
or a thiol —SH and a H$_2$C=C— enyl group, Y being formed through a thiol-ene click chemistry reaction.
When Y represents:

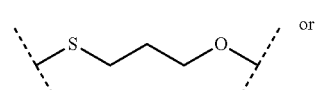
(8')

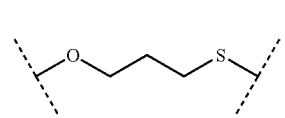
(8bis')

Y co-precursors are for instance:
a thiol —SH and a H$_2$C=C—CH$_2$—O— group, or
a thiol SH and a LG-(CH$_2$)$_3$—O— group, wherein LG is a leaving group, such as a halide, a mesyl or a tosyl, in particular a bromide.
Examples of chemical functions chosen to form the bond between A and L, or L and Z are:
—NH2 and H—CO—, aforesaid bond being formed by reductive amination, or
—NH2 and a leaving group, such as a halide, a mesyl or a tosyl, or
—NH2 and an activated ester, aforesaid activated ester being chosen from all the activated esters known by those skilled in the art, in particular an activated ester obtain from the corresponding carboxylic acid, N,N'-Dicyclohexylcarbodiimide (DCC) and 4-dimethylaminopyridine (DMAP).

In an advantageous embodiment, the present invention relates to a process of preparation of a compound of formula (I) described above, wherein Y or W is of the following formula:

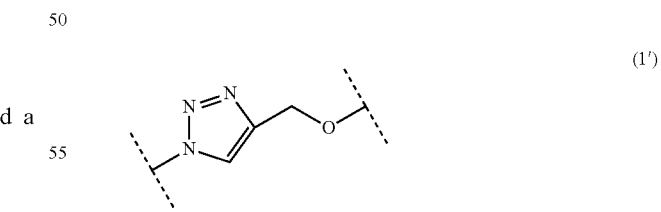
(1')

said process of preparation comprising a reaction between:
A-(N$_3$)$_n$, wherein A and n are as defined above;

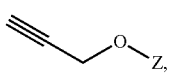

wherein Z is as defined above to obtain a compound of formula (I) A-(X)$_n$, wherein X corresponds to formula —Y—Z (1a) or —W—Z, wherein Y or W is of the following formula:

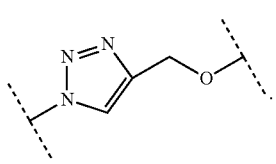
(1')

The present invention also relates to a process of preparation of a compound of formula (I):

$$A\text{-}X_n \qquad (I)$$

wherein:
A is chosen from cyclodextrins and their derivatives, in particular alkylated cyclodextrins, A being more particularly selected from the group comprising:

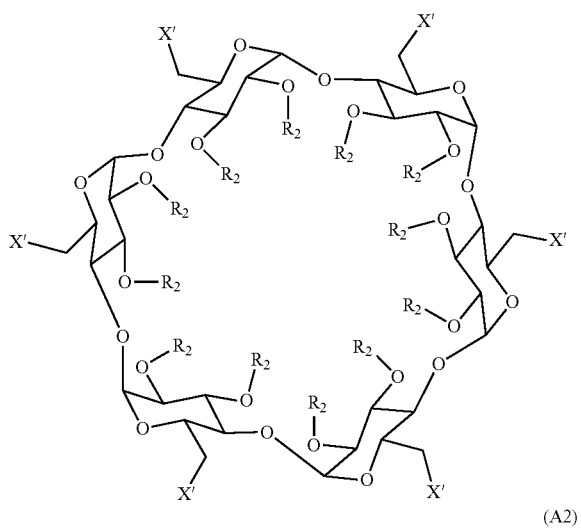
(A1)

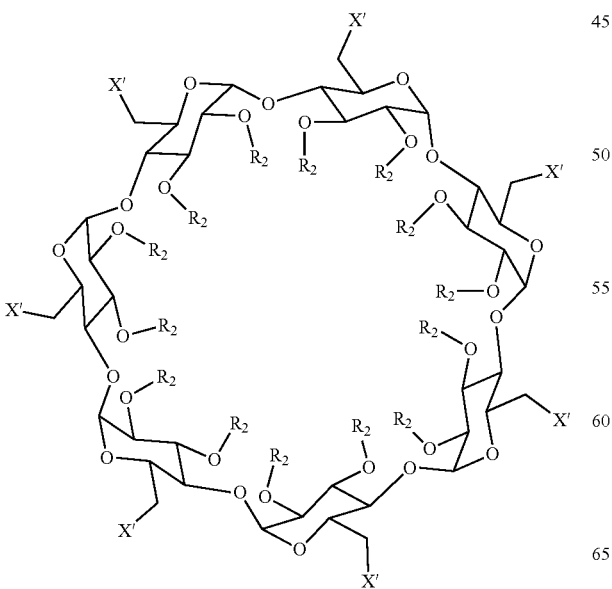
(A2)

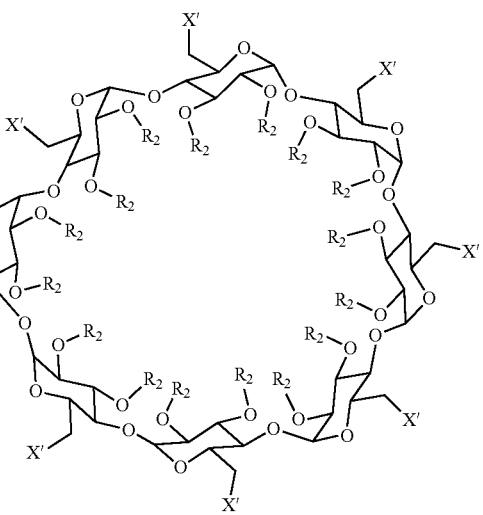
(A3)

wherein
X' is chosen from the group comprising —OH and -----, wherein ----- represents a bond to X;
R$_2$ is chosen from the group comprising hydrogen and a linear or branched (C$_1$-C$_7$)-alkyl;
n is an integer comprised from 3 to 8, in particular from 6 to 8;
X represents a group of the following formula (1):

$$-\text{W}_p\text{-L}_r\text{-Y}_s\text{—Z} \qquad (1)$$

wherein:
p, r, and s are integers independently from each other equal to 0 or 1, provided that:
when r is equal to 0, p and s are such as the sum p+s is equal to 1,
when r is equal to 1, p and s are such as the sum p+s is equal to 2;
W is chosen from:

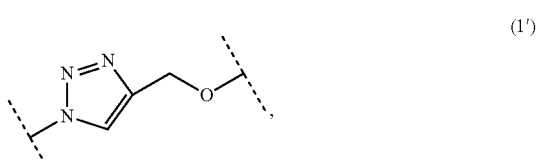
(1')

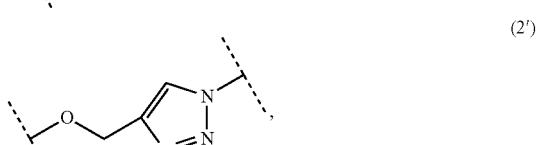
(2')

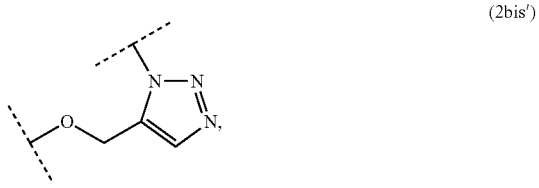
(2bis')

Y is chosen from:

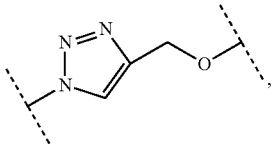
(1′)

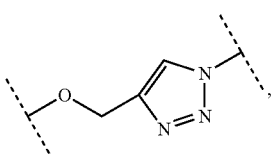
(2′)

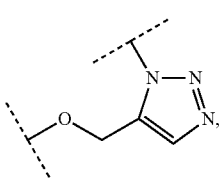
(2bis′)

Z is chosen from:

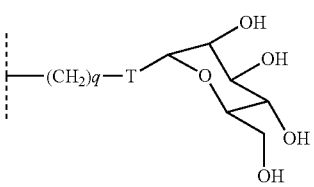
(1″)

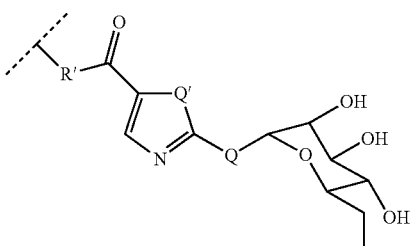
(2″)

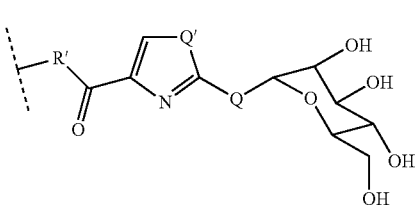
(2bis″)

L represents a linker of one of the following formulae:

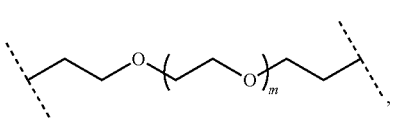
(I₁)

(I₅)

m being an integer comprised from 0 to 20, in particular from 0 to 10,

Q and Q' representing independently from each other NH, O or S;

Q and Q' representing in particular NH and S, respectively;

T representing O, S or CH₂, in particular O;

R' representing a group selected from:
- a linear or branched (C₁-C₇)-alkane diyl,
- a linear or branched (C₂-C₇)-alkene diyl,
- a linear or branched (C₂-C₇)-alkyne diyl,
- a (C₃-C₇)-cycloalkane diyl,
- a (C₅-C₇)-cycloalkene diyl,
- a (C₃-C₇)-heterocycloalkane diyl,
- a (C₅-C₇)-heterocycloalkene diyl,
- an arene diyl, said arene being an aromatic or heteroaromatic group,
- a group -arene₁-arene₂- wherein arene₁ and arene₂ are independently to each other an aromatic or heteroaromatic arene;
- a group of the following formula:

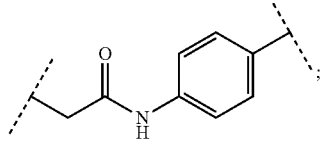

said (C₁-C₇)-alkane diyl, (C₂-C₇)-alkene diyl, (C₂-C₇)-alkyne diyl, (C₃-C₇)-cycloalkane diyl, (C₅-C₇)-cycloalkene diyl, (C₃-C₇)-heterocycloalkane diyl, (C₅-C₇)-heterocycloalkene diyl, arene diyl, arene₁ and arene₂ being substituted or not by one or more substituent(s), each independently selected from:
- a linear or branched (C₁-C₇)-alkyl,
- a linear or branched (C₂-C₇)-alkenyl,
- a linear or branched (C₂-C₇)-alkynyl,
- a (C₃-C₇)-cycloalkyl,
- a (C₅-C₇)-cycloalkenyl,
- a (C₃-C₇)-heterocycloalkyl,
- a (C₅-C₇)-heterocycloalkenyl,
- an aryl, wherein the aryl is an aromatic or heteroaromatic group
- an alkyl aryl, wherein the aryl is an aromatic or heteroaromatic group,
- a CHO,
- a CO—(C₁-C₇)-alkyl,
- a CO-aryl, wherein aryl is an aromatic or heteroaromatic group,
- a CO₂H,
- a CO₂—(C₁-C₇)-alkyl,
- a CONH—(C₁-C₇)-alkyl,
- a halogen selected from the group comprising F, Cl, Br, and I,
- CF₃,
- OR_a, wherein R_a represents:

H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group, $NR_bR_c$, wherein $R_b$ and $R_c$ represent independently from each other:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group, $NO_2$,
CN;

R' representing in particular a linear or branched $(C_1-C_7)$-alkane diyl, more particularly —$CH_2$—, or a group of the following formula:

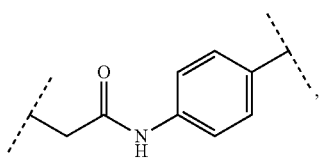

when r=0, said process of preparation comprising a reaction between:
A-$(G_1)_n$, wherein A and n are as defined above and $G_1$ is the first co-precursor of Y or W, and
$G_2$-Z, wherein Z is as defined above and $G_2$ is the second co-precursor of Y or W
to obtain a compound of formula (I) A-$(X)_n$, wherein X corresponds to formula —Y—Z (1a) or —W—Z, $G_1$ and $G_2$ having reacted together to form Y or W,
said group $G_1$ representing —$N_3$ or

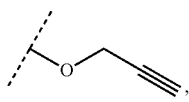

said $G_2$ group representing respectively

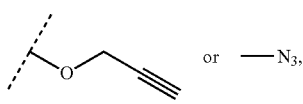

said groups $G_1$ and $G_2$ forming Y or W in particular in presence of copper sulphate and sodium ascorbate in DMF,
or
when r=1, said process of preparation comprises:
a) a reaction between:
A-$(G_1)_n$, wherein A and n are as defined above and $G_1$ is the first co-precursor of W;
$F_2$-L-$F_3$, wherein L is as defined above, $F_2$ is the second co-precursor of W, and $F_3$ is a precursor of the first co-precursor $F_4$ of Y, $F_3$ being in particular a leaving group or the first co-precursor of Y bearing an appropriate protective group;
to obtain a compound of formula A-$(W-L-F_3)_n$; $G_1$ and $F_2$ having reacted together to form W;
b) a reaction, in particular a reaction of substitution or deprotection, starting from A-$(W-L-F_3)_n$ to obtain A-$(W-L-F_4)_n$, wherein $F_4$ is the first co-precursor of Y;

c) a reaction between:
A-$(W-L-F_4)_n$, and
$G_2$-Z, wherein Z is as defined above and $G_2$ is the second co-precursor of Y,
to obtain a compound of formula (I) A-$(X)_n$, wherein X corresponds to formula (1b) —W-L-Y—Z, $F_4$ and $G_2$ having reacted together to form Y,
said group $G_1$ representing —$N_3$ or

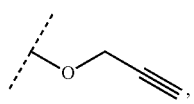

said $F_2$ group representing respectively

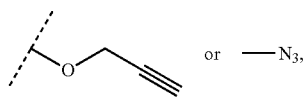

said groups $G_1$ and $F_2$ forming W in particular in presence of copper sulphate and sodium ascorbate in DMF,
said group $F_4$ representing —$N_3$ or

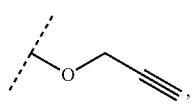

said $G_2$ group representing respectively

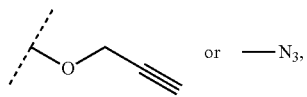

said groups $F_4$ and $G_2$ forming Y in particular in presence of copper sulphate and sodium ascorbate in DMF,
said group $F_3$ representing in particular —Cl, —Br or -mesyl when $F_4$ represents —$N_3$, or

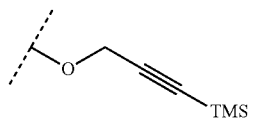

when $F_4$ represents

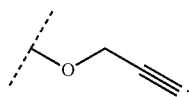

In an advantageous embodiment, the present invention relates to a process of preparation of a compound of the following formula (IIc):

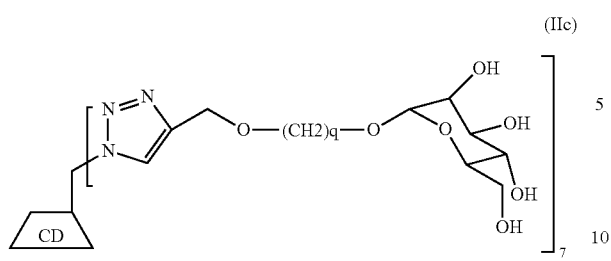 (IIc)

wherein q is as defined above, q being in particular equal to 7,
said process of preparation comprising a reaction between:

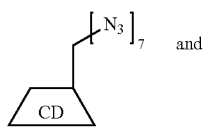 and

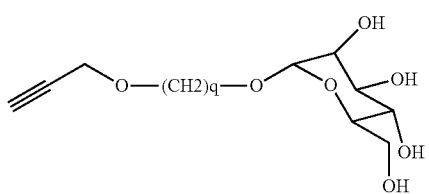

to obtain, in particular in presence of copper sulphate and sodium ascorbate in DMF, aforesaid compound of formula (IIc.)

In an advantageous embodiment, the present invention relates to a process of preparation of a compound of formula (I) described above, wherein W and Y are of the following formula:

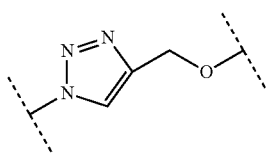 (1')

said process of preparation comprising:
a) a reaction between:
   $A\text{-}(N_3)_n$, wherein A and n are as defined above;

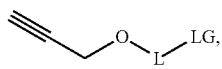

wherein L is as defined above and LG is a leaving group, in particular a halide, a mesyl, or a tosyl,
to obtain, in particular in presence of copper sulphate and sodium ascorbate in DMF, a compound of formula $A\text{-}(W\text{-}L\text{-}LG)_n$;

b) a reaction of substitution between $A\text{-}(W\text{-}L\text{-}LG)_n$ and $M\text{-}N_3$, wherein M is a metal chosen from sodium and potassium, in particular sodium,
to obtain a compound of formula $A\text{-}(W\text{-}L\text{-}N_3)_n$;

c) a reaction between:
   $A\text{-}(W\text{-}L\text{-}N_3)_n$ and

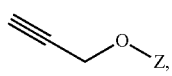

wherein Z is as defined above
to obtain, in particular in presence of copper sulphate and sodium ascorbate in DMF, a compound of formula (I) $A\text{-}(X)_n$, wherein X corresponds to formula (1b) —W-L-Y—Z, wherein W and Y are of the following formula:

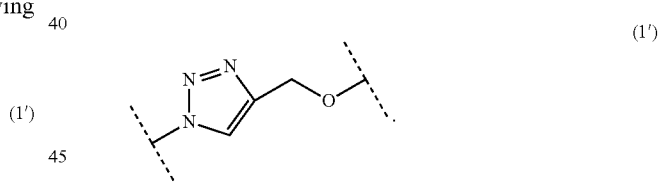 (1')

In an advantageous embodiment, the present invention relates to a process of preparation of a compound of formula (IIf):

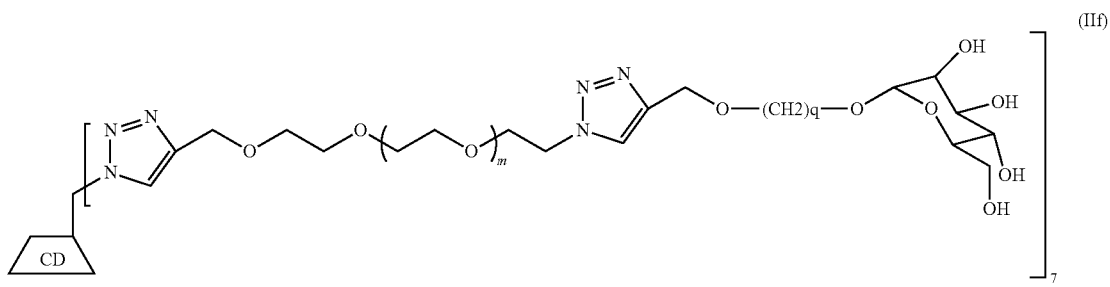 (IIf)

wherein m and q are as defined above, m being in particular equal to 1, q being in particular equal to 7, said process of preparation comprising:

a) a reaction between:

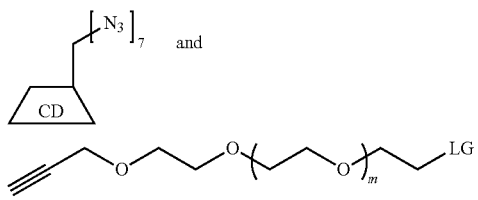 and

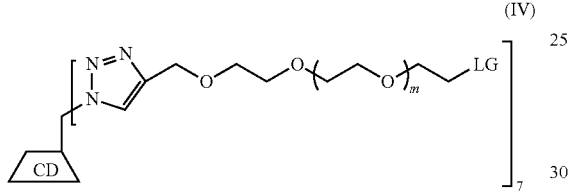

wherein n and m are as defined above, and wherein LG is a leaving group, in particular a halide, a mesyl, or a tosyl, to obtain, in particular in presence of copper sulphate and sodium ascorbate in DMF, a compound of formula:

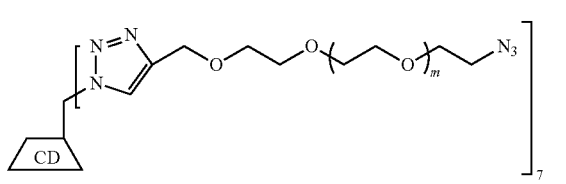

(IV)

b) a reaction between aforesaid compound of formula (IV) and M-$N_3$, wherein M is a metal chosen from sodium and potassium, in particular sodium, to obtain a compound of formula (V):

(V)

c) a reaction between aforesaid compound of formula (V) and

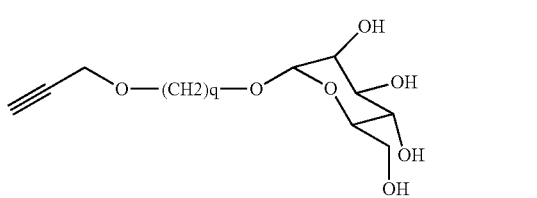

to obtain, in particular in presence of copper sulphate and sodium ascorbate in DMF, aforesaid compound of formula (IIf).

The present invention also relates to a compound of the following formula (IV):

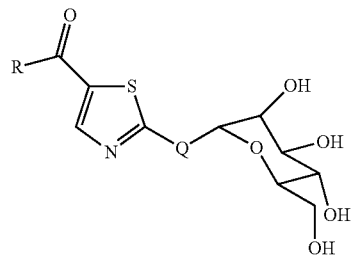

(IV)

wherein:

Q represents NH, O or S, in particular NH;

R represents:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, said aryl being an aromatic or heteroaromatic group,
- an alkyl aryl, wherein the aryl is an aromatic or heteroaromatic group,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- $CF_3$,
- adamantyl, said ($C_1$-$C_7$)-alkyl, ($C_2$-$C_7$)-alkenyl, ($C_2$-$C_7$)-alkynyl, ($C_3$-$C_7$)-cycloalkyl, ($C_5$-$C_7$)-cycloalkenyl, ($C_3$-$C_7$)-heterocycloalkyl, ($C_5$-$C_7$)-heterocycloalkenyl, CO—($C_1$-$C_7$)-alkyl, $CO_2$—($C_1$-$C_7$)-alkyl, CONH—($C_1$-$C_7$)-alkyl, aryl, alkyl aryl and CO-aryl being substituted or not by one or more substituent(s), each independently selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, wherein the aryl is an aromatic or heteroaromatic group
- an alkyl aryl, wherein the aryl is an aromatic or heteroaromatic group,
- a CHO,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl,
- a halogen selected from the group comprising F, Cl, Br, and I,
- $CF_3$,
- $OR_a$, wherein $R_a$ represents:
  - H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group, NR$_b$R$_c$, wherein R$_b$ and R$_c$ represent independently from each other:
   H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
NO$_2$,
CN.

The present invention also relates to a compound of the following formula (IV) or (IVbis):

(IV)

(IVbis)

wherein:
Q and Q' represent independently from each other NH, O or S;
Q representing in particular NH; Q' representing in particular S;
R represents:
   a linear or branched (C$_1$-C$_7$)-alkyl,
   a linear or branched (C$_2$-C$_7$)-alkenyl,
   a linear or branched (C$_2$-C$_7$)-alkynyl,
   a (C$_3$-C$_7$)-cycloalkyl,
   a (C$_5$-C$_7$)-cycloalkenyl,
   a (C$_3$-C$_7$)-heterocycloalkyl,
   a (C$_5$-C$_7$)-heterocycloalkenyl,
   an aryl, said aryl being an aromatic or heteroaromatic group,
   an alkyl aryl, wherein the aryl is an aromatic or heteroaromatic group,
   CF$_3$,
   adamantyl,
   OR$_a$, wherein R$_a$ represents H, a linear or branched (C$_1$-C$_7$)-alkyl, a linear or branched (C$_2$-C$_7$)-alkenyl, a linear or branched (C$_2$-C$_7$)-alkynyl, a (C$_3$-C$_7$)-cycloalkyl, a (C$_5$-C$_7$)-cycloalkenyl, a (C$_3$-C$_7$)-heterocycloalkyl, a (C$_5$-C$_7$)-heterocycloalkenyl, an aryl, wherein the aryl is an aromatic or heteroaromatic group, an alkyl aryl, wherein the aryl is an aromatic or heteroaromatic group, a CHO, a CO—(C$_1$-C$_7$)-alkyl, or CO-aryl, wherein aryl is an aromatic or heteroaromatic group, a CO$_2$H, a CO$_2$—(C$_1$-C$_7$)-alkyl, or a CONH—(C$_1$-C$_7$)-alkyl,
   NR$_b$R$_c$, wherein R$_b$ and R$_c$ represent independently from each other any of the groups defined for R$_a$, R$_b$ representing in particular H,
said (C$_1$-C$_7$)-alkyl, (C$_2$-C$_7$)-alkenyl, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl and CO-aryl being substituted or not by one or more substituent(s) R', each independently selected from:
   a linear or branched (C$_1$-C$_7$)-alkyl,
   a linear or branched (C$_2$-C$_7$)-alkenyl,
   a linear or branched (C$_2$-C$_7$)-alkynyl,
   a (C$_3$-C$_7$)-cycloalkyl,
   a (C$_5$-C$_7$)-cycloalkenyl,
   a (C$_3$-C$_7$)-heterocycloalkyl,
   a (C$_5$-C$_7$)-heterocycloalkenyl,
   an aryl, wherein the aryl is an aromatic or heteroaromatic group
   an alkyl aryl, wherein the aryl is an aromatic or heteroaromatic group,
   a CHO,
   a CO—(C$_1$-C$_7$)-alkyl,
   a CO-aryl, wherein aryl is an aromatic or heteroaromatic group,
   a CO$_2$H,
   a CO$_2$—(C$_1$-C$_7$)-alkyl,
   a CONH—(C$_1$-C$_7$)-alkyl,
   a halogen selected from the group comprising F, Cl, Br, and I,
   CF$_3$,
   OR$_a$, wherein R$_a$ represents:
      H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
   NR$_b$R$_c$, wherein R$_b$ and R$_c$ represent independently from each other:
      H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
   NHR", wherein R" represents any of the groups defined for R$_b$,
   NO$_2$,
   CN.

The present invention also relates to a compound of the following formula (IV) or (IVbis):

(IV)

(IVbis)

wherein:

Q and Q' represent independently from each other NH, O or S;

Q representing in particular NH; Q' representing in particular S;

R represents:
- a linear or branched ($C_1$-$C_7$)-alkyl, in particular methyl or tert-butyl,
- an aryl selected from phenyl and naphthyl,
- an heteroaryl selected from thiophenyl, thiazolyl and triazolyl,
- an alkyl aryl, wherein the aryl is selected from phenyl, naphthyl, thiophenyl,
- thiazolyl and triazolyl,
- adamantyl,
- $NHR_c$, wherein $R_c$ represents any of the groups defined for $R_a$,
- $CF_3$, said ($C_1$-$C_7$)-alkyl, adamantyl, aryl and alkyl aryl being substituted or not by one or more substituent(s) R', as defined above.

In an advantageous embodiment, the present invention relates to a compound selected from the group comprising:

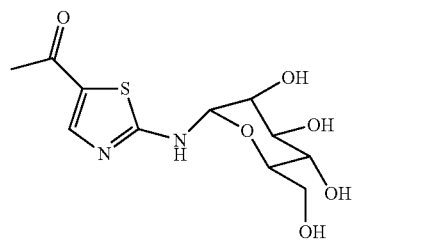

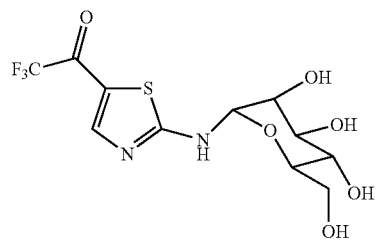

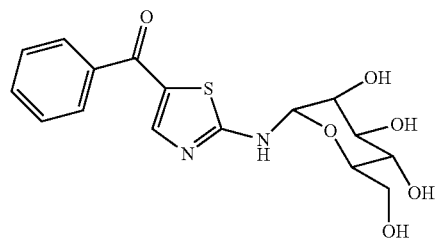

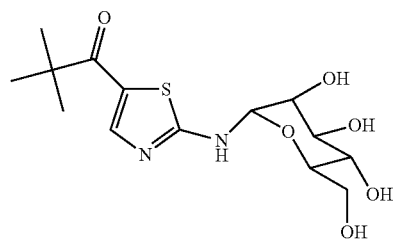

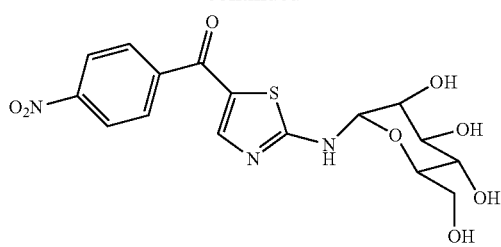

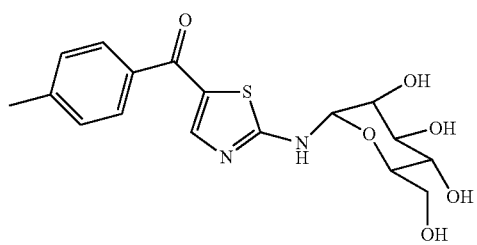

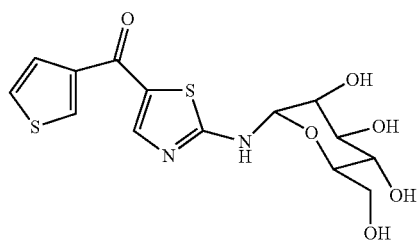

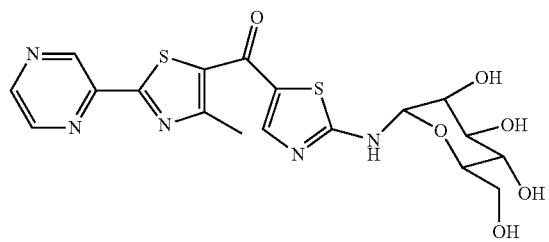

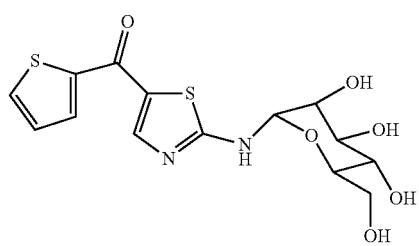

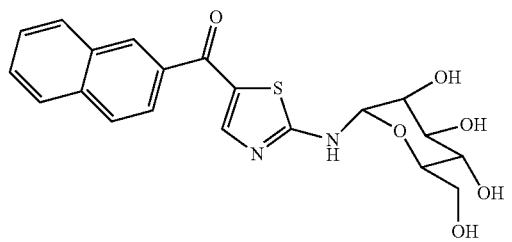

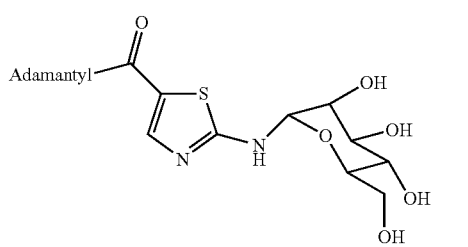

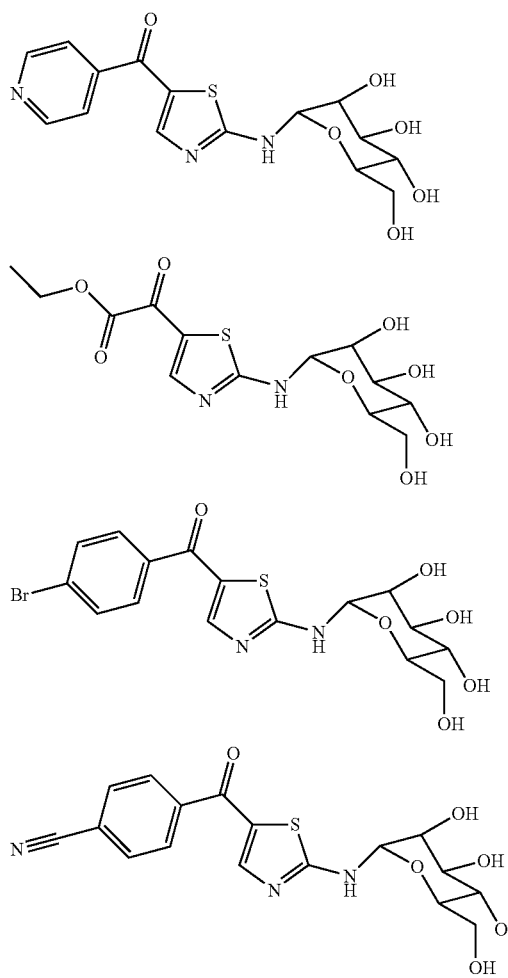
In an advantageous embodiment, the present invention relates to a compound selected from the group comprising:
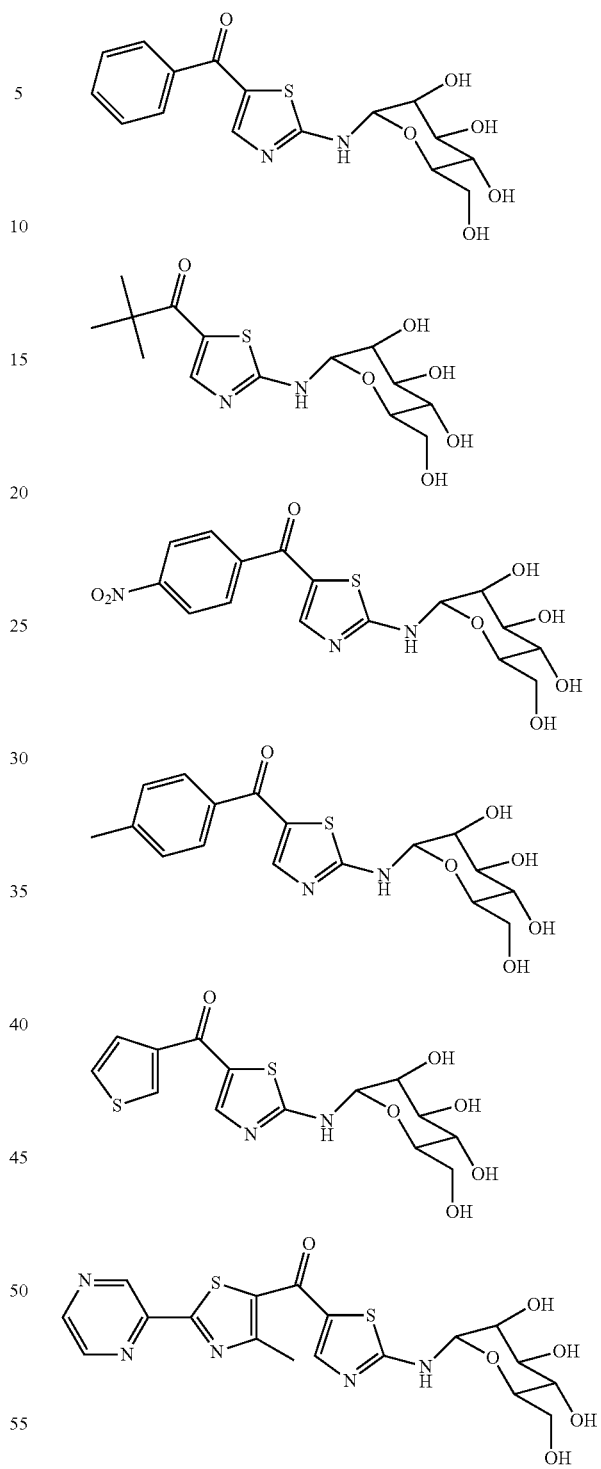

117
-continued
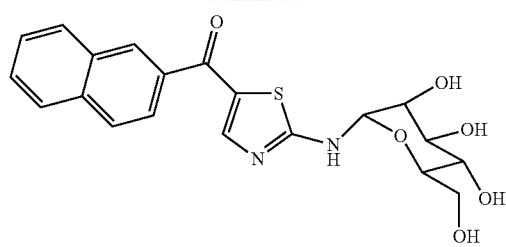
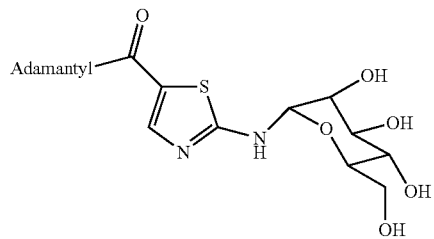
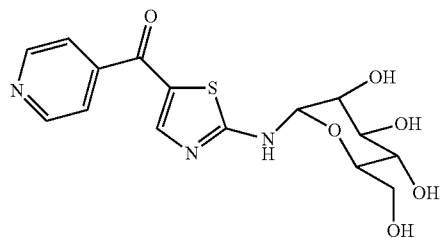
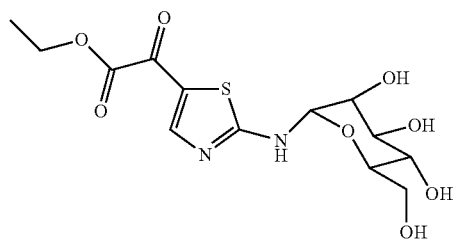
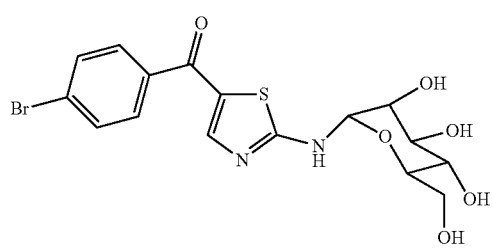
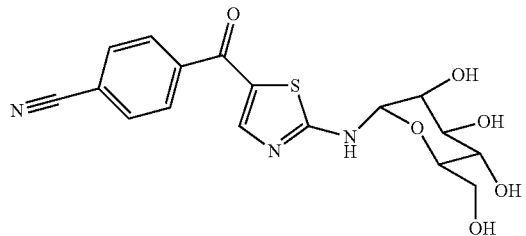
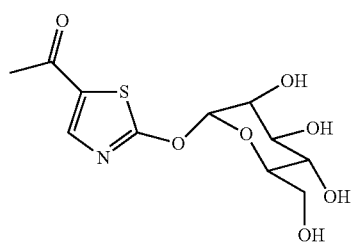
118
-continued
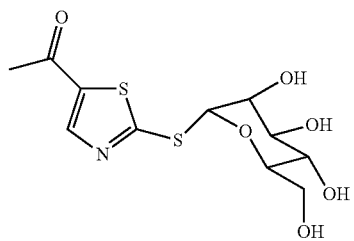
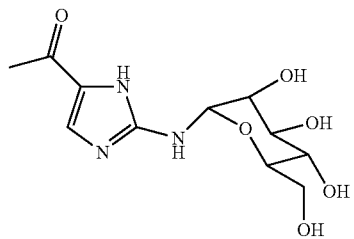
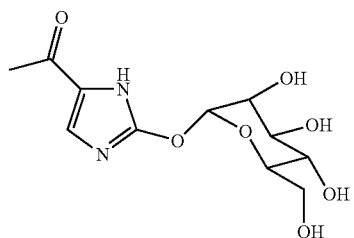
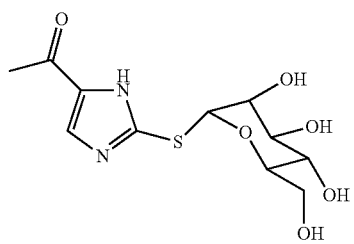
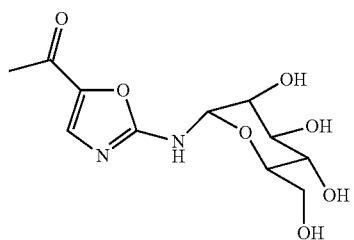
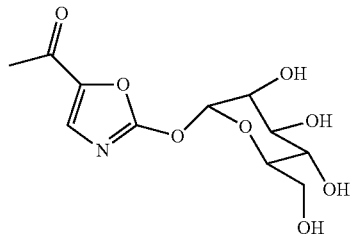
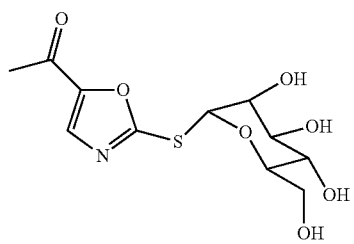

-continued

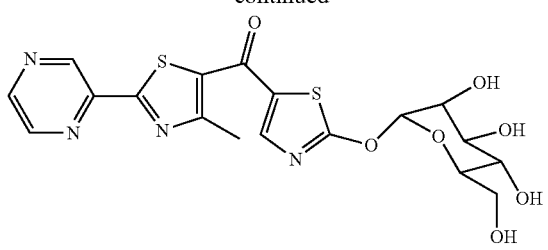

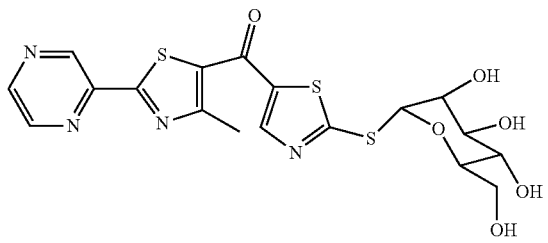

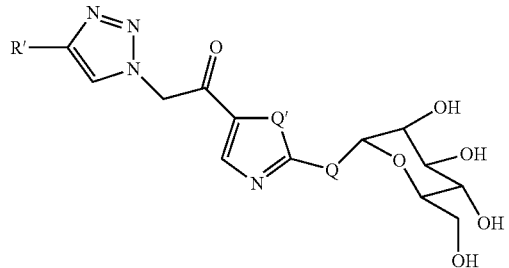

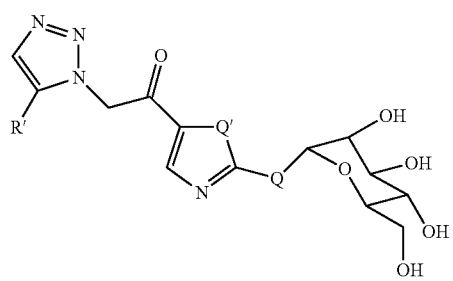

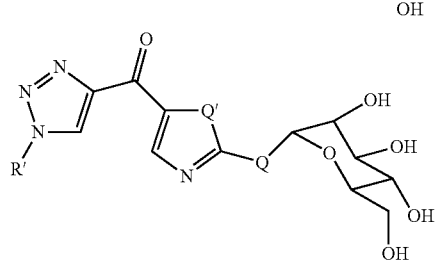

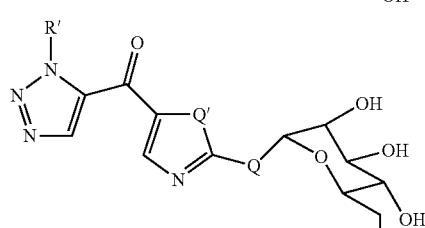

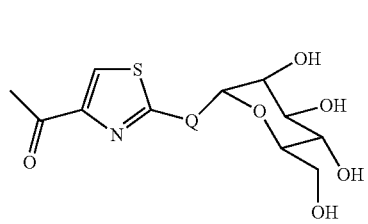

-continued

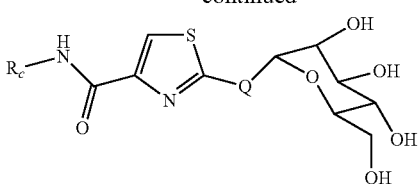

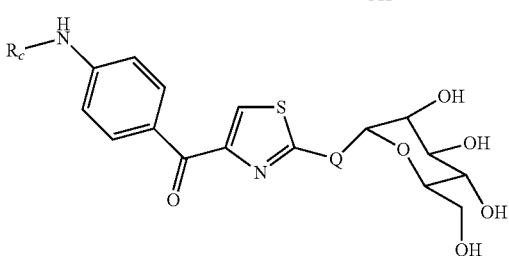

Q, Q', R' and $R_c$ being as defined above.

In another aspect, the present invention relates to a pharmaceutical composition comprising, as active substance, a compound of formula (IV) described above, in association with a pharmaceutically acceptable vehicle.

In another aspect, the present invention relates to a pharmaceutical composition comprising, as active substance, a compound of formula (IV) or (IVbis) described above, in association with a pharmaceutically acceptable vehicle.

In an advantageous embodiment, the present invention relates to a pharmaceutical composition, wherein said active compound is of the following formula:

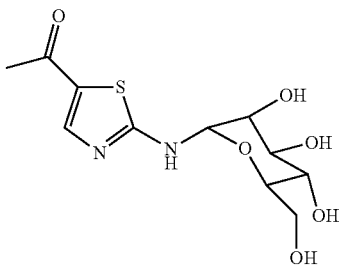

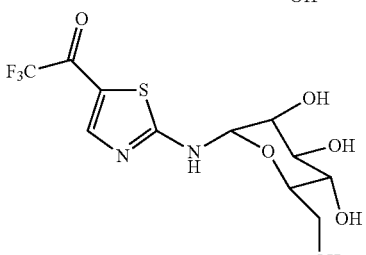

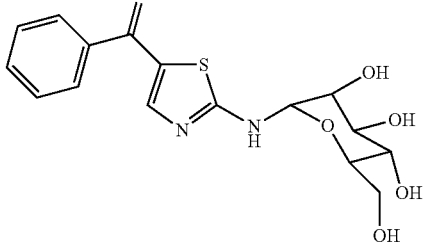

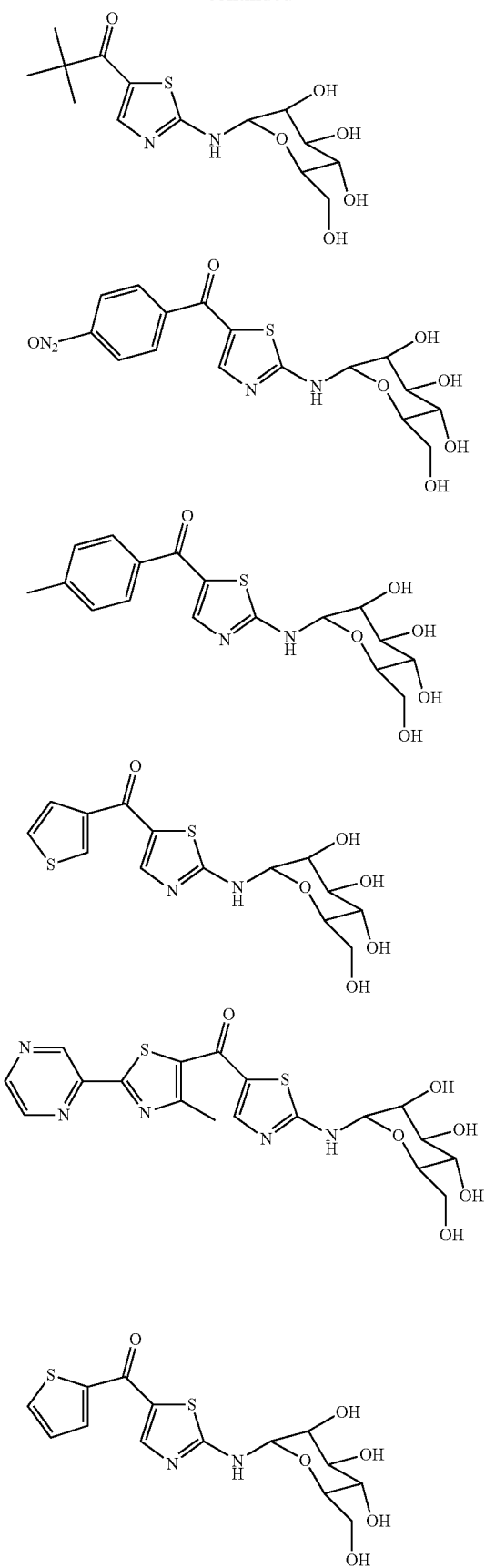
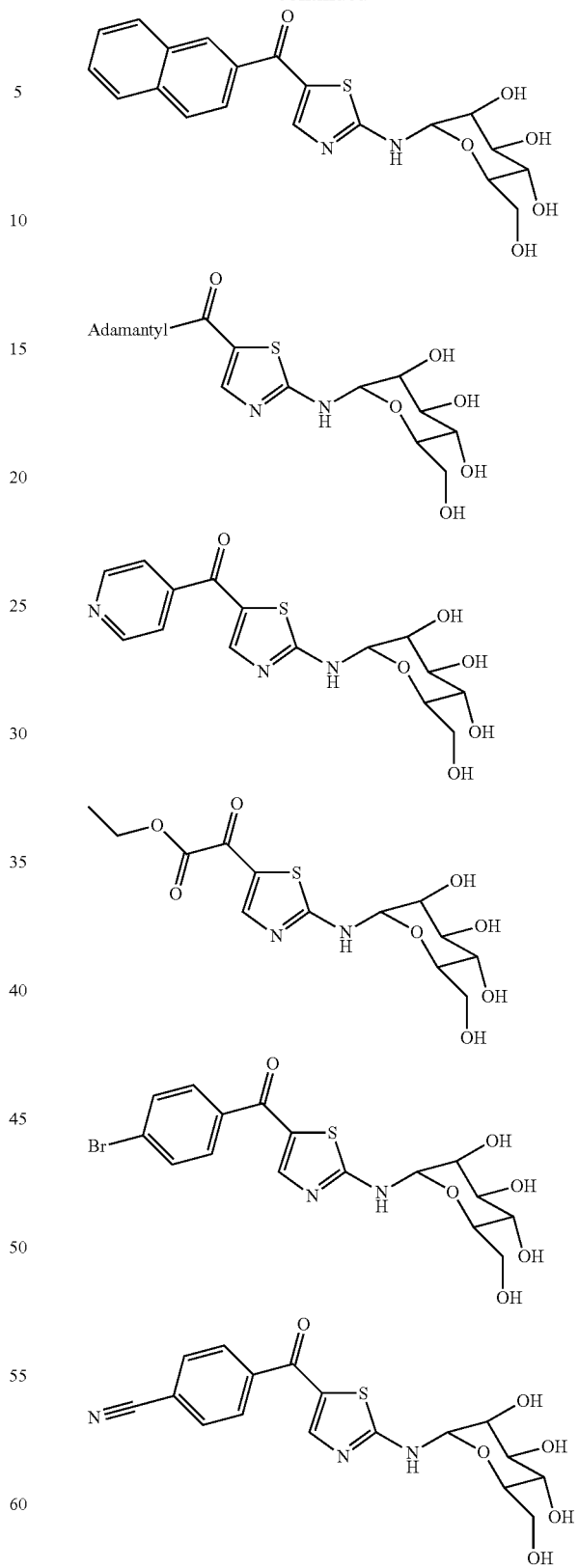
In an advantageous embodiment, the present invention relates to a pharmaceutical composition, wherein said active compound is of the following formula:

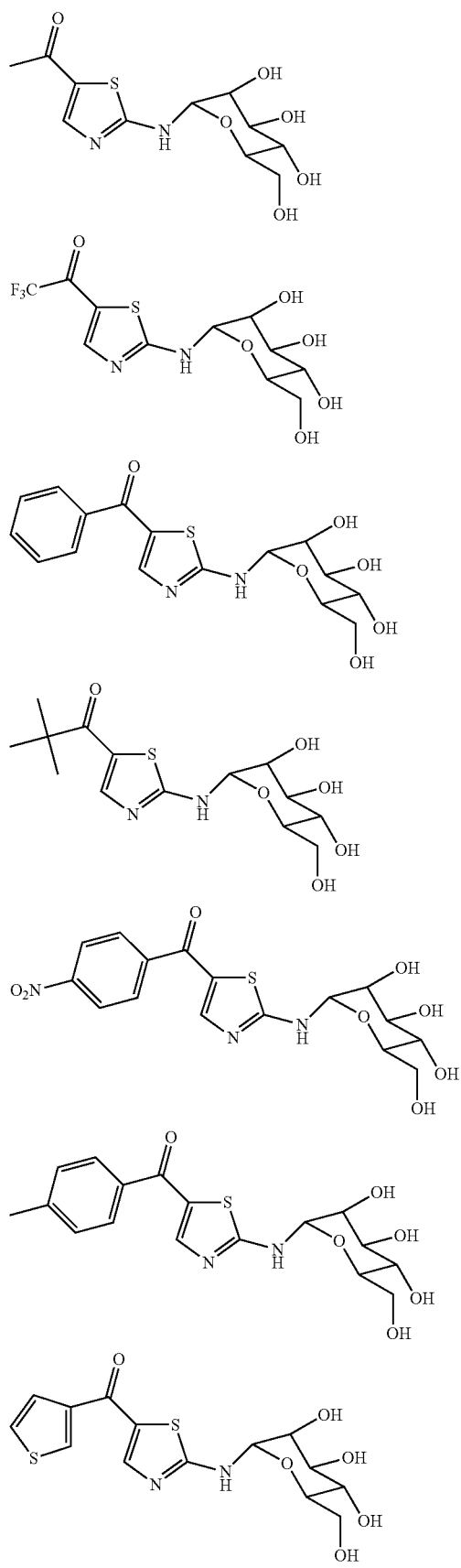
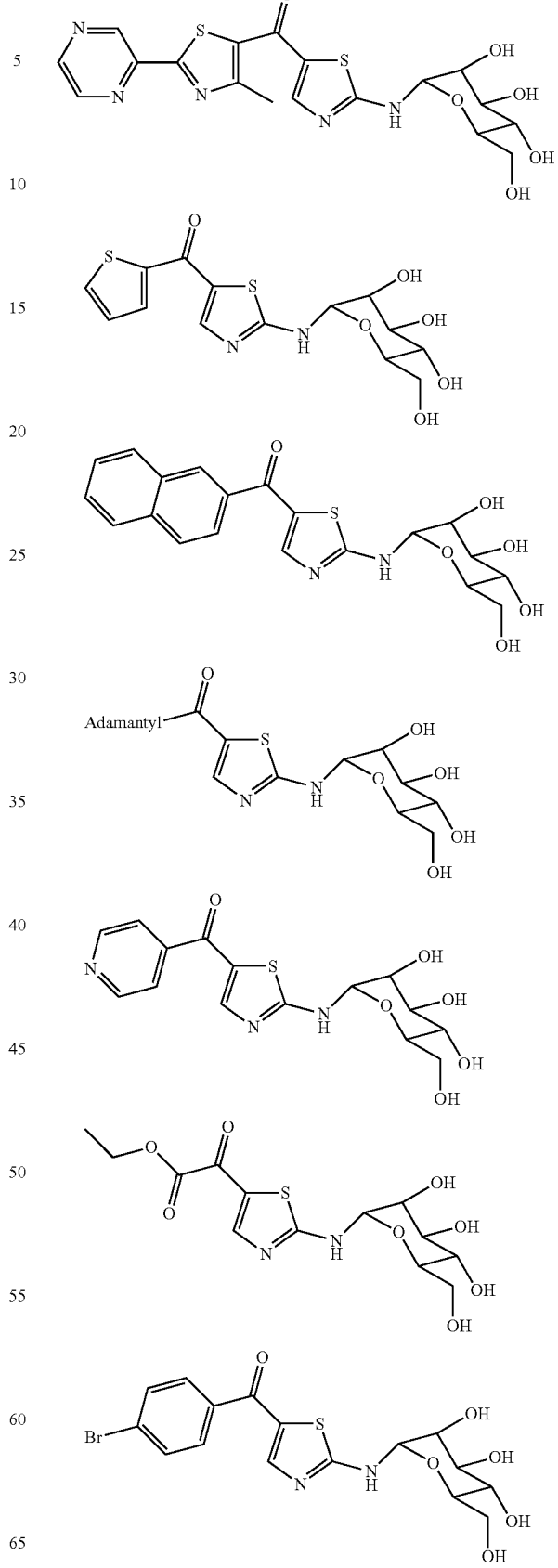

125
-continued
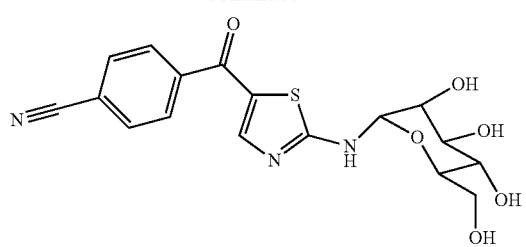
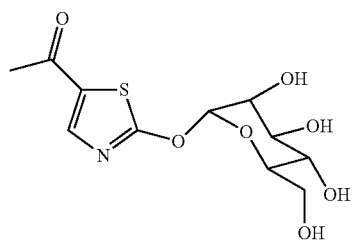
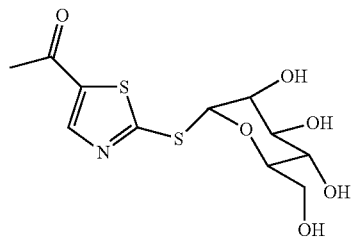
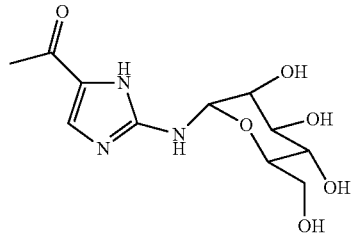
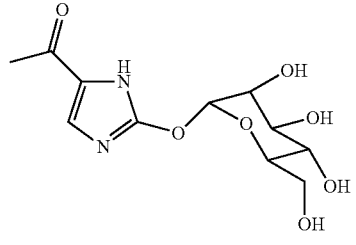
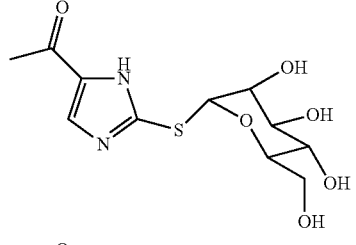
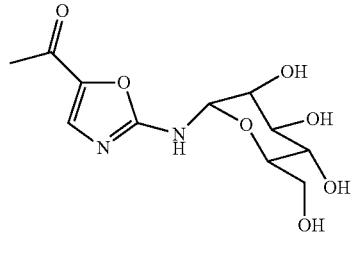
126
-continued
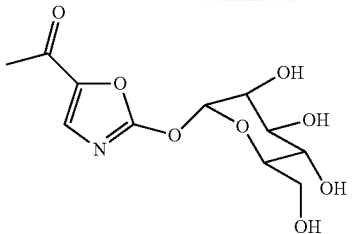
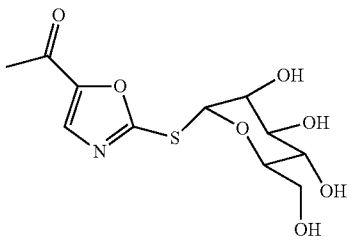
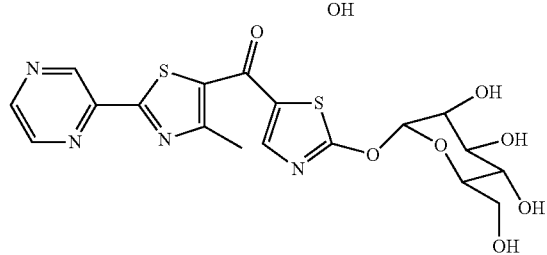
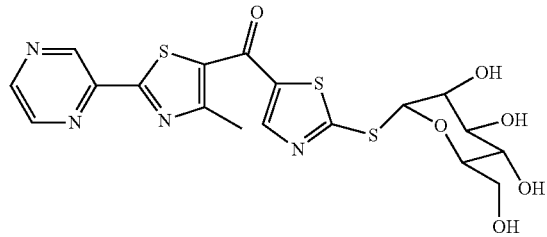
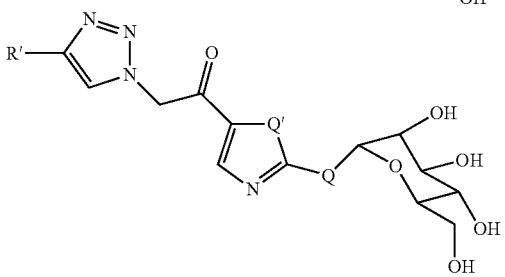
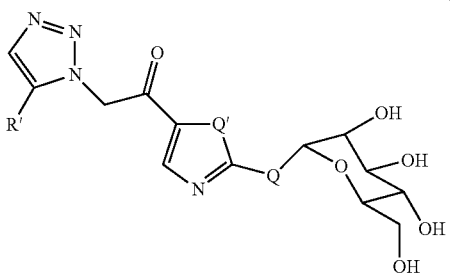
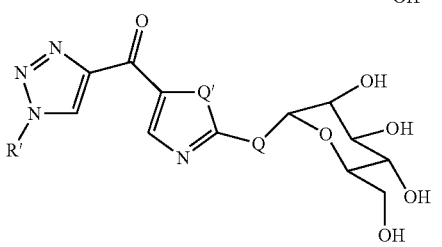

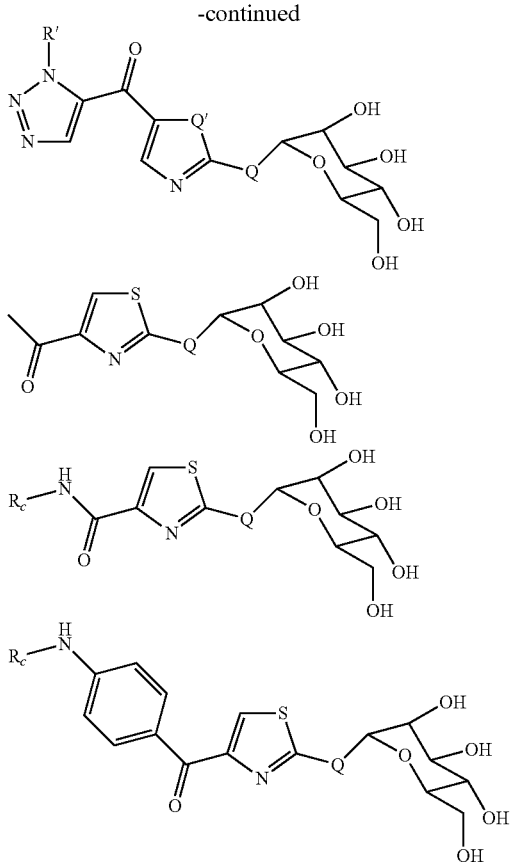

Q, Q', R' and $R_c$ being as defined above.

In an advantageous embodiment, the present invention relates to a pharmaceutical composition as described above, said composition being in a form administrable by at least one route selected from the group consisting of oral, intravenous, subcutaneous, nasal, inhalatory, intramuscular, intraperitoneal and suppository, in particular oral or intravenous route.

In an advantageous embodiment, the present invention relates to a pharmaceutical composition as described above, administrable by oral route at a dose comprised from about 0.1 mg/kg to about 100 mg/kg of body weight.

In an advantageous embodiment, the present invention relates to a pharmaceutical composition as described above, under a form liable to be administrable by oral route, under the form of a unit dose comprised from 100 mg to 2,000 mg, in particular from 100 mg to 1,000 mg, in particular from 100 to 500 mg.

In an advantageous embodiment, the present invention relates to a pharmaceutical composition as described above, administrable by intravenous route at a dose comprised from about 10 µg/kg to about 10 mg/kg.

In an advantageous embodiment, the present invention relates to a pharmaceutical composition as described above, under a form liable to be administrable by intravenous, under the form of a unit dose comprised from 0.1 mg to 1000 mg, in particular from 10 mg to 1,000 mg, in particular from 10 to 500 mg, in particular from 10 to 100 mg.

Said pharmaceutical composition can be administered 1 to 4 times per day, preferably 2 or 3 times per day.

In another aspect, the present invention relates to a vaccine composition comprising, as active substance, a compound of formula (IV) described above, in association with a pharmaceutically acceptable adjuvant.

In another aspect, the present invention relates to a vaccine composition comprising, as active substance, a compound of formula (IV) or (IVbis) described above, in association with a pharmaceutically acceptable adjuvant.

In another aspect, the present invention relates to a compound of formula (IV) described above, for its use for the treatment of pathologies caused by *Escherichia coli* and mediated by interactions between *Escherichia coli* lectins and host cell surface glycans, in particular pathologies caused by *Escherichia coli* and mediated by interactions between *Escherichia coli* FimH adhesin and host cell surface glycans.

In another aspect, the present invention relates to a compound of formula (IV) or (IVbis) described above, for its use for the treatment of pathologies caused by *Escherichia coli* and mediated by interactions between *Escherichia coli* lectins and host cell surface glycans, in particular pathologies caused by *Escherichia coli* and mediated by interactions between *Escherichia coli* FimH adhesin and host cell surface glycans.

In an advantageous embodiment, said pathologies belong to the group consisting of:
  inflammatory bowel diseases, in particular Crohn's disease,
  urinary tract infections, in particular painful bladder syndrome and cystitis, more particularly interstitial cystitis, and
  urinary tract infections in patients with a metabolic disease correlated with enhanced apoptosis, in particular diabetes.

In another aspect, the present invention relates to a combination of a compound of formula (IV) described above, and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides, for simultaneous, separated or sequential use in treatment of said diseases.

In another aspect, the present invention relates to a combination of a compound of formula (IV) or (IVbis) described above, and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides, for simultaneous, separated or sequential use in treatment of said diseases.

In another aspect, the present invention relates to a complex between a compound of formula (IV) described above and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides.

In another aspect, the present invention relates to a complex between a compound of formula (IV) or (IVbis) described above and an antibiotic selected from the group comprising beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides.

DESCRIPTION OF THE DRAWINGS

FIG. 3 presents the solution affinity measurements for compound 6 by inhibition FimH binding to amino-octyl α-D-mannoside immobilized onto a CM5 sensor chip (Biacore3000).

FIG. 11A presents the residual adhesion (in percentage) of the AIEC LF82 strain to intestinal epithelial cells T84 in the presence of different inhibitors at a concentration of 1 μM. Results were expressed as mean±sem, four independent experiments, except for compound HM (two experiments).

FIG. 11B presents the residual adhesion (in percentage) of the AIEC LF82 strain to intestinal epithelial cells T84 in the presence of different inhibitors at a concentration of 10 μM. Results were expressed as mean±sem, four independent experiments, except for compound HM (two experiments).

Figure 1:
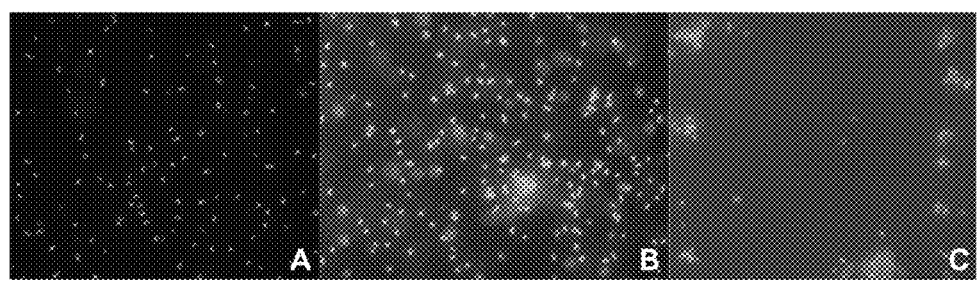
FIG. 1 presents the epifluorescence of acridin orange colored type-1 fimbriated *E. coli* strain UTI89: A. UTI89 B. UTI89+100 04 of compound 4 C. UTI89+1 mM of compound 2.

Matching between the compounds numbering used in the priority document and the one used in the present application, in particular in the above-mentioned figures, is as follows:

| Compounds numbering in the priority document | Compounds numbering in the present application |
|---|---|
| NM46 | 6 |
| X | 1 |
| 7X | 2 |
| P142 | 1 |
| P134 | 2 |

EXAMPLES

Example 1: Synthesis of Heptylmannoside Cyclodextrin Compound 2

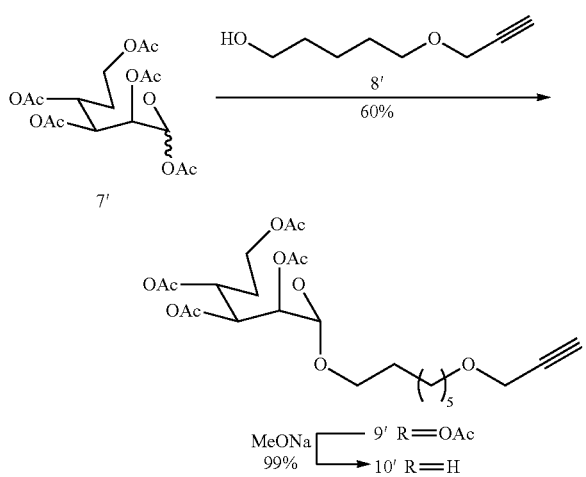

8-Oxaundec-10-ynyl 2,3,4,6-tetra-O-acetyl-α-D-mannopyranoside 9'

Mannosyl pentaacetate (229 mg, 0.587 mmol), compound 8' (150 mg, 0.882 mmol) and silver trifluoroacetate (194 mg, 0.878 mmol) were dissolved in dry dichloromethane (3 mL). A solution of $SnCl_4$ 1 M in dichloromethane (585 μL) was added and the mixture was stirred at rt for 3 h under argon atmosphere. The solution was diluted in dichloromethane (10 mL) and washed with $NaHCO_3$ satd. (2×10 mL). The organic layer was dried, filtered and evaporated under reduced pressure. The residue was chromatographied on silica gel with ethyl acetate-cyclohexane (2-8) to (3-7) to afford 9' as a colorless oil (128 mg, 44%). Analytical data were identical as previously described [Gouin, S. G.; Wellens, A.; Bouckaert, J.; Kovensky, J. *Chem Med Chem.* 2009, 5, 749-755].

8-Oxaundec-10-ynyl-α-D-mannopyranoside 10'

9 (400 mg, 800 μmol) was dissolved in MeOH (10 mL). A solution of freshly prepared sodium methanolate 1 M in methanol (500 μL) was added and the mixture was stirred at rt for 4 h. Amberlyst IR120 (H+) was added and the mixture stirred until pH reached 5. The resin was filtered off and the solution was evaporated to dryness leading to unprotected product 10' (263 mg, 99%).

$[α]_D$=+96 (c=0.2, MeOH); $^1$H NMR (300 MHz, $CD_3OD$) δ=4.76 (1H, d, J=1.6 Hz, H-1), 4.14 (2H, d, J=2.4 Hz, $OCH_2C$), 3.82-3.80 (2H, m, H-2, H-3), 3.75-3.69 (3H, m, H-5, 2×H-6), 3.64 (1H, t, J=9.3 Hz, H-4), 2.84 (1H, t, CCH), 1.61-1.55 (4H, br, 2×$CH_2$), 1.39 (6H, br, 6×$CH_2$); $^{13}$C NMR (125 MHz, $D_2O$): δ=102.4 (C1), 76.5 (CCH), 75.5, 73.5, 73.1, 71.8 (C-2, -3, -4, -5), 69.4 ($CH_2O$), 59.6 ($CH_2CCH$), 31.4, 31.3, 31.1, 28.1, 28.0 ($CH_2$); HRMS (ES+). Found 355.1732 $C_{16}H_{28}O_7Na$ requires 355.1733.

Figure 32A:
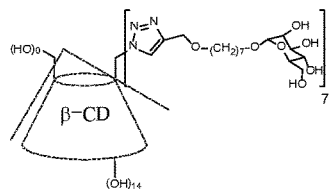
FIGS. 32A-32G show the formulae of various compounds identified in the Examples.

Heptylmannoside Cyclodextrin Compound 2—See FIG. 32A

Alkynyl-saccharide 10' (48 mg, 144 μmol) and heptakis-6-azido-6-deoxy-beta-cyclodextrin (22 mg, 17.1 μmol) were dissolved in a $DMF/H_2O$ mixture (2/0.5 mL). Copper sulfate (8.2 mg, 51 μmol) and sodium ascorbate (20 mg, 100 μmol) were added and the mixture was stirred at 70° C. for 45 minutes under μW irradiation. An ethylenediamine tetraacetic acid trisodium salt solution (50 mg, 127 μmol) in water (5 mL) was added and the mixture was stirred for 30 minutes at rt. The mixture was evaporated under reduced pressure and the residue purified by preparative HPLC leading to 2 (23 mg, 37%) as a white powder after lyophilisation.

$[α]_D$=+36 (c=0.2, $H_2O$); Tr=34 min; $^1$H NMR (500 MHz, DMSO) δ=7.91 (7H, s, $H_{triazol}$), 6.00-5.90 (9H, br, OH), 5.06 (7H, s, H-1$^{I-VII}$), 4.79, 4.69, 4.57, 4.50 (27H, 4 s, 7×H-1$^{HM}$, 20×OH), 3.75-3.00 (90H, m, H-2, -3, -4, -5, -6, $^{I-VII}$, 7×-2, -3, -4, -5, -6$^{HM}$, 7×O—$CH_2$triazol, 14×$OCH_2$), 1.44, 1.36, 1.19 (70H, br, $CH_2$), $^{13}$C NMR (125 MHz, $D_2O$): δ=144.0 (C=$CH_{triazol}$), 125.2 (CH=$C_{triazol}$), 101.6 (C1$^{I-VII}$), 99.7 (C1$^{HM}$), 82.7 (C4$^{I-VII}$), 73.8, 71.0, 70.4, 70.3, 69.7, 66.3, 63.0, 61.2, 61.0 (C2, -3, -5$^{I-VII}$, C2, -3, -4, -5, -6$^{HM}$, $CH_2O$), 49.5 (C6$^{I-VII}$), 29.2, 29.1, 28.8, 27.9, 25.8, 25.7 ($CH_2$); HRMS (ES+). Found 3657.6952 $C_{58}H_{97}N_{21}O_{77}$ requires 3657.6895.

Figure 32B:
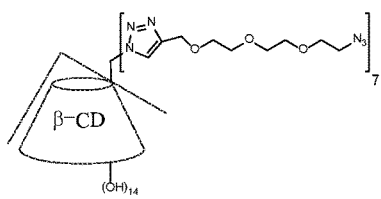

Example 2: Synthesis of Heptylmannoside Cyclodextrin Compound 4 compound 16' of the formula shown in FIG. 32B

Compound 15' (112 mg, 423 μmol) of the following formula:

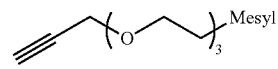

and heptakis-6-azido-6-deoxy-beta-cyclodextrin (60 mg, 47 μmol) were dissolved in a $DMF/H_2O$ mixture (5/1.6 mL). Copper sulfate (15 mg, 94 μmol) and sodium ascorbate (37 mg, 187 μmol) were added and the mixture was stirred at rt for 19 h. The mixture was evaporated under reduced pressure and the residue dissolved in DMF (15 mL) with sodium azide (121 mg, 1.86 mmol). The mixture was stirred at 70° C. for 36 h. The mixture was evaporated under reduced pressure and the residue purified by preparative HPLC leading to 16' (21 mg, 15%) as a white powder after lyophilisation.

$[α]_D$=+84 (c=0.1, $H_2O$); Tr=36 min; $^1$H NMR (500 MHz, DMSO) δ=7.95 (7H, s, $H_{triazol}$), 6.00, 5.88 (14H, br, OH), 5.08 (7H, br, H-1$^{I-VII}$), 4.50-4.00 (36H, H-4$^{I-VII}$, 14×OH, 7×$OCH_2Tri$), 3.70-3.40 (126H, H-2, -3, -4, -5, -6, $^{I-VII}$, 42×$CH_2CH_2$); $^{13}$C NMR (125 MHz, DMSO): δ=144.5 (C=$CH_{triazol}$), 127.0 (C=$CH_{triazol}$) 102.0, 99.7 (C1$^{I-VII}$, C1$^{HM}$), 83.0 (C4$^{I-VII}$), 72.9, 72.1, 70.5, 70.1, 69.9, 69.7, 69.6 (C2, -3, -5$^{I-VII}$, C6$^{I-VII}$, C2, -3, -4, -5, -6$^{HM}$, $CH_2O$), 63.5 ($OCH_2Tri$), 60.8 ($CH_2$), 50.6 ($CH_2N_3$); HRMS (ES+). Found 942.06488 $C_{105}F_{170}O_{49}N_{42}Na_3$ requires 942.06610.

Figure 32C:
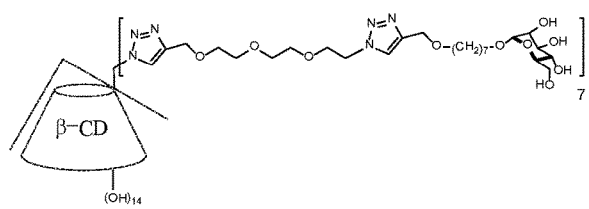

Heptylmannoside Cyclodextrin Compound 4—See FIG. 32C

Compound 16' (18 mg, 6.4 μmol) and 10' (21 mg, 63 μmol) were dissolved in water (1.5 mL). Copper sulfate (4 mg, 25 μmol) and sodium ascorbate (10 mg, 50 μmol) were added and the mixture was stirred at 70° C. for 45 minutes under μW irradiation. An ethylenediamine tetraacetic acid trisodium salt solution (20 mg, 50 μmol) in water (2.5 mL) was added and the mixture was stirred for 30 minutes at rt. The mixture was evaporated under reduced pressure and the residue purified by preparative HPLC leading to 4 (15 mg, 45%) as a white powder after lyophilisation.

$[α]_D$=+6 (c=1, $H_2O$); Tr=21 min; $^1$H NMR (500 MHz, $D_2O$) δ=8.03 (14H, s, $H_{triazol}$), 5.18 (7H, br, H-1$^{HM}$), 4.80-4.00 (H-1$^{I-VII}$, OH, H-2$^{HM}$, H-3$^{HM}$), 3.80-2.80 (209H, H-2, -3, -4, -5, -6, $^{I-VII}$, 7×H-4, -5, -6$^{HM}$, 14×O—$CH_2$-triazol, 77×$CH_2$), 1.53 (28H, br, 14×$CH_2$), 1.27 (42H, br, 21×$CH_2$), $^{13}$C NMR (125 MHz, DMSO): δ=144.1, 143.8 (C=$CH_{triazol}$), 126.5, 125.3 (CH=$C_{triazol}$), 102.7, (C1$^{I-VII}$), 99.7 (C1$^{HM}$), 72.7, 70.1, 69.7, 69.5, 69.1, 68.7, 67.7, 66.7, 63.0, 62.7, 60.9 (C2, -3, -4, -5$^{I-VII}$, C6$^{I-VII}$, C2, -3, -4, -5, -6$^{HM}$, $CH_2O$), 50.3, 49.9 ($CH_2N$, C6$^{I-VII}$), 28.5, 28.3, 28.2, 25.3, 25.2 ($CH_2$); HRMS (ES+). Found 5148.4577 $C_{217}H_{360}N_{42}O_{98}Na_3$ requires 5148.4592.

Example 2bis: Synthesis of Heptylmannoside Cyclodextrin Radiolabeled and Reference Compounds

Figure 32D:
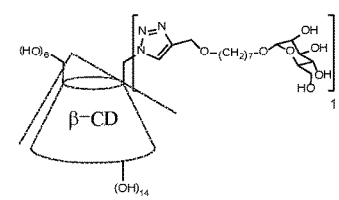

Heptylmannoside Cyclodextrin Compound 1—See FIG. 32D

Alkynyl-saccharide 10' (29 mg, 87 μmol) and mono-6-azido-6-deoxy-beta-cyclodextrin (50 mg, 43 μmol) were dissolved in a DMF/H$_2$O mixture (2/0.5 mL). Copper sulfate (6.9 mg, 43 µmol) and sodium ascorbate (17 mg, 86 µmol) were added and the mixture was stirred at 70° C. for 30 minutes under µW irradiation. Ethylenediamine tetraacetic acid trisodium salt (50 mg, 127 µmol) was added and the mixture was stirred for 10 minutes at rt. The mixture was evaporated under reduced pressure and the residue purified by preparative HPLC leading to 1 (33 mg, 51%) as a white powder after lyophilisation.

[α]$_D$=+130 (c=0.1, MeOH); Tr=17 min; $^1$H NMR (500 MHz, D$_2$O) δ=8.23 (1H, s, H$_{triazol}$), 5.51, 5.36, 5.30 (7H, 3s, H-1$^{I-VII}$), 5.15 (1H, s, H-1$^{HM}$), 4.20-3.20 (54H, br, H-2, -3, -4, -5, -6, $^{I-VII}$, H-2, -3, -4, -5, -6$^{HM}$, O—CH$_2$-triazol, 2×CH$_2$), 1.72, 1.65, 1.47 (10H, br, (×CH$_2$), $^{13}$C NMR (125 MHz, D$_2$O): δ=146.1 (C=CH$_{triazol}$), 123.8 (C=CH$_{triazol}$), 102.1, 101.8, 99.9 (C1$^{I-VII}$, C1$^{HM}$), 83.1, 81.7, 80.9, 80.3 (C4$^{I-VII}$), 72.1, 71.0, 70.4, 68.6, 67.0, 66.5, 63.0, 60.7, 59.8, 58.8 (C2, -3, -5$^{I-VII}$, C6$^{II-VII}$, C2, -3, -4, -5, -6$^{HM}$, CH$_2$O), 51.5 (C6$^I$), 29.1, 28.5, 28.0, 25.7, 25.1 (CH$_2$); HRMS (ES+): Found 1514.5564 C$_{58}$H$_{97}$N$_3$O$_{41}$Na requires 1514.5495.

Figure 32E:
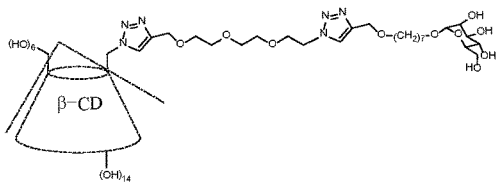

Heptylmannoside Cyclodextrin Compound 3—See FIG. 32E

Mono-6-azido-6-deoxy-beta-cyclodextrin (23 mg, 111 µmol) and 13

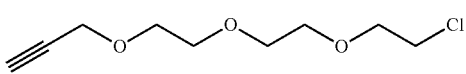

(100 mg, 86 µmol) were dissolved in a DMF/H$_2$O mixture (3/1 mL). Copper sulfate (8 mg, 50 µmol) and sodium ascorbate (16.2 mg, 82 µmol) were added and the mixture was stirred at 70° C. for 45 minutes under µW irradiation. Tetrabutylammonium iodide (2 mg, 5 µmol) and sodium iodide (28 mg, 430 µmol) were added and the mixture was heated at 80° C. for 24 h. Compound 10' (80 mg, 241 µmol), copper sulfate (18 mg, 113 µmol) and sodium ascorbate (36 mg, 182 µmol) were added and the mixture was stirred at 70° C. for 2 h under µW irradiation. The mixture was evaporated under reduced pressure and the residue purified by preparative HPLC leading to 3 (31 mg, 23%) as a white powder after lyophilisation.

[α]$_D$=+115 (c=0.2, H$_2$O); Tr=24 min; $^1$H NMR (500 MHz, DMSO) δ=8.03, 8.00 (2H, s, H$_{triazol}$), 5.73 (14H, br, OH), 5.03 (1H, br, H-1$^{HM}$), 5.00-3.80 (23H, H-1$^{I-VII}$, OH, H-2$^{HM}$, H-3$^{HM}$), 3.80-2.80 (72H, 7×H-4, -5, -6$^{HM}$, 2×O—CH$_2$-triazol, 11×CH$_2$), 1.46 (4H, br, 2×CH$_2$), 1.27 (6H, br, 3×CH$_2$), $^{13}$C NMR (125 MHz, DMSO): δ=144.0, 143.8 (C=CH$_{triazol}$), 124.9, 124.2 (C=CH$_{triazol}$), 102.0 (C1$^{II-VII}$), 101.3 (C1$^I$), 99.7 (C1$^{HM}$), 83.4, 82.1, 81.5, 81.0 (C4$^{I-VII}$), 72.1, 71.0, 69.9, 69.5, 68.7, 66.2, 63.3, 61.3, 60.2, 60.0, 59.0 (C2, -3, -5$^{I-VII}$, C6$^{II-VII}$, C2, -3, -4, -5, -6$^{HM}$, CH$_2$O), 50.3, 49.3 (CH$_2$N, C6$^I$), 29.1, 29.0, 28.7, 25.7 (CH$_2$); HRMS (ES+): Found 1727.6538 C$_{67}$H$_{110}$N$_6$O$_{44}$Na requires 1727.6609.

Figure 32F:
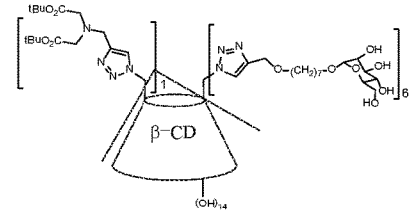

Heptylmannoside Cyclodextrin 17'—See FIG. 32F

Heptakis-6-azido-6-deoxy-beta-cyclodextrin (120 mg, 91.6 µmol), 10' (182 mg, 548 µmol) and 16'

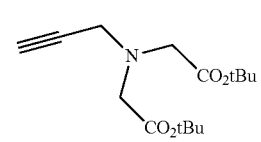

(25.9 mg, 91.5 µmol) were dissolved in a dioxane/water mixture (7.5/1.5 mL). Copper sulfate (29 mg, 182 µmol) and sodium ascorbate (72 mg, 363 µmol) were added and the mixture was stirred at 90° C. for 1 h30 under µW irradiation. Ethylenediamine tetraacetic acid trisodium salt (150 mg, 50 µmol) was added and the mixture was stirred for 30 minutes at rt. The mixture was evaporated under reduced pressure and the residue purified by preparative HPLC leading to 17' (54 mg, 16%), as a white powder after lyophilisation.

[α]$_D$=+21 (c=0.3, H$_2$O); Tr=36 min; $^1$H NMR (500 MHz, DMSO) δ=7.95, 7.90, 7.86, 7.71 (7H, s, H$_{triazol}$), 6.01, 5.89 (12H, br, OH), 5.05 (7H, s, H-1$^{I-VII}$), 4.65-4.00 (H-4$^{I-VII}$, 3×CH$_2$, OH, 6×OCH$_2$Tri, 6×H-1$^{HM}$), 3.60-3.20 (99H, br, H-2, -3, -5, $^{I-VII}$, 6×H-2, -3, -4, -5, -6$^{HM}$, 14×CH$_2$), 1.50-1.20 (78H, m, 30×CH$_2$, 6×CH$_3$), $^{13}$C NMR (125 MHz, DMSO): δ=170.0 (CO), 144.8 (C=CH$_{triazol}$), 125.3 (C=CH$_{triazol}$) 101.7 (C1$^{I-VII}$) 99.8 (C1$^{HM}$), 82.8, 80.3 (C4$^{I-VII}$), 73.9, 71.1, 70.4, 69.7, 66.2, 63.0, 61.3 (C2, -3, -5$^{I-VII}$, C2, -3, -4, -5, -6$^{HM}$, CH$_2$), 54.5, 49.5 (C6$^{I-VII}$), 29.0, 28.8 (CH$_2$), 27.8 (CH$_3$), 25.7 (CH$_2$); HRMS (ES+). Found 3608.6622 C$_{153}$H$_{254}$N$_{22}$O$_{74}$Na requires 3608.6843.

Figure 32G:
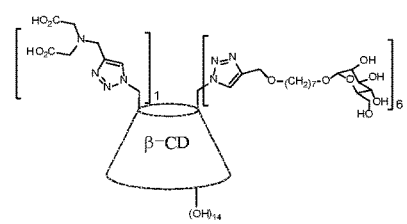

Heptylmannoside Cyclodextrin 20'—See FIG. 32G

Compound 17' (10 mg, 2.8 µmol) was dissolved in pure TFA (2 mL) and the solution was stirred at rt. for 4 h. The solvent was removed under reduced pressure and the residue was lyophilized to lead to 20' quantitatively.

[α]$_D$=+23 (c=0.6, H$_2$O); $^1$H NMR (500 MHz, DMSO) δ=8.01, 7.94, 7.91, 7.85 (7H, s, H$_{triazol}$), 5.92 (2H, br, OH), 5.07 (7H, s, H-1$^{I-VII}$), 4.65-4.00 (H-4$^{I-VII}$, 3×CH$_2$, OH, 6×OCH$_2$Tri, 6×H-1$^{HM}$), 3.60-3.20 (99H, br, H-2, -3, -5, -6, $^{I-VII}$ 6×H-2, -3, -4, -5, -6$^{HM}$, 14×CH$_2$), 1.45-1.20 (60H, m, 30×CH$_2$), $^{13}$C NMR (125 MHz, DMSO): δ=171.4 (CO), 143.9 (C=CH$_{triazol}$), 125.3 (C=CH$_{triazol}$), 101.7 (C1$^{I-VII}$), 99.8 (C1$^{HM}$), 82.8 (C4$^{I-VII}$), 73.9, 71.1, 70.4, 69.7, 66.3, 63.1, 61.3 (C2, -3, -5$^{I-VII}$, C2, -3, -4, -5, -6$^{HM}$, CH$_2$), 53.4, 49.5, 48.2 (C6$^{I-VII}$), 29.2, 29.0, 28.8, 25.8, 25.7 (CH$_2$); HRMS (ES+): Found 3472.5642 C$_{145}$H$_{236}$N$_{22}$O$_{74}$ requires 3472.562.

Heptylmannoside Cyclodextrin Radiolabeled Compound 5

Labelling of 20' with [$^{99m}$Tc(CO)$_3$]$^+$ to obtain compound 5 was performed in a glass vial under nitrogen, 200 µl of 1×10$^{-4}$ M aqueous solution of compound 20' was added to 1.2 mL of [$^{99m}$Tc(OH$_2$)$_3$(CO)$_3$]$^+$ in NaCl 0.9% (pH=7) prepared using an Isolink kit (Mallinckrodt Medical, Petten, The Netherlands) and the mixture was incubated for 45 min at 100° C. The resulting complex was analyzed by RP-HPLC (Column: Analytical, C4 column 214TP53, 0.32×25 cm, Grace Vydac, Flow: 0.5 mL/min; γ detection) (Rt=12 min) and the labelling yield was higher than 95%. The eluent was 0.1% TFA in $H_2O$ (solvent A) and $CH_3CN$ (solvent B). For the analytical control the method was as follows: 0-3 min., 0% B; 3-3.1 min., 0-25% B; 3.1-9 min., 25-100% B; 9-20 min., 100% solvent B.

General Procedure 1 for the Cyclocondensation

Halogenoketone (b, 2 eq.) and triethylamine (c, 2 eq.) were added to a solution of 2-[(2,3,4,6-tetra-O-acetyl-α-D-mannopyranosyl)amino]-4-dimethylamino-1,3-thiazabuta-1,3-diène 5 (a, 1 eq.) in dry THF (5 mL). The reaction mixture was stirred at 60° C. for 16 h. The mixture was diluted in dichloromethane (d) and washed with water (e). The aqueous layer was extracted with dicholomethane (f). Then the organic layers were combined, dried with magnesium sulfate, filtered and evaporated under reduced pressure. The residue was purified by chromatography on a silica gel column with petroleum spirit/ethyl acetate (g) as eluent to afford the corresponding tetra-O-acetyl-mannopyranosylaminothiazole.

TABLE 1

| Compound | Conditions of cyclocondensation | | | | | | |
|---|---|---|---|---|---|---|---|
| | a | b | c | d | e | f | g |
| 6a | 161.0 mg | 48.0 μL | 100 μL | 20 mL | 3 × 10 mL | 2 × 10 mL | 5/5 |
| 7a | 209.3 mg | 95 μL | 125 μL | 20 mL | 3 × 10 mL | 2 × 10 mL | 4/6 |
| 8a | 187.6 mg | 175.8 mg | 120 μL | 20 mL | 3 × 10 mL | 2 × 10 mL | 5/5 |
| 9a | 194.7 mg | 130 μL | 125 μL | 20 mL | 3 × 10 mL | 2 × 10 mL | 4/6 |
| 10a | 202.6 mg | 220.1 mg | 125 μL | 20 mL | 3 × 10 mL | 3 × 10 mL | 4/6 |
| 11a | 204.2 mg | 196.3 mg | 125 μL | 20 mL | 3 × 10 mL | 2 × 10 mL | 4/6 |
| 12a | 121.19 mg | 116.1 mg | 70 μL | 20 mL | 3 × 10 mL | 2 × 10 mL | 4/6 |
| 13a | 100.3 mg | 150.2 mg | 65 μL | 20 mL | 3 × 10 mL | 2 × 10 mL | 4/6 |
| 14a | 210.2 mg | 216.3 mg | 125 μL | 20 mL | 3 × 10 mL | 2 × 10 mL | 4/6 |
| 15a | 207.2 mg | 232.7 mg | 125 μL | 20 mL | 3 × 10 mL | 2 × 10 mL | 3/7 |
| 16a | 205.6 mg | 229.4 mg | 125 μL | 20 mL | 3 × 10 mL | 2 × 10 mL | 3/7 |
| 17a | 203.9 mg | 255.6 mg | 125 μL | 150 mL | 3 × 100 mL | 2 × 100 mL | 3/7 |
| 18a | 209.1 mg | | 125 μL | 125 μL | 20 mL | 3 × 10 mL | 2 × 10 mL | 8/2 |

General Procedure 2 for the Deprotection with Sodium Methanolate

A solution of sodium methanolate 0.1 M (y, 1 eq.) was added to a solution of tetra-O-acetyl-mannopyranosylaminothiazole (x, 1 eq.) in methanol (5 mL), and the mixture was stirred at r.t. for 3 h. The mixture was diluted with osmosed water (5 mL) and neutralized with Amberlite IRA-120 ($H^+$) ion-exchange resin, filtered and evaporated under reduced pressure. The residue was chromatographed on a C-18 column with 100/0 to 0/100 water/methanol (linear gradient) as eluent to afford the corresponding mannosylaminothiazoles.

TABLE 2

| conditions of deprotection | | |
|---|---|---|
| | x | y |
| 6 | 137.7 mg | 60 μl |
| 7 | 133.2 mg | 100 μl |
| 8 | 93.5 mg | 135 μl |
| 9 | 153.3 mg | 145 μl |
| 10 | 117.4 mg | 130 μl |
| 11 | 162.9 mg | 140 μl |
| 12 | 70.6 mg | 65 μl |
| 13 | 72.6 mg | 65 μl |
| 14 | 108.5 mg | 100 μl |
| 15 | 119.0 mg | 100 μl |
| 16 | 117.1 mg | 100 μl |
| 17 | 41.2 mg | 40 μl |
| 18 | 105.2 mg | 100 μl |
| 19 | 101.9 mg | 80 μl |
| 20 | 88.6 mg | 80 μl |

Example 3: Synthesis of 5-acetyl-2-((α-D-mannopyranosyl)amino)thiazole [6]

5-acetyl-2-((2,3,4,6-tetra-O-acetyl-α-D-mannopyranosyl)amino)thiazole [6a]

Prepared according to general procedure 1.
$C_{19}H_{24}N_2O_{10}S$
MW=472.47 g/mol
White solid
Yield=83%
α and β ratio (9/1):

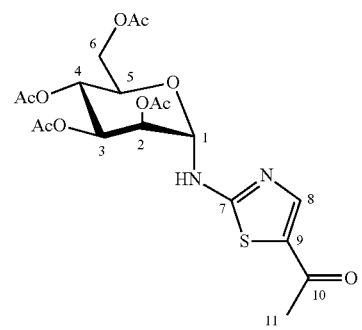

$^1$H NMR (300 MHz, $CDCl_3$) δ=9.00 (br, 1H, NH), 7.98 (s, 0.9H, H$8_α$), 7.79 (s, 0.1H, CH$8_β$), 5.52 (dd, $J_{2,1}$=1.8 Hz, $J_{2,3}$=2.7 Hz, 1H, H2), 5.34-5.24 (m, 2H, H4 and H3), 5.14 (d, 1H, $J_{1,2}$=1.8 Hz, H1$_α$), 4.32 (dd, 1H, $J_{6b,6a}$=12.0 Hz, $J_{6b,5}$=5.4 Hz, H6$_b$), 4.11-4.01 (m, 2H, H6$_a$ and H5), 2.43 (s, 3H, H11), 2.18, 2.06, 2.01, 2.00 (4 s, 12H, $CH_3CO$).

$^{13}$C NMR (300 MHz, $CDCl_3$) δ=189.8 (C10), 173.1 (C7), 170.8, 170.2, 169.7 (4$CH_3CO$), 146.7 (C8), 131.5 (C9), 82.5 (C1), 69.4 (C5+C3 or C4), 69.1 (C2), 66.0 (C3 or C4), 62.2 (C6), 26.2 (C11), 20.7 (4$CH_3CO$).

MS (CI) m/z=473 [M+H]$^+$.

HRMS (MALDI): calcd. for $C_{19}H_{24}N_2O_{10}S$ H $[M+H]^+$ 473.1224. found 473.1241.
$[\alpha]^{26}_D$+87 (c 0.175, CHCl$_3$)

5-acetyl-2-(($\alpha$-D-mannopyranosyl)amino)thiazole [6]

Prepared according to general procedure 2.
$C_{11}H_{16}N_2O_6S$
MW=304.32 g/mol
White solid
Yield=quant
$\alpha$ and $\beta$ ratio (9/1):

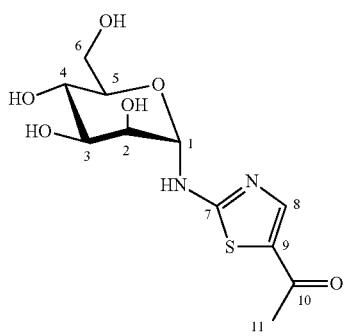

1H NMR (300 MHz, D$_2$O) $\delta$=7.99 (s, 0.9H, H8$_\alpha$), 7.95 (s, 0.1H, H8$_\beta$), 5.22 (s, 1H, $J_{1,2}$=1.7, H1$_\alpha$), 5.15 (d, 1H, $J_{1,2}$=1.1 Hz, H1$_\beta$), 4.09 (dd, $J_{2,1}$=1.7 Hz, $J_{2,3}$=3.3 Hz, 1H, H2$_\alpha$), 4.05 (dd, $J_{2,1}$=0.9z, $J_{2,3}$=3.0 Hz, 1H, H2$_\beta$), 3.91-3.46 (m, 5H, H3, H4, H5, H6), 2.45 (s, 3H, H11).
$^{13}$C NMR (300 MHz, D$_2$O) $\delta$=192.0 (C10), 149.1 (C8), 85.1 (C1), 75.4, 72.4, 71.5, 68.6, 62.7 (C2, C3, C4, C5 and C6); 23.8 (C11).
HRMS (MALDI): calcd. for $C_{11}H_{16}N_2O_6S$ Na $[M+Na]^+$ 327.06213. found 327.06049.
$[\alpha]^{26}$D+46 (c 0.5, CH$_3$OH).

Example 4: Synthesis of 2-($\alpha$-D-mannopyranosyl) amino-5-trifluoroacetylthiazole [7]

2-(2,3,4,6-tetra-O-acetyl-$\alpha$-D-mannopyranosyl) amino-5-trifluoroacetylthiazole [7a]

$C_{11}H_{13}F_3N_2O_6S$
MM=526.44 g/mol
White solid
Yield=83%
$\alpha$ and $\beta$ ratio (9/1):

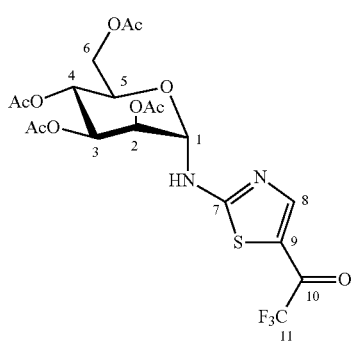

$^1$H NMR (300 MHz, CDCl$_3$) $\delta$=8.96 (br, 1H, NH), 8.19 (s, 0.9H, H8$_\alpha$), 8.06 (s, 0.1H, H8$_\beta$), 5.52 (dd, 1H, $J_{2,1}$=1.5 Hz, $J_{2,3}$=2.4 Hz, H2), 5.34-5.19 (m, 2H, H4 and H3), 5.19 (d, 1H, $J_{1,2}$=1.5 Hz, H1$_\alpha$), 4.35 (dd, 1H, $J_{6b,6a}$=12.0 Hz, $J_{6b,5}$=5.4 Hz, H6$_b$), 4.12, 3.99 (m, 2H, H6$_a$ and H5), 2.20, 2.07, 2.03, 2.02 (4 s, 12H, CH3CO).
$^{13}$C NMR (300 MHz, CDCl$_3$) $\delta$=174.2 (C10), 170.7, 170.4, 170.1, 169.5 (4CH3CO), 151.0 (C8), 124.3 (C9), 118.2, 114.4 (C11 and C9), 82.2 (C1), 69.7 (C5), 68.7 (C4 or C3), 68.2 (C2), 65.7 (C3 or C4), 61.9 (C6).

MS (CI) m/z=473 $[M+H]^+$.
HRMS (MALDI): calcd. for $C_{19}H_{24}N_2O_{10}S$ Na $[M+Na]^+$ 549.0762. found 549.0773.

2-($\alpha$-D-mannopyranosyl)amino-5-trifluoroacetylthiazole [7]

$C_{11}H_{13}F_3N_2O_6S$
MW=358.29 g/mol
White solid
Yield=quant
$\alpha$ and $\beta$ ratio (9/1):

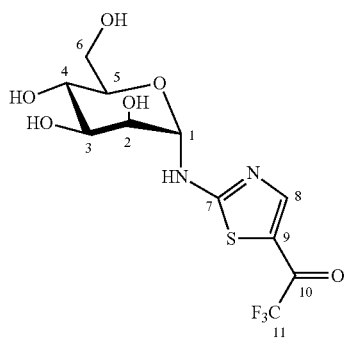

$^1$H NMR (300 MHz, MeOD) $\delta$=8.28 (s, 0.8H, J=, H8$_\alpha$), 7.27 (s, 0.1H, H8$_\beta$), 5.32 (s, 1H, $J_{1,2}$=1.8, H1$_\alpha$), 5.23 (d, 1H, $J_{1,2}$=1.2 Hz, H1$_\beta$), 4.09-3.46 (m, 6H, H2, H3, H4, H5, H6), 2.45 (s, 3H, H11).
$^{13}$C NMR (300 MHz, MeOD) $\delta$=192.0 (C10), 153.5 (C8), 83.7, 82.1, 77.5, 73.4, 66.5, 60.7 (C1, C2, C3, C4, C5 and C6), 23.8 (C11).
HRMS (MALDI): calcd. for $C_{11}H_{13}F_3N_2O_6S$ Na $[M+Na]^+$ 381.03386. found 381.03195.

Example 5: Synthesis of 2-($\alpha$-D-mannopyranosyl)amino-5-benzoylthiazole [8]

2-(2,3,4,6-tetra-O-acetyl-$\alpha$-D-mannopyranosyl) amino-5-benzoylthiazole [8a]

$C_{19}H_{24}N_2O_{10}S$
MW=534.53564 g/mol
White solid
Yield=86%
Exact mass: 534.130815

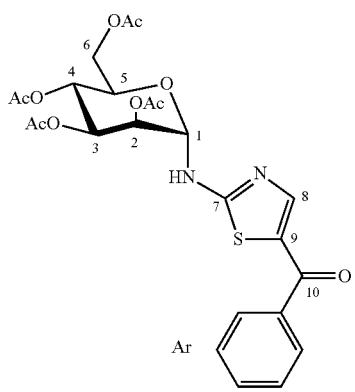

$^1$H NMR (300 MHz, CDCl$_3$) δ=7.84-7.77 (m, 3H, 2H$_{Ar}$+H8), 7.57-7.42 (m, 3H, H$_{Ar}$), 5.53 (dd, J$_{2,1}$=1.8 Hz, J$_{2,3}$=3.3 Hz, 1H, H2), 5.40-5.27 (m, 2H, H4 and H3), 5.21 (d, 1H, J$_{1,2}$=1.8 Hz, H1), 4.37 (dd, 1H, J$_{6b,6a}$=12.3 Hz, J$_{6b,5}$=6.0 Hz, H6$_b$), 4.13-4.03 (m, 2H, H6$_a$ and H5), 2.19, 2.09, 1.98, 1.89 (4 s, 12H, CH$_3$CO).

$^{13}$C NMR (300 MHz, CDCl$_3$) δ=186.9 (C10), 172.8 (C7), 170.9, 170.2, 170.1, 169.6 (4CH$_3$CO), 148.1 (C8), 137.9 (C9), 132.2 (Car), 131.2 (Car), 128.9 (2Car), 128.6 (2Car), 82.5 (C1), 69.3 (C5), 68.9 (C3 or C4), 68.6 (C2), 66.1 (C3 or C4), 62.0 (C6), 20.9, 20.7, 20.5 (4CH$_3$CO).

2-(α-D-mannopyranosyl)amino-5-benzoylthiazole [8]

C$_{16}$H$_{18}$N$_2$O$_6$S
MW=366.38892 g/mol
Yellow solid
Yield=quant
Monoisotopic Mass=366.088556
α and β ratio (7/3):

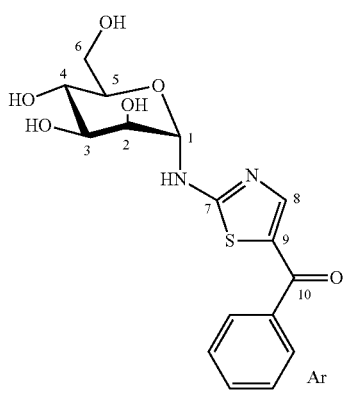

1H NMR (300 MHz, MeOD) δ=7.78-770 (m, 3H, H8 and Har), 7.61-7.49 (m, 3H, Har), 5.33 (d, 1H, J$_{1,2}$=1.8, H1$_α$), 5.15 (d, 0.3H, J$_{1,2}$=0.9 Hz, H1$_β$), 4.01-3.35 (m, 6H, H2, H3, H4, H5, H6).

$^{13}$C NMR (300 MHz, MeOD) δ=188.9 (C10), 170.5 (C7), 150.9 (C8) 139.5 (C9), 133.3, 129.7, 129.6 (Car), 85.2 (C1$_α$), 83.7 (C1$_β$), 79.6, 75.6, 75.5, 72.4, 72.1, 68.5, 68.1, 62.6 (C2, C3, C4, C5, C6 α and β)

HRMS (MALDI): calcd. for C$_{11}$H$_{16}$N$_2$O$_6$S Na [M+Na]$^+$ 327.06213. found 327.06049.

Example 6: Synthesis of 2-(α-D-mannopyranosyl)amin-5-tert-butylcarbonylthiazole [9]

2-(2,3,4,6-tetra-O-acetyl-α-D-mannopyranosyl)amino-5-tert-butylcarbonylthiazole [9a]

C$_{22}$H$_{30}$N$_2$O$_{10}$S
MW=514.546 g/mol
Yellow solid
Yield=89%
Monoisotopic Mass=514.162115

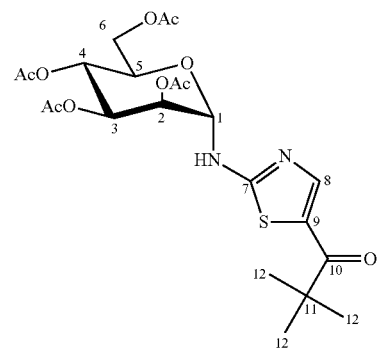

$^1$H NMR (300 MHz, CDCl$_3$) δ=9.14 (br, 1H, NH), 8.00 (s, 1H, H8), 5.55 (dd, J$_{2,1}$=1.5 Hz, J$_{2,3}$=2.7 Hz, 1H, H2), 5.37-5.24 (m, 2H, H4 and H3), 5.11 (d, 1H, J$_{1,2}$=1.5 Hz, H1), 4.33 (dd, 1H, J$_{6b,6a}$=12.9 Hz, J$_{6b,5}$=6.0 Hz, H6$_b$), 4.07-3.98 (m, 2H, H6$_a$ and H5), 2.15, 2.03, 1.97, 1.94 (4 s, 12H, CH$_3$CO), 1.28 (s, 9H, H12)

$^{13}$C NMR (300 MHz, CDCl$_3$) δ=198.3 (C10), 171.6 (C7), 170.7, 170.1, 170.0, 169.6 (4CH$_3$CO), 144.3 (C8), 130.3 (C9), 82.6 (C1), 69.0 (C5), 68.9 (C3 or C4), 68.4 (C2), 65.9 (C3 or C4), 61.9 (C6), 43.6 (C11), 28.1, 29.0 (C12), 20.8, 20.7, 20.6, 20.5 (4CH$_3$CO).

2-(α-D-mannopyranosyl)amin-5-tert-butylcarbonylthiazole [9]

C$_{14}$H$_{22}$N$_2$O$_6$S
MW=346.39928 g/mol
Yellow solid
Yield=quant
Monoisotopic Mass=346.119856

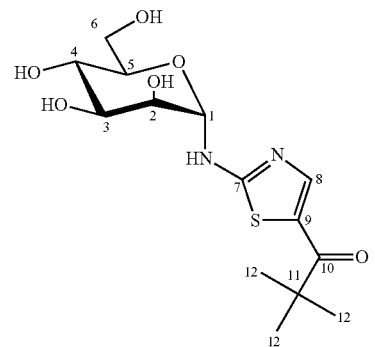

$^1$H NMR (400 MHz, DMSO) δ=9.11 (d, J$_{NH,1}$=4.0 Hz, 1H, NH), 8.1 (s, 1H, H8), 5.12, (d, J$_{2,1}$=4.0 Hz, 0.7H, H1), 4.92 (d, J=3.0 Hz, OH2), 4.80 (d, J=3.3 Hz, 1H, OH4), 4.67 (d, J=3.3 Hz, 1H, OH3), 4.37 (t, J=4.5 Hz, 1H, OH6), 3.76 (m, 1H, H2), 3.67 (m, 1H, H3), 3.58 (m, 1H, H6$_a$), 3.54-3.45 (m, 2H, H4 and H6$_b$), 3.30-3.23 (m, 1H, H5), 1.27 (s, 1H, H12).

$^{13}$C NMR (400 MHz, DMSO) δ=197.1 (C10), 171.6 (C7), 146.1 (C8), 127.2 (C9), 83.3 (C1), 74.7 (C5), 70.6 (C3), 69.6 (C2), 67.2 (C4), 60.9 (C6), 42.9 (C11), 27.9 (C12).

Example 7: Synthesis of 2-(α-D-mannopyranosyl)amino-5-(4-nitrobenzoyl)thiazole [10]

2-(2,3,4,6-tetra-O-acetyl-α-D-mannopyranosyl)amino-5-(4-nitrobenzoyl)thiazole [10a]

$C_{24}H_{25}N_3O_{12}S$
MW=579.5332 g/mol
Yellow solid
Yield=46%
Monoisotopic Mass=579.115893

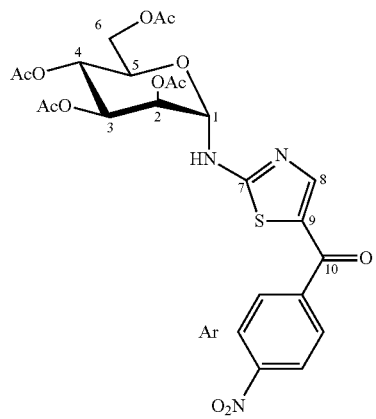

$^1$H NMR (300 MHz, CDCl$_3$) δ=9.25 (br, 1H, NH), 8.29 (d, J=8.7 Hz, 2H, H$_{Ar}$), 7.95 (d, J=8.7 Hz, 2H, H$_{Ar}$), 7.87 (s, 1H, H8), 5.54 (m, 1H, H2), 5.34-5.26 (m, 2H, H4 and H3), 5.18 (s, 1H, H1), 4.35 (dd, 1H, J$_{6b,6a}$=12.3 Hz, J$_{6b,5}$=5.7 Hz, H6$_b$), 4.13-3.80 (m, 2H, H6$_a$ and H5), 2.19, 2.09, 2.00, 1.88 (4 s, 12H, CH$_3$CO).

$^{13}$C NMR (300 MHz, CDCl$_3$) δ=184.9 (C10), 173.7 (C7), 170.9, 170.3, 169.6 (4CH$_3$CO), 149.8 (CNO$_2$), 149.1 (C8), 143.0 (C9), 130.7, 129.9, 129.7 (3Car), 123.9 (2Car), 82.6 (C1), 69.4 (C5), 69.1 (C3 or C4), 68.3 (C2), 65.7 (C3 or C4), 62.0 (C6), 20.7, 20.6 (4CH$_3$CO).

2-(α-D-mannopyranosyl)amino-5-(4-nitrobenzoyl)thiazole [10]

$C_{16}H_{17}N_3O_8S$
MW=411.38648 g/mol
Yellow solid
Yield=quant
Monoisotopic Mass=411.073635
α and β ratio (9/1):

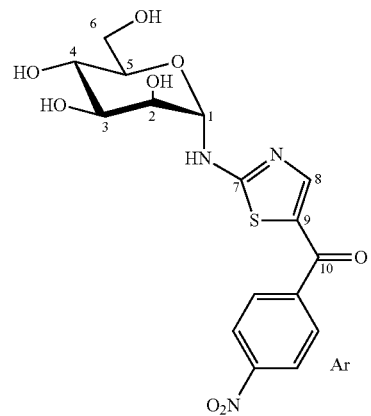

$^1$H NMR (400 MHz, DMSO) δ=9.53 (s, 1H, NH), 8.34 (dd, J=1.2 Hz, J=5.1 Hz, 1H, Har), 7.99 (dd, J=1.2 Hz, J=5.1 Hz, 1H, Har), 7.81 (s, 1H, H8), 5.18 (s, 1H, H1), 5.00 (d, J=2.4 Hz, 1H, OH2), (d, J=1.5 Hz, 1H, OH3), 4.76 (d, J=3.6 Hz, 1H, OH4), 4.41 (t, J=1.5 Hz, 1H, OH6), 3.81-3.79 (m, 1H, H2), 3.71-3.67 (m, 1H, H3), 3.65-3.60 (m, 1H, H6a), 3.55-3.52 (m, 2H, H4 H6b), 3.45-3.35 (m, 1H, H5)

$^{13}$C NMR (400 MHz, DMSO) δ=184.0 (C10), 173.8 (C7), 151.3, 149.1, 143.4 (C8, C9, Car), 129.6, 127.5, 123.7 (Car), 83.5 (C1), 75.1, 70.6, 69.5, 67.1, 60.9 (C2, C3, C4, C5 and C6).

Example 8: Synthesis of 2-(α-D-mannopyranosyl)amino-5-(4-methylbenzoyl)thiazole [11]

2-(2,3,4,6-tetra-O-acetyl-α-D-mannopyranosyl)amino-5-(4-methylbenzoyl)thiazole [11a]

$C_{25}H_{28}N_2O_{10}S$
MW=548.56222 g/mol
Yellow solid
Yield=79%
Monoisotopic Mass=548.146465

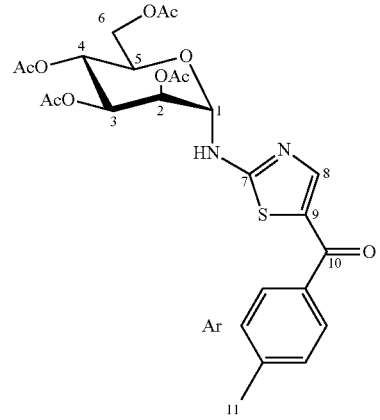

$^1$H NMR (300 MHz, CDCl$_3$) δ=8.77 (br, 1H, NH), 7.81 (s, 1H, H8), 7.72 (d, J=7.8 Hz, 2H, H$_{Ar}$), 7.24 (d, J=7.8 Hz, 2H, H$_{Ar}$), 5.53 (m, 1H, H2), 5.40-5.26 (m, 2H, H4 and H3), 5.22 (s, 1H, H1), 4.37 (dd, 1H, J$_{6b,6a}$=12.3 Hz, J$_{6b,5}$=5.7 Hz, H6$_b$), 4.13-4.00 (m, 2H, H6$_a$ and H5), 2.38 (s, 3H, H11), 2.19, 2.09, 1.98, 1.91 (4 s, 12H, CH$_3$CO).

$^{13}$C NMR (300 MHz, CDCl$_3$) δ=186.5 (C10), 170.9 (C7), 170.9, 170.3, 170.2, 169.7 (4CH$_3$CO), 147.8 (C8), 143.2 (C9), 135.4 (Car), 131.5 (Car), 129.4 (2Car), 129.1 (2Car), 82.1 (C1), 69.7 (C5), 69.1 (C3 or C4), 68.6 (C2), 66.1 (C3 or C4), 62.0 (C6), 21.8 (C11), 21.0, 20.8, 20.7 (4CH$_3$CO).

2-(α-D-mannopyranosyl)amino-5-(4-methylbenzoyl)thiazole [11]

C$_{17}$H$_{20}$N$_2$O$_6$S
MW=380.4155 g/mol
Yellow solid
Yield=quant
Monoisotopic Mass=380.104206
α and β ratio (9/1):

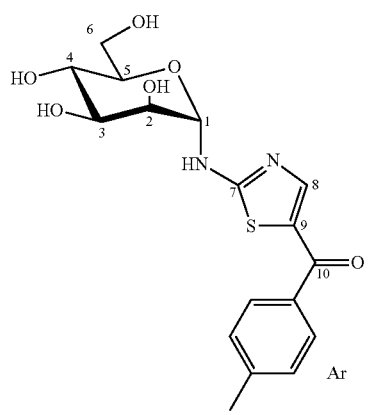

$^1$H NMR (300 MHz, DMSO) δ=9.53 (s, 1H, NH), 8.34 (dd, J=1.2 Hz, J=5.1 Hz, 1H, Har), 7.99 (dd, J=1.2 Hz, J=5.1 Hz, 1H, Har), 7.81 (s, 1H, H8), 5.18 (s, 1H, H1), 5.00 (d, J=2.4 Hz, 1H, OH2), (d, J=1.5 Hz, 1H, OH3), 4.76 (d, J=3.6 Hz, 1H, OH4), 4.41 (t, J=1.5 Hz, 1H, OH6), 3.81-3.79 (m, 1H, H2), 3.71-3.67 (m, 1H, H3), 3.65-3.60 (m, 1H, H6a), 3.55-3.52 (m, 2H, H4 H6b), 3.45-3.35 (m, 1H, H5)

Example 9: Synthesis of 2-(α-D-mannopyranosyl)amino-5-(thiophene-3-carbonyl)thiazole [12]

2-(2,3,4,6-tetra-O-acetyl-α-D-mannopyranosyl)amino-5-(thiophene-3-carbonyl)thiazole [12a]

C$_{22}$H$_{24}$N$_2$O$_{10}$S$_2$
MW=540.56336 g/mol
Yellow solid
Yield=92%
Monoisotopic Mass=540.087235

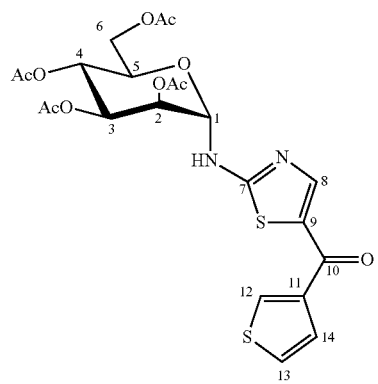

$^1$H NMR (300 MHz, CDCl$_3$) δ=8.93 (br, 1H, NH), 8.15 (dd, J$_{12,13}$=1.2 Hz, J$_{12,14}$=2.7 Hz, 1H, H12), 8.03 (s, 1H, H8), 7.57 (dd, J$_{14,15}$=5.1 Hz, 1H, H14), 7.37 (qq, 1H, H15), 5.59 (dd, J$_{2,1}$=1.5 Hz, J$_{2,3}$=3.0 Hz, 1H, H2), 5.40-5.30 (m, 2H, H4 and H3), 5.22 (d, 1H, H1), 4.40 (dd, 1H, J$_{6b,6a}$=12.3 Hz, J$_{6b,5}$=6.0 Hz, H6$_b$), 4.15-4.06 (m, 2H, H6$_a$ and H5), 2.22, 2.16, 2.03, 1.97 (4 s, 12H, CH$_3$CO).

$^{13}$C NMR (300 MHz, CDCl$_3$) δ=180.0 (C10), 172.7 (C7), 170.9, 170.3, 170.2, 169.7 (4CH$_3$CO), 146.6 (C8), 140.7 (C9), 131.9 (C13), 128.0 (C14), 126.4 (C15), 82.7 (C1), 69.3 (C5), 69.1 (C3 or C4), 68.5 (C2), 66.0 (C3 or C4), 62.1 (C6), 20.9, 20.8, 20.7 (4CH$_3$CO).

2-(α-D-mannopyranosyl)amino-5-(thiophene-3-carbonyl)thiazole [12]

C$_{14}$H$_{16}$N$_2$O$_6$S$_2$
MW=372.41664 g/mol
Orange solid
Yield=83%
Monoisotopic Mass=372.044976
α and β ratio (5/5):

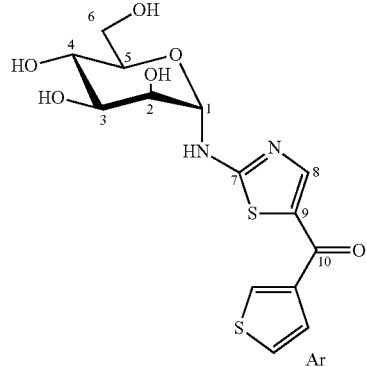

$^1$H NMR (400 MHz, DMSO) δ=9.30 (d, J=5.1 Hz, 0.5H, NH), 8.91 (d, 6.6 Hz, 0.5H, NH), 8.33 (dd, J=1.2 Hz, J=3.3 Hz, 1H, Har), 7.99 (s, 0.5H, H8β), 7.96 (s, 0.5H, H8a), 7.67 (dd, J=2.4 Hz, J=3.3 Hz, 1H, Har), 7.49 (dd, J=2.4 Hz, J=1.2 Hz), 5.23-5.17 (m, 1H, H1), 3.80-3.20 (m, 6H, H2, H3, H4, H5, H6).

$^{13}$C NMR (400 MHz, DMSO) δ=179.1 (C10), 172.7 (C7), 148.4 (C8), 140.3 (C9), 131.6, 128.6, 128.5, 127.4, 127.2 (Car), 85.4, 81.8 (C1), 78.9, 74.9, 73.9, 70.6, 70.3, 69.6, 67.1, 66.7, 61.2, 60.9 (C2, C3, C4, C5, C6 α and β).

Example 10: Synthesis of 2-(α-D-mannopyranosyl)amino-5-(4-methyl-2-(pyrazin-2-yl)thiazole-5-carbonyl)thiazole [13]

2-(2,3,4,6-tetra-O-acetyl-α-D-mannopyranosyl)amino-5-(4-methyl-2-(pyrazin-2-yl)thiazole-5-carbonyl)thiazole [13a]

$C_{26}H_{27}N_5O_{10}S_2$
MW=633.65008 g/mol
Yellow solid
Yield=96%
Monoisotopic Mass=633.119932

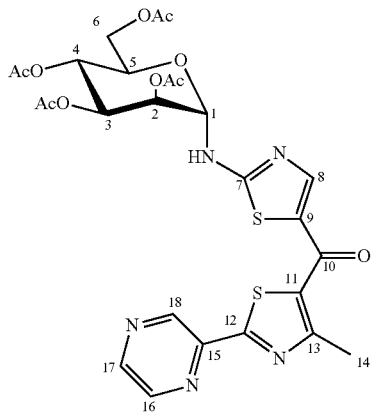

1H NMR (300 MHz, CDCl$_3$) δ=9.39 (d, 1H, $J_{18,17}$=1.5 Hz, H18), 8.60 (d, 1H, $J_{16,17}$=2.5 Hz, H16), 8.50 (dd, 1H, $J_{17,18}$=2.5 Hz, $J_{17,16}$=1.5 Hz, H17), 8.11 (s, 0.9H, H8$_\alpha$), 7.94 (s, 0.1H, H8$_\beta$), 5.52 (dd, 1H, $J_{2,1}$=1.8 Hz, $J_{2,3}$=2.4 Hz, H2), 5.40-5.14 (m, 2H, H4, H3 and H1), 4.36 (dd, 1H, $J_{6b,6a}$=12.9 Hz, $J_{6b,5}$=5.7 Hz, H6$_b$), 4.12-3.99 (m, 2H, H6$_a$ and H5), 2.70 (s, 3H, H14), 2.16, 2.07, 2.00, 1.90 (4 s, 12H, CH$_3$CO).

$^{13}$C NMR (300 MHz, CDCl$_3$) δ=177.6 (C10), 172.8 (C7), 170.9, 170.5, 170.3, 169.7 (4CH$_3$CO), 166.65, 160.48 (Car), 147.7 (C8), 146.1 (C16), 144.14 (C17), 142.0 (C18), 132.8 (C11) 129.8 (C9), 82.3 (C1), 71.53 (C3 or C4), 69.5 (C2), 68.6 (C5), 66.0 (C3 or C4), 62.0 (C6), 20.7 (4CH$_3$CO).

MS (CI) m/z=634.21 [M+H]$^+$.

2-(α-D-mannopyranosyl)amino-5-(4-methyl-2-(pyrazin-2-yl)thiazole-5-carbonyl)thiazole [13]

$C_{18}H_{19}N_5O_6S_2$
MW=465.50336 g/mol
Yellow solid
Yield=quant
Monoisotopic Mass=465.077673
α and β ratio (65/35)

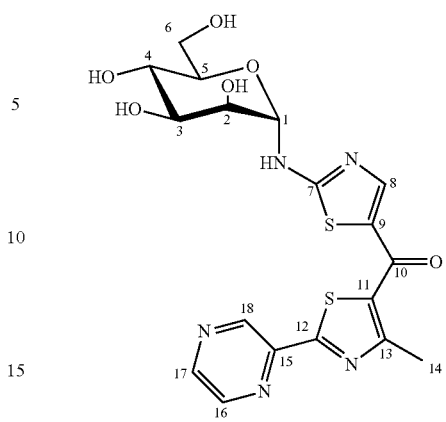

$^1$H NMR (400 MHz, DMSO) δ=9.40 (s, 1H, H18), 8.70 (d, 1H, $J_{16,17}$=2.4 Hz, H16), 8.68 (d, 1H, $J_{17,18}$=2.4, H17), 8.00 (m, 1H, H8$_{\alpha\ et\ \beta}$) 5.33 (d, 0.65H, $J_{1,2}$=1.8 Hz, H1$_\alpha$), 5.26 (d, 0.35H, $J_{1,2}$=1.8 Hz, H1$_\beta$), 5.40-5.14 (m, 6H, H2, H3, H4, H5 and H6)

Example 11: Synthesis of 2-(α-D-mannopyranosyl)amino-5-(thiophene-2-carbonyl)thiazole [14]

2-(2,3,4,6-tetra-O-acetyl-α-D-mannopyranosyl)amino-5-(thiophene-2-carbonyl)thiazole [14a]

$C_{22}H_{24}N_2O_{10}S_2$
MW=540.56336 g/mol
Yellow solid
Yield=92%
Monoisotopic Mass=540.087235

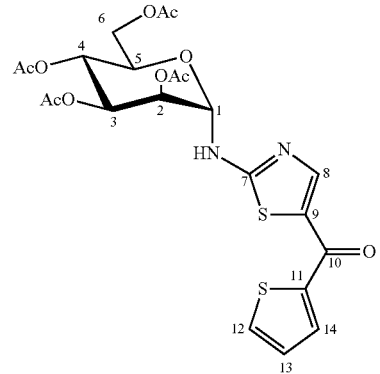

$^1$H NMR (300 MHz, CDCl$_3$) δ=8.12 (s, 1H, H8), 7.88, (dd, J=3.9 Hz, J=1.2 Hz, 1H, H12 or H14), 7.65 (dd, J=1.2 Hz, J=4.8 Hz, H12 or H14), 7.15 (dd, J=5.1 Hz, J=4.8 Hz, 1H, H13), 5.57 (dd, $J_{2,1}$=2.1 Hz, $J_{2,3}$=3.3 Hz, 1H, H2), 5.42-5.28 (m, 2H, H4 and H3), 5.22 (d, 1H, H1), 4.38 (dd, 1H, $J_{6b,6a}$=12.3 Hz, $J_{6b,5}$=6.0 Hz, H6$_b$), 4.15-4.05 (m, 2H, H6$_a$ and H5), 2.21, 2.10, 2.02, 1.98 (4 s, 12H, CH$_3$CO).

$^{13}$C NMR (300 MHz, CDCl$_3$) δ=177.5 (C10), 172.2 (C7), 170.9, 170.4, 170.3, 169.7 (4CH$_3$CO), 146.2 (C8), 142.7 (C9), 133.1, 132.1 (C12, C14), 131.0 (C11), 128.1 (C13), 82.4 (C1), 69.5 (C5), 69.1 (C3 or C4), 68.6 (C2), 66.1 (C3 or C4), 62.1 (C6), 21.0, 20.8, 20.7 (4CH$_3$CO).

2-(α-D-mannopyranosyl)amino-5-(thiophene-2-carbonyl)thiazole [14]

C$_{14}$H$_{16}$N$_2$O$_6$S$_2$
MW=372.41664 g/mol
Yellow solid
Yield=quant
Monoisotopic Mass=372.044976
α and β ratio (6/4):

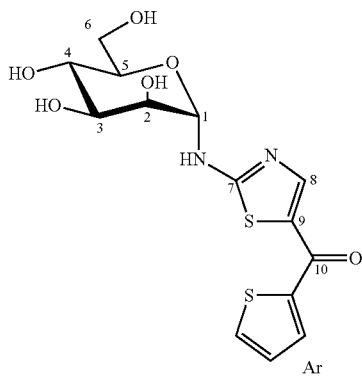

$^1$H NMR (400 MHz, DMSO) δ=8.09 (s, 0.6H, H8$_α$), 8.06 (s, 0.4H, H1$_β$), 7.91 (m, 1H, Har), 7.85 (dd, 1H, J=5.1 Hz, J=0.9 Hz, 1H, Har), 7.24 (dd, J=3.6 Hz, J=7.8 Hz, 1H, Har), (5.32, d, J$_{1,2}$=2.1 Hz, 0.6H, H1$_α$), 5.24 (d, J$_{1,2}$=1.8 Hz, 1H, H1$_β$), 4.05-3.40 (m, 6H, H2, H3, H4, H5, H6).
$^{13}$C NMR (400 MHz, DMSO) δ=(179.0 (C10), 172.7 (C7), 148.3 (C8), 140.3 (C9), 131.6, 128.6, 128.5, 127.4, 127.2 (Car), 83.35, 81.8 (C1 α and β), 7.9, 74.9, 73.9, 70.6, 70.3, 69.6, 67.1, 66.7, 61.2, 60.9 (C2, C3, C4, C5 and C6).

Example 12: Synthesis of 2-(α-D-mannopyranosyl)amino-5-(2-naphthoyl)thiazole [15]

2-(2,3,4,6-tetra-O-acetyl-α-D-mannopyranosyl)amino-5-(-2-naphthoyl)thiazole [15a]

C$_{28}$H$_{28}$N$_2$O$_{10}$S
MW=584.59432 g/mol
Yellow solid
Yield=87%
Monoisotopic Mass=584.146465 Da

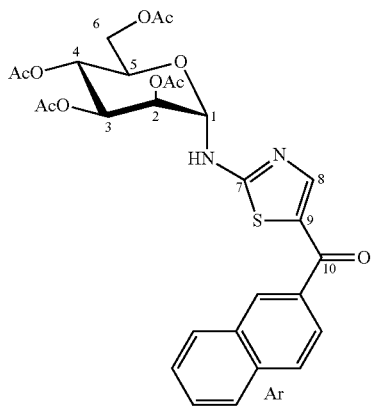

$^1$H NMR (300 MHz, CDCl$_3$) δ=8.35 (s, 1H, Har), 8.00-7.85, (m, 5H, Har and H8), 7.56 (dq, J=7.5 Hz, J=1.5 Hz, Har), 5.55 (dd, J$_{2,1}$=2.4 Hz, J$_{2,3}$=3.0 Hz, 1H, H2), 5.41-5.27 (m, 2H, H4 and H3), 5.26 (d, 1H, H1), 4.41 (dd, 1H, J$_{6b,6a}$=12.3 Hz, J$_{6b,5}$=6.3 Hz, H6$_b$), 4.18-4.04 (m, 2H, H6$_a$ and H5), 2.22, 2.13, 1.98, 1.80 (4 s, 12H, CH$_3$CO).
$^{13}$C NMR (300 MHz, CDCl$_3$) δ=186.7 (C10), 172.9 (C7), 170.9, 170.1, 169.6 (4CH$_3$CO), 148.1 (C8), 135.15, 132.4, 131.4, 130.0, 129.4, 128.6, 128.2, 127.8, 126.8, 125.1 (C9 and Car), 82.5 (C1), 69.3 (C5), 68.9 (C3 or C4), 68.6 (C2), 66.2 (C3 or C4), 62.0 (C6), 20.9, 20.6, 20.3 (4CH$_3$CO).

2-(α-D-mannopyranosyl)amino-5-(2-naphthoyl)thiazole [15]

C$_{20}$H$_{20}$N$_2$O$_6$S
MW=416.4476 g/mol
Yellow solid
Yield=89%
Monoisotopic Mass=416.104206

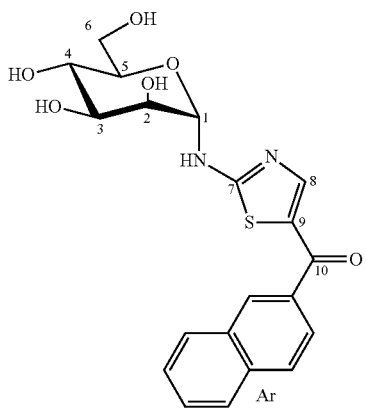

$^1$H NMR (400 MHz, DMSO) δ=9.00 (d, J=6.6 Hz, 1H, NH), 8.43 (s, 1H, Har), 8.14 (d, J=5.7 Hz, 1H, Har), 8.03 (dd, J=6.6 Hz, J=10.8 Hz, 1H, Har), 7.87 (s, 1H, H8), 7.81 (dd, J=1.5 Hz, J=6.3 Hz, 2H, Har), 5.26 (d, J$_{2,1}$=6.6 Hz, 1H, H1), 4.98 (d, J=3.9 Hz, 1H, OH2), 4.80 (d, J=3.9 Hz, 1H, OH4), 4.75 (d, J=3.9 Hz, 1H, OH3), 4.45 (t, J=2.7 Hz, 1H, OH6), 3.77-3.75 (m, 1H, H2), 3.72-3.67 (m, 1H, H6a), 3.49-3.37 (m, H4, H3, H6), 3.17-3.13 (m, 1H, H5).
$^{13}$C NMR (400 MHz, DMSO) δ=185.7 (C10), 173.4 (C7), 149.9 (C8), 135.2, 134.4, 132.1, 129.3, 129.2, 128.3, 128.1, 128.0, 127.6, 126.8, 124.7 (C9 and Car), 81.8 (C1), 79.0 (C5), 73.9 (C3 or C4), 70.4 (C2), 66.7 (C4 or C3), 61.2 (C6).

Example 13: Synthesis of 5-((3r,5r,7r)-adamantane-1-carbonyl)-2-(α-D-mannopyranosyl)aminothiazole [16]

5-((3r,5r,7r)-adamantane-1-carbonyl)-(2,3,4,6-tetra-O-acetyl-α-D-mannopyranosyl)aminothiazole [16a]

C$_{28}$H$_{36}$N$_2$O$_{10}$S
MW=592.65784 g/mol
Yellow solid
Yield=95%
Monoisotopic Mass=592.209065

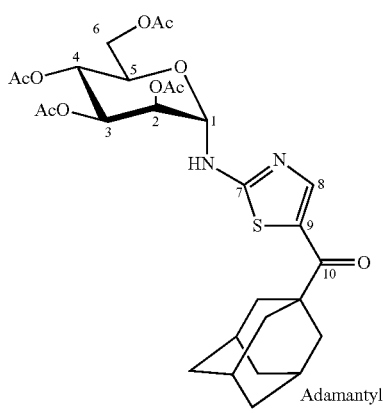

Adamantyl

¹H NMR (300 MHz, CDCl₃) δ=8.14 (s, 1H, H8), 5.60 (dd, $J_{2,1}$=1.8 Hz, $J_{2,3}$=2.4 Hz, 1H, H2), 5.40-5.27 (m, 2H, H4 and H3), 5.14 (d, 1H, H1), 4.38 (dd, 1H, $J_{6b,6a}$=12.9 Hz, $J_{6b,5}$=6.0 Hz, H6$_b$), 4.11-4.02 (m, 2H, H6$_a$ and H5), 2.21-1.69 (m, 27H, 4CH₃CO H$_{Adamantyl}$).

¹³C NMR (300 MHz, CDCl₃) δ=197.1 (C10), 170.4 (C7), 170.4, 169.8, 169.0, 168.6 (4CH₃CO), 142.9 (C8), 129.6 (C9), 81.6 (C1), 68.1 (C3 or C4), 67.9 (C5), 67.4 (C2), 64.8 (C3 or C4), 60.9 (C6), 45.4, 38.8, 38.6, 37.7, 35.5, 27.3, 27.2, 26.9 (C$_{Adamantyl}$), 19.8, 19.7, 19.5 (4CH₃CO).

5-((3r,5r,7r)-adamantane-1-carbonyl)-2-(α-D-mannopyranosyl)aminothiazole [16]

C₂₀H₂₈N₂O₆S
MW=424.51112 g/mol
Yellow solid
Yield=quant
Monoisotopic Mass=424.166807
α and β ratio (7/3):

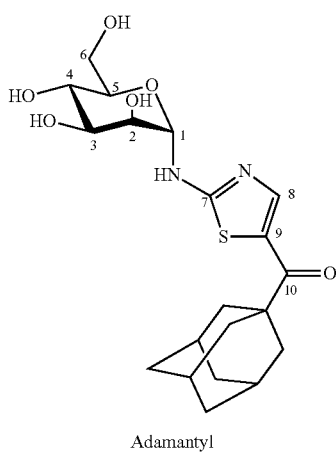

Adamantyl

¹H NMR (400 MHz, DMSO) δ=8.08 (s, 0.7H, H8α), 8.05 (s, 0.3H, H8β), 5.27 (d, $J_{1,2}$=1.8 Hz, 0.7H, H1α), 5.17 (d, J=0.9 Hz, 0.3H, H1β), 4.00-3.30 (m, 6H, H2, H3, H4, H5, H6), 2.12-1.85 (m, 16H, Hadamantyl)

¹³C NMR (400 MHz, DMSO) δ=196.8 (C10), 178.4 (C7), 145.6 (C8), 127.3 (C9), 81.9 (C1), 78.9 (C5), 73.9 (C3 or C4), 70.3 (C2), 66.7 (C4 or C3), 61.2 (C6), 45.5, 36.0, 27.7 (Cadamantyl)

Example 14: Synthesis of 2-(α-D-mannopyranosyl)amino-5-isonicotinoylthiazole [17]

2-(2,3,4,6-tetra-O-acetyl-α-D-mannopyranosyl)amino-5-isonicotinoylthiazole [17a]

C₂₃H₂₅N₃O₁₀S
MW=535.5237 g/mol
Yellow solid
Yield=50%
Monoisotopic Mass=535.126064

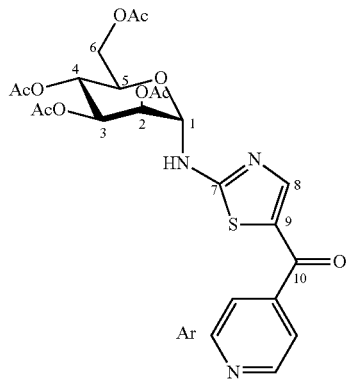

¹H NMR (300 MHz, CDCl₃) δ=8.80 (d, J=5.7 Hz, NH and H$_{Ar}$), 7.90 (s, 1H, H8), 7.64 (d, 2H, H$_{Ar}$), 5.54 (dd, $J_{2,1}$=1.8 Hz, $J_{2,3}$=3.0 Hz, 1H, H2), 5.34-5.29 (m, 2H, H4 and H3), 5.20 (d, 1H, H1), 4.40 (dd, 1H, $J_{6b,6a}$=12.3 Hz, $J_{6b,5}$=5.7 Hz, H6$_b$), 4.15-4.04 (m, 2H, H6$_a$ and H5), 2.22, 2.13, 2.03, 1.92 (4 s, 12H, CH₃CO).

¹³C NMR (300 MHz, CDCl₃) δ=185.2 (C10), 173.8 (C7), 170.8, 170.3, 170.2, 169.6 (4CH₃CO), 150.6 (Car), 149.4 (C8), 144.5 (Car), 130.3 (C9), 122.3 (Car), 82.6 (C1), 69.4 (C5), 69.1 (C3 or C4), 68.3 (C2), 65.8 (C3 or C4), 62.0 (C6), 20.9, 20.7, 20.5 (4CH₃CO).

2-(α-D-mannopyranosyl)amino-5-isonicotinoylthiazole [17]

C₁₅H₁₇N₃O₆S
MW=367.37698 g/mol
Yellow solid
Yield=97%
Monoisotopic Mass=367.083805
α and β ratio (9/1):

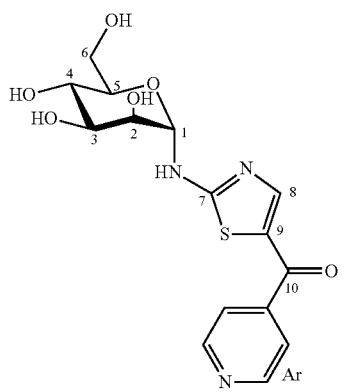

¹H NMR (400 MHz, DMSO) δ=8.74 (dd, J=1.8 Hz, J=4.5 Hz, 2H Har), 7.80 (s, 0.9H, H8α), 7.77 (s, 0.1H, H8β), 7.71 (dd, J=1.5 Hz, J=4.5 Hz, 2H, Har), 5.32 (d, J$_{1,2}$=2.1 Hz, 0.9H, H1α), 5.26 (d, J=0.9 Hz, 0.1H, H1β), 3.89 (m, 0.9H, H2α), 3.94 (m, 0.1H, H2β), 3.82-3.72 (m, 4H, H3, H4, H6), 3.50-3.43 (m, 1H, H5)

¹³C NMR (400 MHz, DMSO) δ=184.2 (C10), 173.9 (C7), 151.5 (C8), 150.1, 144.9, 127.3, 122.0 (C9, Car), 83.5 (C1), 75.1 (C5), 70.6 (C3 or C4), 69.5 (C2), 67.1 (C4 or C3), 60.9 (C6).

Example 15: Synthesis of 2-(α-D-mannopyranosyl)amino-5-(2-ethoxy-2-oxoacetyl)thiazole [18]

2-(2,3,4,6-tetra-O-acetyl-α-D-mannopyranosyl)amino-5-(2-ethoxy-2-oxoacetyl)thiazole [18a]

$C_{21}H_{26}N_2O_{12}S$
MW=530.50234 g/mol
Yellow solid
Yield=95%
Monoisotopic Mass=530.120644

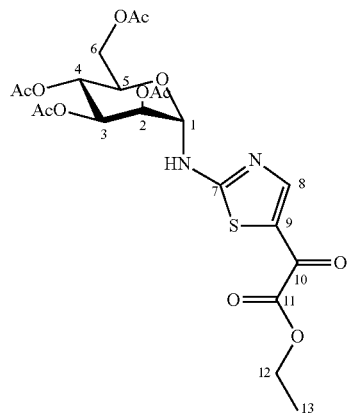

¹H NMR (300 MHz, CDCl$_3$) δ=8.43 (s, 1H, H8), 5.48 (dd, J$_{2,1}$=2.1 Hz, J$_{2,3}$=3.0 Hz, 1H, H2), 5.40-5.32 (m, 2H, H4 and H3), 5.22 (d, 1H, H1), 4.38 (m, 3H, J$_{12,13}$=7.2 Hz, H6$_b$ and H12), 4.13-4.00 (m, 2H, H6$_a$ and H5), 2.20, 2.08, 2.05, 2.04 (4 s, 12H, CH$_3$CO), 1.39 (t, 3H, H13).

¹³C NMR (300 MHz, CDCl$_3$) δ=174.4 (C10), 173.9 (C7), 170.4, 170.2, 169.7 (4CH$_3$CO), 161.0 (C11) 151.6 (C8), 127.6 (C9), 82.1 (C1), 69.7 (C5), 68.8 (C3 or C4), 68.6 (C2), 66.2 (C3 or C4), 63.0 (C12), 62.1 (C6), 20.9, 20.8 (4CH$_3$CO), 14.1 (C13).

2-(α-D-mannopyranosyl)amino-5-(2-ethoxy-2-oxoacetyl)thiazole [18]

$C_{13}H_{18}N_2O_8S$
MW=362.35562 g/mol
Yellow solid
Yield=quant
Monoisotopic Mass=362.078386

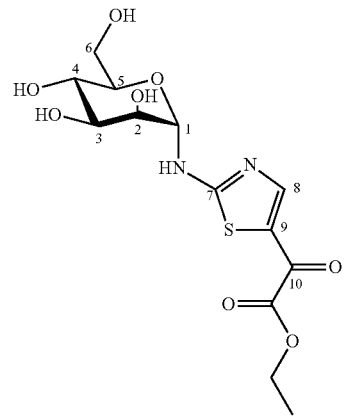

Example 16: Synthesis of 2-(α-D-mannopyranosyl)amino-5-(4-bromobenzoyl)thiazole [19]

2-(2,3,4,6-tetra-O-acetyl-α-D-mannopyranosyl)amino-5-(4-bromobenzoyl)thiazole [19a]

$C_{24}H_{25}BrN_2O_{10}S$
MW=613.4317 g/mol
Yellow solid
Yield=97%
Monoisotopic Mass=612.04132 Da

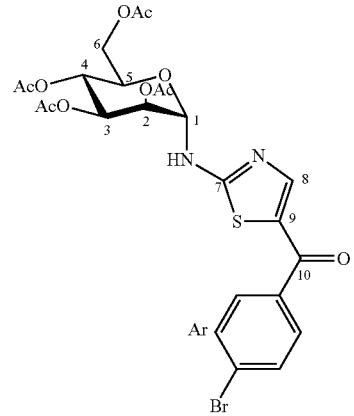

¹H NMR (300 MHz, CDCl$_3$) δ=8.80 (d, J=5.7 Hz, NH and H$_{Ar}$), 7.90 (s, 1H, H8), 7.64 (d, 2H, H$_{Ar}$), 5.54 (dd, J$_{2,1}$=1.8 Hz, J$_{2,3}$=3.0 Hz, 1H, H2), 5.34-5.29 (m, 2H, H4 and H3), 5.20 (d, 1H, H1), 4.40 (dd, 1H, J$_{6b,6a}$=12.3 Hz, J$_{6b,5}$=5.7 Hz, H6$_b$), 4.15-4.04 (m, 2H, H6$_a$ and H5), 2.22, 2.13, 2.03, 1.92 (4 s, 12H, CH$_3$CO).

¹³C NMR (300 MHz, CDCl$_3$) δ=185.2 (C10), 173.8 (C7), 170.8, 170.3, 170.2, 169.6 (4CH$_3$CO), 150.6 (Car), 149.4 (C8), 144.5 (Car), 130.3 (C9), 122.3 (Car), 82.6 (C1), 69.4 (C5), 69.1 (C3 or C4), 68.3 (C2), 65.8 (C3 or C4), 62.0 (C6), 20.9, 20.7, 20.5 (4CH$_3$CO).

2-(α-D-mannopyranosyl)amino-5-(4-bromobenzoyl)thiazole [19]

$C_{16}H_{17}BrN_2O_6S$
MW=445.28498 g/mol
Yellow solid

Yield=quant
Monoisotopic Mass=443.999061

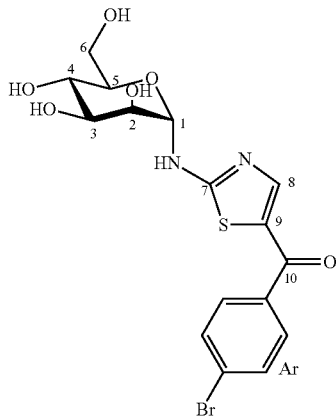

$^1$H NMR (400 MHz, DMSO) δ=8.74 (dd, J=1.8 Hz, J=4.5 Hz, 2H Har), 7.80 (s, 0.9H, H8a), 7.77 (s, 0.1H, H8β), 7.71 (dd, J=1.5 Hz, J=4.5 Hz, 2H, Har), 5.32 (d, $J_{1,2}$=2.1 Hz, 0.9H, H1α), 5.26 (d, J=0.9 Hz, 0.1H, H1β), 3.89 (m, 0.9H, H2a), 3.94 (m, 0.1H, H2β), 3.82-3.72 (m, 4H, H3, H4, H6), 3.50-3.43 (m, 1H, H5)

$^{13}$C NMR (400 MHz, DMSO) δ=184.5 (C10), 173.7 (C7), 151.0 (C8), 141.8, 132.7, 129.0, 127.4, 118.2, 127.4 (C9, Car), 81.9 (C1), 79.0 (C5), 73.8 (C3 or C4), 70.3 (C2), 66.6 (C4 or C3), 61.2 (C6).

Example 17: Synthesis of 2-(α-D-mannopyranosyl) amino-5-(4-cyanobenzoyl)thiazole [20]

2-(2,3,4,6-tetra-O-acetyl-α-D-mannopyranosyl) amino-5-(4-cyanobenzoyl)thiazole [20a]

$C_{25}H_{25}N_3O_{10}S$
MW=559.5451 g/mol
Yellow solid
Yield=97%
Monoisotopic Mass=559.126064

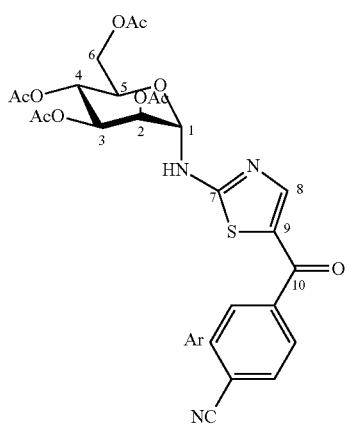

$^1$H NMR (300 MHz, CDCl$_3$) δ=8.80 (d, J=5.7 Hz, NH and H$_{Ar}$), 7.90 (s, 1H, H8), 7.64 (d, 2H, H$_{Ar}$), 5.54 (dd, $J_{2,1}$=1.8 Hz, $J_{2,3}$=3.0 Hz, 1H, H2), 5.34-5.29 (m, 2H, H4 and H3), 5.20 (d, 1H, H1), 4.40 (dd, 1H, $J_{6b,6a}$=12.3 Hz, $J_{6b,5}$=5.7 Hz, H6$_b$), 4.15-4.04 (m, 2H, H6$_a$ and H5), 2.22, 2.13, 2.03, 1.92 (4 s, 12H, CH$_3$CO).

2-(α-D-mannopyranosyl)amino-5-(4-cyanobenzoyl) thiazole [20]

$C_{17}H_{17}N_3O_6S$
MW=391.39838 g/mol
Yellow solid
Yield=98.5%
Monoisotopic Mass=391.083805
α and β ratio (8/2):

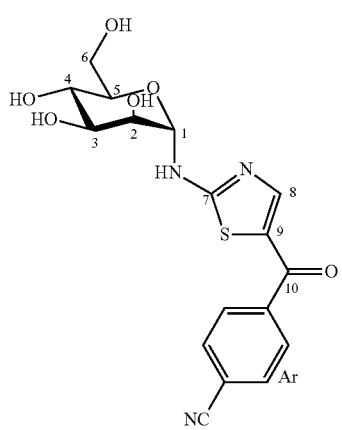

$^1$H NMR (400 MHz, DMSO) δ=9.44 (m, 0.8H, NH), 9.06 (d, J=8.0 Hz, 0.2H, NH), 7.80 (s, 1H, H8), 7.76 (m, 4H, Har), 5.20 (m, 1H, H1), 5.00 (m, 1H, OH2), 4.85 (m, 1H$_2$OH4), 4.43 (m, 1H, OH3), 4.42 (m, 1H, OH6), 3.87-3.40 (m, 6H, H2, H3, H4, H5, H6)

$^{13}$C NMR (400 MHz, DMSO) δ=184.6 (C10), 173.3 (C7), 150.17 (C8), 137.0, 131.7, 130.3, 128.8, 127.8, 125.9, 125.6 (C9, Car, CN), 83.4 (C1), 75.0 (C5), 70.6, 69.6, 67.1, 66.7, 60.9, 54.9 (C2, C3, C4, C5, C6).

Example 17bis: Synthesis of Heterocyclic Reference Compounds 1-(2,3,4,6-tetra-O-acetyl-α-D-mannopyranosyl)-4-methylsulfanylpyrimidine-2(1H)-(thi)one (13b)

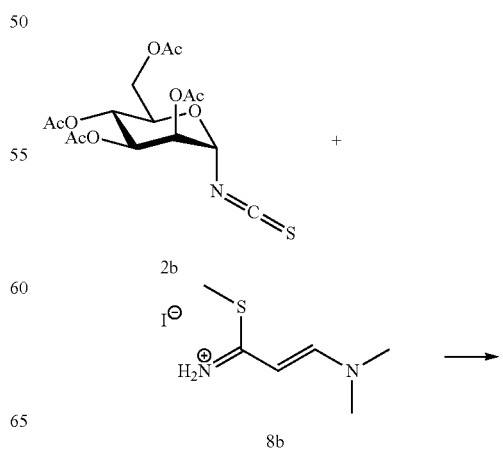

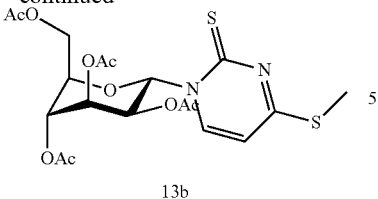

13b

To a solution of mannosylisothiocyanate 2b (1.54 mmol; 2 eq.) in dichloromethane (30 mL) was added thiazadiene 8b (1.3 mmol; 1 eq.). After 15 min of stirring at RT, triethylamine (1.69 mmol; 2.2 éq.) was added and the resulting mixture was stirred for 30 minutes. The organic phase is washed with water (2×20 mL) and dried over magnesium sulfate. After evaporation under reduced pressure, the residue was purified by silica gel chromatography (Ethylacetate/petrol ether: 4/6).

Yellow solid
Quantitative yield.
RMN 1H (CDCl3): 7.59 (d, 1H, J1, 2=9.6 Hz, H1); 7.55 (d, 1H, J6p, 5p=7.2 Hz, H6 pyrimidine); 6.53 (d, 1H, J5p, 6p=7.2 Hz, H5 pyrimidine); 5.47 (t, 1H, J3, 4=3.3 Hz, H3); 5.27-5.31 (m, 1H, H2); 5.00 (d, 1H, J4, 3=3.6 Hz, H4); 4.59 (dd, 1H, J6b, 6a=12.0 Hz, J6b, 5=8.4 Hz, H6b); 4.49 (dd, 1H, J6a, 6b=12 Hz, J6a, 5=5.7 Hz, H6a); 4.32-4.36 (m, 1H, H5); 2.61 (s, 3H, SCH3); 2.26 (s, 3H, CH3CO); 2.18 (s, 3H, CH3CO); 2.09 (s, 3H, CH3CO); 1.98 (s, 3H, CH3CO).
RMN 13C (CDCl3): 181.8 (C2 pyrimidine); 172.9 (C4 pyrimidine); 170.6, 169.9 and 169.2 (4CH3CO); 139.6 (C6 pyrimidine); 108.4 (C5 pyrimidine); 80.0 (C1); 76.5 (C5); 68.4 and 68.3 (C3 and C4); 67.4 (C2); 60.4 (C6); 21.0, 20.9, 20.8 and 20.7 (4CH3CO); 13.2 (S—CH3).
MS (CI); m/z: 489 [M+H]+.
$[\alpha]_D^{20}$: +27.8° (c=1 DCM).

4-amino-1-(2,3,4,6-tetrahydroxy-α-D-mannopyranosyl)pyrimidine-2(1H)-(thi)one (NM34)

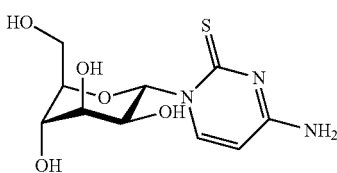

Compound 13b was dissolved in a 7 M solution of ammonia in methanol (5 mL) and the mixture was stirred at RT for one day. After evaporation under reduced pressure, the residue was purified by silica gel chromatography (MeOH/CH2Cl2:30/70).
MM=289,321 g/mol
White soli
Yield=86%
RMN 1H (MeOD): 7.93 (d, 1H, J6p, 5p=7.8 Hz, H6 pyrimidine); 7.19 (d, 1H, J=9.0 Hz, H1); 6.23 (d, 1H, J5p, 6p=7.5 Hz, H5 pyrimidine); 4.37 (dd, 1H, J6b, 6a=12.3 Hz, J6b, 5=9.0 Hz, H6b); 4.11-4.07 (m, 2H, H2 and H4); 4.01 (dd, 1H, J5, 6=9.3 Hz, J5, 4=4,2 Hz, H5); 3.84 (d, 1H, J=2.7 Hz, H3); 3.63 (dd, 1H, J6a, 6b=12.0 Hz, J6a, 5=4.5 Hz, H6a).
RMN 13C (MeOD): 184.2 (C2 pyrimidine); 162.0 (C4 pyrimidine); 143.9 (C6 pyrimidine); 100.1 (C5 pyrimidine); 83.8 (C5); 83.2 (C1); 73.6 (C2 or C4); 70.9 (C3); 68.4 (C2 or C4); 60.6 (C6).

MS (CI); m/z: 290 [M+H]+.
$[\alpha]_D^{20}$: +47.2° (c=1H2O).

1-(2,3,4,6-tetrahydroxy-α-D-mannopyranosyl)-4-methoxypyrimidine-2(1H)-(thi)one (NM30)

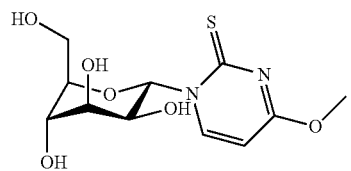

Sodium methanolate (0.75 mmol; 5 eq.) was added to a solution of 13b in methanol (5 mL). The mixture was stirred at RT for 3 hours. After evaporation under reduced pressure, the residue was purified by silica gel chromatography (MeOH/CH2Cl2:30/70).
White solid
Yield=61%
RMN 1H (CDCl3): 8.24 (d, 1H, J=7.5 Hz, H6 pyrimidine); 7.25 (d, 1H, J1, 2=8.7 Hz, H1); 6.47 (d, 1H, J5p, 6p=7.5 Hz, H5 pyrimidine); 4.31 (dd, 1H, J6b, 6a=12.0 Hz, J6b, 5=8.7 Hz, H6b); 4.04-4.12 (m, 3H, H2H4 and H5); 4.01 (s, 3H, OCH3); 3.88 (d, 1H, J=2.4 Hz, H3); 3.70 (dd, 1H, J6a, 6b=12.3 Hz, J6a, 5=4.2 Hz, H6a).
RMN 13C (CDCl3): 186.2 (C2 pyrimidine); 167.3 (C4 pyrimidine); 147.0 (C6 pyrimidine); 102.1 (C5 pyrimidine); 84.0 and 83.9 (C1 and C2 or C5 or C6); 73.4 (C2 or C5 or C6); 70.8 (C3); 69.0 (C2 or C5 or C6); 60.8 (C6); 55.6 (S—CH3).
MS (CI); m/z: 305 [M+H]+.
HRMS (MALDI); m/z: calculated for C11H16N2O6S [M+Na]+=327.0621; measured=327.0633; Δ=3.7 ppm.
$[\alpha]_D^{20}$: +20.7° (c=1 MeOH).

Example 17ter: Synthesis of 1-((5-acetylthiazol-2-yl)oxy)-α-D-mannopyranose 2-amino-5-acétylthiazol

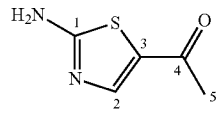

White powder
M=142.02 g·mol$^{-1}$
C5H6N2OS
1H NMR (400 MHz, DMSO): δ (ppm): 7.96 (bs, 2H NH2), 7.91 (s, 1H, H2), 2.34 (s, 3H, H5)
13C NMR (100 MHz, DMSO): δ (ppm): 188.34 (C4), 174.42 (C1), 149.35 (C2), 127.59 (C3), 25.56 (C5)
mP=176-178° C.
MS, ei m/z=141.93
General Procedure for Sandmeyer Reaction
The aminothiazol (1 eq) was solubilised in HCl 37%, and cooled to −5° C. A solution of sodium nitrite (3 eq) in a minimum of water was added over 1 h, and then stirred 30 min. a solution of CuSO4.H2O (4 eq), and NaCl (20 eq) in water was added over 40 min, and the green solution was then stirred 30 min, then heated to 60° C. for 1 h. The mixture was extracted by DCM, then washed by a solution of saturated NaHCO3, dried on MgSO4, filtrated on a silica pad, eluted with DCM, and concentrated under vacuum. 71% yield, as a yellow powder.

2-chloro-5-acétylthiazol

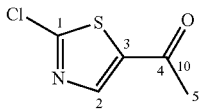

White cristal
M=160.97 g·mol$^{-1}$
C$_5$H$_4$ClNOS $^1$H NMR (400 MHz, CDCl$_3$): δ (ppm): 8.06 (s, 1H, H2), 2.55 (s, 3H, H5)

$^{13}$C NMR (100 MHz, CDCl$_3$): δ (ppm): 189.61 (C4), 159.30 (C1), 145.76 (C2), 142.67 (C3), 27.21 (C5)

mP=48.8-49.9° C.

SM, Ci m/z: [m+H$^+$]=161.9

General Procedure for the Formation of Alcohol.

The chlorothiazol (1 eq) was solubilised in a solution of NaOH 1 M (5 mL/mmol), and potassium iodide (0.2 eq) was added. The solution was warmed to 80° C. for 2 h, and then cooled. HCl 1 M was until the color change, and the mixture was extracted by AcOEt, dried on MgSO4, and concentrated under vacuum. the crude product was purified by column chromatography on silica gel (column chromatography (EP/AcOEt, 1:1-3:7)). 66% yield, as a yellow powder.

2-hydroxy-5-acétylthiazol

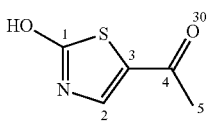

yellow solid
M=143.01 g·mol$^{-1}$
C$_5$H$_5$NO$_2$S $^1$H NMR (400 MHz, DMSO): δ (ppm): 12.13 (bs, 1H, OH), 8.17 (s, 1H, H2), 2.41 (s, 3H, H5)

$^{13}$C NMR (100 MHz, DMSO): δ (ppm): 189.06 (C4), 172.39 (C1), 133.51 (C2), 120.64 (C3), 24.89 (C5)

mP=158.2-159° C.

MS, Ci m/z: [m+H$^+$]=143.9, [m+NH$_4^+$]=160.93

Silylation of Mannose

α-D-mannose (1 eq) was dissolved in pyridine, under argon atmosphere and magnetical stirring. HMDS (8.6 eq) and TMSCl (7.12 eq) were added and the mixture became white. the mixture was heated to 75° C. during 90 min, then quenched by water and extracted by pentane, dried on MgSO4, and concentrated under vacuum. Several co-evaporations were done to remove pyridine residues. The white oil was used without further purification.

Quantitative yield 2,3,4,6-penta-O-trimethylsilyl-α-D-mannopyranose

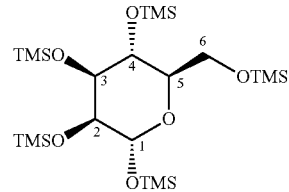

Colorless oil
M=540.26 g·mol$^{-1}$
C$_{21}$H$_{52}$O$_6$Si$_5$ 1-((5-acetylthiazol-2-yl)oxy)-α-D-mannopyranose In a flask under argon atmosphere and magnetical stirring, the hydroxythiazol (1 eq) was dissolved in DCM, tetrabutyl ammonium iodide (6 eq) and diisopropylamine (13 eq) were added. After addition of 3Å sieve, the mixture was stirred for 1 hour.

In an other flask, penta-O-trimethylsilyl-mannose was dissolved in DCM, cool to ° C., and iodide trimethylsilyl was added. The mixture was stirred 10 min, and the solvent was removed by co-evaporation with benzene. After 3 addition of benzene, the residue was dissolved in DCM, add to the first mixture and stirred during 20 h.

The mixture was filtrated, and then dissolved in methanol. H+ amberlyst was added and the medium was stirred 1 hour, then filtered concentrated under vacuum, and purified on silicagel column chromatography (DCM/MeOH, 95:5-8-2) to obtain a yellow powder.

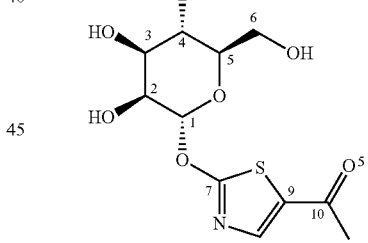

White powder
M=305.03 g·mol$^{-1}$
C$_{11}$H$_{15}$NO$_7$S $^1$H NMR (400 MHz, MeOH): δ (ppm): 8.21 (s, 1H, H8), 5.57 (d, $^3$J=1.2 Hz, 1H, H1), 3.97 (dd, $^3$J=1.2/3.2 Hz, 1H, H2), 3.90 (dd, $^3$J=2.3/12.1 Hz, 1H, H6), 3.80 (dd, $^3$J=5.2/12.1 Hz, 1H, H6'), 3.75 (t, $^3$J=9.6 Hz, 1H, H4), 3.64 (dd, $^3$J=3.2/9.5 Hz, 1H, H3), 3.44 (ddd, $^3$J=2.3/5.2/9.6 Hz, 1H, H5), 2.41 (s, 3H, H11)

$^{13}$C NMR (100 MHz, CDCl$_3$): δ (ppm): 191.4, 172.3, 135.7, 120.3, 83.5, 81.5, 74.9, 71.3, 67.5, 62.3, 25.0

FT-IR: (ATR en cm$^{-1}$)

[α]$_D$=

MS, ESI m/z: [m+Na$^+$]=328.0

HRMS, ESI: [MNa$^+$]$_{calc}$=328.04614 Da, [MNa$^+$]$_{mes}$=328.04562 Da

Example 18: Cellular Binding Studies of Mannose-Derivatised Cyclodextrin Compounds 1-4 Regarding *E. coli* Urinary Tract Infections

Example 18.1: Results

Haemagglutination Inhibition Assay (HIA)

Inhibitions of the haemagglutination (HIA) mediated by the FimH adhesion that is displayed as the fimbrial tip adhesin of type-1 fimbriated *Escherichia coli* uropathogenic strains, allow a first biological evaluation of the multivalent character of the newly synthesized glycoconjugates. Haemagglutination is observed as the red blood cells being held in suspension through the formation of a space-filling cross-linked network with the fimbriated bacteria.

Binding affinities of the mannose-deriatized β-cyclodextrin compounds 1 (example 2bis), 2 (example 1), 3 (example 2bis) and 4 (example 2) for type-1 piliated clinical *E. coli* isolate UTI89 were evaluated by HIA. Assays were repeated three times at three different bacteria concentrations. n-heptyl α-D-mannoside (HM), a potent monovalent FimH inhibitor, has been included in the assay as a reference. Multivalent effects were estimated by comparing monovalent derivatives 1 and 3 with heptavalent ligands 2 and 4, respectively.

The dramatically decreased affinity for FimH evidenced by ITC upon tethering HM to the β-cyclodextrin (CD) core is also reflected in the haemagglutination assay (Table 3). Indeed, a >16 fold increased titer is observed when comparing monovalent derivatives 1 and 3 with HM in the different bacteria concentration. This significant loss in affinity is likely due to the CD core rather than the triazole or tether moities. Indeed, we previously shown that monovalent HM references bearing the latter functional group conserves the bacterial affinity in HAI (Gouin, S. G. et al., *Chem Med Chem* 5, 749-55 (2009); Almant, M. et al. *Chem. Eur. J.* 17: 10029-10038 (2011).

High relative inhibitory potency (RIP) value, ranging from 62 to 256, are obtained with the titer ratios 2/1 and 4/3. On a per mannose molar basis (values divided by the seven tethered epitopes), this corresponds to a significant multivalent effect, with a 9 to 36 fold enhancement. However, these values may be overestimated and should be interpreted with caution considering that monovalent derivatives 1 and 3 are several ten-fold less potent than HM. When HM was selected as reference, RIP values ranged from 2 to 8 for 2/HM and 4/HM, indicative of a statistical enhancement at best. These results clearly highlight the difficulty in selecting a relevant reference to estimate potential multivalent effects. In particular, it shows that monovalent ligands having the closest chemical structures with their multivalent counterparts are not necessarily the most relevant references.

TABLE 3

Minimal inhibitory concentrations (MIC, in μM) of HM and of the synthetic glycoconjugates 1-4 on the haemagglutination by the UTI89 *E. coli* strain of guinea pig erythrocytes. Different bacterial concentrations latter are expressed in number of colony forming units (CFU) per ml), the lowest is just above the hemagglutination titer. Relative inhibitory potencies (RIP) present the improvement in MIC compared to a selected reference.

| UTI89 (CFU/ml) | HM | 1 | 2 | 3 | 4 |
|---|---|---|---|---|---|
| 7 10$^7$ | 0.98 | 63 | 0.24 | 31 | 0.5 |
| 1.4 10$^8$ | 1.50 | 100 | 0.39 | 50 | 0.2 |
| 1.2 10$^9$ | 12.5 | >200 | 1.56 | 200 | 3.1 |

| RIP | 2/1 | 4/3 | HM/1 | HM/3 | 2/HM | 4/HM |
|---|---|---|---|---|---|---|
| | 263 | 62 | 64 | 32 | 4 | 2 |
| | 256 | 250 | 67 | 33 | 3 | 7 |
| | >128 | 65 | >16 | 16 | 8 | 3 |

Isothermal Calorimetry, Affinity for FimH

The interactions of 1, 2, 3 and 4 with the monovalent lectin domain of FimH were measured using isothermal calorimetry (ITC). Each compound was titrated into a FimH solution in the VP-ITC measurement cell, to obtain the overall binding enthalpy and entropy. Also, FimH was titrated in the reverse manner to the ligands 2 and 4 in the cell, to observe distinct binding events consequent to locally high, but overall limiting, FimH concentrations. These latter conditions can be more biologically relevant in the context of the encounter of type 1-fimbriated *E. coli* with high-mannosylated glycoproteins on epithelial membranes. The affinity of FimH for the monovalent ligands 1 and 3 were in the micromolar range (Table 4), which is significantly less than for free HM but indicative of the recognition of only mannose. This is possibly a result of the inclusion of the hydrophobic part of HM in the γ-CD cone.

Figure 20:
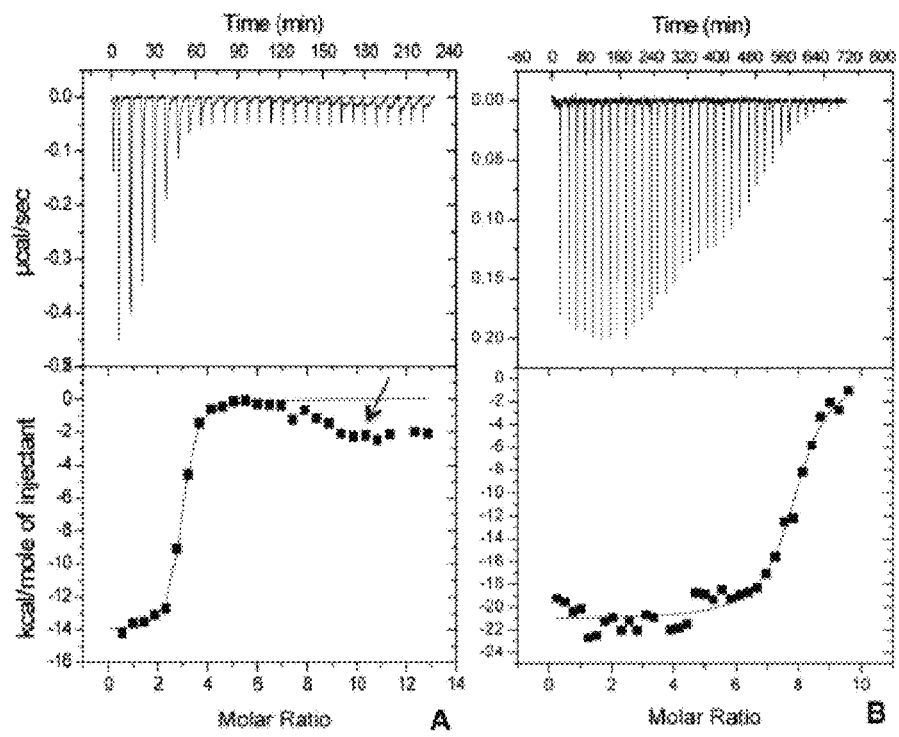
FIG. 20 presents reverse ITC with compound 2 (FIG. 20A) and 4 (FIG. 20B).
Figure 21:
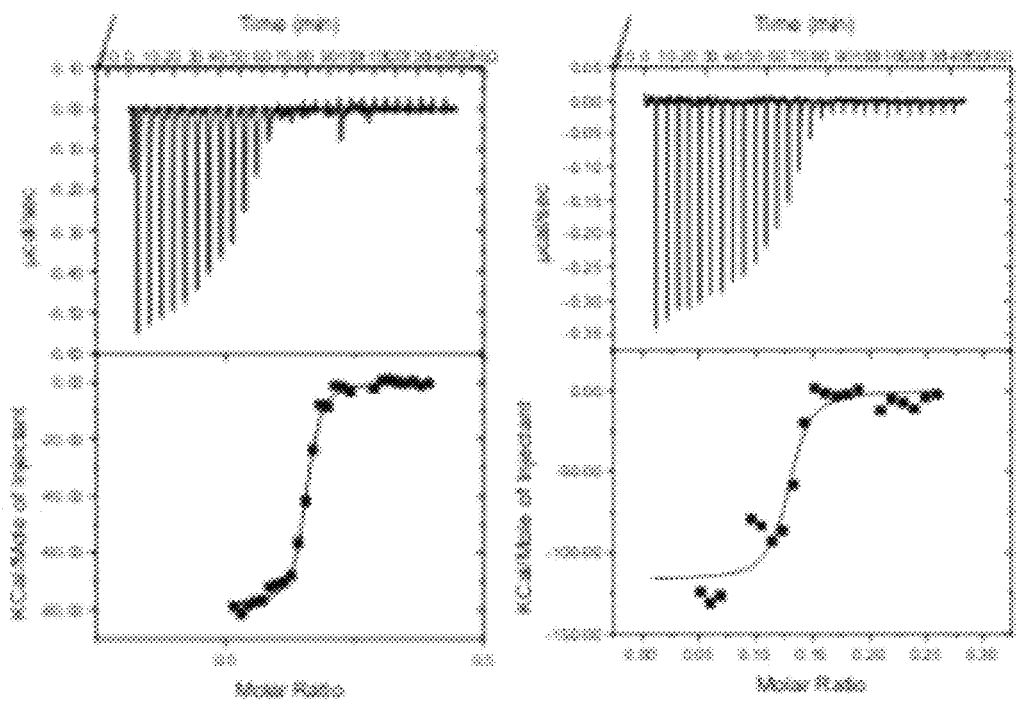
FIG. 21 presents direct titrations of 30 μM of ligand 2 into 20 μM of the FimH lectin domain (left) and of 12 μM of ligand 4 into 10 μM FimH.

The ITC data show that both 2 and 4 have nanomolar affinities for FimH and are functionally multivalent (Table 4, FIGS. 20 and 21). Titrations with heptavalent ligand 4 have a larger molar ratio n, near the structural valency of 7, confirmed by a larger enthalpy contribution compensated by a larger entropic loss compared to 2. Ligand 2 has a similar affinity for FimH as 4 despite its lower functional valency with molar ratio n=3 from the resulting fit of the reverse titration.

We propose that the high-affinity complex ($K_d$=2.86±0.03 nM) of 3 FimH molecules with 2 is trapped under the reverse titration conditions of locally high, but overall limiting, FimH concentrations (Table 4). In contrast, derivative 4 reaches full occupancy (n=7-8) with FimH in a single step. Apparently, the longer ethylene glycol linkers to the HM ligand make it easier for FimH to bind all seven mannosides simultaneously.

TABLE 4

| Cpd | $K_d$ (nM) | ΔG° (kcal·mol⁻¹) | ΔH° (kcal·mol⁻¹) | ΔS° (cal/mol/deg) | Molar ratio $n^{meas}$ |
|---|---|---|---|---|---|
| 1[1] | 1639 (±884) | −7.8 | −7.2 (±0.7) | 2.2 | 0.35 (±0.03) |
| 1[2] | 625 (±123) | −8.4 | −5.6 (±0.1) | 9.7 | 0.36 (±0.007) |
| 2 | 18.2 (±2.8) | −10.5 | −77.5 (±0.9) | −227 | 0.12 (±0.001) |
| 3[1] | 4566 (±953) | −7.2 | −10.0 (±0.8) | −9.6 | 0.45 (±0.03) |
| 3[2] | 1946 (±534) | −7.7 | −4.8 (±0.9) | 9.9 | 0.57 (±0.02) |
| 4 | 6.6 (±3.2) | −11.0 | −123.8 (±6.2) | −382 | 0.13 (±0.002) |
| 2 | 2.9 (±0.03) | −11.6 | −19.2 (±0.4) | −25.9 | 3.01 (±0.03) |
| 4 | 33.0 (±6.6) | −10.1 | −21.0 (±0.2) | −37.1 | 7.77 (±0.06) |

Direct isothermal titrations demonstrate low, mannose-like affinities for derivatives 1 and 3 and HM-like affinities for 2 and 4. The calorimetric data was processed to include the whole binding event[1], or exclude spiky heat signals[2]. Discrepancy in molar ration is observed for 2, depending on the direction of the titration. In the normal titration, compounds 1, 2, 3, 4 were injected into a FimH solution in the measurement cell. In the reverse titration, a solution of FimH was injected into a solution of compounds 1, 2, 3, 4 in the measurement cell. Values obtained during reverse titration experiments are indicated in the final two rows of the table.

Bacterial Crosslinking Due to Multivalency

The possibility to capture living bacteria in solution with β-CD-based glycol-clusters 2 and 4, using epi-fluorescence microscopy was investigated.

It was decided to evaluate if the FimH aggregation evidenced in ITC, DLS and SAXS could also occur when the lectin is attached at the tip of the bacteria pili. *E. coli* strain UTI89 expressing type-1 fimbriae. Said bacteria were diluted from the culture medium into PBS and glycoconjugated in a ten-fold dilution series of 2 or 4 were added. Bacterial cells were then colored with acridin orange.

Glycopolymers with high ligand valencies have been previously shown to promote bacterial clustering in solution (Disney, M. D. et al. *J. Am. Chem. Soc.* 126: 13343-13346 (2004). The same phenomena was also observed with the β-CD-based glycol-clusters 2 and 4 (FIG. 1). The formation of bacterial clusters by the glycoconjugates can be explained by their potency to cross-link at least two FimH belonging to different bacteria. These results are coherent with the ITC experiments, showing that multivalent 2 and 4 aggregates FimH molecules.

Anti-Adhesives for Bacterial Bladder Cell Binding

The anti-adhesive capacities of the HM-derivatized cyclodextrins 1-4 were tested in vitro on the bladder cell line 5637, in a procedure analogous as previously described (Wellens, A. et al., *PLoS ONE* 3: e2040 (2008)). The CD conjugates 1-4 were diluted in a ten-fold series. The minimum inhibitory concentrations (MIC) indicate the concentrations of sugars at which we see some inhibition of binding of FimH to the bladder cells, they do however not indicate complete inhibition. MIC values for the CD-conjugates 1-4 followed a similar trend as the inhibitory concentrations recorded in HIA. Heptavalent compounds 2 and 4 were much more potent than their monovalent analogues at inhibiting the bacterial adhesion to the bladder cells. The heptavalent CD-conjugate 2 with short-size linkers still displayed one of the highest inhibitory potencies.

TABLE 5

Anti-adhesive potency of the CD conjugates 1-4 on bladder cell line 5637

| | HM | 1 | 2 | 3 | 4 |
|---|---|---|---|---|---|
| MIC (μM) | 4 | >400 | 0.4 | >400 | 4 |

Reduction of Bacterial Load In Vivo—Preventing Urinary Tract Infections

Figure 19:
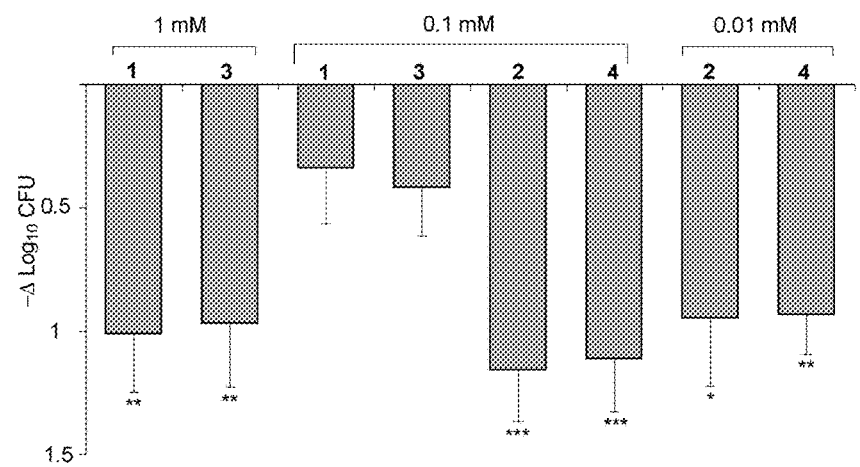
FIG. 19 presents the in vivo-inhibition in the murine cystitis model. The bar diagrams means the logarithmic average bacterial count reduction per group (n=10) compared to untreated mice (n=14, baseline). Y error bars represent the standard error of the mean and asterisks the significant statistical results of each treated group comparing to the untreated group by Mann-Whitney test. * $p<0.001$  $p<0.01$ * $p<0.05$.

In vivo inhibition was evaluated by instilling 1-4 together with the UTI89 strain via a catheter in the bladder of C3H/HeN mice. The present study is the first in vivo evaluation of multivalent anti-adhesive compounds in the UTI mouse model. Instillations of the designed glycoconjugates with the *E. coli* strain UTI89 inhibit the binding of FimH to mannosylated uroplakins displayed at the epithelial linings of the bladder. A group of ten animals was used for each concentration of antagonists. Reduction in the bacterial counts are expressed by substracting the mean value obtained for the untreated animals (n=14, 5.47±0.18 $Log_{10}$ CFU, baseline of FIG. 19). The animals were sacrificed at a 6 h post infection time.

The level of infection was reduced 10-fold for instillations of 1 mM of the monovalent derivatives 1 and 3. We previously observed a similar level of inhibition with 5 mM of HM in the mouse bladder at 1 hour post infection, for the same significance (Wellens, A.; Garofalo, C.; Nguyen, H.; Van Gerven, N.; Slättegård, R.; Hernalsteens, P.; Wyns, L.; Oscarson, S.; De Greve, H.; Hultgren, S. J.; Bouckaert, J. *PLoS ONE* 2008, 3, e2040). Decreasing the concentration of monovalent HM derivatives 1 and 3 to 0.1 mM led to an important drop in the inhibition efficiency. High concentrations of HM and HM conjugates 1 and 3 are therefore required for a significant inhibitory efficiency in vivo.

Importantly, the reduction of infection was much higher with heptavalent derivatives 2 and 4 at lower concentrations. A 100-fold lower concentrations (10 μM) of multivalent derivatives 2 and 4 compared to the monovalent HM derivatives 1 and 3 (1 mM) still achieve an equivalent bacterial reduction. Multivalent 2 and 4 were injected to the animals at very low dose of 1.8 and 2.5 μg respectively. The spacer arm length did not significantly impact the inhibitory values, the two sets of compounds 1,3 and 2,4 behave very similarly at the different concentrations tests.

Example 18.2: Materials and Methods

Inhibition of Haemagglutination

The UIT89 clinical isolate was grown statically 37° C. for 48 hours in LB medium and analysed for haemagglutination of guinea pig red blood cells. Both bacteria and red blood cells (RBCs) were washed 3 times in ice-cold PBS (17 mM K/$NaH_2PO_4$, 150 mM NaCl). PBS was used for all dilutions. 96-well round-bottom microtiter plates were used for the dilutions. The titer for agglutination was determined in a 2-fold dilution series in PBS of the bacteria in a volume of 25 μL. Well 1 is a negative control without bacteria but 25 μL PBS. 25 μL PBS and 50 μL 5% RBCs were added to a final 100 μL volume. Upon 1 hour at 4° C., the titer was determined as the lowest concentration of bacteria that led to haemagglutination.

A bacterial concentration of twice the determined haemagglutination titer was kept constant in the haemagglutination inhibition assays. First, a 2-fold dilution series of the inhibitory compounds was performed in 25 μL PBS. Instead, in well 1 only 25 μL PBS was added as a negative control. 25 μL of the bacterial solution and 50 μl of 5% red blood cells were added to reach a final volume of 100 μL. The plate was left at 4° C. for 1 hour before read-out minimum inhibition concentration (MIC) is here presented.

Epifluorescence Microscopy:

UTI189 *E. coli* strains were grown statically overnight in LB at 37° C., washed (3 times) and diluted in PBS (137 mM NaCl, 2.7 mM KCl, 10 mM $Na_2HPO_4$, 1.76 mM $K_2HPO_4$, pH 7.4) to an $OD_{600\ nm}=1$. 100 μl of glycoconjugate-agglutinated *E. coli* were washed in 1 ml PBS, resuspended in 200 μl 0.1% acridin orange and left at room temperature for 2.5 hours. The bacterial cells were washed again in 1 ml PBS to remove unbound acridin orange. A microscope glass was rinsed with 100% EtOH and next dried at the air. A 5 μl cell suspension was put on the microscope glass, dried at the air and visualised using a laser with excitation wavelength of 408 nm.

Bladder Cell Binding

The anti-adhesive capacities of the n-heptyl α-D-mannoside-derivatized cyclodextrins 1-4 were tested in vitro on the bladder cell line 5637, in a procedure analogous to as described in (Wellens, A. et al., PLoS ONE 3: e2040 (2008)). The ligands have been diluted 10-fold and this is also the resolution limit of these tests.

Procedure for In Vivo Experiments

A murine model of urinary tract infection was used to test the ability of the compounds to inhibit the colonization of UTI89 in the bladder [Hung C. S.; Dodson, K. W., Hultgren S. J. *Nat. Protoc.* 2009, 4, 1230-1243 and Wellens A.; Garofalo C.; Nguyen H.; Van Gerven N.; Slättegård R.; Hernalsteens, J.-P.; Wyns, L.; Oscarson, S.; De Greve H.; Hultgren S. J.; Bouckaert, J. *PLoS ONE* 2008, 3, e2040]. The solution with high concentration of compounds was added to the resuspension of UTI89 before given to the mice. The eight-week old Female C3H/HeN mice (Harlan, Horst, The Netherlands) were anesthetized and infected via transurethral catheterization of $10^7$ CFU UTI89 in solution in PBS, or in PBS with the compound in the mentioned concentration. The mice were sacrificed at 24 hours post infection and the bladders were harvested, homogenized and resuspended in PBS. The serial dilutions were spot on LB medium agar plates. The bacterial load was determined by counting the CFU recovered from the bladder. The animal experiments were approved by the Ethical Committer for Animal Experiments of Vrije Universiteit Brussel and complied with all relevant national legislation and institutional policies. The Mann-Whitney test was applied for the comparison of the data obtained from the untreated group and inhibition group in GraphPad Prism version 5.1 and two tailed P value were shown (GraphPad software).

Figure 2:
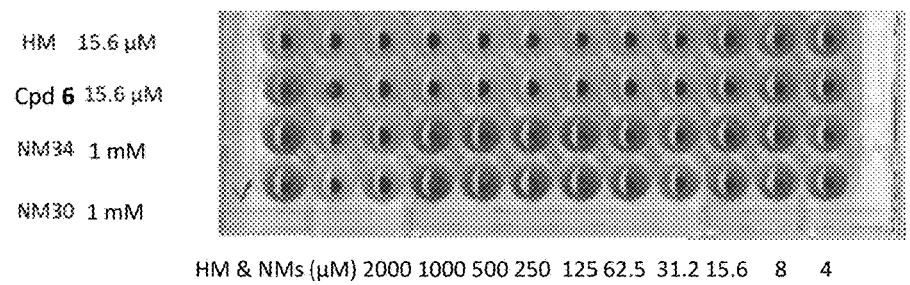
FIG. 2 presents the inhibitory potency of the compound 6 (example 3), mannoside derivative that is equivalent to the one for HM. The non-effectiveness of heterocycles NM34 (example 17bis) and NM30 (example 17 bis) directly coupled to the mannose ring is demonstrated.

Example 19: In Vitro Binding Studies of Heterocycle-Mannoside Compound 6 (Example 3) Regarding *E. coli* Infections Inhibition of Haemagglutination Interaction of *E. coli* FimH adhesins with the glycocalyx of guinea pig erythrocytes forms a cross-linked network into the wells. Glycoconjugates added in a two-fold dilution series prevents the agglutination reaction. The inhibition titer is defined as the lowest concentration of the glycoconjugate at which haemagglutination is still inhibited. UTI89 *E. coli* were grown statically overnight in LB at 37° C., washed three times in ice-cold phosphate-buffered saline and resolubilized. A two-fold dilution of glycoconjugates was prepared in 25 μL 20 mM HEPES pH 7.4 with 150 mM NaCl, starting from 1 mM as the highest concentration. The bacterial solution (25 μL) was added to the two-fold dilution series of the compound. Finally 50 μl of guinea pig red blood cells, washed in buffer and diluted to 5%, were added to a final 100 μL and left on ice for 30 min. before read-out. Due to serial dilutions, the maximal error is ±one well, or a factor two (FIG. 2).

Surface Plasmon Resonance

The affinity of the compounds was first evaluated and then measured in a surface plasmon resonance solution competition assay. The lectin domain of FimH was expressed as described previously and purified at pH 4.0 in 50 mM HCOOH on a SPFF (sulfopropyl fast flow) ion exchange column (GE Healthcare). A CM5 sensor chip (Biacore, GE Healthcare) has been coated with a layer of amino-functionalized monovalent heptyl mannoside to 60 RU (response units) and the kinetics of FimH binding to the sensor chip has been determined. All data collection have been performed in HBS buffer complemented with 3 mM EDTA and 0.01% Tween20. Regeneration was done with a single 10 s injection of 100 mM NaOH in water. A solution affinity inhibition experiment was set up as follows: a constant FimH concentration (concentration B, a parameter that is fitted in the solution affinity equation) was inhibited with a series of 24 increasing concentrations (0-750 nM) of the compound (concentrations A, a variable in the solution affinity equation). The kinetic constants, $k_a$ and $k_d$, and $R_{max}$, derived from the prior experiment, were kept constant to determine the non-inhibited FimH concentrations that displayed binding to the heptyl mannoside on the chip.

The solution affinity provided by the Biacore software uses the equation $(B-A-Kd)/2+(0.25*(A+B+Kd)^2-A*B)^{0.5}$, with B presenting the uninhibited concentration of FimH, and A the variable compound concentration.

TABLE 6

Solution affinity measurements for NM30 (example 17 bis), NM34 (example 17 bis), and compound 6 (example 3) by inhibition FimH binding to amino-octyl α-D-mannoside immobilized onto a CM5 sensor chip (Biacore3000). Results were repeated with 2 different batches of purfied FimH protein and synthesized compound 6.

| Compound | Kd (nM) |
|---|---|
| NM30 (example 17 bis) | 920 |
| NM34 (example 17 bis) | 2370 |
| Compound 6 (measurement 1) | 216 |
| Compound 6 (measurement 2) | 220 ± 7.71 |

Isothermal Titration Calorimetry

Figure 4:
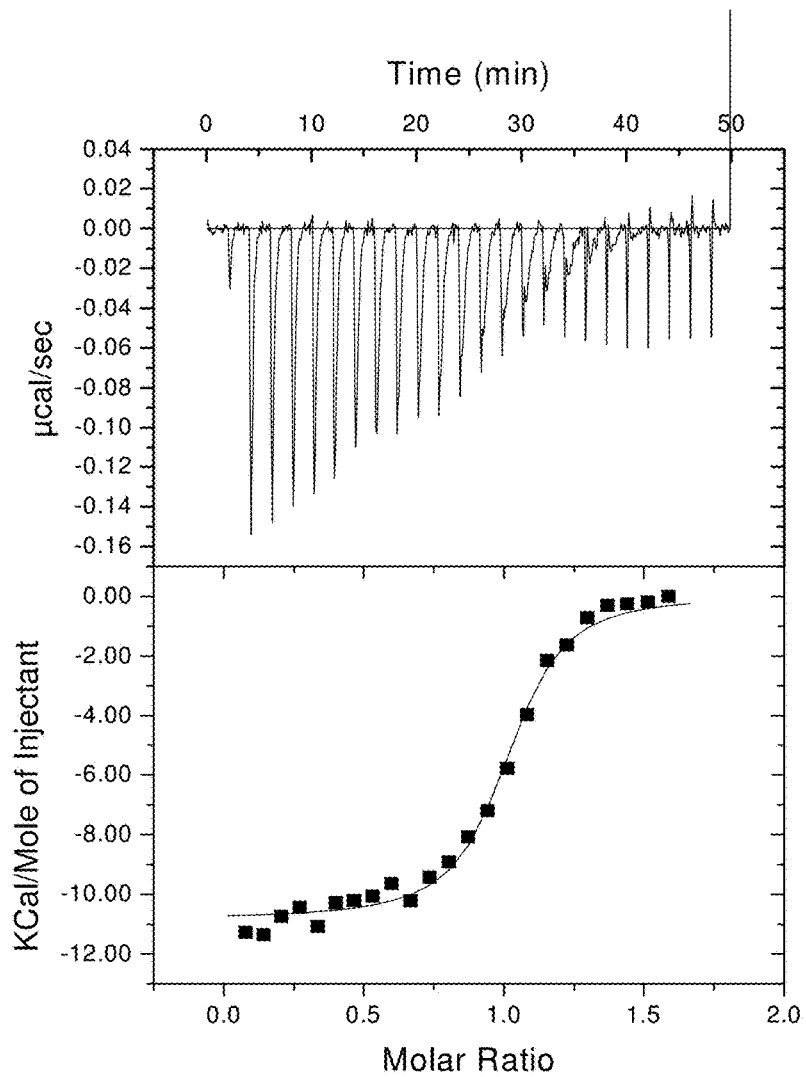
FIG. 4 presents calorimetric measurements with compound 6.

For compound 6 (example 3), the enthalpy, the affinity equilibrium constant $K_a$ and the molar ratio have moreover been measured using ITC. Integrated heat effects were analyzed by nonlinear regression using a single-site binding model (Origin 7.0). The experimental data fitted to a theoretical titration curve gave the association constant (Ka), the enthalpy of binding (ΔH) and the molar ratio n. The entropic contribution to the affinity and the change in Gibbs free energy (ΔG) have been calculated from the equation ΔG=ΔH−TΔS=−RTlnKa, where T is the absolute temperature and R is the molar gas constant (8.314 J·mol−1·K−1). ITC measurements indicate an affinity of 197 nM of FimH for compound 6, very similar to the values reported using surface plasmon resonance measurements (FIG. 4).

Crystal Structure of FimH in Complex with Heterocycle Derivatized Mannoside Compound 6

Figure 5:
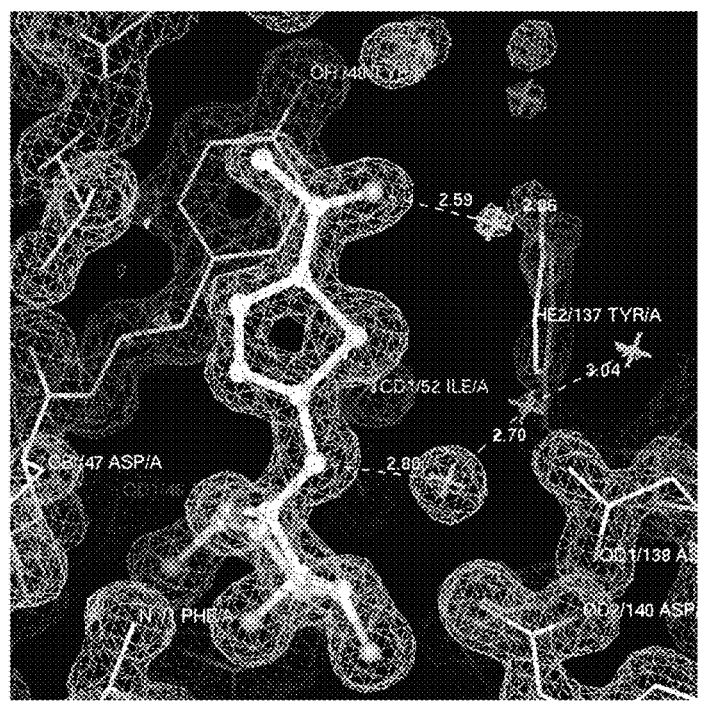
FIG. 5 presents interactions of compound 6 with FimH in a crystal obtained by FimH-compound 6 co-crystallization. The electron density is displayed in blue.

The crystals resulted from co-crystallizations of 10 mg/ml FimH with 2 mM of compound 6 in a sitting drop vapour diffusion experiment using 20 mM Na/K phosphate, 0.1 M Bis Tris propane pH 6.5, 20% (w/v) PEG 3350 as the precipitant solution. The molecular interactions between FimH and compound 6 in the crystals consist of aromatic stacking interactions with tyrosines 48 and 137 (mature FimH sequence numbering) as well as water-mediated hydrogen bonding through the carboxylmethyl group with Tyr137 (FIG. 5).

Example 20: Pharmacokinetics Using Dynamic Imaging, Pharmacokinetics and -Distribution Using Dissections, In Vivo Inhibition of Colonization of the Mouse Bladder Example 20.1: Results In Vivo Pharmacokinetics and -Distribution, Bladder Targeting and Retention each dose at the later time points of 1 h, 3 h, 6 h and 24 h only for the lowest dose. Dissection allowed measurement of activity per gram (% of the injected activity per gram organ) in the kidneys, the liver and bladder. These time points were chosen to cover the pathogenic cycle of UTI89 in the C3HHeN mouse: 0-6 hours adhesion, invasion and early IBC (intracellular bacterial communities) formation, 6-12 h (maturation into mid-IBCs), from 16 h and on: fluxing out of bladder wall, spreading in filamentous shape into the bladder lumen and re-initiation of the IBC cascade (Justice, S. S. et al. *Proc. Natl. Acad. Sci. U.S.A.* 101: 1333-1338 (2004)). All radioactivity measurements have been corrected for decay. The pharmaco-distributions experiments made use of 3 concentrations (3/60/300 µg) to examine the effect of dose on bio-distribution. The final dissection of heart, lungs, kidneys and liver and blood collection was performed to understand how much of the compound remained in the animal.

The blood distribution curve (FIG. 7B) confirms the low activity remaining in the blood after 30 minutes. The highest dose of 300 µg shows a clearly elevated blood activity, which can equally be observed in the distribution analyses by dissection (Table 7).

TABLE 7

Activities of 5 in mouse organs, including the bladder

| | 3 µg % IA/G | | | | | 60 µg % IA/G | 300 µg % IA/G |
|---|---|---|---|---|---|---|---|
| Time | 30 min | 1 h | 3 h | 6 h | 24 h | 30 min | 30 min |
| Heart | 4.08 ± 0.85 | 3.66 ± 0.96 | 2.93 ± 0.26 | 2.91 ± 0.29 | 3.27 ± 0.26 | 1.80 ± 0.34 | 0.96 ± 0.16 |
| Lungs | 2.33 ± 0.42 | 2.34 ± 0.44 | 1.69 ± 0.23 | 1.93 ± 0.36 | 1.58 ± 0.09 | 1.64 ± 0.32 | 1.49 ± 0.29 |
| Liver | 6.50 ± 1.26 | 5.56 ± 0.77 | 4.98 ± 0.45 | 5.10 ± 0.63 | 5.69 ± 0.50 | 4.26 ± 0.36 | 2.43 ± 0.14 |
| KidneyL | 3.83 ± 0.80 | 1.89 ± 0.26 | 1.57 ± 0.08 | 1.64 ± 0.20 | 1.51 ± 0.28 | 3.07 ± 1.04 | 4.36 ± 0.38 |
| KidneyR | 3.33 ± 0.41 | 1.98 ± 0.41 | 1.61 ± 0.15 | 1.46 ± 0.12 | 1.44 ± 0.26 | 4.72 ± 2.80 | 4.00 ± 0.70 |
| Blood | 0.66 ± 0.19 | 0.27 ± 0.02 | 0.21 ± 0.01 | 0.18 ± 0.04 | 0.10 ± 0.01 | 0.77 ± 0.09 | 1.45 ± 0.34 |
| Bladder | 5.06 ± 4.21 | 2.92 ± 1.36 | 1.37 ± 0.17 | 1.39 ± 0.24 | 2.08 ± 0.79 | 1.22 ± 0.46 | 2.19 ± 2.82 |

Dynamic Imaging

Figure 6:
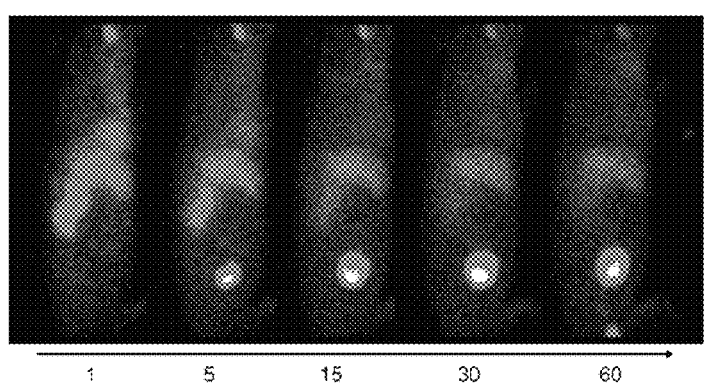
FIG. 6 presents an image sequence of dynamic acquisition. Image acquisition was performed with a left lateral positioning using a γ-camera, mounted with a pinhole collimator, for 60 images of 1 minute. C3H/HeN mice (n=3) were intravenously injected with 57-76 MBq of Tc-labeled compound 5 (3 μg/animal) to allow real time imaging.

C3H/HeN mice (n=3) were intravenously injected with 57-76 MBq of compound 5 (radiolabeled compound 5, example 2bis) (3 µg/animal) to allow real time imaging of the glyco-conjugated CD derivatives (FIG. 6). Image acquisition was performed with a left lateral positioning of the animal using a γ-camera, mounted with a pinhole collimator, for 60 images of 1 minute.

The image processing took into account a sensitivity correction for the pinhole opening. Regions Of Interest (ROIs) were drawn over the total body, liver, kidneys, bladder and heart and results were expressed in % of injected activity (% IA).

Figure 7:
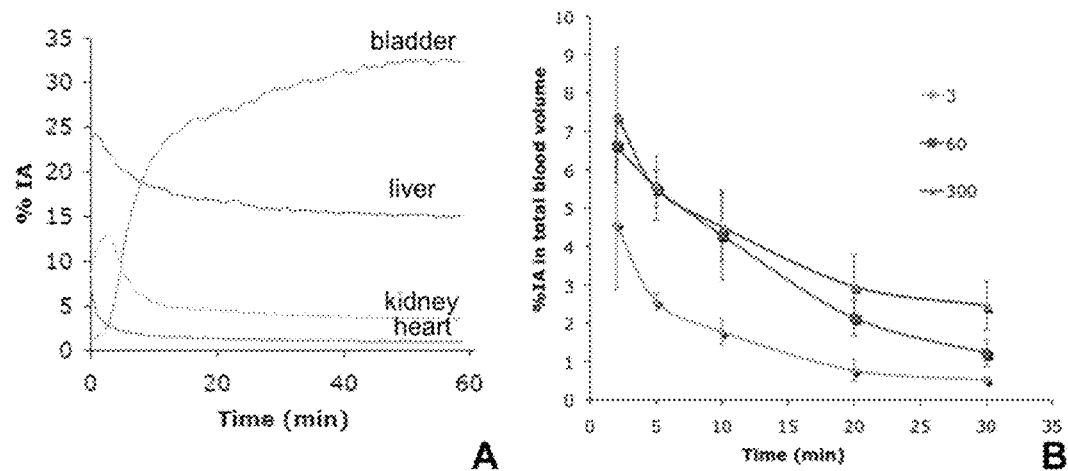
FIG. 7A presents the distribution of Tc-labeled 5 (example 2bis) in the heart, liver, kidney and bladder by processing of dynamic images.
FIG. 7B presents the percentage of injected activity in blood versus time. The blood curves (3, 60 or 300 μg) show a rapid clearance of 5 through the kidneys (no recycling) into the bladder.

Image processing allowed quantification of the tracer compound 5 in the bladder (locus of potential bacterial infections) (FIG. 7). The activities are decrease in the heart, liver and kidney, but not in the bladder. Analyses of these preliminary results in three mice indicate that 20% of 5 reached the bladder in only about 5 minutes upon injection and more than 30% of tracer 5 after 1 h (FIG. 7A). 15-20% settles in the liver and less than 5% remains in the kidneys (indicating no recycling) (FIG. 7B).

Blood sampling was performed at 2, 5, 10, 20 and 30 minutes time points using three different doses (3 µg, 60 µg and 300 µg) of the $^{99m}$Tc-chelated tracer molecule 5, with four mice for each time point. Moreover, the distribution of 5 in major mouse organs was followed by dissections, for The activities in the other organs: lungs, kidneys, blood and bladder, keep on decreasing over the 24 hours period, indicating that the kidneys not recycle the compound and that the blood can unhinderedly clear the glyco-conjugate 5 from the blood through the kidneys into the bladder.

Liver and heart demonstrate an almost stable activity of 5 over 24 h. Increasing the dose of 5 decreases their percentage of activity (30 min. time point), whereas the percentage increases in the blood. This means that 5 is retained less in the liver and heart but more in the blood before being filtered through the kidneys into the bladder. Higher doses of 5 thus give rise to higher concentrations of the β-CD derivatives in the bladder.

In Vivo Inhibition in a Murine Cystitis Model

Figure 8:
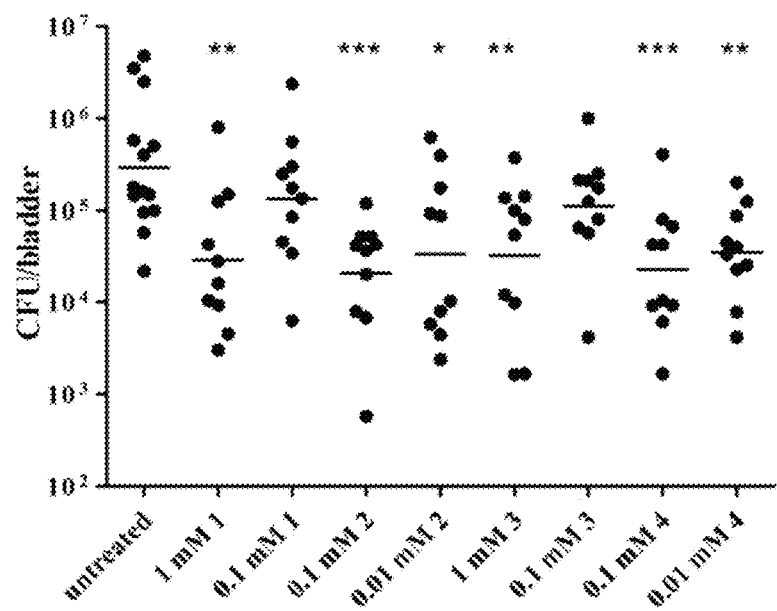
FIG. 8 presents the In vivo inhibition assay in the murine cystitis model C3H/HeN. The horizontal line in each column means the average in each group. Asterisks represent the significant statistical results of each treated group comparing to the untreated group by Mann-Whitney test. * $p<0.001$  $p<0.01$ * $p<0.05$.

In vivo inhibition was evaluated by instilling glycoconjugate compounds 1-4 together with the UTI89 strain via a catheter in the bladder of C3H/HeN mice. A limited number of papers described the in vivo efficiency of anti-adhesive mannosides to treat UTIs. Interesting studies have shown that monovalent mannosides bearing hydrophobic aglycons can reduce bacterial level in vivo. To the best of the knowledge of the inventors, the present study is the first in vivo evaluation of multivalent anti-adhesive compounds in the UTI mouse model. Instillations of the designed glycoconjugates with the *E. coli* strain UTI89 inhibit the binding of FimH to mannosylated uroplakins displayed at the epithelial linings of the bladder (FIG. 8). The level of infection was reduced by 5-10 folds when the heptavalent derivatives 2 and 4 were added at 0.01 mM (which corresponds to a dose of only 2 µg per mouse). A 1 mM concentration of the monovalent derivatives 1 and 3 has to be employed to achieve equivalent levels of inhibition. Monovalent 3 and heptavalent 4 with the longer spacers were better inhibitors than their analogues 1 and 2 bearing short-linkers, respectively. Such level of invasion inhibition (p≤0.01) was previously observed with HM, but at the higher concentration of 5 mM (1 hour, dissecting invasion and luminal).

Altogether, the results suggest that the multivalent HM-conjugate reach and accumulate quickly in the bladder with a long retention time in the body, and these are two important requirements for a treatment of UTI by a (single-shot) intravenous injection. An injected mass of 60 µg would have a significant inhibitory effect on bacterial adhesion, in the case that 20% (12 µg) reaches the bladder as pointed out by the dynamics study (FIG. 7A). Indeed, this dose would surpass the 2 µg (0.01 mM) of 2 or 4 required in the bladder for a significant bacterial reduction (FIG. 8). After 24 h, the concentration of multivalent antagonists would continue to inhibit the bacterial adhesion as suggested by the pharmacodistributions performed with 3 µg of 5, where the % IA/g are only reduced to about 40% between 30 min to 24 h (Table 7).

Only around 2 µg of heptavalent 2 and 4 instilled in the mouse bladder significantly reduced the urinary tract infection after 24 h, and at around 100-fold lower doses than the monovalent references 1 and 3 or HM. It seems therefore that designing multivalent HM derivatives is not only relevant for the in vitro inhibition of bacterial adhesion but also give supplementary improvements in vivo. These results strongly suggest that multivalent ligands may not only increase anti-adhesive properties in vitro but also in vivo by reducing the initial number of bacteria able to adhere to and invade bladder epithelial linings.

In contrast to monovalent mannosides, multivalent derivatives are less likely to be orally available. However, the long retention times of β-CD HM derivatives in the body at concentrations in the bladder sufficient to inhibit bacterial adhesion make these FimH antagonists suitable drug candidates against urinary tract infections by single-shot intravenous administration. The multivalent FimH antagonists 2 and 4 may also be of interest for the treatment of other infections involving type 1 piliated *E. coli*, thus to evaluate their anti-adhesive effect on adherent-invasive *E. coli* inducing gut inflammation in patients with Crohn's disease.

Example 20.2: Materials and Methods for Dynamic Imaging and Pharmacodistributions Dynamic Imaging Injection of tracer compound 5 with activities of 2.014 mCi, 1.644 mCi and 1.554 mCi, respectively, in the eye vein of three C3HHeN mice was done to allow real time imaging in C3H/HeN. Image acquisition was performed with a left lateral positioning total-body pinhole SPECT scan using a dual-head γ-camera, mounted with 2 multi-pinhole collimators (3 pinholes of 1.5 mm in each collimator, 200-mm focal length, 80-mm radius of rotation, e.cam180; Siemens Medical Solutions), for 60 images of 1 minute. On both modalities, the animals were imaged in the same animal holder, which included 2 plastic discs, each containing three $^{57}$Co (3.7 MBq) sources (Canberra-Packard). A micro-CT scan was performed using a dual-source CT scanner with 60 kV and 615 mA at a resolution of 83 mm. The six $^{57}$Co sources were detected on both micro-CT and pinhole SPECT and used for alignment of CT and SPECT images. Image reconstruction was performed using filtered back-projection (Nrecon; Skyscan). Image processing took into account a sensitivity correction for the pinhole opening. Analyses of total body, liver, kidneys, bladder and heart outputs of distributions the bifunctional CD 5 in the regions of interest (ROI) expressed in % of injected activity (% IA).

Distribution by Dissections and Blood Curves

Quantitative samplings of 5 was performed using three different doses (3 µg, 60 µg and 300 µg), between 2' and 30' post-injection, with for each time point four mice. Blood curves were composed over this time period. Dissections were also performed at the later time points of 1 h, 3 h, 6 h and 24 h for the lowest dose. Dissection allowed measurement of activity per gram (% of the injected activity) in kidney, liver and bladder. These time points were chosen to cover the pathogenic cycle of UTI89 in the C3H/HeN mouse: 0-6 hours adhesion, invasion and early IBC (intracellular bacterial communities) formation, 6-12 h (maturation into mid-IBCs), from 16 h and on: fluxing out of bladder wall, spreading in filamentous shape into the bladder lumen and re-initiation of the IBC cascade (Justice S.; Hung C., Theriot J.; Fletcher D.; Anderson G.; Footer M.; Hultgren S. *PNAS* 2004, 101, 1333-8). All radioactivity measurements have been corrected for decay.

Procedure for In Vivo Experiments:
  As described in example 18.2.

Example 21: Adhesion Assays in Presence of Heptylmannoside-Cyclodextrin Compounds Example 21.1: Adhesion Assays in Presence of Heptylmannoside-Cyclodextrin Compounds of *E. coli* Adhesion Bacterial Strain and Cell Line

*E. coli* strain LF82 was isolated from a chronic ileal lesion of a patient with Crohn's disease (CD). Bacteria were grown routinely in Luria-Bertani (LB) broth overnight at 37° C. Intestinal epithelial cells T84 derived from colonic adenocarcinoma were maintained in an atmosphere containing 5% CO2 at 37° C. in DMEM/F12 (50/50) medium supplemented with 10% (v/v) heat-inactivated fetal calf serum (FCS), 1% L-glutamine, 100 000 U·l$^{-1}$ penicillin, 100 mg·l$^{-1}$ streptomycin, 25 µg·l$^{-1}$ amphotericin B.

Adhesion Assays in Presence of Mannosidic Inhibitors of *E. coli* Adhesion

T84 cells were seeded in 48-well tissue culture plates with 1.5×10$^5$ cells per well and grown for 48 h. Cells were incubated 1 h prior infection with each mannoside at a final concentration of 100; 10; 1 or 0.1 µM in complete medium without antibiotics, containing heat inactivated fetal calf serum (FCS) and were next infected with AIEC LF82 strain at a multiplicity of infection (MOI) of 10 bacteria per cell. After a 3 h incubation period at 37° C., the monolayers were washed in phosphate-buffered saline (PBS; pH 7.2). The epithelial cells were then lysed with 1% Triton X-100 in deionized water. Samples were diluted and plated onto Luria Bertani agar plates to determine the number of cfu recovered from the lysed monolayers.

Results were expressed in percentage of residual adhesion, considering adhesion level of AIEC LF82 without mannoside treatment as 100%.

Results

Figure 9:
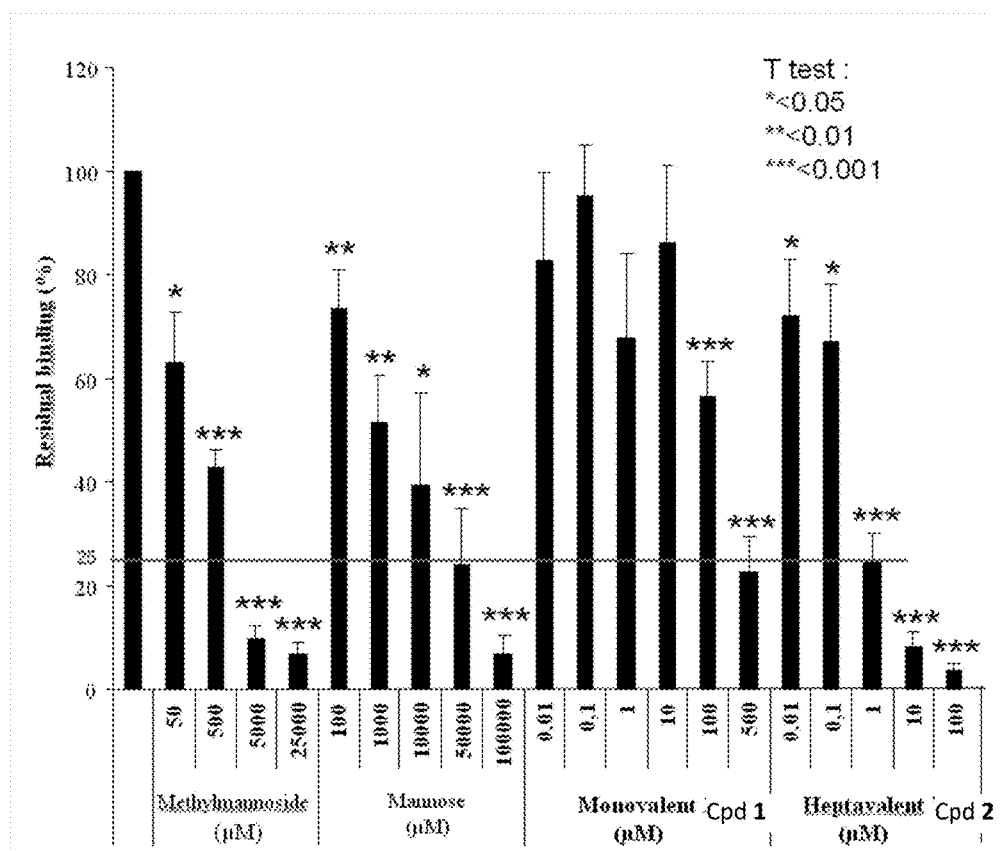
FIG. 9 presents the inhibition of AIEC bacteria adhesion to T84 intestinal epithelial cells.

Mannose, methyl-mannoside, compounds 1 (example 2bis) and 2 (example 1) were assessed on T84 intestinal epithelial cells, as inhibitors to compete with the interaction CEACAM6/FimH of AIEC bacteria (FIG. 9). Results clearly showed that increasing the potency of monovalent mannoside inhibitors for FimH (i.e. compound 1) and displaying 1 in multivalent copies on a common scaffold (i.e. compound 2) can be successfully combined to greatly reduced the AIEC bacteria adhesion to the T84 cells. Indeed, mannose, 1, 2, reached around 75% of binding inhibition (25% line), at 50000, 500, and 1 micromolar concentrations, respectively.

Example 21.2: Adhesion Assays on Intestinal Epithelial Cells of Adherent-Invasive E. coli Strains in Presence of Heptylmannoside-Cyclodextrin Compounds: Pre-, Co- and Post-Incubation Experiments Bacterial Strain and Cell Line E. coli strain LF82 was isolated from a chronic ileal lesion of a patient with Crohn's disease (CD). Bacteria were grown routinely in Luria-Bertani (LB) broth overnight at 37° C. Intestinal epithelial cells T84 derived from colonic adenocarcinoma were maintained in an atmosphere containing 5% $CO_2$ at 37° C. in DMEM/F12 (50/50) medium supplemented with 10% (v/v) heat-inactivated fetal calf serum (FCS), 1% L-glutamine, 100 000 $U·l^{-1}$ penicillin, 100 $mg·l^{-1}$ streptomycin, 25 $µg·l^{-1}$ amphotericin B.

Adhesion Assays of Adherent-Invasive E. coli Strains on Intestinal Epithelial Cells in Presence of Mannosidic Inhibitors.

T84 were seeded in 48-well plates at a concentration of $1.5×10^5$ cells per well and grown for 48 h. AIEC LF82 bacteria were incubated 1 h with each mannoside prior the cell infection (pre-incubation protocol) or they were added simultaneously onto the cells (co-incubation protocol) in complete medium without antibiotics, containing heat inactivated fetal calf serum (FCS). Heptyl-mannose or compound 2 (example 1) were tested at a dose of 100; 10; 1 or 0.1 µM. D-D-mannose was tested at a dose of 10 000; 1 000; 100 or 10 µM and compound 1 (example 2bis) was tested at a concentration of 500; 100; 10 or 1 µM. Cells were infected with AIEC LF82 bacteria at a multiplicity of infection (MOI) of 10 bacteria per cell for 3 h at 37° C. For the post-incubation protocol, mannosides were incubated with cells for 3 h after bacterial infection. A washing step was realized before this post-incubation to eliminate non-adherent bacteria. Monolayers were washed in phosphate-buffered saline (PBS; pH 7.2) and cells were then lysed with 1% Triton X-100 in deionized water. Samples were diluted and plated onto Luria Bertani agar plates to determine the number of colony-forming units (CFU) recovered from the lysed monolayers. Results were expressed as percentages of residual adhesion, considering adhesion level of AIEC LF82 without mannoside treatment as 100%.

Results

For pre- and co-incubation experiments, results clearly indicated that increasing the potency of monovalent mannoside inhibitors for FimH (i.e. monovalent cyclodextrin 1) by displaying 1 in multivalent copies on a common scaffold (i.e. multivalent cyclodextrin 2) can successfully greatly reduced the AIEC bacteria adhesion to T84 cells. Indeed, in pre-incubation assay, D-mannose, monovalent cyclodextrin 1, heptyl-mannose and multivalent cyclodextrin 2, led to decreased adhesion levels of at least 50% at 1000, 500, 10 and 0.1 µM respectively.

Interestingly, very good efficacy of the 2 compound was obtained in the post-incubation protocol, with a significant decreased adhesion at 10 µM, whereas the monovalent cyclodextrin 1, even at a dosage of 500 µM was not able to eliminate more than 40% of the bacteria adherent to intestinal epithelial cells. This effect was not related to any toxicity effect since we did not observe, even at the highest dose of each compound, any death of intestinal epithelial cells or bacteria.

Example 21.3: Adhesion Ability of Adherent-Invasive E. coli Strains in Presence of Heptylmannoside-Cyclodextrin Compounds Using Colonic Loops of Transgenic Mice Expressing CEACAM6

Bacterial Strain and Transgenic Mouse Model

E. coli strain LF82 was isolated from a chronic ileal lesion of a patient with Crohn's disease (CD). Bacteria were grown routinely in Luria-Bertani (LB) broth overnight at 37° C.

The transgenic mouse model CEABAC10 expressing the human CEACAM6 protein is available in the UMR Inserm/Université d'Auvergne 1071 led by Professor Arlette Darfeuille-Michaud at Clermont-Ferrand. This model is particularly suitable to reproduce the abnormal colonization by AIEC bacteria through the interaction with CEACAM6 molecules that were observed abnormally expressed in the ileal mucosa of Crohn's disease patients.

Adhesion Assays of Adherent-Invasive E. coli Strains in Colonic Loops from CEABAC10 Mice in Presence of Mannosidic Inhibitors.

Three colonic loops were realized in anesthetized CEABAC10 mice. A volume of 100 µl of a bacterial suspension containing $6×10^6$ bacteria/mL with or without inhibitory compound was injected into the loops (here, compound 2, example 1) or heptyl-mannose at a concentration of 100 µM). After an incubation period of 4 h, mice were euthanized and each loop was longitudinally opened, extensively washed and homogenized to numerate adherent LF82 bacteria. Bacterial adhesion was expressed as percentages of residual adhesion (100% corresponds to the adhesion in absence of any compound).

Figure 31:
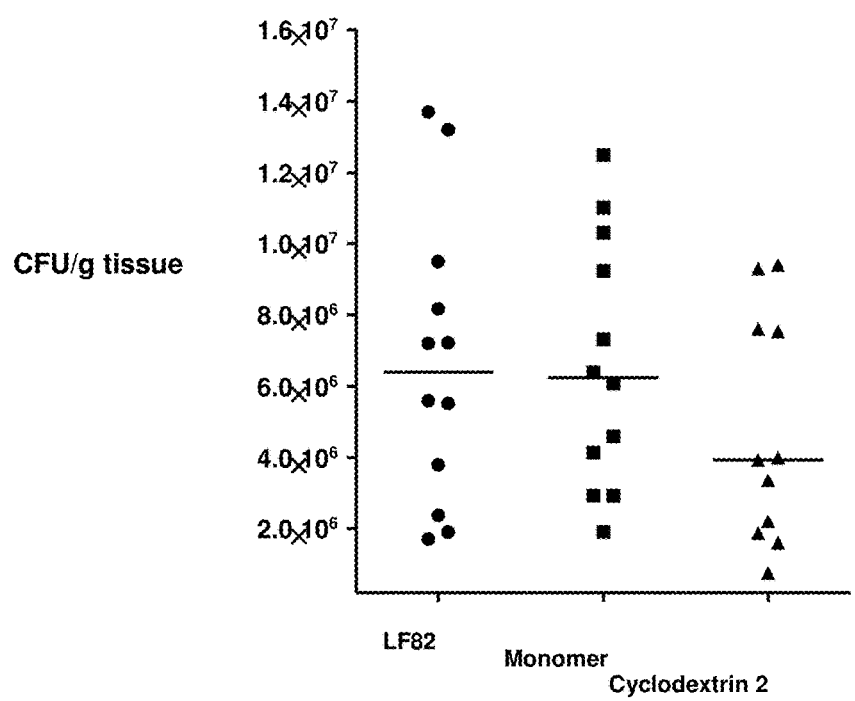
FIG. 31 presents adhesion assays of Adherent-Invasive *E. coli* strains on colonic tissue isolated from transgenic mice expressing CEACAM6 in presence of heptylmannoside-cyclodextrin compound 2 or heptyl-mannose.

Results indicated that heptyl-mannoside did not decrease significantly the bacterial adhesion at a dose of 0.1 µmol. In contrast, at this dose, cyclodextrin 2 was able to induce a two-fold decreased adhesion, compared to the adhesion observed in the absence of inhibitor (FIG. 31).

Example 22: Assays in Presence of Heterocylic Mannoside Compounds

Example 22.1: Binding Affinity for FimH

Figure 22:
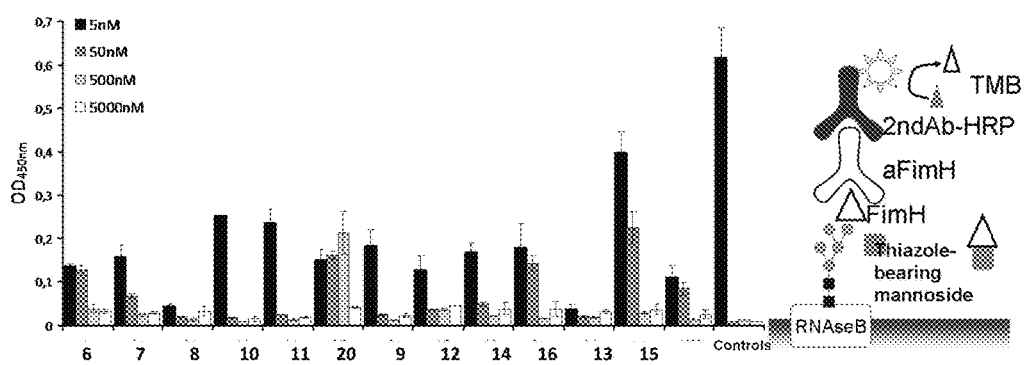
FIG. 22 presents the affinity testing of thiazolylaminomannosides toward oligomannose glyco-epitopes using enzyme-linked immunosorbent assay (ELISA). The X-axis indicates the compounds used for testing; the Y-axis represents the optical density of TMB chromophore absorbance at 450 nm. The controls are (from left to right): FimH alone (positive control—black bar), aFimH (dark gray), aFimH+2ndAb-HRP (light gray), 2ndAb-HRP (white), TMB (negligible, not shown). The schematic principle of the assay is shown on the right. Briefly, oligomannose glycans of RNAseB (as the best suited natural FimH target) and the studied inhibitors compete for binding of FimH lectin, then bound FimH is detected by antibodies. In the case of the absence of inhibitor or a weak inhibitor, FimH will bind to RNAseB sorbed onto a plate and will produce a high signal of absorbance, while a strong inhibitor will bind to FimH and prevent it from binding to RNAseB on a plate, resulting in a low optical density signal.

The binding affinity of the synthetic thiazolylaminomannosides 6-16 and 20 towards FimH was first evaluated by competitive ELISA. Heptylmannoside (HM) was also included in the assay as a reference displaying a strong nanomolar affinity for FimH (Mol. Microbiol. 2005, 55, 441-455). The RNAseB protein, which possesses a complex mixture of oligomannose glycans ($Man_5GlcNAc_2$, $Man_7GlcNAc_2$, and $Man_8GlcNAc_2$-Prien, J. M.; Ashline, D. J.; Lapadula, A. J.; Zhang, H.; Reinholda, V. N. J. Am. Soc. Mass. Spectr. 2009, 20, 539-556), was used as the FimH substrate (FIG. 22). The intensity of FimH binding to the substrate is represented by the optical density of chromophore absorbance at 450 nm, and decreases in the presence of inhibitors in a dose-dependent manner. The thiazolylaminomannosides 6-16 and 20 showed a strong affinity for FimH. Compared to the control (FimH alone), most of the inhibitors, including HM, already significantly inhibited FimH binding at 5 nM. The marked signal reduction obtained with HM at nanomolar concentrations is consistent with the low dissociation constants of 5 nM (*J. Am. Soc. Mass. Spectr.* 2009, 20, 539-556) and 7 nM (*Biochemistry* 2012, 51, 4790-4799) previously reported for the HM-FimH complex by Surface Plasmon Resonance (SPR) and Isothermal Titration calorimetry (ITC), respectively. Different inhibitory profiles were observed depending on the nature of the substituents attached to the thiazole ring. This clearly shows that improved affinity for FimH may still be expected with pharmacophores situated at rather large distances from the mannose binding site. As can be seen from FIG. 22, thiazolylaminomannosides 8 and 13 were able to block FimH binding towards oligomannose glycans at the low concentration of 5 nM, while mannosides 7, 9, 11, 12 and 14 effectively blocked its binding at a higher concentration of 50 nM. A significantly higher level of inhibition was observed with 8 and 13 compared to the HM reference.

Example 22.2: Prevention of Bacterial Attachment to Erythrocytes

A widely used cell-based assay (hemagglutination—HAI) was selected to evaluate the anti-adhesive potency of the glycoconjugates 6-16 and 20 toward the CD-associated *E. coli* strain AIEC LF82. AIEC adhesion to the gut occurs through the binding of FimH adhesins to the mannosylated glycans of intestinal cells. This scenario was first mimicked here with the highly mannosylated glycocalyx of guinea pig erythrocytes.

A two-fold dilution series of the antagonists was added to wells containing guinea pig erythrocytes and AIEC LF82 bacteria. The formation of the cross-linked network (hemagglutination) due to the interaction of the *E. coli* FimH adhesins with the glycocalyx of the erythrocytes was prevented at a certain concentration of inhibitors. The lowest concentration at which hemagglutination is still inhibited is defined as the inhibition titer of the antagonist. HM was included in the assay to obtain a relative inhibitory concentration (rIC) for the antagonists by dividing the inhibitory concentration (IC) of the substance of interest by the value for HM. In fact, rICs are more accurate than rough inhibition titers to compare the potency of antagonists evaluated in different assays.

Figure 23:
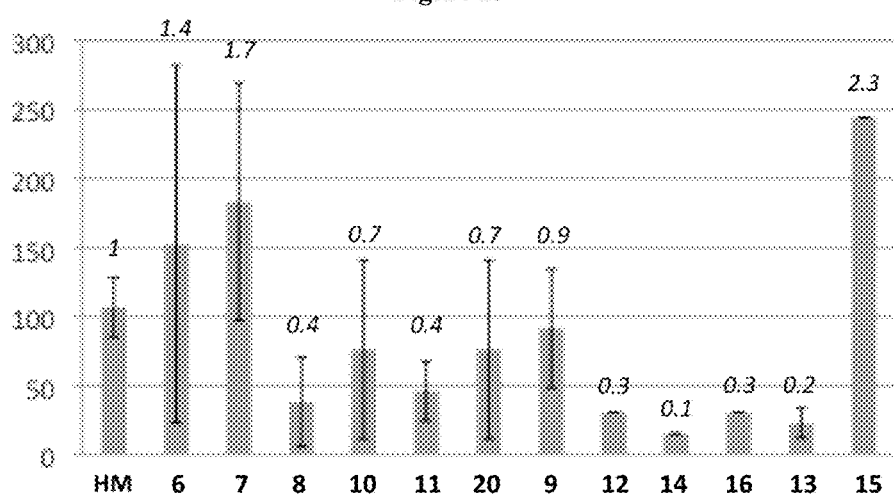
FIG. 23 presents inhibition of hemagglutination (HAI): inhibition of guinea pig red blood cell hemagglutination by the type-1 piliated AIEC strain LF82 by the newly synthesized glycoconjugates. The error bars indicate the variation in inhibitory concentrations for the two assays with variable *E. coli* LF82 bacterial numbers. rICs relative to HM are indicated in italic.
Figure 24:
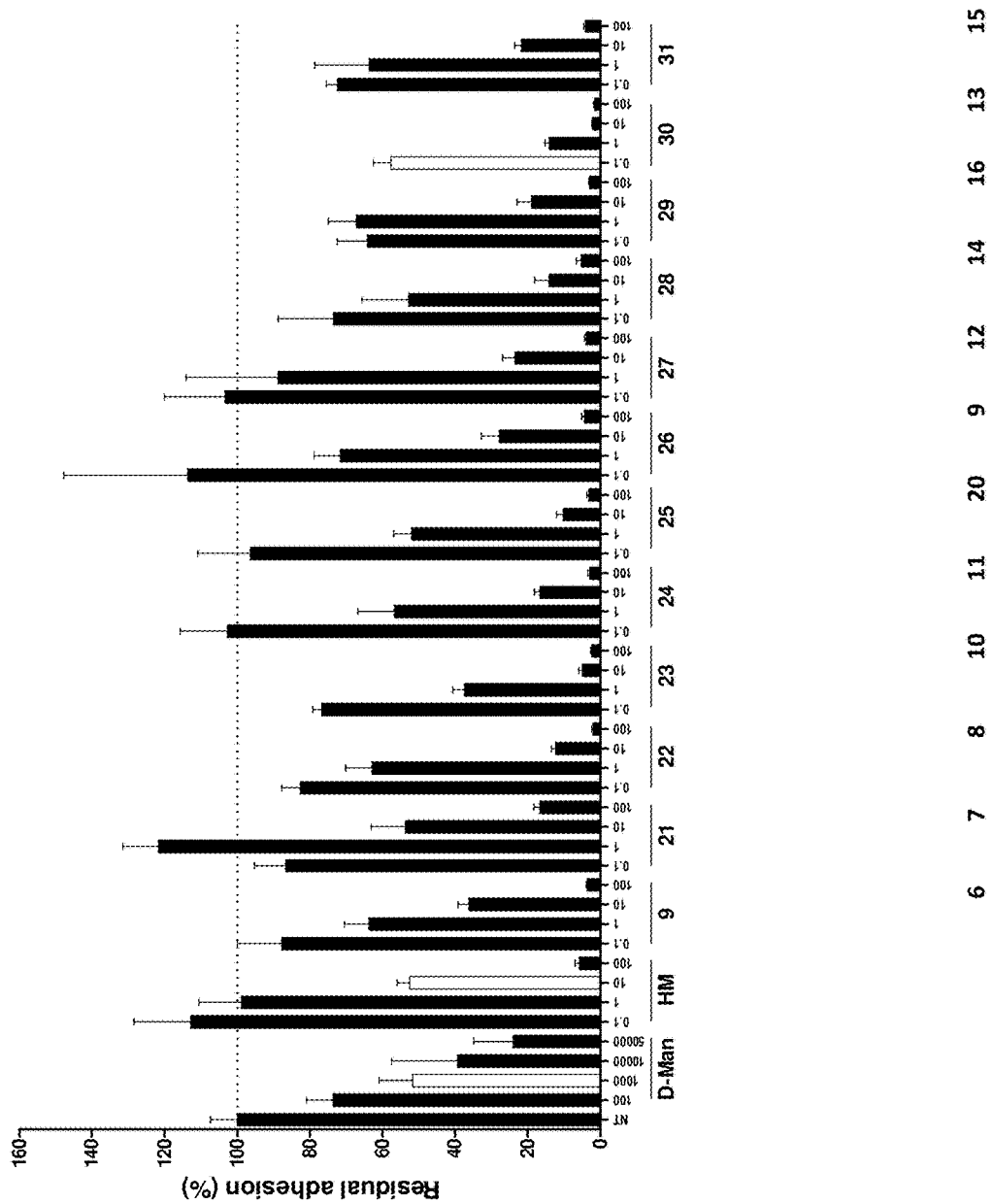
FIG. 24 presents the dose-dependent inhibitory effects of various molecules (D-Man, HM, 6-16 and 20) on the ability of the AIEC strain LF82 to adhere to T84 cells. Horizontal scale: concentration of inhibitors expressed in µM. Results are expressed in percentage of bacteria adherent to cells (means±sem); 100% corresponds to adhesion in the absence of any treatment (NT for non-treated). All the mannosides tested exerted a dose-dependent inhibitory effect on AIEC LF82 adhesion. α-D-Mannose, HM and all the compounds tested displayed very large differences when concentration values corresponding to $IC_{50s}$ were considered. For example, similar residual adhesion levels (51.6%, 52.4% and 57.6%) were observed with 1000 µM of α-D-mannose, 10 µM of HM and 0.1 µM of compound 13, respectively (FIG. 24, white bars). The inhibitory potency of compound HM was therefore 100 times greater than that of α-D-mannose, indicating that the anti-adhesive effect observed on AIEC bacteria greatly benefits from the anomeric heptyl chain of HM. Importantly, compound 13 exhibited a dose-dependent inhibition similar to HM but at a 100-fold lower concentration (rIC~0.01).
Figure 25:
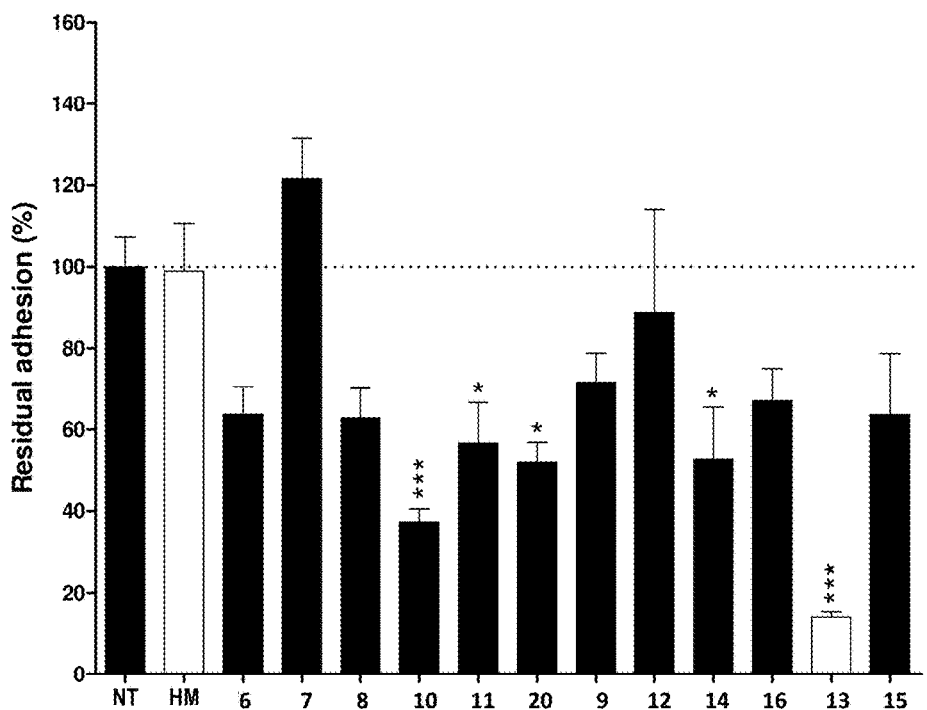
FIG. 25 presents the comparison of the inhibitory effects on the AIEC strain LF82 adhesion to T84 cells obtained with HM, 6-16 and 20 at 1 µM concentration. Results are expressed in percentage of bacteria adherent to the cells (means±sem); 100% corresponds to adhesion in the absence of any treatment (NT for non-treated). *: p<0.05; : p<0.01; *: p<0.001 (One-way ANOVA). No significant decrease in bacterial adhesion was observed with HM at this concentration, while only 14% of AIEC remained attached to the cells when 13 was applied (p<0.001). These results are in good agreement with the previous assays (competitive ELISA and HAI) and show the very strong anti-adhesive properties of 13 on AIEC.
Figure 26:
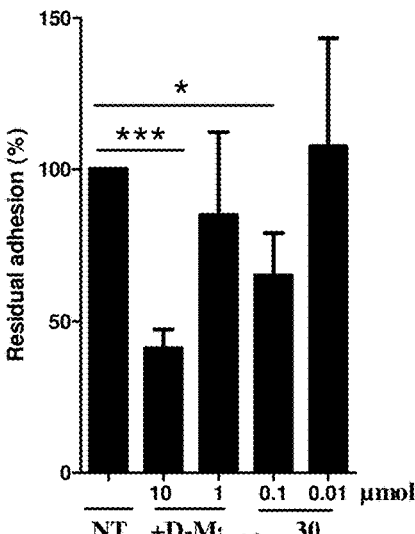
FIG. 26 presents the comparison of the inhibitory effects on AIEC bacterial adhesion to the colonic tissue of transgenic CEABAC10 mice obtained with D-Man and 13. Results are expressed as percentage of bacteria adherent to the colonic mucosa (means±sem, n=5 to 8 mice). 100% corresponds to bacterial adhesion in the absence of treatment (NT for non-treated). *: p<0.05; ***: p<0.001 (One-way ANOVA).
Figure 27:
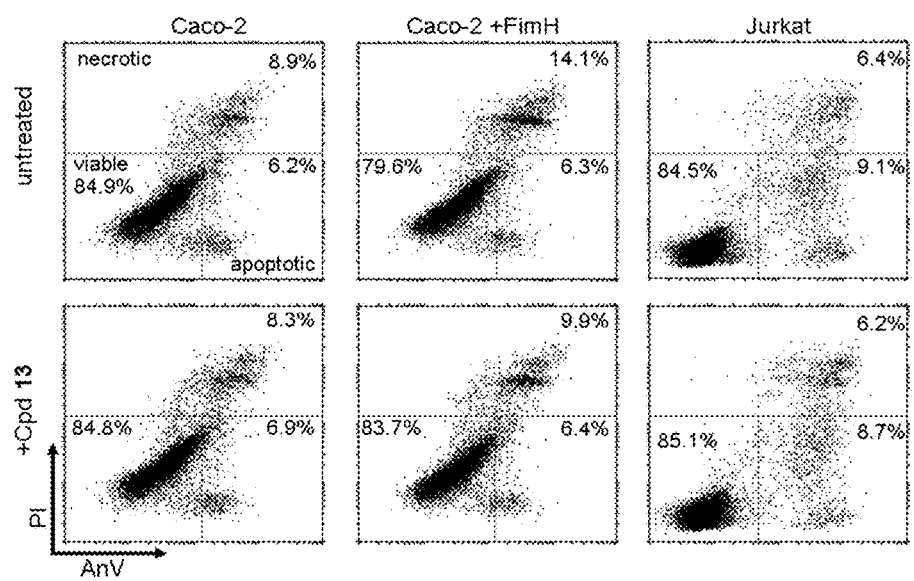
FIG. 27 presents the analysis of cell viability by flow-cytometry after incubation with FimH and Cpd 13 for 20 h. Incubation of Caco-2 cells with FimH immobilized on microspheres (Upper Middle) exhibited significantly increased cytotoxicity when compared to untreated Caco-2 cells (Upper Left), while incubation with only 100 nM of cpd 13 (Lower Middle) was enough to abrogate FimH cytotoxicity. At the same time the cpd 13 at 100 nM was not toxic for both Caco-2 cells (LL) and Jurkat human T-cells (LR) for 20 h. Detection of viable (annexinV-negative (AnV), propidium iodine-negative), apoptotic (AnV-positive, PI-negative) and necrotic (PI-positive) cells. It is noted that most necrotic cells are also AnV-positive, that is secondary necrotic (converted from apoptotic cells). The typical dot plot from 3 replicates are shown, their mean values of cells in each category are indicated with numbers.
Figure 28:
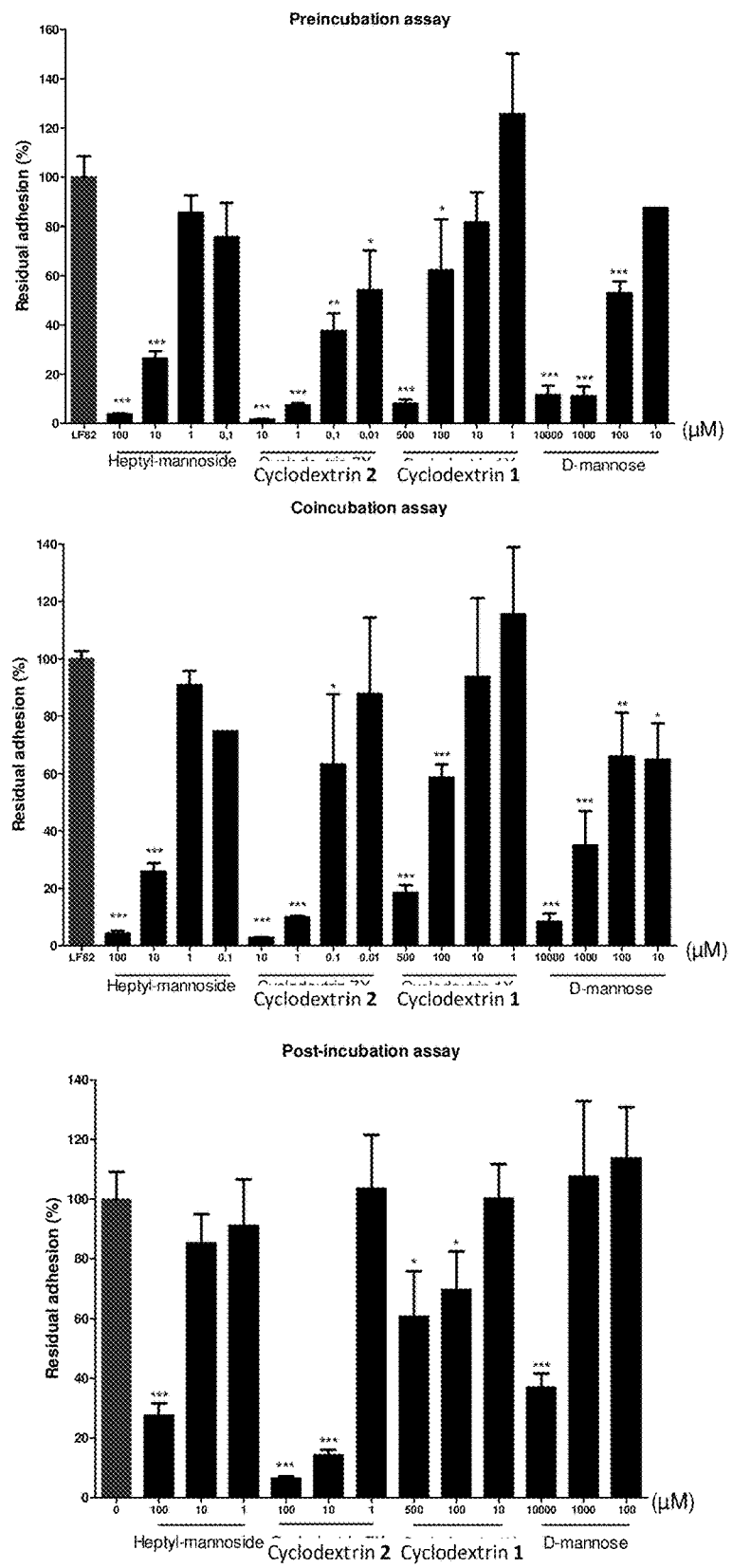
FIG. 28 presents the assays of D-mannose, heptyl-mannoside, compounds 1 (example 2bis) and 2 (example 1) on T84 intestinal epithelial cells as inhibitors to compete with the interaction CEACAM6/FimH of AIEC bacteria in three different protocols: pre-, co- and post-incubation experiments.

HAI titers confirmed the good to excellent inhibitory potencies of the thiazole antagonists. Analogues less potent than HM in this assay were 6, 7 and 15 (FIG. 23). Antagonist 7, bearing the highly electron-withdrawing group $CF_3$, was significantly less potent than 6 with the $CH_3$ group. The same tendency was also observed in the aromatic series. Compounds 10 and 20 with $NO_2$ and CN groups were less potent than the unsubstituted phenyl analogue 8. The electron-withdrawing groups probably hamper interactions with the Tyr48 side chain. Alkyl-armed thiazoles 6 and 9, bearing a methyl and a tert-butyl group, showed a similar inhibitory profile to HM. A significant improvement was observed with compound 16 bearing a bulky adamantyl group. The most potent FimH inhibitor 13 identified in the ELISA was also shown to be the second most potent compound to prevent AIEC attachment to guinea pig erythrocytes.

Example 22.3: Adhesion Assays in Presence of Heterocylic Mannoside Compounds of *E. coli* Adhesion T84 Intestinal Epithelial cells (overexpressing the receptor CEACAM6) were beforehand incubated for 1 h with the synthetic thiazolylaminomannosides 6-20 (examples 3-17) at different concentrations. Each compound was tested four times at concentrations of 0.1, 1, 10 and 100 µM.

Figure 10:
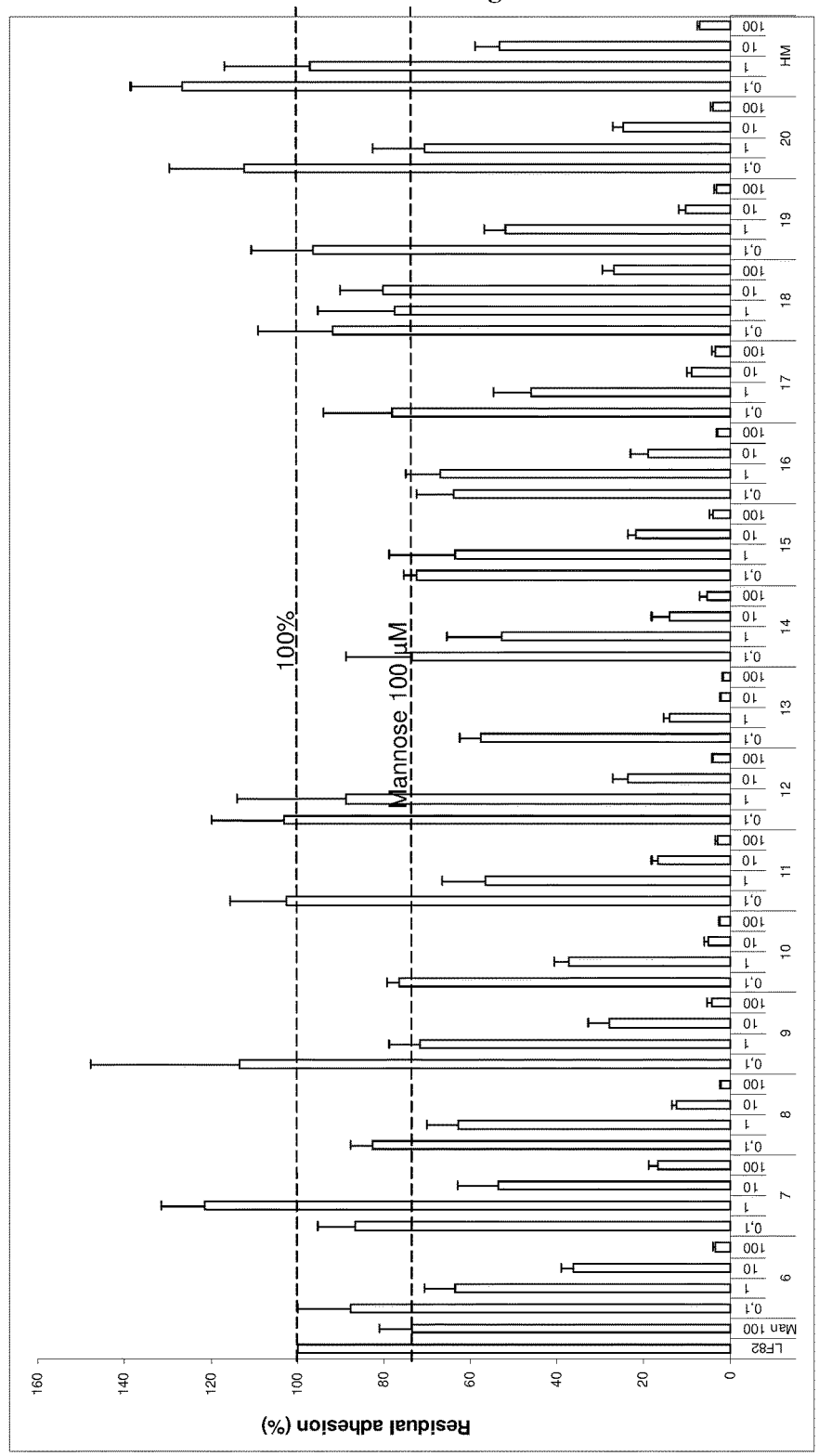
FIG. 10 presents the residual adhesion (in percentage) of the AIEC LF82 strain to intestinal epithelial cells T84 in the presence of increasing concentrations of inhibitors 6-20 (examples 3-17) (0.1, 1, 10 and 100 mM). Results were expressed as mean±sem, four independent experiments, except for compound HM (two experiments). LF82=bacterial adhesion without any treatment, Man=Mannose at 100 μM.
Figure 12:
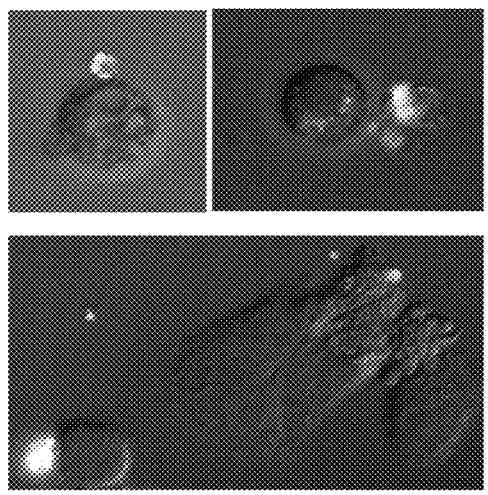
FIG. 12 presents the binding of FimH to apoptotic and necrotic cells and apoptotic blebs. Upper row—aged human PMN cells, lower row—human HeLa cells irradiated with UV-B. FimH is labeled with FITC and fluorescence in green. Cells are counterstained with propidium iodine (PI, red fluorescence). Overlapping of FimH-FITC and PI signals produce yellow color (indicating FimH binding to dead cells, indicated with asterisk). Fluorescent signal was overlayed with DIC image.

The cells were then infected in the presence of inhibitory compounds by the AIEC strain of reference LF82 for 3 hours at a multiplicity of infection of 10 bacteria to a cell. After 3 h of incubation, the monolayer was washed and the number of AIEC bacteria associated with cells was counted. The level of adhesion of AIEC LF82 strain in the presence of inhibitors (residual adhesion) was expressed relatively to the level of adherence in the absence of any treatment (considered 100%) (FIG. 10).

Compounds exhibit good adhesion inhibitory ability of AIEC bacteria to epithelial cells T84. Inhibitors 8, 10, 13, 15, 16 showed a significant inhibitory effect at 100 nM (FIG. 10). At this concentration, the reference compound HM (heptylmannose) showed no significant effect.

At a concentration of 100 µM, mannose reduces by about 25% adherence to intestinal epithelial cells. At this concentration, all compounds induced a significant decrease ($P<0.001$) greater than 95%. To achieve a similar percentage of residual adhesion with mannose, a concentration of 100 mM is necessary, that is to say a concentration that is 1000 times greater. There is therefore a much higher efficiency of mannosides with a functionalized thiazole (FIG. 10).

At 10 µM, all compounds 6-20 had a significant effect on bacterial adhesion. The compound 13 is the most effective compound with 2.12% of residual adhesion and other compounds 10, 17 and 19 have a greater than 90% inhibition (FIG. 11B).

Example 22.4: Adhesion Assays of Adherent-Invasive *E. coli* Strains on Colonic Tissue Isolated from Transgenic Mice Expressing CEACAM6 in Presence of Synthetic Thiazolylaminomannoside Compound 13 ("Ex-Vivo" Analyses)

Materials and Methods

*E. coli* strain LF82 was isolated from a chronic ileal lesion of a patient with Crohn's disease (CD). Bacteria were grown routinely in Luria-Bertani (LB) broth overnight at 37° C.

Adhesion assay of AIEC LF82 bacteria were performed using colonic tissue from transgenic mice expressing the human CEACAM6 protein (C. H. Chan, C. P. Stanners "Novel mouse model for carcinoembryonic antigen-based therapy", *Mol Ther.* 2004; 9, 775-785). Briefly, 10 to 12-week-old FVB/N CEABAC10 transgenic mice were anesthetized, euthanized by cervical dislocation and colons were removed. Colons were washed twice in phosphate buffer saline (PBS) and were segmented in 4 independent loops of ≈0.6 cm. A volume of 100 µL of LF82 bacteria at $2 \times 10^6$ bacteria/mL in PBS or of a mix of LF82 bacteria+D-mannose (1 µmol and 10 µmol) or compound 13 (0.1 µmol and 0.01 µmol) were injected into the loops. Loops were incubated 1 h at 37° C. in an atmosphere containing 5% of $CO_2$, and then opened and washed 4 times in PBS. Tissues were homogenized, appropriately diluted and plated onto Luria-Bertani agar plates containing ampicillin (100 µg/mL) and erythromycin (20 µg/mL) to select AIEC LF82 bacteria.

Results

Entire colons from CEABAC10 mice were collected and washed two times with PBS. The colon was divided in 4 isolated loops and 100 µL of a bacterial suspension containing $6 \times 10^6$ bacteria/mL with or without inhibitory compounds were injected into the loops. D-mannose was tested at a dose of 1 and 10 µmol and monovalent 13 was tested at a dose of 0.01 and 0.1 µmol. After a 1 h-period of incubation, samples were extensively washed and homogenized to numerate adherent bacteria. Bacterial adhesion was expressed as percentages of residual adhesion (100% corresponds to the adhesion in absence of any compound).

D-mannose decreased bacterial adhesion to 41% when administered at a dose of 10 µmol whereas no decrease was observed at 1 µmol. For the monovalent 13, a significant decrease of the adhesion was obtained at 0.1 µmol. Thus, the monovalent molecule 13 was 100-fold more efficient than D-mannose.

Example 22.5: Cytotoxicity of 13 and Blockage of the Pro-Apoptotic Effect of FimH It was shown that upon binding of FimH adhesin to uroplakin UPIIIa its cytoplasmic tail undergoes phosphorylation on a specific threonine residue by casein kinase II, followed by an elevation of intracellular calcium triggering apoptosis (Thumbikat, P.; Berry, R. E.; Zhou, G.; Billips, B. K.; Yaggie, R. E.; Zaichuk, T.; Sun, T.-T.; Schaeffer, A. J.; Klumpp, D. J. *PLoS Pathog* 2009, 5, e1000415). Recently it was demonstrated (Bilyy, R.; Stoika, R. *Autoimmunity* 2007, 40, 249-53.) that apoptotic cells produces subcellular microparticles (apoptotic bodies) of two types—one exposing increased sialidase activity on their surface, which results from caspase-3 dependent activation of plasma membrane associated Neu1, and being able to desialylate their neighbours (Shkandina, T.; Herrmann, M.; Bilyy, R. *Autoimmunity* 2012, 45, 574-578.) and potentially stimulate efferocytosis due to desialylation (Meesmann, H. M.; Fehr, E.-M.; Kierschke, S.; Herrmann, M.; Bilyy, R.; Heyder, P.; Blank, N.; Krienke, S.; Lorenz, H.-M.; Schiller, M. *J Cell Sci* 2010, 123, 3347-3356), and second, resulting from ER-derived membranes ezposed on cell surface, bearing olimanosidde glycans and being rapidly cleared by macrophages (Bilyy R. O.; Shkandina, T.; Tomin, A.; Muñoz, L E.; Franz, S.; Antonyuk, V.; Kit, Y. Y.; Zirngibl, M.; Fürnrohr, B. G.; Janko, C.; Lauber, K.; Schiller, M.; Schett, G.; Stoika, R. S.; Herrmann, M., *J. Biol. Chem.* 2012, 287, 496-503). To evaluate the potency of thiazole-bearing mannoside 13 to block the pro-apoptotic effect of FimH we have utilized the previously described approaches of conjugation proteins with nanoparticles (Bilyy, R; Podhorodecki, A.; Nyk, M.; Stoika, R.; Zaichenko, A.; Zatryb, G.; Misiewicz, J.; Strek, W. *Physica E,* 2008, 81, 2096-2099; Bilyy, R.; Tomyn, A.; Kit, Y.; Podhorodecki, A.; Misiewicz, J.; Nyk, M.; Strek, W.; Stoika, R. *Materialwiss. Werkst.* 2009, 24, 234-237) and have conjugated purified (Wellens, A.; Garofalo, C.; Nguyen, H.; Van Gerven, N.; Slattegard, R.; Hernalsteens, J. P.; Wyns, L.; Oscarson, S.; De Greve, H.; Hultgren, S.; Bouckaert, J. *PloS one* 2008, 3, e2040.) FimH lectin with the surface of fluorescent 1 µm microspheres, which provided us the following advantages: 1. conjugation greatly enhances stability of otherwise hydrophobic FimH lectin; 2. lectin-nanoparticles complex most closely resembles the interaction with FimH-bearing bacteria, as FimH molecules on the surface of microsperes allow one to mimic the spatial lectin organization yet still to study a pure system devoid of other bacterial proteins; 3. due to microparticles' fluorescence they are easily trackable. Addition of microparticles-FimH to the sub-confluent culture resulted in increase of dead cells, detected by both flow cytometry as apoptotic (AnnexinV-positive and PI-negative) and secondary necrotic (both AnnexinV-positive and PI-positive) (FIG. S2) and by counting in hematocytometric chamber with trypan blue staining. It is needed to mentioned that according to our observations that Caco2 cells, unlike human blood cells, (Bilyy R. O.; Shkandina, T.; Tomin, A.; Muñoz, L E.; Franz, S.; Antonyuk, V.; Kit, Y. Y.; Zirngibl, M.; Fürnrohr, B. G.; Janko, C.; Lauber, K.; Schiller, M.; Schett, G.; Stoika, R. S.; Herrmann, M., *J. Biol. Chem.* 2012, 287, 496-503) are very quickly converted from apoptotic to secondary necrotic (PI-positive). Treatment of epithelial colorectal cell of Caco2 line with 1 µl of microparticle-FimH suspension (containing $4.5*10^{10}$ particle in ml) per each ml of cell culture medium increased the amount of the dead cell in population from 15% (typical for normal cell culture) to above 20% ($p<0.01$). At the same time action of thiazole-bearing mannoside 13 in concentration 100 nM had no significant effect on amount of dead cell in population, while co-treatment with microparticles-FimH and 100 nM 13 resulted in the 16.5% of dead cells in population, being significantly distinct from that of microparticles-FimH action alone ($p<0.05$) and not significantly distinct from normal population. Also 13 was tested for it toxicity towards human blood cells using as a model human Jurkat T-cell line, and was shown to be nontoxic in concentration (100 nM) already abrogating cytotoxic action of FimH (FIG. S2). Thus 13 was effective in abrogating the cytotoxic effect of FimH even at very small concentrations (100 nM) in epithelial colorectal Caco2 cells at same being itself non-toxic to the treated cells.

Materials and Methods

Cell Culture.

Human colorectal adenocarcinoma Caco-2 cells were cultured in the RPMI 1640 (Sigma Chemical Co., St. Louis, USA) culture medium supplemented with 4 mM L-glutamine, 10 mM HEPES buffer, 50 µg/gentamicin. RPMI 1640 was further supplemented with 10% (v/v) heat inactivated fetal calf serum (FCS) (Gibco-BRL, Eggenstein, Germany). Cell viability was assessed by a trypan blue exclusion test. Cells were cultured in 5% $CO_2$ at 37° C.

Flow Cytometry.

Apoptotic cells were identified by using annexin V-FITC and PI, according to the manufacturer's protocol. Cells were washed in Ringer solution. Cells were then resuspended in a solution of annexin V-FITC and PI prepared in Ringer buffer, incubated 30 min at 4° C. in the dark, and analyzed on a FACS scan flow cytometer (BD Biosciences). A minimum of 10,000 events per sample was recorded. With this method, viable cells remain unlabeled, apoptotic cells with intact membrane integrity are labeled only by annexin V-FITC, and necrotic cells are labeled by both stains.

Covalent Coupling of Proteins to Carboxylated Polystyrene Microparticles.

Covalent coupling of FimH lectin to Fluoresbrite® BB Carboxylate Microspheres 1.00 µm (Polysciences, Inc., USA) was done according to manufactures' protocol. We used 0.25 ml of 2.5% carboxylated microparticles and after covalent coupling of FimH this microparticles were resuspend in 0.25 ml Storage buffer (1×PBS, 1% BSA, 0.1% sodium azide, 5% glycerol). In total 0.88 of FimH protein was conjugated with 1 ml of microparticles, containing $4.55*10^{10}$ particles per ml.

Example 23: Example 23.1

Bacterial Oligomannose-Specific Adhesin FimH Binds to Apoptotic Cells and Apoptotic Blebs We evaluated the binding of FimH to apoptotic cells and distinct types of apoptotic blebs with the perspective to determine the role of FimH binding in provoking persistent urinary tract infections.

While fluorescent microscopy revealed weak binding (if any) of FimH to viable HeLa cells, its binding was prominent to HeLa cells induced to apoptosis using UV-B irradiation, both primary apoptotic (PI-negative) and secondary necrotic (PI-positive). Previously we developed a method for induction of (preferentially ER-derived) blebs by causing ER-stress with glibenclamide, a compound inhibiting ATP-sensitive potassium channels in ER followed by UV-B treatment (UA Patent 60626, Method for induction of membranous blebs formation, inventor: R. Bilyy). Induction of ER-derived bleb caused prominent binding of FimH to both formed blebs and cells undergoing blebbing.

Figure 13:
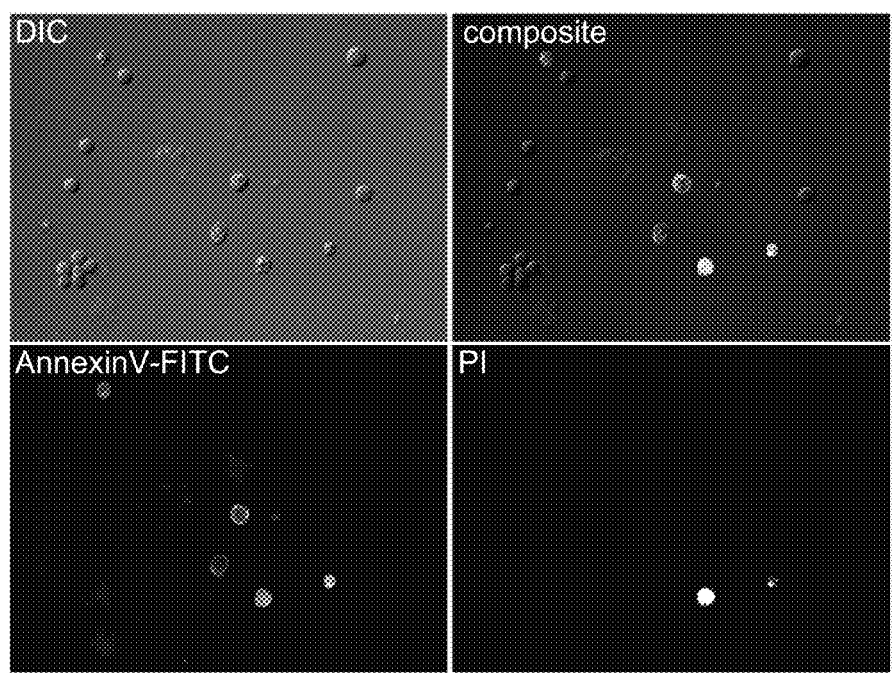
FIG. 13 shows that Lectin FimH (10 μg/ml, 12 h of incubation) causes the apoptosis of the Jurkat human T-cell line. Staining with PI for necrotic and annexinV-FITC for apoptotic cell. Necrotic cells are double-positive.
Figure 14:
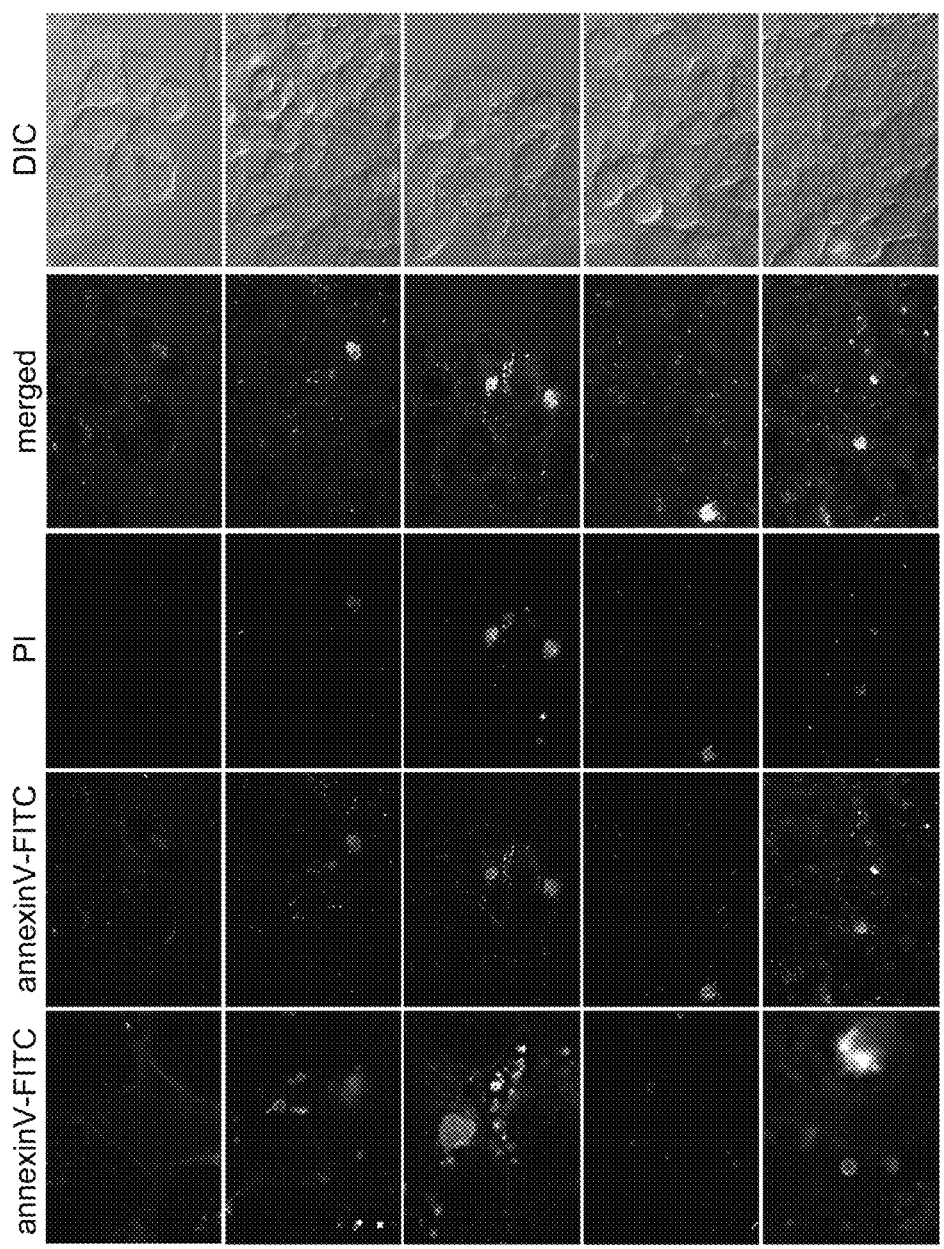
FIG. 14 presents HeLa cells at different time of incubation after adding FimH lectin, 10 μg/ml. Staining with PI for necrotic and annexinV-FITC for apoptotic cell. A pronounced formation of apoptotic (annexinV positive) blebs is visible after incubation with FimH. Lower panel represent enlarged areas of annexinV-FITC stained cells.

Example 23.2: Bacterial Oligomannose-Specific Adhesin FimH Induces Cell Apoptosis and Apoptotic Bleb Formation We evaluated the ability of FimH to induce cell death by apoptosis and necrosis by incubating human Jurkat cells and human HeLa cells with FimH and performing subsequent fluorescent microscopy/DIC microscopy AnnexinV-FITC was used to discriminate apoptotic cells while propidium iodine (PI) was used to discriminate dead (necrotic) cells (which were also positive for Annexin-V). As seen from FIG. 13, incubation of Jurkat cells with FimH caused mainly apoptotic (green cells) and not necrotic (orange cells) cell death. As can be seen from FIG. 14, incubation of HeLa cells with FimH caused the formation of apoptotic cell blebs (AnnexinV—positive) and in the induction of apoptotic cell death.

Figure 15:
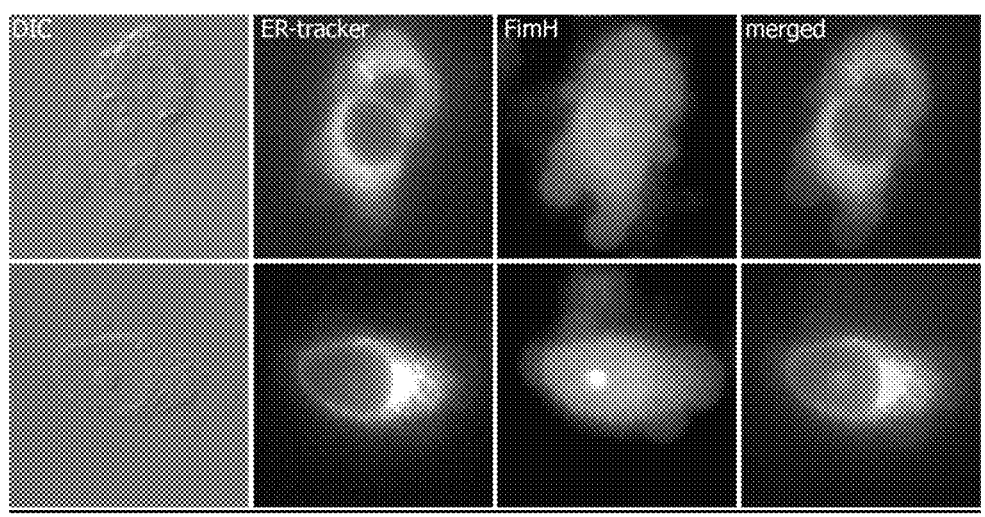
FIG. 15 presents the fluorescent microscopy of HeLa cells, previtally stained with ER-tracker (green), induced to blebbing by UV-B irradiation and stained with FimH-TexasRed (red). Co-localization of images demonstrated binding of FimH to ER-derived blebs.

Example 23.3: Bacterial Oligomannose-Specific Adhesin FimH Binds to ER-Derived (Oligomannose) Blebs We evaluated the binding of FimH to apoptotic cells and distinct types of apoptotic blebs with the perspective to determine the role of FimH binding in provoking persistent urinary tract infections. To test the ability of FimH to bind with ER-derived blebs the FimH protein was labeled with TexasRed dye according to [Hermanson, Bioconjugate Techniques. 1996. 1-785], while HeLa cell's ER was vitally stained with ER-tracker green, in dilution 1:15000 for 20 min as described [Haugland, Invitrogen: A Guide to Fluorescent Probes and Labeling Technologies. 2005.]. Cell blebbing was performed by irradiating HeLa cells with UV-B for 90 s, 90 mJ/cm2, cells were incubated with FimH-TexasRed (~2 µg/ml) for 5 min with subsequent fluorescent microscopy. Fluorescent microscopy revealed the presence on cells of blebs being both positive for FimH and ER-tracker signals, as shown on FIG. 15. Thus FimH binds to ER-blebs, rich in oligomannose glycans.

Figure 16:
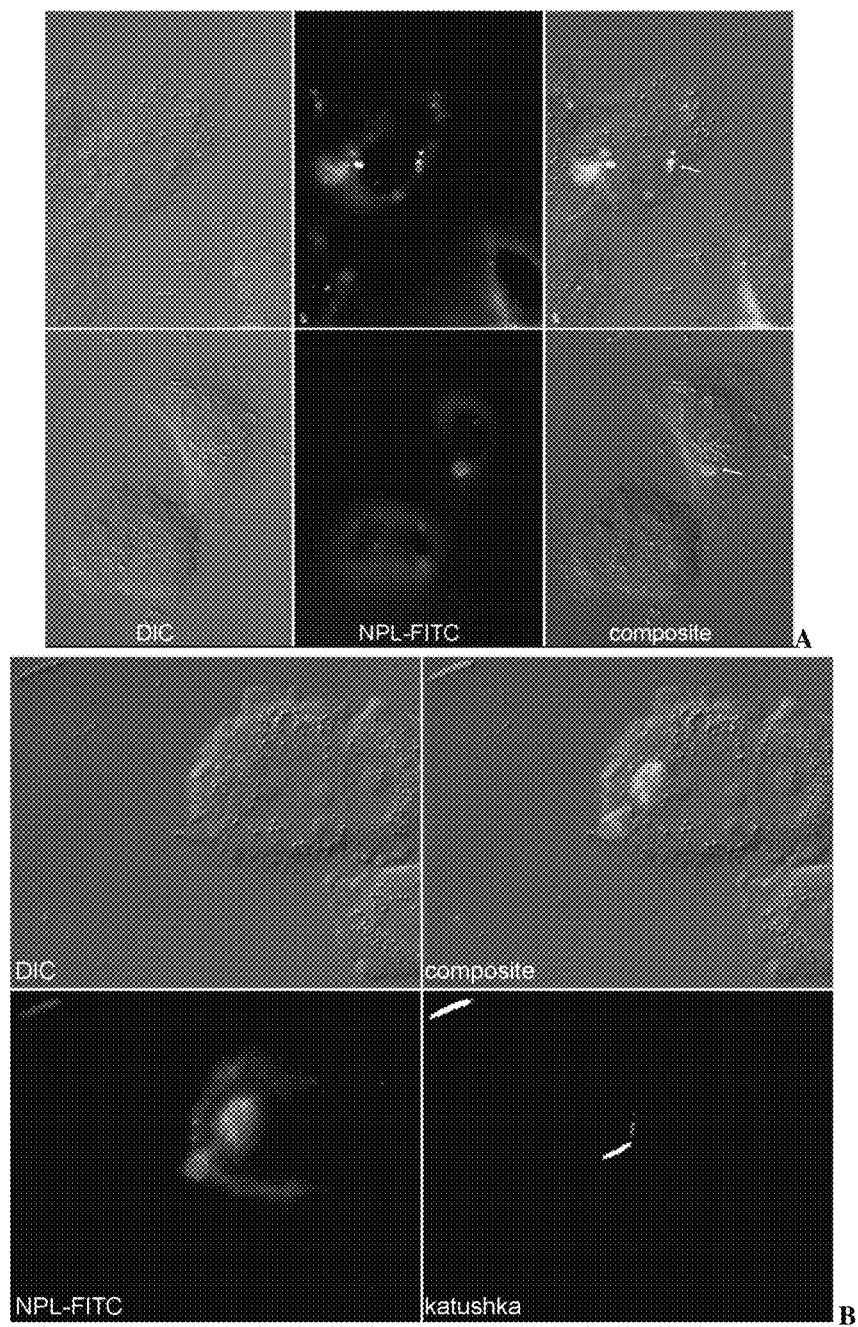
FIG. 16 presents the uropathogenic *E. coli* binding to oligomannose blebs on apoptotic cells.
A—*E. coli* cells (UTI89, pBlue-PtetO NirFP670) were co-incubated with HeLa cells for 6 h. Mannose rich blebs were detected with NPL-FITC lectin.
B—*E. coli* cells (DHSalpha, pDONR221-nadBUTI89:cat-kat) were co-incubated with HeLa cells for 6 h. Mannose rich brebs were detected with NPL-FITC lectin.

Example 23.4: Uropathogenic E. coli Bind to Oligomannose Blebs on Apoptotic Cells Eventually, we tested whether FimH is able to bind to oligomannose blebs on HeLa cells. We used NPL lectin (FITC labels) to track ER-derived glycans. By adding E. coli bacterial cells to HeLa cells and incubating for 6 h we observed: 1. induction of formation of ER-derived blebs (no apoptotic stimuli was present in the media!). 2. Binding of bacterial to ER-derived blebs (FIG. 16).

Thus, we suppose that binding of apoptotic cells or apoptosis-related blebs possessing oligomannose glycans by the FimH adhesin in E. coli fimbriae can be the site of bacterial entry into the epithelia of urinary tract.

Figure 17:
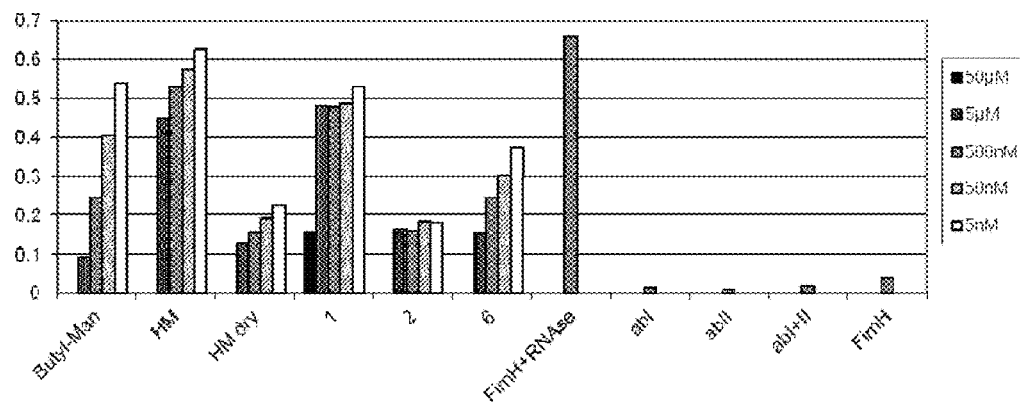
FIG. 17 presents the inhibon of FimH binding with oligomannose glycans of RNAseB after simultaneous treatment of FimH and indicated inhibitor compound 1 (example 2bis), compound 2 (example 1) or compound 6 (example 3). HM—heptylmannoside after 1 month storage in dissolved form. HM dry—immediately dissolved HM. FimH+RNAseB—positive control (maximal signal) of FimH binding with oligonanose glycans. abI—primary anti-FimH antibody. abII—secondary antibody, HRP-labeled.

Example 23.5: Compounds of the Invention are Effective in Blocking Interaction of FimH with Oligomannose Glycans To test the ability of tested compounds to block FimH interaction with oligomannose glycans we have developed an ELISA-based method for testing of lectin affinity towards natural occurring oligomannose substrates by using the RNAseB as binding target by sorbing it to activated immunological plates. RNAse B possesses a complex mixture of Man5GlcNAc2, Man7GlcNAc2, and Man8GlcNAc2 glycans [Prien, Ashline, Lapadula, Zhang and Reinhold, The High Mannose Glycans from Bovine Ribonuclease B Isomer Characterization by Ion Trap MS. Journal of the American Society for Mass Spectrometry, 2009. 20.539-556]—which are the glycans synthesized in the ER of higher eukaryotic cells. Tested compounds were added to wells following with FimH treatment. As one can see from FIG. 17 the most potent inhibition of oligomannoside binding was observed for compound 2 (example 1).

As one can see HM is loosing activity in dissolved form. While maximal inhibition of binding was observed for compound 2.

Thus compound 2 was effective in preventing FimH interaction with oligomannose glycans.

Figure 18:
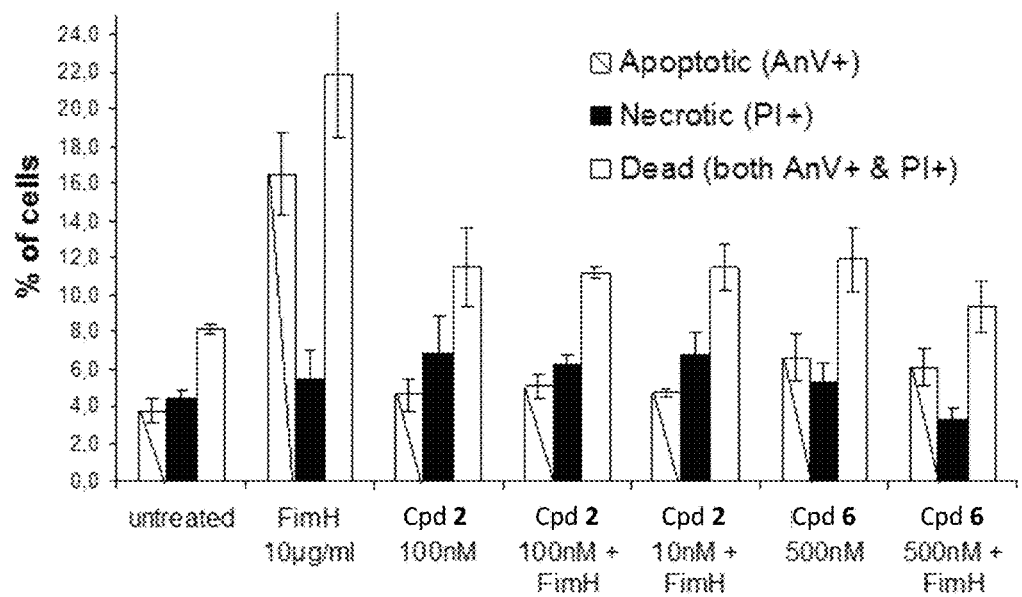
FIG. 18 presents the percentage of apoptotic and necrotic Jurkat T-cell in population, after 24 h co-incubation with the indicated compounds compound 2 (example 1) and compound 6 (example 3).

Example 23.6: The Patented Compounds (Inhibitors) are Effective in Blocking Interaction of FimH with Cells and in Prevention Eukariotic Cell Apoptosis Eventually, we tested the ability of mannose-based inhibitors to prevent the induction of cell death of human Jurkat cells under the treatment with FimH. We cultures cells with the indicated compound for 24 h and counter percentage of viable (AnV−/Pi−), apoptotic (AnV+/Pi−) and necrotic cells (AnV+/PI+). As one can see from FIG. 18: 1. FimH treatment increase the amount of apoptotic and not necrotic cells (also shown in thesis 2 above). 2. The tested compounds 2 and 6 (example 3) were not toxic to cells in the tested concentrations. 3. Compound 6 effectively prevented apoptosis induction by FimH at concentration of 500 nM compound 2 effectively prevented apoptosis induction by FimH at concentration of 100 nM and 10 nM.

Thus, binding of apoptotic cells or apoptosis-related blebs possessing oligomannose glycans by the FimH adhesin in E. coli fimbriae can be the site of bacterial entry into the epithelia of urinary tract. Treatment with synthetic mannose-based compound is effective in prevention of FimH-induced apoptotic cells death and, probably, bacterial interaction with host cells.

Example 23.7: Materials and Methods

Cells and Clinical Material:

Lymphocytes and polymorphonuclear neutrophils (PMN) from healthy donors were isolated after informed consent from blood of patients by centrifugation in ficoll-verografin or LymphoPrep® gradient according to manufacture's recommendations. Monocytes were isolated from peripheral blood by LymphoPrep® gradient according to manufacture's recommendations. Plastic-attached cells were then cultured for 7 days in the presence of GM-CSF (100 U/ml) and autologous serum to emerge monocyte-derived phagocytes as described by us previously [Meesmann, Fehr, Kierschke, Herrmann, Bilyy, Heyder, Blank, Krienke, Lorenz and Schiller, Decrease of sialic acid residues as an eat-me signal on the surface of apoptotic lymphocytes. J Cell Sci, 2010. 123.3347-3356].

Human cell of cervical carcinoma HeLa line from the Cell Culture Collection of Institute of Cell Biology, National Academy of Sciences of Ukraine (Lviv, Ukraine) were used in the research. Cells lines were maintained in RPMI-1640 medium (Sigma Chemical Co., USA). Culture medium was supplemented with 10% heat-inactivated fetal calf serum (Sigma) and gentamycin (50 µg/ml, Sigma). Bacterial cell culturing was done on standard LB medium.

Induction of Cell Death and Detection of Apoptosis.

Apoptosis was induced by UV-B irradiation with 90 mJ/cm$^2$, apoptosis of human PMN cells was induced by 24 h aging. To quantify the rate of apoptosis, cells were analyzed by flow cytometry or fluorescent microscopy. Amongst other features, apoptosis is characterized by blebbing of the cellular membrane, leading to a decrease in the forward scatter (FSC) and an increase in the sideward scatter (SSC). For detection of phosphatidylserine (PS) exposure on the cell surface staining with FITC conjugated annexin V (Böhringer, Mannheim, Germany) in combination with propidium iodide (PI) (AxV/PI) was performed. 200.000 cells were stained for 30 minutes at 4° C. with 200 ng of AxV-FITC and 500 ng propidium iodide (PI) in 500 µl Ringer's solution [Nicoletti, Migliorati, Pagliacci, Grignani and Riccardi, A rapid and simple method for measuring thymocyte apoptosis by propidium iodide staining and flow cytometry. J Immunol Methods, 1991. 139.271-9]. The samples were immediately analyzed by flow cytometry of fluorescent microscopy.

Biofunctionalization and fluorescent labeling of lectins (FimH lectin) was done as previously described, where general principles of lectin chemistry [Rhodes and Milton, Lectin methods and protocols. Methods in molecular medicine, 1997. 1-650] and bioconjugate techniques [Hermanson, Bioconjugate Techniques. 1996. 1-785] were used.

ELISA for Testing Affinity Toward Oligomannose Glycoepitopes (Inhibitor Testing).

Plates were coated with 100 µl of 10 mg/ml solution of RNAse-B in 100 mM carbonate/bicarbonate buffer pH 9.6. Plates were incubated at 4° C. overnight and then washed (300 µl/well) three times with 10 mM phosphate-buffered saline (PBS) containing 0.15% Tween-20. All wells were blocked with 250 µl 3% bovine serum albumin (BSA) in 10 mM phosphate-buffered saline (PBS) containing 0.15% Tween-20 and incubated at 37° C. 2 h. Then washed three times with 10 mM PBS containing 0.05% Tween-20. FimH (or other compound to be tested for affinity towards oligomannose glycoepitopes/or combination of these compound with specific inhibitor) were diluted in 10 mM PBS containing 0.05% Tween-20 at a series of dilutions, and 100 µl of sample was added to each well of plate and incubated for 1 h at room temperature. Wells were washed three times with 10 mM PBS+0.05% Tween-20. 100 µl of anti-body conjugated to horseradish peroxidase (1:5000) was added in buffer and incubated for 1 h at room temperature. Then washed three times with 10 mM PBS+0.05% Tween-20. Added 100 µl of TMB and incubated in dark for 2-5 min. The reaction was stopped with 100 µl/well 1N sulfuric acid. Plate absorbance was analyzed at 450 nm using microplate reader.

Visualization of Endoplasmic Reticulum (ER) Components.

Fluorescently labeled *Narcissus pseudonarcissus* lectin (NPL, specific to oligomannose glycans [Glycomics, Glycan DB. http://functionalglycomics.org, 2012.] and concanavalin A (ConA) specific to glucosylated oligomannose residues [Haugland, Invitrogen: A Guide to Fluorescent Probes and Labeling Technologies. 2005.], both specific to ER-originated glycans, were used to detect ER-derived blebs as described previously [Bilyy, Shkandina, Tomin, Munoz, Franz, Antonyuk, Kit, Zirngibl, Furnrohr, Janko, Lauber, Schiller, Schett, Stoika and Herrmann, Macrophages Discriminate Glycosylation Patterns of Apoptotic Cell-derived Microparticles. J Biol Chem, 2012. 287.496-503]. Lectin binding was analyzed by fluorescent microscopy of flow cytometry. Additionally, ER-Tracker™ Green (Invitrogen), an ER-specific fluorescent stain for live-cell imaging [Haugland, Invitrogen: A Guide to Fluorescent Probes and Labeling Technologies. 2005.] was used to visualized ER.

Fluorescent microscopy with DAPI, FITC-conjugates of lectins and Annexin V, and propidium iodide staining was done using Zeiss AxioImager A1 epifluorescent/DIC microscope, equipped with AxioCam MRm camera and corresponding fluorescent filters (all from Zeiss, Germany) and additional Canon camera (Canon, Japan).

Example 24: Effect of Heptylmannoside-Cyclodextrin Compounds or Synthetic Thiazolylaminomannosides on Colonization of Transgenic Mice Expressing CEACAM6 by Adherent-Invasive *E. coli* Bacteria and on the Related Signs of Colitis Bacterial Strain and Transgenic Mouse Model

*E. coli* strain LF82 was isolated from a chronic ileal lesion of a patient with Crohn's disease (CD). Bacteria were grown routinely in Luria-Bertani (LB) broth overnight at 37° C. Transgenic mouse model CEABAC10 expressing the human CEACAM6 protein is available in the UMR Inserm/Université d'Auvergne 1071 of the Professor Arlette Darfeuille-Michaud at Clermont-Ferrand. This model is particularly suitable to reproduce the abnormal colonization by AIEC bacteria through the interaction with CEACAM6 molecules that were observed abnormally expressed in the ileal mucosa of Crohn's disease patients.

AIEC Colonization Assessment in CEABAC10 Mice Treated with Heptylmannoside-Cyclodextrin or Synthetic Thiazolylaminomannosides Compounds.

Compounds were analyzed for their anti-adhesive effect on a pre-established LF82 colonization in CEABAC10 mice (curative therapy). CEABAC10 mice were given 0.5% of DSS in drinking water. Two days later, mice were treated per os with streptomycin sulfate, 5 mg/mouse. Twenty four hours later, (corresponding to day "0"), a five-hour culture of AIEC LF82 bacteria in LB broth was concentrated to reach $5 \times 10^9$ bacteria/mL and was administered by gavage 2 h after the intragastric administration of cimetidine at 50 mg/kg in order to ablate gastric secretion. An orally administration of inhibitory compounds (cyclodextrin compound 1, example 2bis and cyclodextrin compound 2, example 1), or heptylmannose, or monovalent 13) at a range from 1 to 1000 µg/mouse (=0.04 to 40 mg/kg) was realized 2 h after LF82 infection. A second administration of inhibitors was realized 18 h later (cimetidine was already given 2 h before administration of the compounds). Body weight and signs of colitis were followed for 5 days. Stools were collected from day 1 to day 5 post-infection to assess bacterial colonization. Mice were euthanized at day +5 and the entire intestine was collected to assess the number of AIEC associated with the gut mucosa, to measure pro- and anti-inflammatory cytokine secretions, to assess neutrophil infiltration in the intestinal tissue by measuring myeloperoxidase activity, to determine the disease activity index and to estimate histological damages of the mucosa.

Similar protocol was realized in testing a prophylactic administration of the compounds (administration of similar doses of compounds 5 h before infection). Compounds were compared for their efficacy, depending on the dose and on the preventive or curative effect. We always checked that the inhibitory effects were not related to toxicity effects by analyzing, even at the highest dose of each compound, the absence of cell death of intestinal epithelial cells or bacteria. No toxic effect was observed with the 4 compounds at the highest dose.

Example 25: Protocols for Measuring Affinity, Specificity and Selectivity of Compounds within the Scope of the Present Invention for the FimH Lectin Domain as Target Molecule 1) Affinity, Specificity and Selectivity of Anti-Adhesives for the Target Molecule, the FimH Lectin Domain The affinity and specificity of the FimH lectin for anti-adhesive molecules is screened predominantly using competition tests in vitro, such as this using surface plasmon resonance detection (SPR). Direct binding assessments are made using Isothermal Titration calorimetry (ITC), crystal and solution structures and quantum chemical calculations. Providing within the scope of the present invention compounds with high specificity and selectivity for the target is of essential importance to subvert off-target specificity. These aspects are learned from thermodynamic and structural studies. Multivalent glycoconjugates have greatly enhanced avidity and, as the results in Example 25.2) suggest, also in selectivity, over monovalent ones. In an alternative strategy, both monovalent ligands as well as the multivalent scaffolds are undergoing Quantitative structure-activity relationship (QSAR) improvement using SPR, ITC, crystallography and solution structures and quantum chemical calculations.

Materials and Methods

One of these competition assays that allows to define very accurately the affinities of series of inhibitors, with very limited amounts of materials, is surface plasmon resonance detection of the binding of the FimH adhesin to an amino-octyl mannose-, or alike, coated carboxymethyl-functionalised gold sensor surface (Biacore, GE healthcare) (Almant, M. et al. (2011), Chemistry. 17, 10029-10038). This competition binding assay measures the amount of free FimH in solution using biosensor chips decorated with immobilised Fab fragments of a monoclonal antibody or with an immobilized octyl or heptyl mannoside carrying an amine group for covalent coupling to the chip. A titration series using stepwise 2-fold dilutions from 4000 nM down to 0.015 nM mannoside inhibitor results in a inhibition curve that can be fitted to the Langmuir model of binding with a 1:1 molar ratio. [FimHnb]=[FimH0]−[FimH-Man] (where [FimHnb] is the concentration of non-bound fraction of FimH, [FimH0] the total FimH concentration and [FimH-Man] the mannoside-bound FimH concentration), the amount of free FimH, measured by the SPR assay, is proportional to the amount of added mannoside and the dissociation constant for the FimH-mannoside binding.

Current state-of-the-art methods are used to measure thermodynamics of the interaction of the complete ligand series within the scope of the present invention with the FimH lectin domain (Wellens, A. et al. (2012), Biochemistry 51, 4790-4799; Bouckaert, J. et al. (2013), Chemistry 19, 7847-7855), as well as current state-of-the-art methods to determine the crystal structures of FimH in complex with this same series of ligands (Wellens et al. ibid; Brument, S. et al. (2013), J. Med. Chem. 56, 5395-5406). Current state-of-the-art methods are used to determine the solution structures of FimH lectin domains complexed onto multivalently modified scaffolds (Bouckaert et al. ibid).

2) Measuring the Non-Selectivity for Off-Target Molecules (Macrophage-Mediated Phagocytosis)

Apoptotic cell clearance prevents the accumulation of dying cells in the organisms, their conversion to secondary necrotic cells, while its failure often leads to chronic inflammations resulting in developing of autoimmune disorders (Gaipl, U. S. et al. (2007) Journal of Autoimmunity 28, 114-12; Munoz, L. E., et al. (2010) Nat Rev Rheumatol 6, 280-289).

Among a rich variety of macrophageal receptors, the receptors specific to mannose residues are well known (Li, W. (2012) Journal of Cellular Physiology 227, 1291-1297), and have been tested in the in vitro system for their affinity towards synthetic mannose-based inhibitors (Scharenberg, M., et al., Journal of Medicinal Chemistry 55, 9810-9816), however, the described system is rather an "artificial" one as does not represent the natural repertoire of mannose-specific receptor present on human macrophages and does not allow to estimate influence on phagocytosis itself, but only affinity towards a specific receptor.

To estimate the influence of mannose-based inhibitors on possible inhibition of phagocytosis we used primary human peripheral venous blood monocyte-derived macrophages and estimated their ability to phagocyte autologous and allogenic human blood-derived PMN cells, as described by us previous (Bilyy, R. O. et al. (2012) J Biol Chem 287, 496-503).

Figure 29:
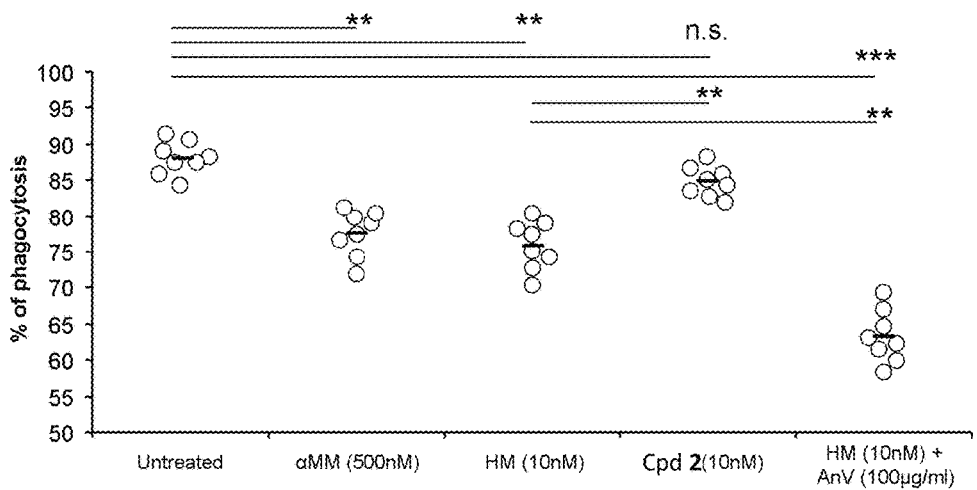
FIG. 29 presents the inhibition of phagocytosis of aged human blood derived PMN cell by autologous human peripheral blood monocyte-derived macrophage in the presence of α-D-methyl mannoside (aMM, 500 nM), hepthyl-mannoside (HM, 10 nM), compound 2 (example 1, 10 nM), and annexin V (AnV, 100 µg/ml) as positive control for inhibiting phosphatidylserine dependent phagocytosis.
Figure 30:
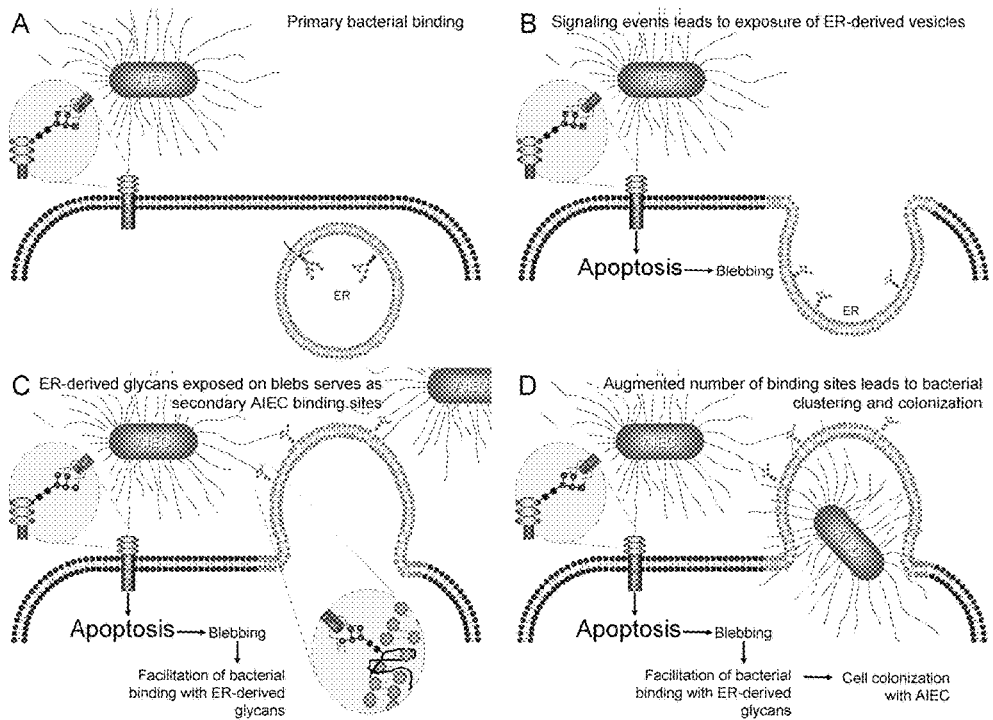
FIG. 30 shows that the induction of apoptosis by AIEC *E. coli* bacteria leads to the exposure of internal oligomannose glycoepitopes. The latter serves as augmented binding sites for bacterial binding and cell colonization.

Monomeric HM at 10 nM as well as αMM at 500 nM significantly decreased phagocytosis rate, while no phagocytosis decrease was observed for multimeric compound 2 at 10 nM (FIG. 29).

Materials and Methods

Patients

Peripheral blood serum samples of 65 patients diagnosed with SLE (with SLEDAI>4 (Gladman, D. et al. (2002) The Journal of Rheumatology 29, 288-291)) were analyzed. An informed consent was obtained from all patients, as it was approved by the Review Board of the Lviv National Medical University, in accordance with the regulations of the Ministry of Health Protection of Ukraine.

Cell Culture and Phagocytosis Assays

Primary human PMN and MoMa from healthy volunteers were used. Monocytes were isolated from peripheral blood by LymphoPrep® gradient according to manufacture's recommendations for isolation of PBMC fraction. Plastic-attached cells of PBMC fraction were then cultured for 7 days in the presence of GM-CSF (100 U/ml) and autologous serum (added at days 1, 3 and 5) to generate MoMa. After 7 days of differentiation, the MoMa population was tested. They typically contain >95% CD11b+ cells, >90% CD14+ cells and >85% CD89+ cells. Phagocytosis was assessed by pre-incubation of PMN (freshly isolated or aged for 24 h) with mannose-based inhibitor for 30 min at 37° C. at Ringer buffer. Cells were thoroughly washed three times with Ringer solution and incubated with human MoMa for 2 hours. Uningested PMN were analyzed by flow cytometry (for this reason cells were pre-stained with CFSE (Rodel, F. et al. (2005) Strahlentherapie and Onkologie: Organ der Deutschen Rontgengesellschaft . . . [et al] 181, 456-462)) or in the hemocytometric chamber using Zeiss AxioImager A1 microscope. The percentage of prey cells that had been bound to or taken up by MoMa (% of phagocytosis) was calculated.

Induction and Inhibition of Apoptosis

Cell viability was controlled by AnnexinV/PI staining Apoptosis was induced by ageing of polymorphonuclear leukocytes (PMN).

Flow Cytometry

Analyses employing fluorescence-labeled lectins (Franz, S. et al. (2006) Cytometry A 69, 230-239) were performed using FACS Scan flow cytometer (BD Biosciences).

Statistics

Statistical significance was assessed employing the Student's t-test. Three levels of significance were depicted with asterisks *—$p<0.05$; —$p<0.01$; *—$p<0.001$, n.s.—$p>0.05$.

The invention claimed is:

1. A compound of the following formula (I):

$$A\text{-}X_n \qquad (I)$$

wherein:

A is selected from the group consisting of:

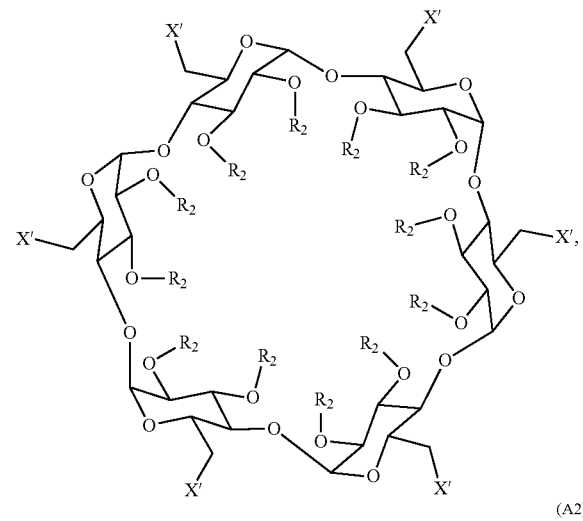

(A1)

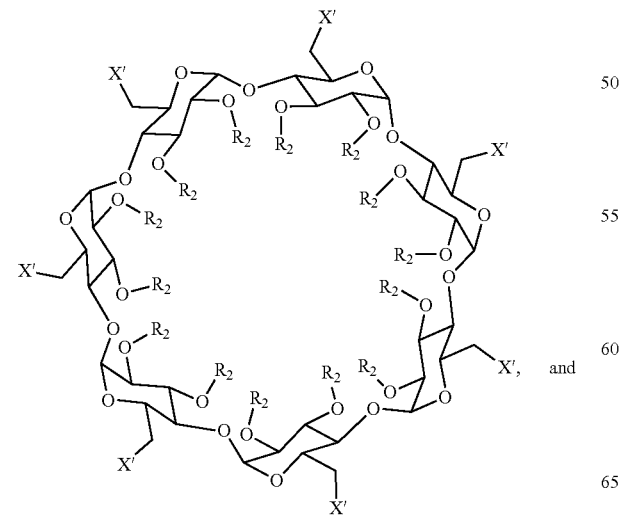

(A2) and

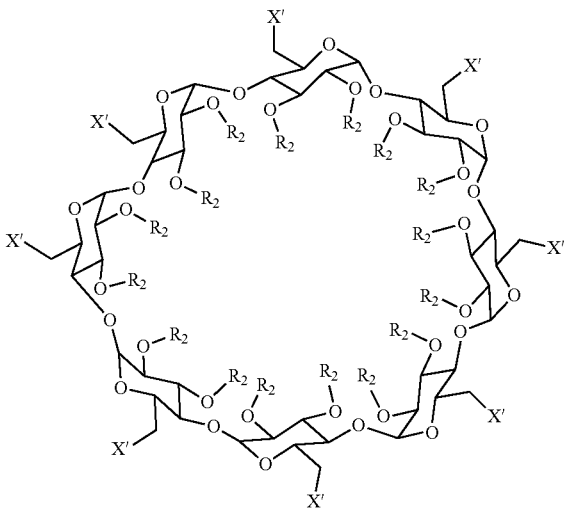

(A3)

wherein

X' is selected from the group consisting of —OH and -----, wherein ----- represents a bond to X;

$R_2$ is selected from the group consisting of hydrogen and a linear or branched ($C_1$-$C_7$)-alkyl;

n is an integer from 6 to 8;

X represents a group according to formula (1):

$$\text{-}W_p\text{-}L_r\text{-}Y_s\text{—}Z \qquad (1)$$

wherein:

p, r, and s are integers independently from each other equal to 0 or 1, provided that:

when r is equal to 0, p and s are such as the sum p+s is equal to 1, when r is equal to 1, p and s are such as the sum p+s is equal to 2;

W is selected from the group consisting of:

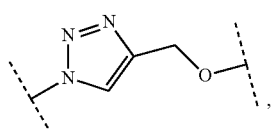

(1')

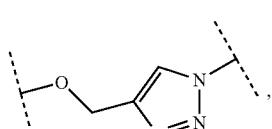

(2')

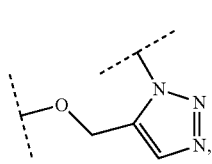

(2bis')

Y is selected from the group consisting of:

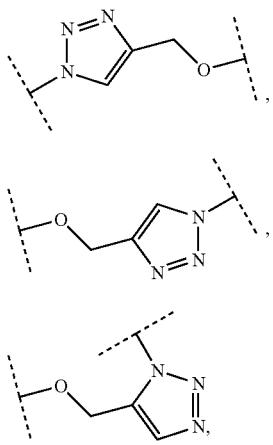

(1')

(2')

(2bis')

Z is selected from the group consisting of:

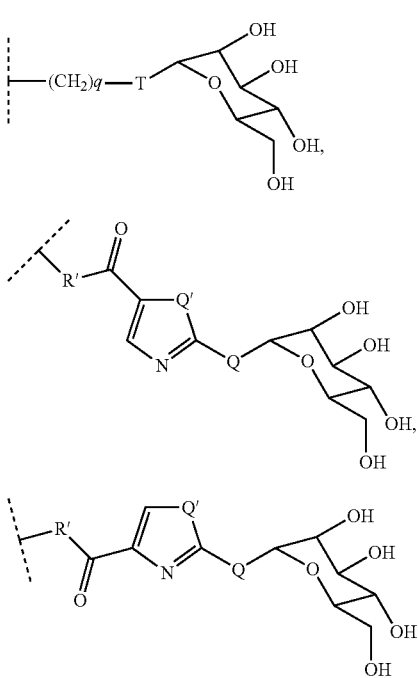

(1")

(2ª)

(2bis")

L represents a linker having a formula:

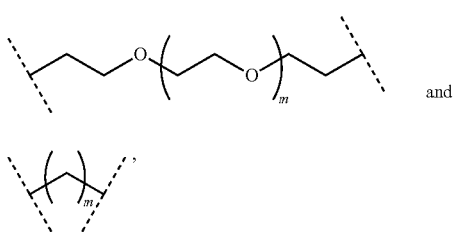

(1₁)

and (1₅)

m being an integer comprised from 0 to 20,
q being an integer chosen from 6, 7, and 8,
Q and Q' representing independently from each other NH, O or S;
T representing O, S or $CH_2$;
R' representing a group selected from the group consisting of:
 a linear or branched ($C_1$-$C_7$)-alkane diyl,
 a linear or branched ($C_2$-$C_7$)-alkene diyl,
 a linear or branched ($C_2$-$C_7$)-alkyne diyl,
 a ($C_3$-$C_7$)-cycloalkane diyl,
 a ($C_5$-$C_7$)-cycloalkene diyl,
 a ($C_3$-$C_7$)-heterocycloalkane diyl,
 a ($C_5$-$C_7$)-heterocycloalkene diyl,
 an arene diyl, said arene being an aromatic or heteroaromatic group,
 a group -$arene_1$-$arene_2$- wherein $arene_1$ and $arene_2$ are independently to each other an aromatic or heteroaromatic arene; and
 a group of the following formula:

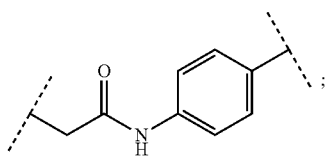

said ($C_1$-$C_7$)-alkane diyl, ($C_2$-$C_7$)-alkene diyl, ($C_2$-$C_7$)-alkyne diyl, ($C_3$-$C_7$)-cycloalkane diyl, ($C_5$-$C_7$)-cycloalkene diyl, ($C_3$-$C_7$)-heterocycloalkane diyl, ($C_5$-$C_7$)-heterocycloalkene diyl, arene diyl, $arene_1$ and $arene_2$ being substituted or not by one or more substituent(s), each independently selected from the group consisting of:
 a linear or branched ($C_1$-$C_7$)-alkyl,
 a linear or branched ($C_2$-$C_7$)-alkenyl,
 a linear or branched ($C_2$-$C_7$)-alkynyl,
 a ($C_3$-$C_7$)-cycloalkyl,
 a ($C_5$-$C_7$)-cycloalkenyl,
 a ($C_3$-$C_7$)-heterocycloalkyl,
 a ($C_5$-$C_7$)-heterocycloalkenyl,
 an aryl, wherein the aryl is an aromatic or heteroaromatic group
 an alkyl aryl, wherein the aryl is an aromatic or heteroaromatic group,
 a CHO,
 a CO—($C_1$-$C_7$)-alkyl,
 a CO-aryl, wherein aryl is an aromatic or heteroaromatic group,
 a $CO_2H$,
 a $CO_2$—($C_1$-$C_7$)-alkyl,
 a CONH—($C_1$-$C_7$)-alkyl,
 a halogen selected from the group consisting of F, Cl, Br, and I,
 $CF_3$,
 $OR_a$, wherein $R_a$ represents:
  H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group,
 $NR_bR_c$, wherein $R_b$ and $R_c$ represent independently from each other:
  H, a linear or branched ($C_1$-$C_7$)-alkyl, a ($C_3$-$C_7$)-cycloalkyl, CO—($C_1$-$C_7$)-alkyl, or CO-aryl, wherein aryl is an aromatic or heteroaromatic group, NO$_2$ and
CN.

2. The compound according to claim 1, of formula (I):

 (I)

wherein A is a cyclodextrin chosen from α-cyclodextrin (α-CD), β-cyclodextrin (β-CD), γ-cyclodextrin (γ-CD), n being 6 when A is α-cyclodextrin or a α-cyclodextrin derivative;

n being chosen from 6 and 7 when A is β-cyclodextrin or a β-cyclodextrin derivative;

n being chosen from 6, 7 and 8 when A is γ-cyclodextrin or a γ-cyclodextrin derivative.

3. A pharmaceutical composition comprising, as active substance, a compound according to claim 2, in association with a pharmaceutically acceptable vehicle.

4. The compound according to claim 2, wherein the compound of formula (I) is selected from the group consisting of:

(i) a compound of formula (I) wherein Z is of formula (1″):

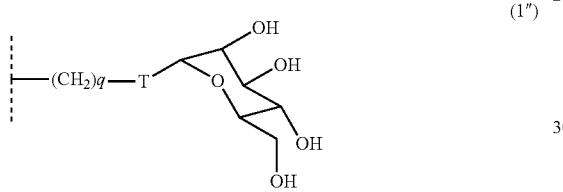 (1″)

T representing O, S or CH$_2$;

(ii) a compound of formula (I) wherein X is of formula (1), wherein p equals 0 and Z is of formula (1″), corresponding to the following formula (2a):

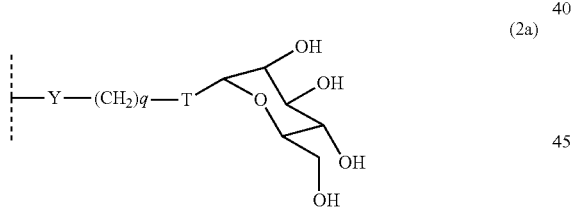 (2a)

wherein Y and q are as defined above, T representing O, S or CH$_2$;

(iii) a compound of formula (I) wherein X is of formula (1), wherein p equals 1 and Z is of formula (1″), corresponding to the following formula (2b):

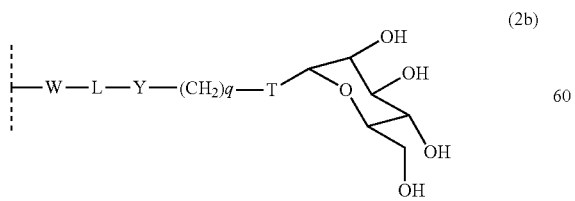 (2b)

wherein W, L, Y and q are as defined above, T representing O, S or CH$_2$;

(iv) a compound of formula (I) wherein X is of formula (1), wherein p equals 0, Y represents (1′) and Z is of formula (1″), corresponding to the following formula (2c):

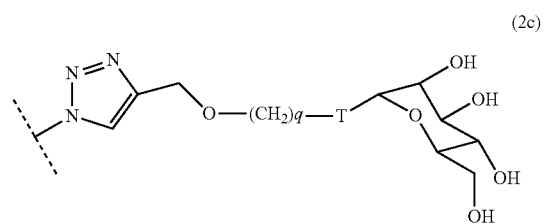 (2c)

wherein q is as defined in above, T representing O, S or CH$_2$;

(v) a compound of formula (I), wherein X is of formula (1), wherein p equals 1, L is of formula (1$_1$), and Z is of formula (1″), corresponding to the following formula (2d):

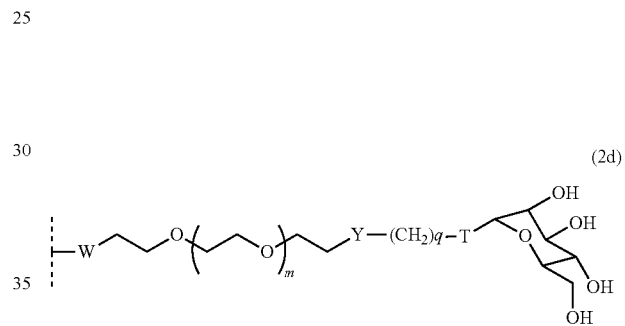 (2d)

wherein W, L, Y, m and q are as defined above, T representing O, S or CH$_2$;

(vi) a compound of formula (I), wherein X is of formula (1), wherein p equals 1, W and Y are of formula (1′), and Z is of formula (1″), corresponding to the following formula (2e):

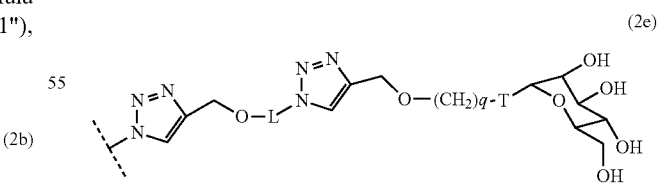 (2e)

wherein L and q are as defined above, T representing O, S or CH$_2$; and (vii) a compound of formula (I), wherein X is of formula (1), wherein p equals 1, W and Y are of formula (1′), and Z is of formula (1″), corresponding to the following formula (2f):

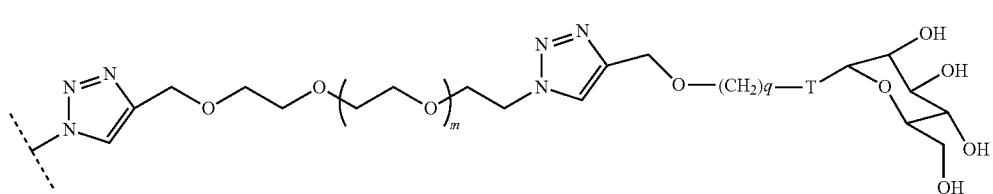

(2f)

wherein m and q are as defined in above, T representing O, S or CH$_2$.

5. The compound according to claim 2, wherein the compound of formula (I) is selected from the group consisting of:

(i) a compound of formula (I), wherein A is a cyclodextrin, X is of formula (1), wherein Z is of formula (1"), corresponding to the following formula:

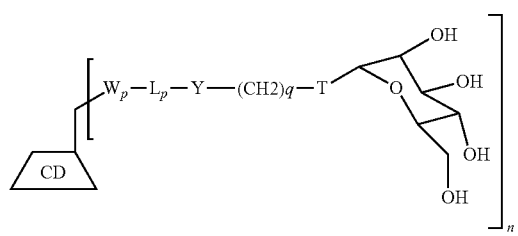

wherein p, n, W, L, Y and q are as defined above, T representing O, S or CH$_2$;

(ii) a compound of formula (I), wherein A is a cyclodextrinX is of formula (1), wherein p equals 0 and Z is of formula (1"), corresponding to the following formula (IIa):

(IIa)

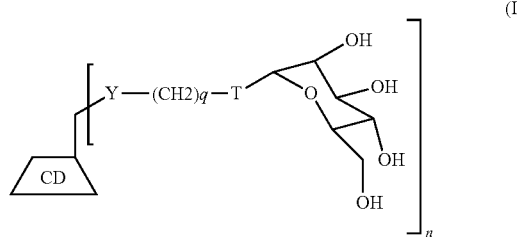

wherein n, Y and q are as defined above, T representing O, S or CH$_2$;

(iii) a compound of formula (I), wherein A is a cyclodextrin, X is of formula (1), wherein p equals 1 and Z is of formula (1"), corresponding to the following formula (IIb):

(IIb)

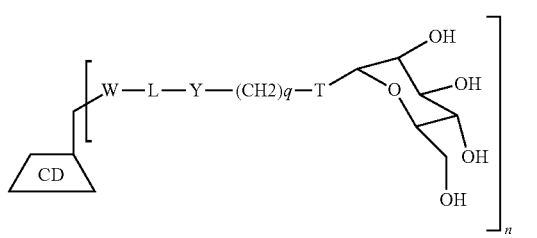

wherein n, W, L, Y and q are as defined above, T representing O, S or CH$_2$;

(iv) a compound of formula (I), wherein A is a cyclodextrin, X is of formula (1), wherein p equals 0, Y represents (1') and Z is of formula (1"), corresponding to the following formula (IIc):

(IIc)

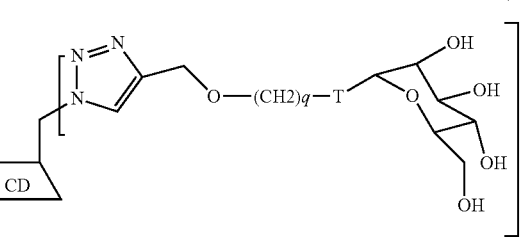

wherein n and q are as defined above, T representing O, S or CH$_2$;

(v) a compound of formula (I), wherein A is a cyclodextrin, X is of formula (1), wherein p equals 1, L is of formula (1$_1$), and Z is of formula (1"), corresponding to the following formula (IId):

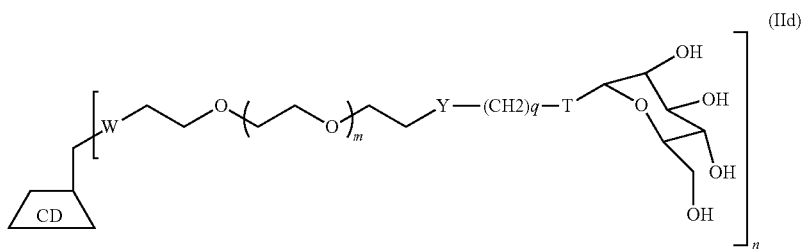

wherein n, W, L, Y, m and q are as defined above, T representing O, S or CH$_2$;

(vi) a compound of formula (I), wherein A is a cyclodextrin, X is of formula (1), wherein p equals 1, W and Y are of formula (1'), and Z is of formula (1''), corresponding to the following formula (IIe):

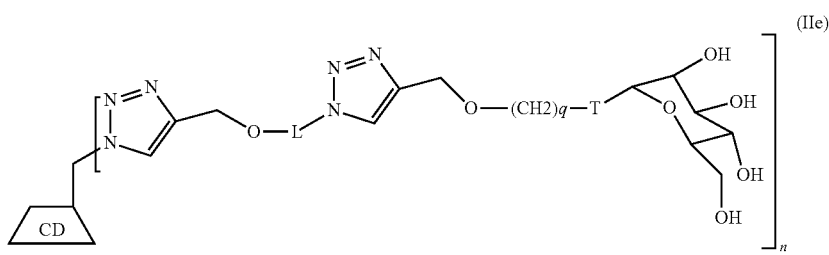

wherein n, L and q are as defined above, T representing O, S or CH$_2$;

(vii) a compound of formula (I), wherein A is a cyclodextrin, X is of formula (1), wherein p equals 1, W and Y are of formula (1'), and Z is of formula (1''), corresponding to the following formula (IIf):

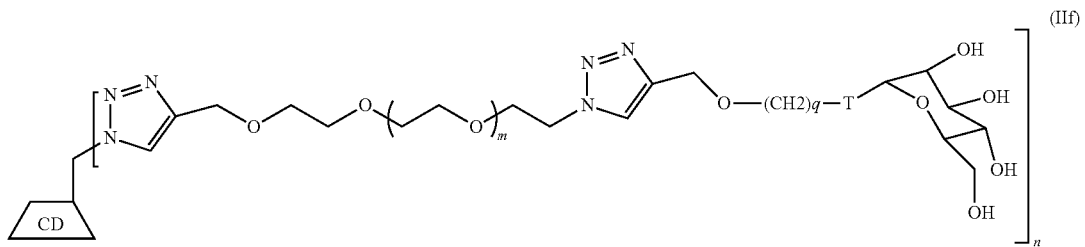

wherein n, m and q are as defined above, T representing O, S or CH$_2$;

(viii) a compound of formula (I), wherein A is a cyclodextrin, X is of formula (1), wherein p equals 0, Y represents (1') and Z is of formula (1''), corresponding to the following formula (IIg):

(IIg)

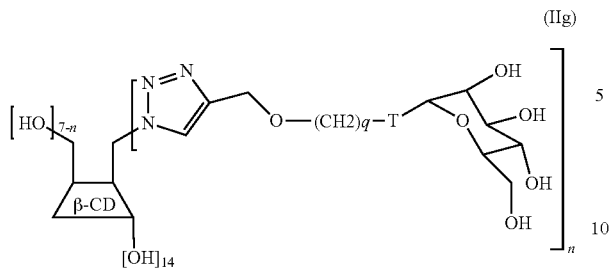

wherein n and q are as defined above, T representing O, S or $CH_2$;

(ix) compound of formula (I), wherein A is a cyclodextrin, X is of formula (1), wherein p equals 1, W and Y are of formula (1'), and Z is of formula (1"), corresponding to the following formula (IIh):

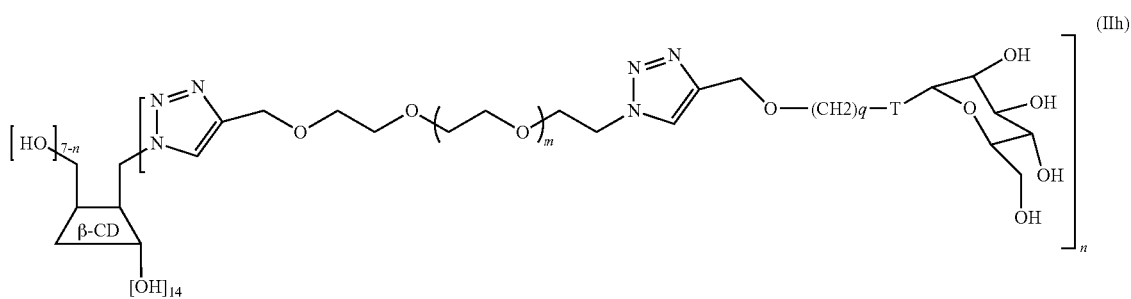

(IIh)

wherein n, m and q are as defined above, T representing O, S or $CH_2$;

(x) a compound of formula (I), wherein A is a cyclodextrin derivative, X is of formula (1), wherein p equals 0, Y represents (1') and Z is of formula (1"), corresponding to the following formula (IIg-bis):

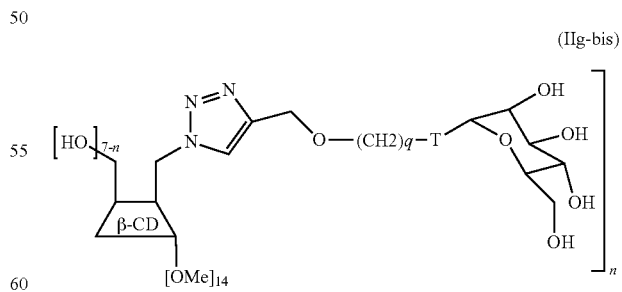

(IIg-bis)

wherein n and q are as defined above, T representing O, S or $CH_2$; and (xi) a compound of formula (I), wherein A is a cyclodextrin derivative, X is of formula (1), wherein p equals 1, W and Y are of formula (1'), and Z is of formula (1"), corresponding to the following formula (IIh-bis):

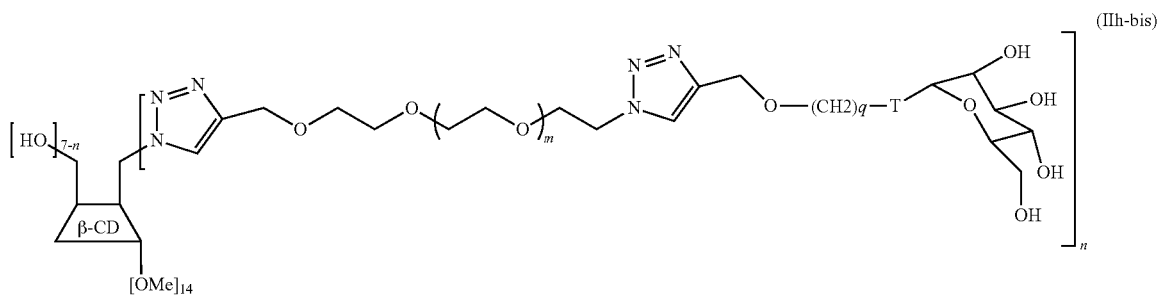
wherein n, m and q are as defined above, T representing O, S or $CH_2$.
6. The compound according to claim 2, wherein n is 7.
7. The compound according to claim 1, wherein q is 7.
8. The compound according to claim 1, selected from the group consisting of:
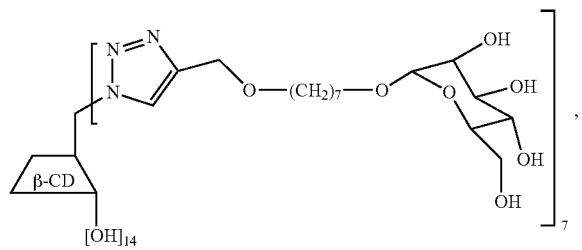
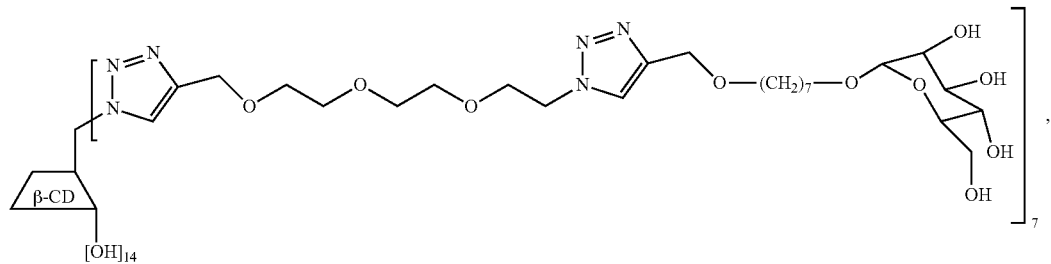
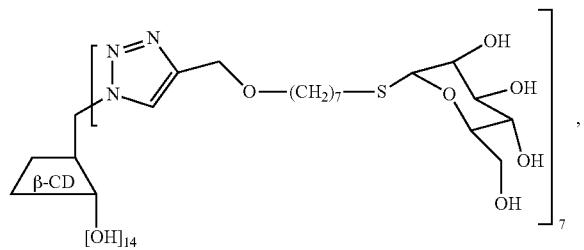
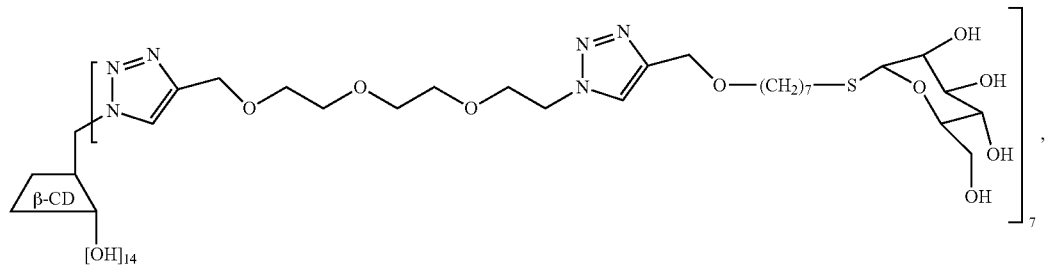

-continued

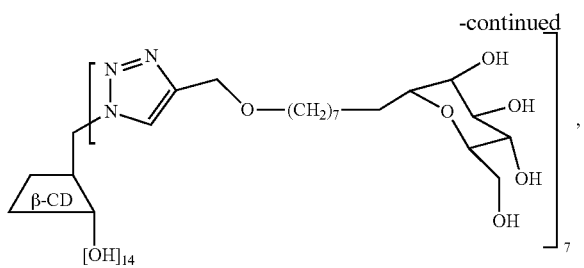

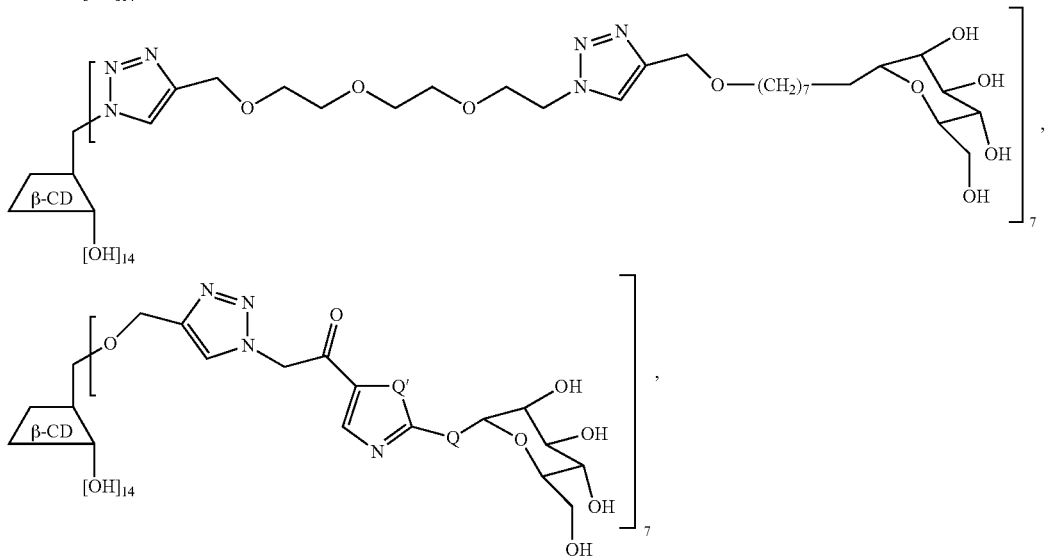

wherein Q and Q' are as defined above,

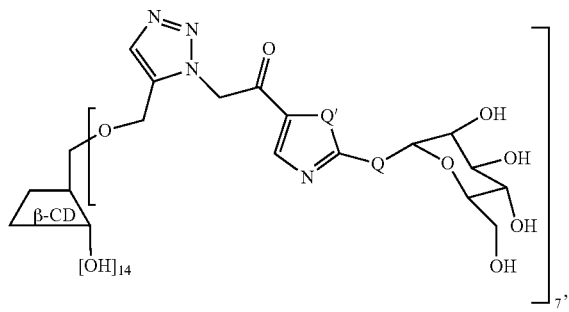

wherein Q and Q' are as defined above,

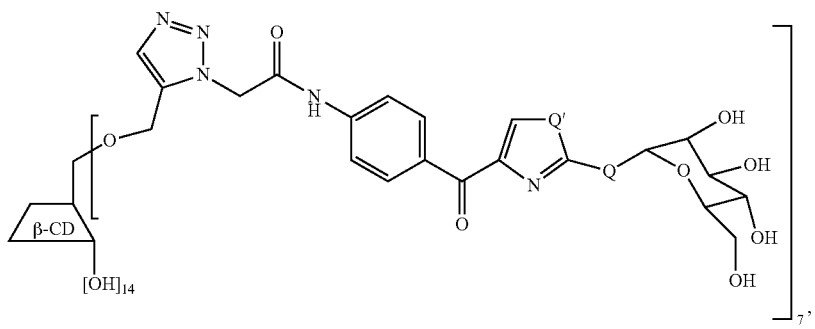

wherein Q and Q' are as defined above.

9. A pharmaceutical composition comprising, as active substance, a compound according to claim 1, in association with a pharmaceutically acceptable vehicle.

10. A vaccine composition comprising, as active substance, a compound according to claim 1, in association with a pharmaceutically acceptable adjuvant.

11. A method for the treatment of pathologies caused by *Escherichia coli* and mediated by interactions between *Escherichia coli* lectins and host cell surface glycans, comprising administering to a patient in need thereof an therapeutically effective amount of the compound according to claim 1.

12. The method according to claim 11, wherein said pathologies belong to the group consisting of:
inflammatory bowel diseases,
urinary tract infections, and urinary tract infections in patients with a metabolic disease correlated with enhanced apoptosis.

13. The method according to claim 12, wherein one of said pathologies is Crohn's disease.

14. A process of preparation of a compound of formula (I):

$$A\text{-}X_n \qquad (I)$$

wherein:

A is selected from the group consisting of:

(A1)

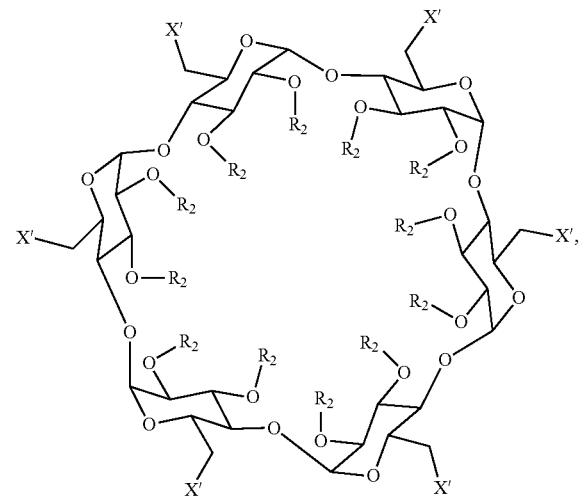

(A2)

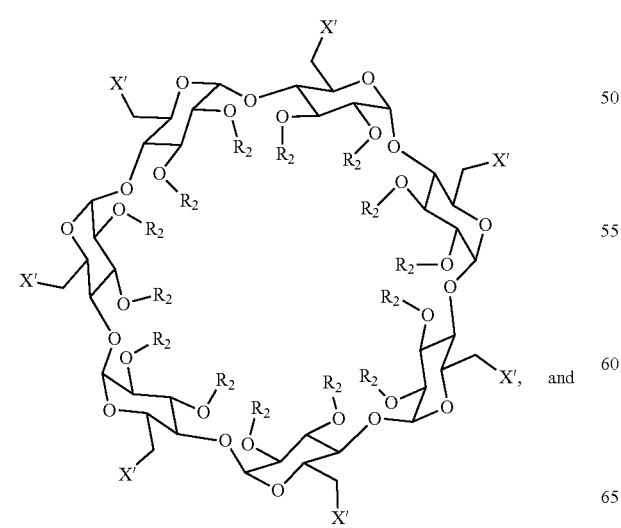

and (A3)

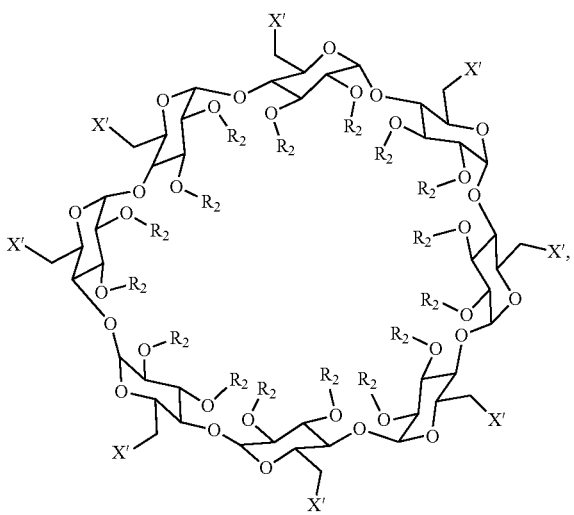

wherein
X' is selected from the group consisting of —OH and -----, wherein ----- represents a bond to X;
$R_2$ is selected from the group consisting of hydrogen and a linear or branched $(C_1\text{-}C_7)$-alkyl;
n is an integer from 6 to 8;
X represents a group of the following formula (1):

$$-W_p\text{-}L_r\text{-}Y_s-Z \qquad (1)$$

wherein:
p, r, and s are integers independently from each other equal to 0 or 1,
provided that:
when r is equal to 0, p and s are such as the sum p+s is equal to 1,
when r is equal to 1, p and s are such as the sum p+s is equal to 2;
W is selected from the group consisting of:

(1')

(2')

(2bis')

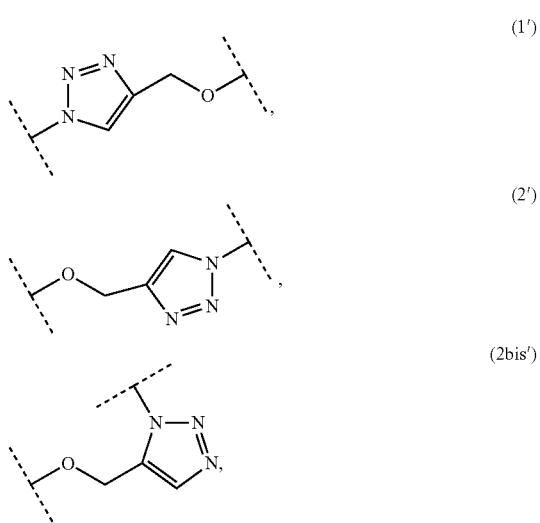

Y is selected from the group consisting of:

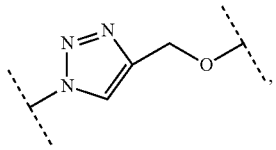
(1')

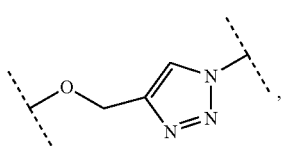
(2')

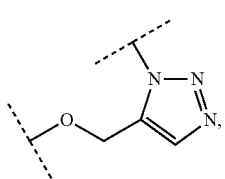
(2bis')

Z is selected from the group consisting of:

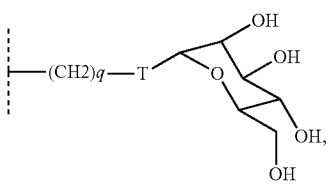
(1")

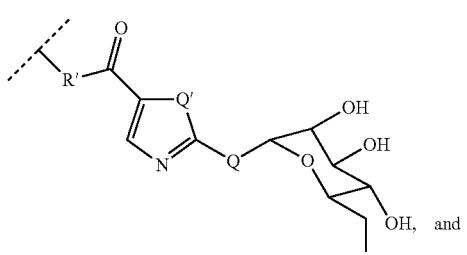
(2")

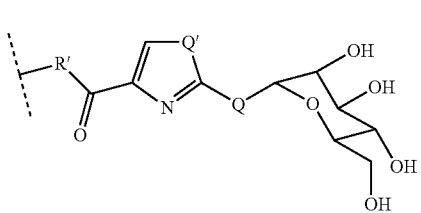
(2bis")

L represents a linker of one of the following formulae:

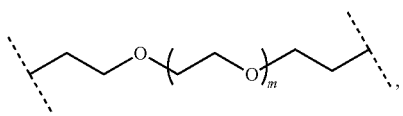
(1₁)

(1₅)

m being an integer comprised from 0 to 20,
q being an integer chosen from 6, 7, and 8,
Q and Q' representing independently from each other NH, O or S;
T representing O, S or CH₂;
R' representing a group selected from the group consisting of:
  a linear or branched (C₁-C₇)-alkane diyl,
  a linear or branched (C₂-C₇)-alkene diyl,
  a linear or branched (C₂-C₇)-alkyne diyl,
  a (C₃-C₇)-cycloalkane diyl,
  a (C₅-C₇)-cycloalkene diyl,
  a (C₃-C₇)-heterocycloalkane diyl,
  a (C₅-C₇)-heterocycloalkene diyl,
  an arene diyl, said arene being an aromatic or heteroaromatic group,
  a group -arene₁-arene₂- wherein arene₁ and arene₂ are independently to each other an aromatic or heteroaromatic arene; and
  a group of the following formula:

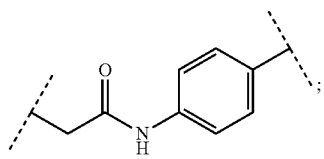

said (C₁-C₇)-alkane diyl, (C₂-C₇)-alkene diyl, (C₂-C₇)-alkyne diyl, (C₃-C₇)-cycloalkane diyl, (C₅-C₇)-cycloalkene diyl, (C₃-C₇)-heterocycloalkane diyl, (C₅-C₇)-heterocycloalkene diyl, arene diyl, arene₁ and arene₂ being substituted or not by one or more substituent(s), each independently selected from the group consisting of:
  a linear or branched (C₁-C₇)-alkyl,
  a linear or branched (C₂-C₇)-alkenyl,
  a linear or branched (C₂-C₇)-alkynyl,
  a (C₃-C₇)-cycloalkyl,
  a (C₅-C₇)-cycloalkenyl,
  a (C₃-C₇)-heterocycloalkyl,
  a (C₅-C₇)-heterocycloalkenyl,
  an aryl, wherein the aryl is an aromatic or heteroaromatic group
  an alkyl aryl, wherein the aryl is an aromatic or heteroaromatic group,
  a CHO,
  a CO—(C₁-C₇)-alkyl,
  a CO-aryl, wherein aryl is an aromatic or heteroaromatic group,
  a CO₂H,
  a CO₂—(C₁-C₇)-alkyl,
  a CONH—(C₁-C₇)-alkyl,
  a halogen selected from the group consisting of F, Cl, Br, and I,
  CF₃,
  OR_a, wherein R_a represents:

H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group, $NR_bR_c$, wherein $R_b$ and $R_c$ represent independently from each other:

H, a linear or branched $(C_1$-$C_7)$-alkyl, a $(C_3$-$C_7)$-cycloalkyl, CO—$(C_1$-$C_7)$-alkyl, or CO-aryl, wherein aryl is an aromatic or heteroaromatic group, $NO_2$ and

CN;

when r=0, said process of preparation comprising a reaction between:

A-$(G_1)_n$, wherein A and n are as defined above and $G_1$ is the first co-precursor of Y or W, and $G_2$-Z, wherein Z is as defined above and $G_2$ is the second co-precursor of Y or W to obtain a compound of formula (I) A-$(X)_n$, wherein X corresponds to formula —Y—Z (1a) or —W—Z, $G_1$ and $G_2$ having reacted together to form Y or W, said group $G_1$ representing —$N_3$ or said $G_2$ group representing respectively or —$N_3$;

or when r=1, said process of preparation comprising:
a) a reaction between:
A-$(G_1)_n$, wherein A and n are as defined above and $G_1$ is the first co-precursor of W;
$F_2$-L-$F_3$, wherein L is as defined above, $F_2$ is the second co-precursor of W, and $F_3$ is a precursor of the first co-precursor $F_4$ of Y;
to obtain a compound of formula A-$(W$-L-$F_3)_n$; $G_1$ and $F_2$ having reacted together to form W;
b) a reaction starting from A-$(W$-L-$F_3)_n$ to obtain A-$(W$-L-$F_4)_n$, wherein $F_4$ is the first co-precursor of Y;
c) a reaction between:
a. A-$(W$-L-$F_4)_n$, and
b. $G_2$-Z, wherein Z is as defined above and $G_2$ is the second co-precursor of Y, to obtain a compound of formula (I) A-$(X)_n$, wherein X corresponds to formula (Ib)

—W-L-Y—Z, $F_4$ and $G_2$ having reacted together to form Y, said group $G_1$ representing —$N_3$ or said $F_2$ group representing respectively or —$N_3$;

said group $F_4$ representing —$N_3$ or said $G_2$ group representing respectively or —$N_3$.

15. The process of preparation according to claim 14, of a compound of the following formula (IIc):

wherein q is as previously defined, said process of preparation comprising a reaction between:

to obtain aforesaid compound of formula (IIc).

16. The process of preparation according to claim 14, of a compound of formula (IIf):

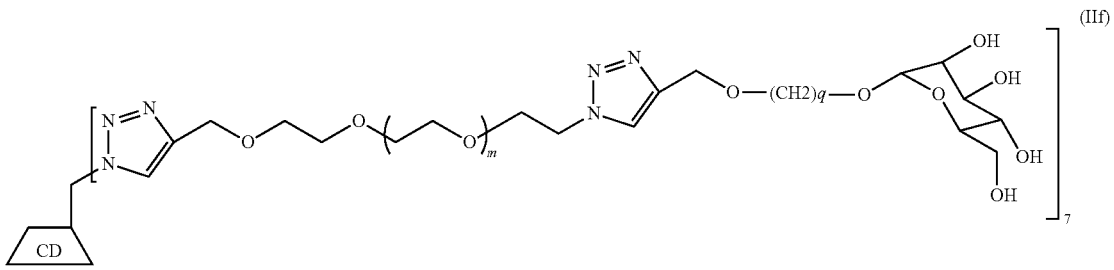

wherein m and q are as previously defined,
said process of preparation comprising:
 a) a reaction between:

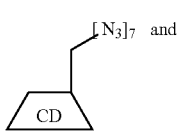

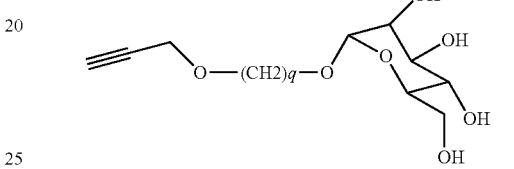

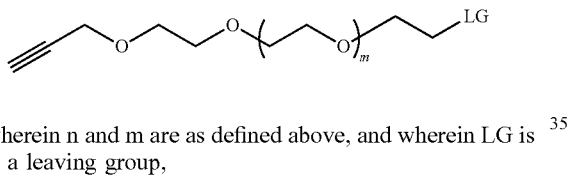

wherein n and m are as defined above, and wherein LG is a leaving group,
to obtain a compound of formula:

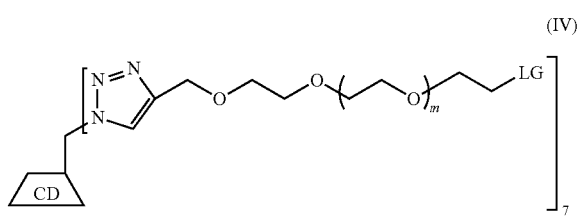

b) a reaction between aforesaid compound of formula (IV) and M-N₃, wherein M is a metal chosen from sodium and potassium,
to obtain a compound of formula (V):

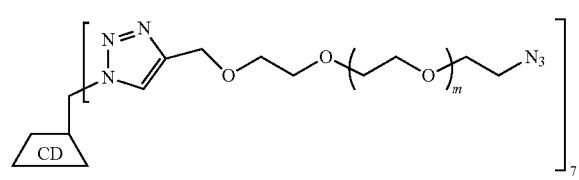

c) a reaction between aforesaid compound of formula (V) and to obtain aforesaid compound of formula (IIf).

17. The process of preparation according to claim 14, wherein A is a cyclodextrin chosen from α-cyclodextrin (α-CD), β-cyclodextrin (β-CD), γ-cyclodextrin (γ-CD);
 n is 6 when A is α-cyclodextrin or a α-cyclodextrin derivative;
 n is chosen from 6 and 7 when A is β-cyclodextrin or a β-cyclodextrin derivative; and
 n is chosen from 6, 7 and 8 when A is γ-cyclodextrin or a γ-cyclodextrin derivative.

18. The process of preparation according to claim 17, wherein the compound of formula (I) is selected from the group consisting of:
 (i) a compound of formula (I), wherein A is a cyclodextrin, X is of formula (1), wherein Z is of formula (1″), corresponding to the following formula:

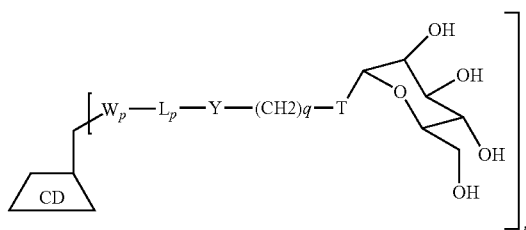

wherein p, n, W, L, Y and q are as defined above, T representing O, S or CH₂;

(ii) a compound of formula (I), wherein A is a cyclodextrin, X is of formula (1), wherein p equals 0 and Z is of formula (1″), corresponding to the following formula (IIa):

(IIa)

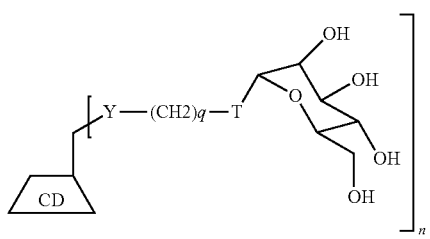

wherein n, Y and q are as defined above, T representing O, S or CH$_2$;

(iii) a compound of formula (I), wherein A is a cyclodextrin, X is of formula (1), wherein p equals 1 and Z is of formula (1"), corresponding to the following formula (IIb):

(IIb)

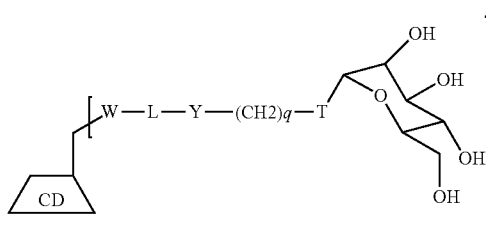

wherein n, W, L, Y and q are as defined above, T representing O, S or CH$_2$;

(iv) a compound of formula (I), wherein A is a cyclodextrin, X is of formula (1), wherein p equals 0, Y represents (1') and Z is of formula (1"), corresponding to the following formula (IIc):

(IIc)

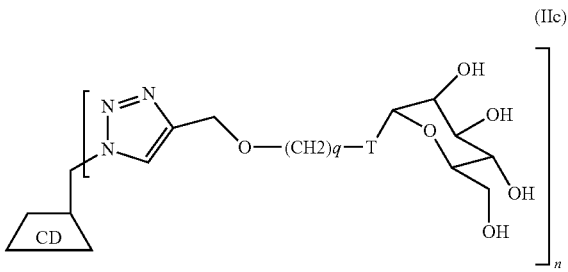

wherein n and q are as defined above, T representing O, S or CH$_2$;

(v) a compound of formula (I), wherein A is a cyclodextrin, X is of formula (1), wherein p equals 1, L is of formula (1$_1$), and Z is of formula (1"), corresponding to the following formula (IId):

(IId)

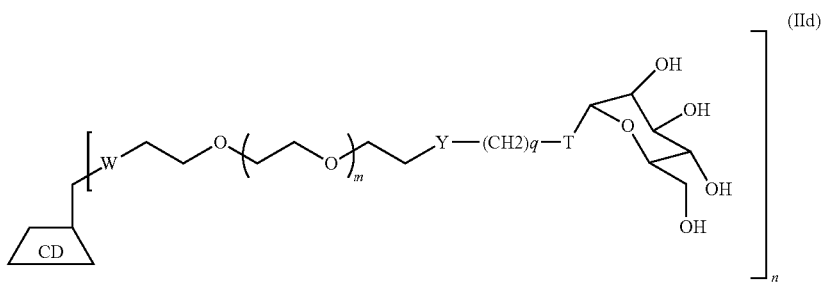

wherein n, W, L, Y, m and q are as defined above, T representing O, S or CH$_2$;

(vi) a compound of formula (I), wherein A is a cyclodextrin, X is of formula (1), wherein p equals 1, W and Y are of formula (1'), and Z is of formula (1"), corresponding to the following formula (IIe):

(IIe)

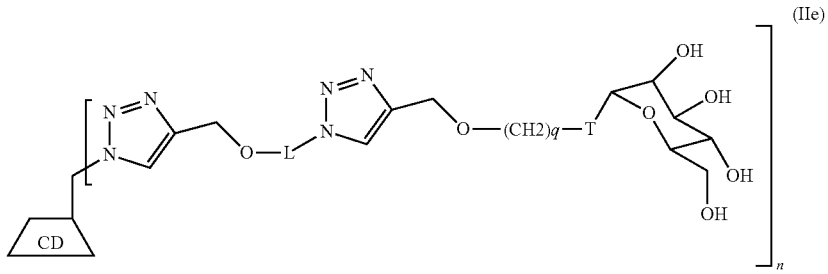

wherein n, L and q are as defined above, T representing O, S or CH$_2$;

(vii) a compound of formula (I), wherein A is a cyclodextrin, X is of formula (1), wherein p equals 1, W and Y are of formula (1'), and Z is of formula (1"), corresponding to the following formula (IIf):

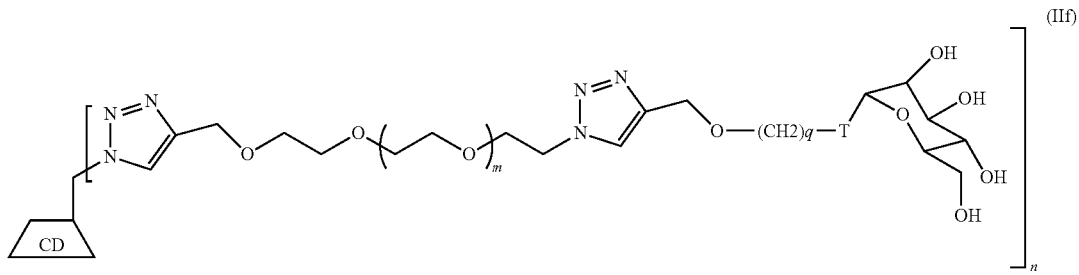

wherein n, m and q are as defined above, T representing O, S or CH$_2$;

(viii) a compound of formula (I), wherein A is a cyclodextrin, X is of formula (1), wherein p equals 0, Y represents (1') and Z is of formula (1"), corresponding to the following formula (IIg):

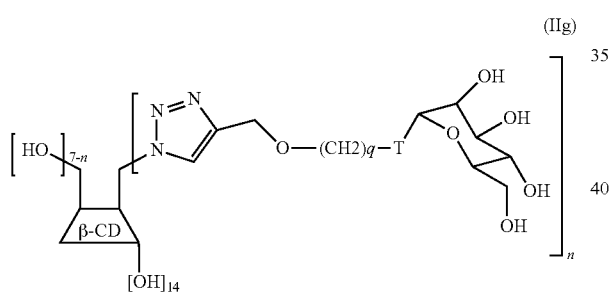

wherein n and q are as defined above, T representing O, S or CH$_2$;

(ix) compound of formula (I), wherein A is a cyclodextrin, X is of formula (1), wherein p equals 1, W and Y are of formula (1'), and Z is of formula (1"), corresponding to the following formula (IIh):

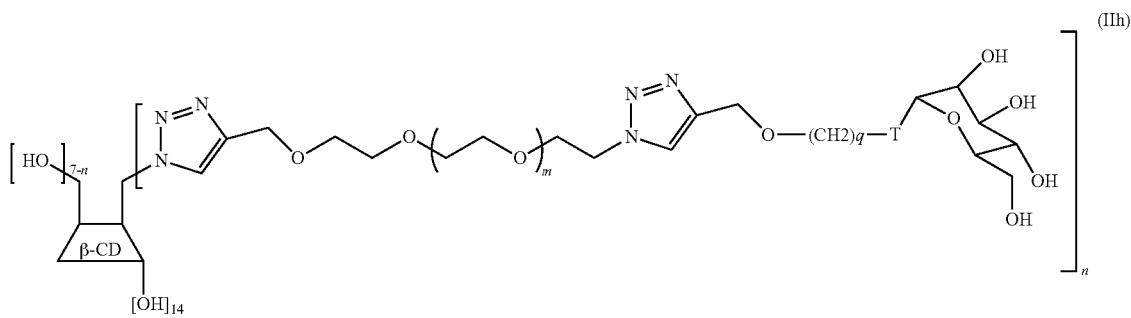

wherein n, m and q are as defined above, T representing O, S or CH$_2$;

(x) a compound of formula (I), wherein A is a cyclodextrin derivative, X is of formula (1), wherein p equals 0, Y represents (1') and Z is of formula (1"), corresponding to the following formula (IIg-bis):

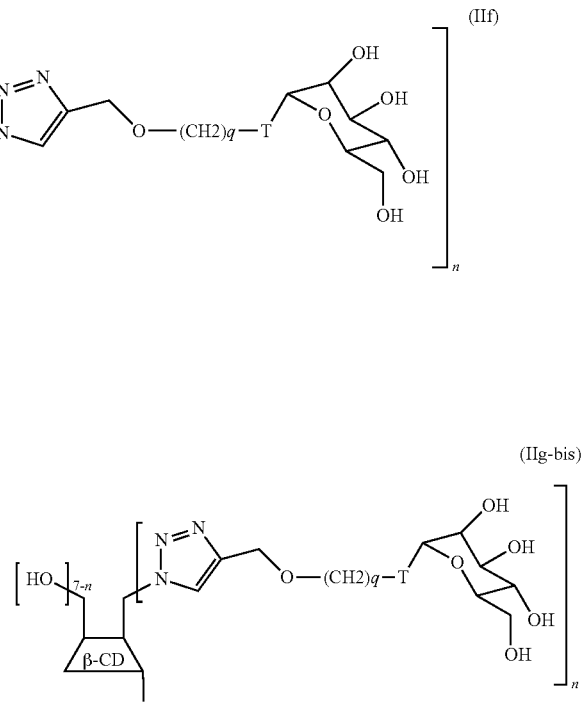

wherein n and q are as defined above, T representing O, S or CH$_2$; and (xi) a compound of formula (I), wherein A is a cyclodextrin derivative, X is of formula (1), wherein p equals 1, W and Y are of formula (1'), and Z is of formula (1"), corresponding to the following formula (IIh-bis):

211 212
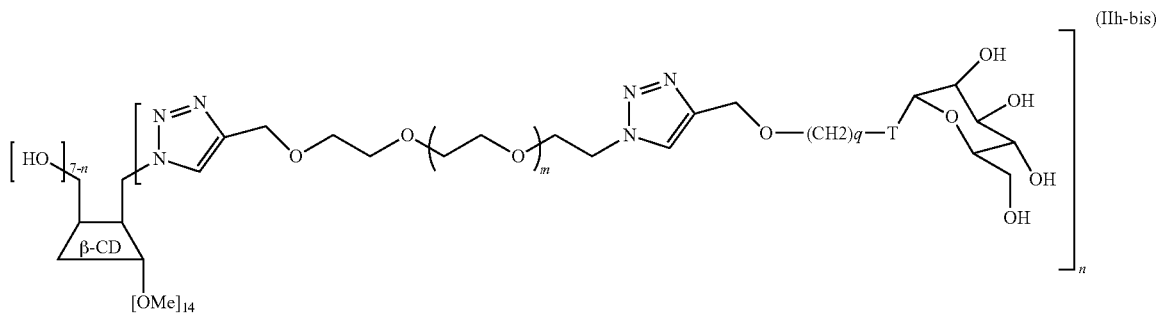
wherein n, m and q are as defined above, T representing O, S or CH$_2$.
19. The process of preparation according to claim 14, wherein the compound is selected from the group consisting of:
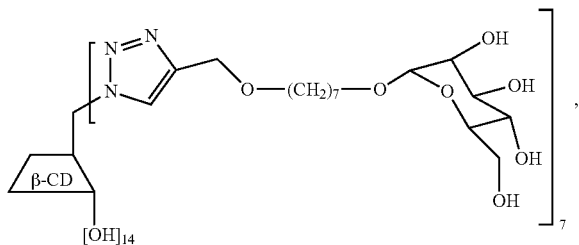
,
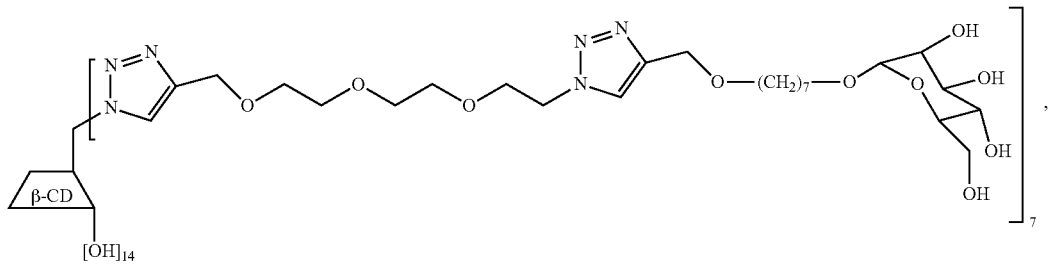
,
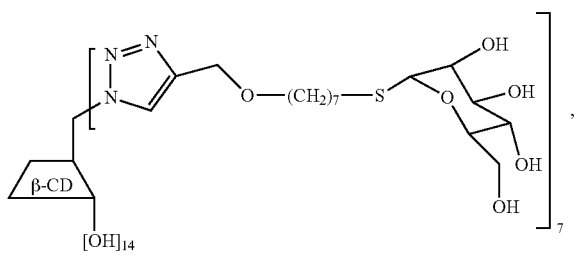
,

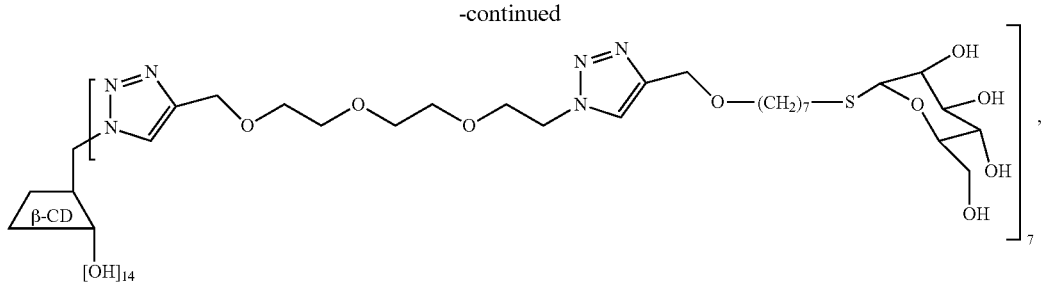
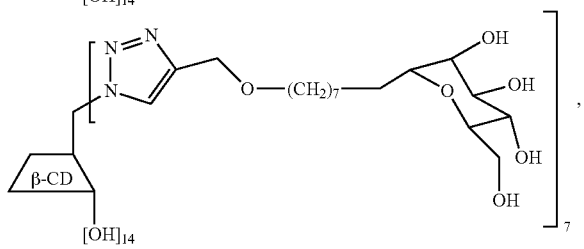
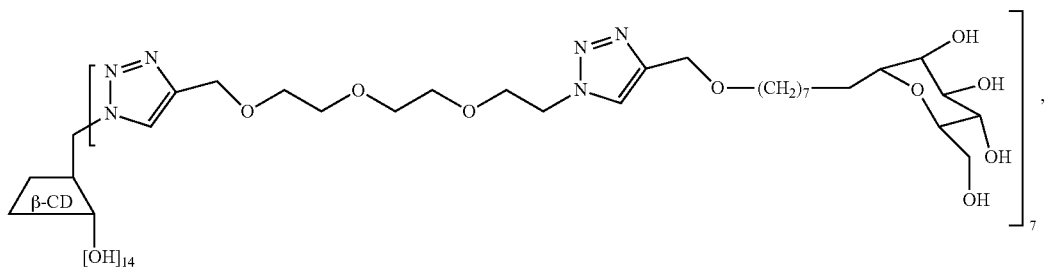
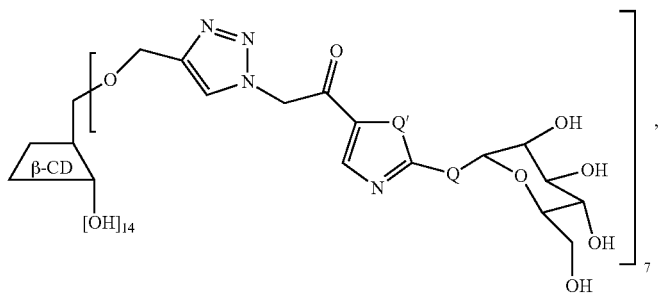
wherein Q and Q' are as defined above,
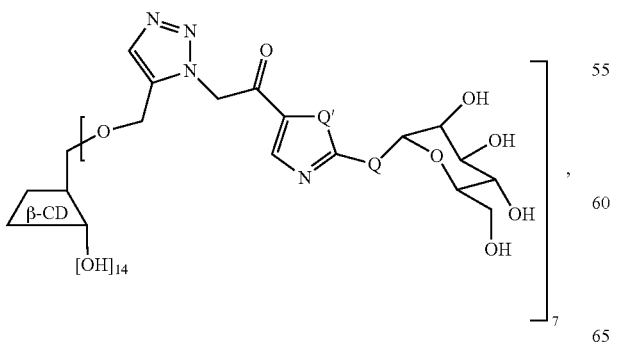
wherein Q and Q' are as defined above,

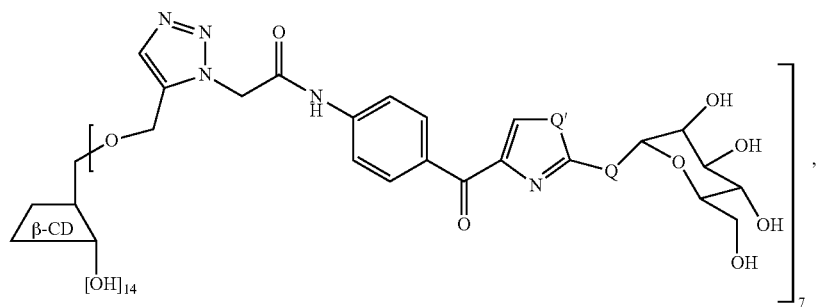
wherein Q and Q' are as defined above.
20. The process of preparation according to claim 14, wherein q is 7.
21. The process of preparation according to claim 14, wherein n is 7.
\* \* \* \* \*